US012784885B2

(12) United States Patent
Ginsburg

(10) Patent No.: US 12,784,885 B2
(45) Date of Patent: Nov. 3, 2026

(54) DATA COMMAND CENTER VISUAL DISPLAY SYSTEM

(71) Applicant: DHRpro, LLC, Merion Station, PA (US)

(72) Inventor: Leonard H. Ginsburg, Merion, PA (US)

(73) Assignee: DHRPRO, LLC, Merion Station, PA (US)

( * ) Notice: Subject to any disclaimer, the term of this patent is extended or adjusted under 35 U.S.C. 154(b) by 0 days.

(21) Appl. No.: 16/802,547

(22) Filed: Feb. 26, 2020

(65) Prior Publication Data

US 2020/0294640 A1 Sep. 17, 2020

Related U.S. Application Data

(60) Provisional application No. 62/810,868, filed on Feb. 26, 2019.

(51) Int. Cl.
*G16H 15/00* (2018.01)
*G16H 10/60* (2018.01)
(Continued)

(52) U.S. Cl.
CPC ............. *G16H 15/00* (2018.01); *G16H 10/60* (2018.01); *G16H 40/20* (2018.01); *G16H 40/63* (2018.01); *G06F 3/04842* (2013.01)

(58) Field of Classification Search
CPC ........ G16H 15/00; G16H 10/60; G16H 40/20; G16H 40/63; G06F 3/04842
See application file for complete search history.

(56) References Cited

U.S. PATENT DOCUMENTS 7,171,277 B2 1/2007 Engleson et al.
7,987,428 B2 7/2011 Handy et al.
(Continued)

FOREIGN PATENT DOCUMENTS

CA 2529213 A1 6/2006
CA 2702079 4/2009
(Continued)

OTHER PUBLICATIONS

Kevin Fogerty, "In the Cloud, Distance Matters for Compute Efficiency," Network Computing, https://www.networkcomputing.com/cloud-networking/in-the-cloud-distance-matters-for-compute-efficiency (Year: 2013).*
(Continued)

*Primary Examiner* — Joshua B Blanchette
(74) *Attorney, Agent, or Firm* — SCHWEGMAN LUNDERG & WOESSNER, P.A.

(57) ABSTRACT

A data command center visual display system presents dynamic data to a display screen. The command center visual display system includes a plurality of adjustable display panels configured to display predetermined combinations of patient identification information and patient medical information. A patient flowsheet is created that includes a table that presents the patient's medical information by medical service, medical procedure, diagnostic test, medication, and diagnosis that is prescribed, ordered, performed, or selected during respective encounters with at least one medical provider. In response to selection by a user, at least two adjustable display panels containing medical information relating to one or more patients in the patient flowsheet are presented to the display in a single view. The user may edit or move the medical information or the patient identification information within the display panels while the display panels are simultaneously open.

93 Claims, 114 Drawing Sheets

(51) Int. Cl.
*G16H 40/20* (2018.01)
*G16H 40/63* (2018.01)
*G06F 3/04842* (2022.01)

(56) References Cited

U.S. PATENT DOCUMENTS 8,126,738 B2 2/2012 Green et al.
8,285,681 B2 10/2012 Prahlad et al.
8,321,383 B2 11/2012 Schumacher et al.
8,666,773 B1 3/2014 Gonzales, Jr. et al.
8,666,774 B1 3/2014 Gonzales, Jr. et al.
9,053,222 B2 6/2015 Lynn et al.
9,104,789 B2 8/2015 Gross et al.
9,240,002 B2 1/2016 Hume et al.
9,483,614 B2 11/2016 Ash et al.
9,582,838 B1 2/2017 Henderson et al.
9,626,479 B2 4/2017 Zaleski
10,541,053 B2 1/2020 Sheffer et al.
10,622,105 B2 4/2020 Von Reden
10,685,743 B2 6/2020 Ginsburg et al.
11,205,505 B2 12/2021 Ginsburg
11,244,745 B2 2/2022 Kamen et al.
11,387,000 B2 7/2022 Saliman et al.
11,610,653 B2 3/2023 Schneider et al.
11,666,702 B2 6/2023 Morawiec et al.
11,701,199 B2 7/2023 Defreitas et al.
11,705,242 B2 7/2023 Pfeiffer et al.
11,710,554 B2 7/2023 De La Torre et al.
11,756,659 B2 9/2023 Ginsburg
11,837,334 B2 12/2023 Ginsburg et al.
12,380,972 B2 8/2025 Ginsburg et al.
2001/0032100 A1 10/2001 Mahmud et al.
2002/0002473 A1 1/2002 Schrier et al.
2002/0198742 A1 12/2002 Kameda et al.
2003/0195775 A1 10/2003 Hampton et al.
2004/0172306 A1 9/2004 Wohl et al.
2005/0234903 A1 10/2005 Makino
2006/0058612 A1 3/2006 Dave et al.
2006/0064020 A1 3/2006 Burnes et al.
2006/0080620 A1 4/2006 Dvorak et al.
2006/0085223 A1 4/2006 Anderson et al.
2006/0265249 A1 11/2006 Follis et al.
2006/0294092 A1 12/2006 Giang et al.
2007/0016441 A1 1/2007 Stroup
2007/0016442 A1 1/2007 Stroup
2007/0143149 A1 6/2007 Buttner et al.
2007/0185390 A1 8/2007 Perkins et al.
2008/0033754 A1 2/2008 Smith et al.
2008/0040151 A1 2/2008 Moore
2008/0086332 A1 4/2008 Hertel et al.
2008/0086333 A1 4/2008 Hertel et al.
2008/0133274 A1 6/2008 Warner
2008/0243548 A1* 10/2008 Cafer .................... G16H 40/67 705/3
2009/0070136 A1 3/2009 Morita et al.
2009/0192823 A1 7/2009 Hawkins et al.
2009/0204421 A1* 8/2009 Guimaraes ............. G16H 10/60 705/2
2009/0217189 A1* 8/2009 Martin .................. G16H 40/63 715/772
2009/0222286 A1* 9/2009 Elsholz .................. G16H 10/60 707/999.1
2009/0265188 A1 10/2009 Lamy et al.
2009/0328176 A1 12/2009 Martin et al.
2010/0057646 A1* 3/2010 Martin .................. G16H 15/00 706/11
2010/0083164 A1 4/2010 Martin et al.
2010/0094649 A1 4/2010 White
2010/0114608 A1 5/2010 Ando
2010/0131293 A1* 5/2010 Linthicum ............. G16H 10/60 715/838
2010/0131482 A1 5/2010 Linthicum et al.
2010/0131883 A1 5/2010 Linthicum et al.
2010/0274584 A1 10/2010 Kim
2010/0280846 A1 11/2010 Clements et al.
2011/0004494 A1 1/2011 Denny, Jr. et al.
2011/0202370 A1 8/2011 Green, III et al.
2011/0218821 A1 9/2011 Walton et al.
2011/0225114 A1 9/2011 Gotthardt
2011/0239113 A1 9/2011 Hung et al.
2011/0258001 A1 10/2011 Green, III et al.
2011/0270630 A1 11/2011 Green, III et al.
2011/0276348 A1 11/2011 Ahn et al.
2011/0295618 A1 12/2011 Naipaul et al.
2012/0078662 A1 3/2012 Olivarez
2012/0078664 A1 3/2012 Hasan et al.
2012/0109686 A1 5/2012 Higbie et al.
2012/0130197 A1 5/2012 Kugler et al.
2012/0130741 A1 5/2012 Sparandara et al.
2012/0131440 A1 5/2012 Rodorff
2012/0131498 A1 5/2012 Gross et al.
2012/0131507 A1 5/2012 Sparandara et al.
2012/0215551 A1 8/2012 Flanagan et al.
2012/0215557 A1 8/2012 Flanagan et al.
2012/0215558 A1 8/2012 Flanagan et al.
2012/0215559 A1 8/2012 Flanagan et al.
2012/0215560 A1 8/2012 Ofek et al.
2012/0232918 A1 9/2012 Mack et al.
2012/0253841 A1 10/2012 Erlandsen et al.
2012/0286955 A1 11/2012 Welch et al.
2013/0024206 A1 1/2013 Hughes et al.
2013/0024213 A1 1/2013 Poon
2013/0027411 A1 1/2013 Hebler et al.
2013/0035961 A1 2/2013 Yegnanarayanan
2013/0041677 A1 2/2013 Nusimow et al.
2013/0080192 A1 3/2013 Bucur et al.
2013/0083185 A1 4/2013 Coleman, III
2013/0159022 A1 6/2013 Verbeek et al.
2013/0191161 A1 7/2013 Churchwell et al.
2013/0290005 A1 10/2013 Vesto et al.
2013/0297348 A1 11/2013 Cardoza et al.
2014/0012597 A1 1/2014 Nolte et al.
2014/0058740 A1 2/2014 Barnett
2014/0068489 A1 3/2014 Wyland et al.
2014/0074509 A1 3/2014 Amarasingham et al.
2014/0100885 A1 4/2014 Stern
2014/0181128 A1 6/2014 Riskin et al.
2014/0188503 A1 7/2014 Balignasay et al.
2014/0207486 A1 7/2014 Carty et al.
2014/0236627 A1 8/2014 Odessky et al.
2014/0236631 A1 8/2014 Perrin et al.
2014/0236635 A1 8/2014 Liberty et al.
2014/0249833 A1* 9/2014 Conti .................... G16H 40/20 705/2
2014/0304005 A1 10/2014 Hughes et al.
2015/0052032 A1 2/2015 Aharoni
2015/0185972 A1* 7/2015 Ash ....................... G16H 40/63 715/810
2015/0254403 A1* 9/2015 LaPerna ................ G16H 10/60 705/3
2015/0269323 A1 9/2015 Ginsburg
2015/0317435 A1 11/2015 Klocek et al.
2016/0063212 A1 3/2016 Monier et al.
2016/0125137 A1 5/2016 Ott
2016/0125149 A1 5/2016 Abramowitz
2016/0162638 A1 6/2016 Albro et al.
2016/0198996 A1 7/2016 Dullen
2016/0253461 A1 9/2016 Sohr et al.
2016/0283664 A1 9/2016 Tubman et al.
2016/0321399 A1 11/2016 Ramachandran
2016/0321404 A1 11/2016 Ginsburg
2016/0328526 A1 11/2016 Park et al.
2016/0357914 A1 12/2016 Morris et al.
2017/0068780 A1 3/2017 Dobrean
2017/0116373 A1 4/2017 Ginsburg et al.
2018/0121605 A1 5/2018 Allen et al.
2018/0130003 A1 5/2018 Sublett et al.
2018/0261306 A1 9/2018 Naito et al.
2018/0330457 A1 11/2018 Hawkins et al.
2018/0336457 A1 11/2018 Pal et al.
2019/0259479 A1 8/2019 Ginsburg
2020/0005916 A1 1/2020 Brooks et al.
2020/0185100 A1 6/2020 Francois
2020/0185103 A1 6/2020 Allen

(56) References Cited

U.S. PATENT DOCUMENTS

| | | | |
|---|---|---|---|
| 2021/0110897 | A1 | 4/2021 | Ginsburg et al. |
| 2021/0174916 | A1 | 6/2021 | Ginsburg et al. |
| 2022/0084641 | A1 | 3/2022 | Ginsburg |
| 2022/0084645 | A1 | 3/2022 | Ginsburg et al. |
| 2022/0084664 | A1 | 3/2022 | Ginsburg |
| 2022/0215919 | A9 | 7/2022 | Ginsburg et al. |
| 2022/0367016 | A1 | 11/2022 | Ginsburg |
| 2023/0073347 | A1 | 3/2023 | Ginsburg et al. |
| 2023/0238090 | A1 | 7/2023 | Ginsburg |
| 2023/0253082 | A1 | 8/2023 | Ginsburg et al. |
| 2024/0257931 | A1 | 8/2024 | Ginsburg et al. |
| 2025/0174323 | A1 | 5/2025 | Ginsburg et al. |
| 2025/0232855 | A1 | 7/2025 | Ginsburg |
| 2025/0384398 | A1 | 12/2025 | Hume et al. |
| 2026/0066070 | A1 | 3/2026 | Ginsburg et al. |

FOREIGN PATENT DOCUMENTS

| | | | |
|---|---|---|---|
| CA | 2887622 | | 4/2014 |
| CA | 3000205 | | 3/2017 |
| DE | 102005034160 | | 2/2007 |
| EP | 1452129 | A1 | 9/2004 |
| EP | 2937799 | | 10/2015 |
| JP | 2004513452 | | 4/2004 |
| JP | 2017510015 | | 4/2017 |
| WO | WO-03005241 | A1 | 1/2003 |
| WO | 2015143455 | | 9/2015 |
| WO | 2015191562 | | 12/2015 |
| WO | WO-2018017927 | A1 | 1/2018 |
| WO | 2018057918 | | 3/2018 |
| WO | 2021042077 | | 3/2021 |
| WO | 2021174169 | | 9/2021 |
| WO | 2021183347 | | 9/2021 |

OTHER PUBLICATIONS

U.S. Appl. No. 16/399,974 U.S. Pat No. 11,205,505, filed Apr. 30, 2019, Medical Services Tracking System and Method.

U.S. Appl. No. 17/456,286, filed Nov. 23, 2021, Medical Services Tracking System and Method.

U.S. Appl. No. 17/008,631, filed Aug. 31, 2020, Dynamic Health Records Visual Display System.

U.S. Appl. No. 17/035,648, filed Sep. 28, 2020, Intelligent, Individualized Medical and Image Management System (CIP).

U.S. Appl. No. 14/666,278 U.S. Pat. No. 10,319,468, filed Mar. 23, 2015, Medical Services Tracking System and Method.

U.S. Appl. No. 15/204,900 U.S. Pat. No. 10,573,407, filed Jul. 7, 2016, Medical Services Tracking Server System and Method.

U.S. Appl. No. 16/865,859, filed May 4, 2020, Data Command Center Visual Display System.

U.S. Appl. No. 15/275,223 U.S. Pat. No. 10,685,743, filed Sep. 23, 2016, Data Command Center Visual Display System.

"International Application Serial No. PCT US2020 052964, International Search Report mailed Dec. 22, 2020", 2 pgs.

"International Application Serial No. PCT US2020 052964, Written Opinion mailed Dec. 22, 2020", 7 pgs.

"U.S. Appl. No. 15/275,223, Preliminary Amendment filed Mar. 16, 2017", 11 pages.

"International Application Serial No. PCT US2015 022091, International Search Report mailed Jun. 29, 2015", 3 pages.

"International Application Serial No. PCT US2015 022091, Written Opinion mailed Jun. 29, 2015", 5 pages.

"International Application Serial No. PCT US2015 022091, International Preliminary Report on Patentability mailed Sep. 29, 2016", 7 pages.

"International Application Serial No. PCT US2017 052993, International Search Report mailed Dec. 1, 2017", 2 pages.

"International Application Serial No. PCT US2017 052993, Written Opinion mailed Dec. 1, 2017", 9 pages.

"U.S. Appl. No. 14/666,278, Non Final Office Action mailed Dec. 21, 2017", 20 pages.

"U.S. Appl. No. 14/666,278, Non Final Office Action mailed Jan. 9, 2018", 22 pages.

"U.S. Appl. No. 15/204,900, Non Final Office Action mailed Jan. 9, 2018", 32 pages.

"U.S. Appl. No. 14/666,278, Response filed Jun. 11, 2018 to Non Final Office Action mailed Jan. 9, 2018", 33 pages.

"Placement of Inventor work by MD Office in EyeNet Extra", distributed as a Supplement to an EyeNetmagazine available in Oct. 2014 at the American Academy of Ophthalmology AAO 2014 Conference, (Oct. 18-21, 2014), 2 pages.

"International Application Serial No. PCT US2017 052993, International Preliminary Report on Patentability mailed Apr. 4, 2019", 11 pages.

"U.S. Appl. No. 15/275,223, Supplementary Preliminary Amendment Filed May 1, 2019", 14 pages.

"Australian Application Serial No. 2015230980, First Examination Report mailed Dec. 24, 2019", 3 pages.

"Medication Ordering Screenshots 1A, 1B, 1C", MDoffice EHR, 3 pages.

"Scheduling Screenshots 2A, 2B, 2C", MDoffice EHR, 3 pages.

"Test Ordering Screenshots 3A, 3B, 3C, 3D, 3E", MDoffice EHR, 5 pages.

"U.S. Appl. No. 15/275,223, Notice of Allowance mailed Feb. 3, 2020", 21 pages.

"U.S. Appl. No. 15/275,223, Corrected Notice of Allowability mailed Mar. 24, 2020", 2 pages.

"U.S. Appl. No. 16/399,974, Preliminary Amendment filed Mar. 3, 2020", 15 pages.

"U.S. Appl. No. 16/399,974, Preliminary Amendment filed Mar. 25, 2021", 13 pages.

"U.S. Appl. No. 17/008,631, Preliminary Amendment filed Dec. 30, 2020", 3 pages.

"U.S. Appl. No. 16/399,974, Examiner Interview Summary mailed Nov. 4, 2021", 3 pages.

"U.S. Appl. No. 16/399,974, Notice of Allowance mailed Nov. 15, 2021", 31 pages.

"U.S. Appl. No. 16/399,974, 312 Amendment filed Nov. 15, 2021", 23 pages.

"U.S. Appl. No. 16/865,859, Preliminary Amendment filed Dec. 23, 2021", 21 pages.

"U.S. Appl. No. 16/865,859, Supplemental Preliminary Amendment Filed Jul. 25, 2022".

"U.S. Appl. No. 17/008,586, Non Final Office Action mailed Jun. 23, 2022", 16 pgs.

"U.S. Appl. No. 17/008,631, Restriction Requirement mailed Aug. 12, 2022", 6 pgs.

"U.S. Appl. No. 17/035,648, Non Final Office Action mailed Sep. 1, 2022", 17 pgs.

"U.S. Appl. No. 17/456,286, Notice of Allowance mailed Jul. 25, 2022", 9 pgs.

"International Application Serial No. PCT/US2020/048849, International Preliminary Report on Patentability mailed Mar. 10, 2022", 9 pgs.

"International Application Serial No. PCT/US2021/020159, International Preliminary Report on Patentability mailed Sep. 9, 2022", 14 pgs.

U.S. Appl. No. 17/686,194, filed Mar. 3, 2022, Dynamic Health Records.

"Australian Application Serial No. 2015230980, Subsequent Examiners Report mailed Jul. 23, 2020", 3 pgs.

"Israel Application Serial No. 265575, Notification of Defects in Patent Application mailed Dec. 31, 2020", with English translation, 10 pages.

"International Application Serial No. PCT US2020 048849, International Search Report mailed Feb. 2, 2021", 6 pgs.

"International Application Serial No. PCT US2020 048849, Written Opinion mailed Feb. 2, 2021", 7 pgs.

"U.S. Appl. No. 17/008,586, Preliminary Amendment filed Dec. 30, 2020", 3 pgs.

"U.S. Appl. No. 17/008,586, Preliminary Amendment filed Feb. 16, 2021", 4 pgs.

"International Application Serial No. PCT US2021 020159, Invitation to Pay Additional Fees mailed Jun. 4, 2021", 7 pgs.

(56) References Cited

OTHER PUBLICATIONS

"International Application Serial No. PCT US2021 020751, International Search Report mailed Jul. 2, 2021", 3 pgs.
"International Application Serial No. PCT US2021 020751, Written Opinion mailed Jul. 2, 2021", 10 pgs.
"International Application Serial No. PCT US2021 020159, International Search Report mailed Aug. 3, 2021", 6 pgs.
"International Application Serial No. PCT US2021 020159, Written Opinion mailed Aug. 3, 2021", 12 pgs.
"U.S. Appl. No. 17/456,286, Non Final Office Action mailed Feb. 16, 2022", 35 pages.
"U.S. Appl. No. 17/456,286, Examiner Interview Summary mailed Apr. 22, 2022", 2 pgs.
"U.S. Appl. No. 17/008,586, Examiner Interview Summary mailed May 5, 2023", 2 pgs.
"U.S. Appl. No. 17/008,586, Final Office Action mailed Mar. 9, 2023", 23 pgs.
"U.S. Appl. No. 17/035,648, Examiner Interview Summary mailed May 30, 2023", 2 pgs.
"U.S. Appl. No. 17/035,648, Final Office Action mailed Mar. 23, 2023", 29 pgs.
"U.S. Appl. No. 17/035,648, Response filed Feb. 1, 2023 to Non Final Office Action mailed Sep. 1, 2022", 15 pgs.
"U.S. Appl. No. 17/035,648, Response filed May 23, 2023 to Final Office Action mailed Mar. 23, 2023", 17 pgs.
"U.S. Appl. No. 17/456,286, Amendment Under 37 CFR 1.114 filed Oct. 24, 2022", 15 pgs.
"U.S. Appl. No. 18/101,873, Preliminary Amendment filed Jan. 26, 2023.", 14 pgs.
"U.S. Appl. No. 17/008,586, Response filed Jun. 9, 2023 to Final Office Action mailed Mar. 9, 2023", 22 pgs.
"U.S. Appl. No. 17/035,648, Advisory Action mailed Jun. 13, 2023", 4 pgs.
"U.S. Appl. No. 17/008,631, Response filed Aug. 2, 2023 to Non Final Office Action mailed Feb. 2, 2023", 11 pgs.
"U.S. Appl. No. 17/008,586, Non Final Office Action mailed Aug. 8, 2023", 19 pgs.
"U.S. Appl. No. 17/035,648, Non Final Office Action mailed Aug. 16, 2023", 17 pgs.
"U.S. Appl. No. 17/008,631, Final Office Action mailed Aug. 16, 2023", 16 pgs.
"U.S. Appl. No. 17/008,586, Response filed Aug. 31, 2023 to Non Final Office Action mailed Aug. 8, 2023", 19 pgs.
"U.S. Appl. No. 17/008,586, Notice of Allowance mailed Sep. 14, 2023", 11 pgs.
"U.S. Appl. No. 17/008,586, Notice of Allowability mailed Sep. 24, 2023", 2 pgs.
"U.S. Appl. No. 18/123,011, Restriction Requirement mailed Nov. 8, 2023", 7 pgs.
"U.S. Appl. No. 17/035,648, Response filed Dec. 18, 2023 to Non Final Office Action mailed Aug. 16, 2023", 10 pgs.
"U.S. Appl. No. 18/123,011, Response filed Jan. 8, 2024 to Restriction Requirement mailed Nov. 8, 2023", 9 pgs.
"U.S. Appl. No. 17/035,648, Final Office Action mailed Jan. 18, 2024", 19 pgs.
U.S. Appl. No. 18/123,011, filed Mar. 17, 2023, Medical Services Tracking System and Method.
U.S. Appl. No. 18/490,466, filed Oct. 19, 2023, Whole-Life, Medication Management, and Ordering Display System.
"U.S. Appl. No. 18/101,873, Non Final Office Action mailed Mar. 18, 2024", 24 pgs.
"U.S. Appl. No. 18/123,011, Non Final Office Action mailed Feb. 23, 2024", 39 pgs.
"U.S. Appl. No. 18/490,466, Non Final Office Action mailed May 23, 2024", 18 pgs.
"U.S. Appl. No. 18/101,873, Examiner Interview Summary mailed Jun. 24, 2024", 2 pgs.
"U.S. Appl. No. 17/686,194, Non Final Office Action mailed Jul. 16, 2024", 18 pgs.
"U.S. Appl. No. 18/101,873, Final Office Action mailed Jul. 30, 2024", 32 pgs.
"U.S. Appl. No. 18/490,466, Examiner Interview Summary mailed Aug. 23, 2024", 2 pgs.
"U.S. Appl. No. 18/490,466, Response filed Aug. 23, 2024 to Non Final Office Action mailed May 23, 2024", 16 pgs.
"U.S. Appl. No. 18/490,466, Final Office Action mailed Sep. 6, 2024", 22 pgs.
"U.S. Appl. No. 18/101,873, Examiner Interview Summary mailed Oct. 8, 2024", 2 pgs.
"U.S. Appl. No. 18/101,873, Response filed Oct. 28, 2024 to Final Office Action mailed Jul. 30, 2024", 19 pgs.
"U.S. Appl. No. 18/101,873, Advisory Action mailed Nov. 5, 2024", 3 pgs.
"U.S. Appl. No. 18/101,873, Response filed Nov. 14, 2023 to Advisory Action mailed Nov. 5, 2024", 20 pgs.
"U.S. Appl. No. 16/802,547, Response filed Nov. 14, 2024 to Advisory Action mailed Apr. 25, 2024", 20 pgs.
"U.S. Appl. No. 17/686,194, Response filed Dec. 16, 2024 to Non Final Office Action mailed Jul. 16, 2024", 14 pgs.
"U.S. Appl. No. 17/686,194, Examiner Interview Summary mailed Dec. 17, 2024", 2 pgs.
"U.S. Appl. No. 17/940,908, Non Final Office Action mailed Jan. 2, 2025", 21 pgs.
"U.S. Appl. No. 18/101,873, Non Final Office Action mailed Jan. 6, 2025", 32 pgs.
"U.S. Appl. No. 16/865,859, Notice of Allowance mailed Oct. 17, 2022", 11 pgs.
"U.S. Appl. No. 17/940,908, Preliminary Amendment filed Nov. 23, 2022", 7 pgs.
"U.S. Appl. No. 17/008,586, Response filed Dec. 19, 2022 to Non Final Office Action mailed Jun. 23, 2022", 14 pgs.
"U.S. Appl. No. 17/008,631, Response filed Jan. 12, 2023 to Restriction Requirement mailed Aug. 12, 2022", 9 pgs.
"U.S. Appl. No. 17/456,286, Notice of Allowance mailed Jan. 26, 2023", 19 pgs.
U.S. Appl. No. 18/101,873, filed Jan. 26, 2023, Data Command Center Visual Dispilay System.
U.S. Appl. No. 17/008,586, filed Aug. 31, 2020, Whole-Life, Medication Management, and Ordering Display System.
U.S. Appl. No. 17/940,908, filed Sep. 8, 2022, Dynamic Health Records.
"U.S. Appl. No. 19/029,684, Non Final Office Action mailed Mar. 21, 2025", 14 pgs.
"U.S. Appl. No. 17/686,194, Final Office Action mailed Mar. 31, 2025", 22 pgs.
"U.S. Appl. No. 17/940,908, Response filed Apr. 2, 2025 to Non Final Office Action mailed Jan. 2, 2025", 16 pgs.
"U.S. Appl. No. 18/101,873, Examiner Interview Summary mailed Apr. 7, 2025", 2 pgs.
"U.S. Appl. No. 18/101,873, Response filed Apr. 7, 2025 to Non Final Office Action mailed Jan. 6, 2025", 24 pgs.
"U.S. Appl. No. 17/940,908, Final Office Action mailed Apr. 22, 2025", 25 pgs.
"U.S. Appl. No. 18/101,873, Notice of Allowance mailed Apr. 30, 2025", 10 pgs.
"U.S. Appl. No. 19/029,684, Examiner Interview Summary mailed May 13, 2025", 2 pgs.
"U.S. Appl. No. 18/101,873, 312 Amendment filed May 16, 2025".
"U.S. Appl. No. 19/029,684, Response filed May 27, 2025 to Non Final Office Action mailed Mar. 21, 2025", 15 pgs.
"U.S. Appl. No. 18/101,873, Notice of Allowability mailed May 29, 2025", 7 pgs.
"U.S. Appl. No. 19/029,684, Final Office Action mailed Jun. 20, 2025", 22 pgs.
"U.S. Appl. No. 17/940,908, Response filed Jun. 23, 2025 to Final Office Action mailed Apr. 22, 2025", 16 pgs.
"U.S. Appl. No. 17/940,908, Advisory Action mailed Jul. 7, 2025", 3 pgs.
"U.S. Appl. No. 17/940,908, Response filed Jul. 21, 2025 to Advisory Action mailed Jul. 7, 2025", 19 pgs.
"U.S. Appl. No. 17/940,908, Notice of Allowance mailed Aug. 15, 2025", 11 pgs.

(56) References Cited

OTHER PUBLICATIONS

"U.S. Appl. No. 17/686,194, Examiner Interview Summary mailed Aug. 25, 2025", 3 pgs.
"U.S. Appl. No. 18/813,965, Non Final Office Action mailed Aug. 26, 2025", 20 pgs.
"U.S. Appl. No. 17/940,908, Corrected Notice of Allowability mailed Aug. 27, 2025", 7 pgs.
"U.S. Appl. No. 17/686,194, Response filed Sep. 2, 2025 to Final Office Action mailed Mar. 31, 2025", 15 pgs.
"U.S. Appl. No. 17/686,194, Notice of Non-Compliant Amendment mailed Sep. 29, 2025", 6 pgs.
"U.S. Appl. No. 17/940,908, PTO Response to Rule 312 Communication mailed Nov. 14, 2025", 2 pgs.
"U.S. Appl. No. 19/029,684, Examiner Interview Summary mailed Dec. 18, 2025", 2 pgs.
"U.S. Appl. No. 19/029,684, Response filed Dec. 22, 2025 to Final Office Action mailed Jun. 20, 2025", 21 pgs.
"U.S. Appl. No. 19/404,963, Preliminary Amendment filed Feb. 13, 2026", 15 pgs.
"U.S. Appl. No. 19/029,684, Non Final Office Action mailed Feb. 24, 2026", 25 pgs.
"U.S. Appl. No. 19/385,789, Restriction Requirement mailed Mar. 6, 2026", 7 pgs.
Ledesma, Andres, "Health timeline: an insight-based study of a timeline visualization of clinical data", BMC Med Inform Decis Mak, 19(1):170, (Aug. 22, 2019), 14 pgs.
Zhu, Xinxin, "Using Timeline Displays to Improve Medication Reconciliation", Telemedicine, and Social Medicine, Cancun, Mexico, (2009), 6 pgs.

* cited by examiner

1900

1905 1910 1920 1930 1940 1950 1960 1970

| | A | | | B | | | | C | | | | | | D | E | F | G |
|---|---|---|---|---|---|---|---|---|---|---|---|---|---|---|---|---|---|
| Patient Name | Date Exam | F / U Appt | E&M Code | Additional CPT Code | Diagnosis ICD-9 | Colon polyp 45385 | Colon Bx 45380 | Colon Dx 45378 | Upper GI / Bx 43242 | Upper GI / Dx 43235 | Sigmoidoscopy 45330 | Lab Results | BP | Other | Notes | EMR | Mssg Billing |
| | | | | | | | | | | | | | | | | | |
| Mr. A | 3.14.15 | | | | | | | | | | | | | | | | |
| Mr. B | 3.14.15 | | | | | | | | | | | | | | | | |
| Mr. C | 3.14.15 | | | | | | | | | | | | | | | | |
| Mr. D | 3.14.15 | | | | | | | | | | | | | | | | |
| Mr. E | 3.14.15 | | | | | | | | | | | | | | | | |
| Mr. F | 3.14.15 | | | | | | | | | | | | | | | | |
| Mr. G | 3.14.15 | | | | | | | | | | | | | | | | |
| Mr. H | 3.14.15 | | | | | | | | | | | | | | | | |
| Mr. I | 3.14.15 | | | | | | | | | | | | | | | | |
| Mr. J | 3.14.15 | | | | | | | | | | | | | | | | |
| | | | | | | | | | | | | | | | | | |
| | | | | | | | | | | | | | | | | | |
| | | | | | | | | | | | | | | | | | |
| | | | | | | | | | | | | | | | | | |
| | | | | | | | | | | | | | | | | | |
| | | | | | | | | | | | | | | | | | |
| | | | | | | | | | | | | | | | | | |
| | | | | | | | | | | | | | | | | | |
| Color coded: | Green if payment paid, yellow if pending, red if denied | | | | | | | | | | | | | | | | |

FIG. 12D

Diabetes Flowsheet Example

3022

| Date | Height | Weight | BMI | Waist Circ | Presenting HbA1c | Current HbA1c | LDL | Trig. | Meds | Vaccines | Hypertension | Last BP | Exams | Assessments | Other | Notes |
|---|---|---|---|---|---|---|---|---|---|---|---|---|---|---|---|---|
| 5/5/2015 | 5' 11" | 195 lbs. | 27.2 | 35 in | 8.9 | 7.6 | 95 mg/dL | 135 mg/dL | Oral | | No | 120/80 | | | | |
| | | | | | | | | | | | | | | | | |
| | | | | | | | | | | | | | | | | |
| | | | | | | | | | | | | | | | | |
| | | | | | | | | | | | | | | | | |

3020

Figure 36

Figure 61
Receive Data
(Industry Standards)
5080
Identify Patient
(Industry Standards)
5081
Standardize Data
(Industry Standards)
5082
Store Data
(Industry Standards)
5083
Evaluate Data
5084

High Level Data Processing Algorithm

Financial Analysis Algorithm
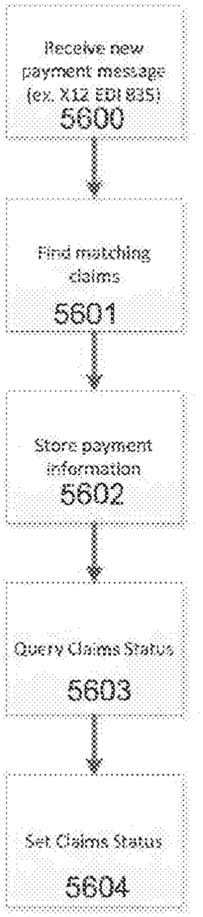
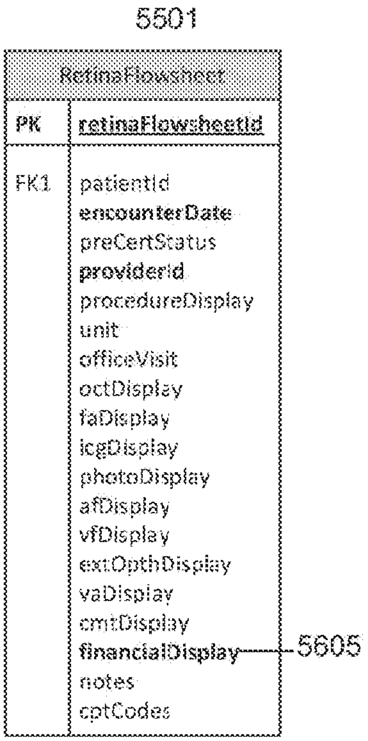
Figure 65

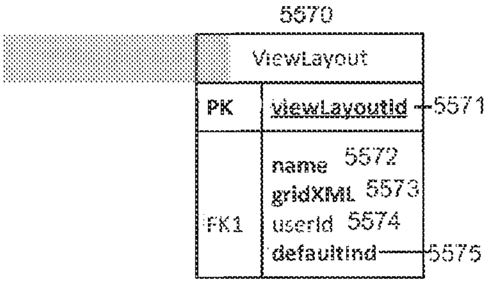

Figure 75

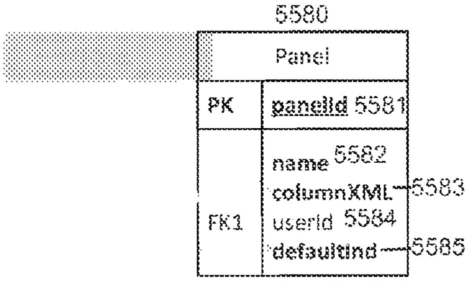

Figure 76

Figure 77

```
<view>
  <panels> 5590
    <panel>
      <panelId></panelId> 5593
      <position></position> 5594 <!-- Based on Flow Style: left, right, top, bottom, center -->
5595  <stacked></stacked> <!-- true,false – if true, creates tabs -- >
      <moveability></moveability> <!-- fixed, adjustable --> 5596
    </panel>
  </panels>
  <tabs> 5591
    <position></position> 5597 <!-- left, right, top, bottom -->
    <tab>
      <panelId></panelId> 5598
      <order></order> 5599
    </tab>
  </tabs>
</view>
```

Figure 78

```
<panel>
  <columns> 5601
    <column>
      <name></name>5602
      <source></source> 5603
      <width></width> 5604
      <order></order> 5605
    </column>
  </columns>
</panel>
```

FIGURE 83 PATIENT SCHEDULER AND TRIAGE SYSTEM
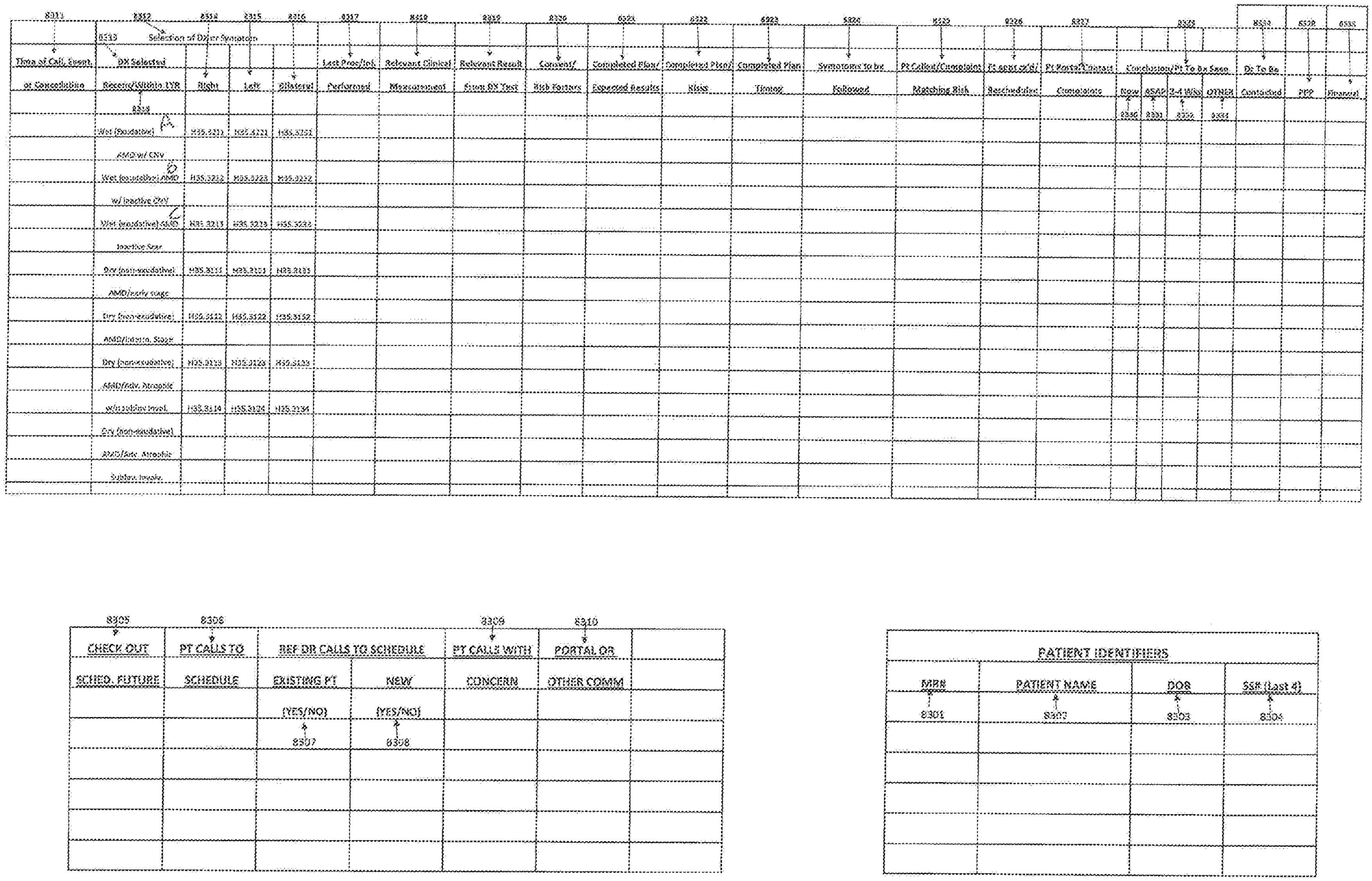

AN EXISTING PATIENT CALLS THE PRACTICE FOR APPOINTMENT

QUESTIONS TO ASK OR LOOK UP AND COMPUTER AUTOMATICALLY INPUTS THE QUESTIONS THAT ARE KNOWN

ALL ASSIGNED RISK NUMBERS BELOW AND QUESTIONS ARE EXAMPLES – A FORMULA WILL ALLOW PRACTICE TO INSERT ANY NUMBER

1. Patient had the following procedures in the last month
    a. Injection in eye (assigned urgent potential risk 10)
    b. Cataract surgery in the last month
    c. Glaucoma surgery in the last month
    d. Other ______________
        i. If surgery, symptoms asked
            1. Sudden pain (urgency risk of 10)
            2. Sudden loss of vision (urgency risk of 10)
            3. Itching eye (urgency rate of 3)
2. Patient had a procedure greater than 1 month to 6 months ago
    a. Injection in eye
        i. Dx of patient auto-populated
            1. If diabetes (risk 7 assigned)
            2. If macular degeneration (risk 9)
            3. If BRVO (risk 7)
3. Patient had a follow up appointment but was not seen
    a. Within 30 days
        i. Previous appointment was < 1 month earlier
        ii. Previous appointment was 1-4 months
        iii. Previous appointment was > 120 days
    b. Within 90 days
        i. Previous appointment before that "missed appointment" was
            1. 1 month earlier
            2. 1-4 months
            3. > 120 days
4. Patient has the following diagnosis (ICD-10) with risk factors associated such that algorithm calculates the risk
    a. No diabetic retinopathy (3)
    b. Minimal diabetic retinopathy (4)
    c. Moderate diabetic retinopathy (5)
    d. Severe diabetic retinopathy (8)
    e. Proliferative diabetic macular edema (8)
    f. Macular edema (8)
    g. Advanced glaucoma (8)
    h. Ocular hypertension (3)

FIG. 84A

- i. Cataracts (3)
- j. Dry eyes (1)

5. Modifying factors auto-populated by computer, which calculate possible need for appointment
    - a. Contact lens wearer
    - b. Over age 60
    - c. Age 50-60
    - d. Under age 60
6. Patient has referring doctor that is an
    - a. Optometrist
    - b. Endocrinologist
    - c. Ophthalmologist
7. Systemic disease
    - a. Lupus
    - b. Diabetes
    - c. Hypertension
8. Patient calling because
    - a. Missed a scheduled appointment
    - b. Never had appointment scheduled from last visit
    - c. Has new symptoms
9. If symptoms assigns a severity
    - a. Loss of vision sudden in one eye or in two eyes
        - i. Partial
        - ii. Complete
        - iii. Just blurred
        - iv. Reading problems only
    - b. Headache
        - i. Visual complaint
        - ii. Over age 50
    - c. Curtain effect
    - d. Floaters
        - i. Few
        - ii. Many
    - e. Flashes of light
    - f. Discharge from eye
    - g. Itching
10. Which doctor patient sees auto-populated and take into consideration what type of doctor and what was done last time you saw that doctor
    - a. Example of how works
        - i. If practice has many specialists, some handle not the severe disease versus those of lesser how risky of a problem can be identified, i.e.,
            1. If optometrist in practice who only prescribed glasses and no ocular needs – low risk
            2. If retina doctor and any time in patient's history the patient had a laser – much higher risk

FIG. 84B

11. DOES PATIENT TAKE ANY OCULAR MEDICATIONS - EACH ASSIGNED A RISK
  A. TEARS 9RISK 10}
  B. GLAUCOMA DROP (RISK 5}
  C. ANTIBIOTIC DROP (RISK 6 BUT DEPENDS ON ICD-10, WHICH COULD RAISE OR LOWER RISK)
  D. STEROID DROP (RISK 7)
12. PATIENT HAD DIAGNOSTIC TEST SCHEDULED
  A. RISK ASSESSED BUT ALSO CORRELATED WITH ICD-10
    I. FLUORESCEIN ANGIOGRARR: (8 RISK FACTOR)
    II . COLOR PHOTOS (2 RISK FACTOR)
    III. VISUAL FIELD (5 RISK FACTOR, BUT IF HISTORY OF GLAUCOMA – 8 RISK FACTOR)
    IV. ERG
13. PROCEDURE HAD BEEN SCHEDULED BUT PATIENT

| | |
|---|---|
| INJECTION IN EYE | 10 RISK FACTOR |
| FOCAL LASER | 7 RISK FACTOR |
| PRP LASER | 8 RISK FACTOR |
| RETINAL TEAR LASER | 10 RISK FACTOR |
| CATARACT SURGERY | 5 RISK FACTOR |
| SLTLASER | 6 RISK FACTOR |

FIG. 84C

EXAMPLE OF FORMULA FOR HOW URGENT APPOINTMENT NEEDED

| DX OF PT | PAST PROCEDURE | WHEN | PAST DX TEST | SYMPTOMS | SCHEDULED BUT MISSED APPT | NO APPT SCHEDULED | NEED TO SEE DOCTOR |
|---|---|---|---|---|---|---|---|
| Diabetes | PRP | 3 mths ago | FA | New floaters | Yes | | Within one mth |
| Macular degeneration | Injection in eye | | OCT | Pain and blurred vision | Yes | | Emergency – get doctor on phone if patient can't be seen in 1 hour |
| Macular degeneration | Injection in the eye 4 mths ago | 3 mths ago | OCT<br>FA | None | Yes | | 1 month |

FORMULA WITH MOST AUTO-POPULATED BY HISTORY IN COMPUTER

| Patient Name | Diagnosis | Procedure in last one month | Procedure last year if any | Missed apt<br>Yes No | Symptoms | How soon patient need to be seen |
|---|---|---|---|---|---|---|
| Written in by call center | Auto-populate | Auto-populate | Auto-populate | Auto-populate | Written in by person taking call | Risk = X |

FIG. 84D

DATA COMMAND CENTER VISUAL DISPLAY SYSTEM

CROSS-REFERENCE TO RELATED APPLICATIONS

The present application is a continuation-in-part application of U.S. patent application Ser. No. 15/275,223, filed Sep. 23, 2016, which is a continuation-in-part application of U.S. patent application Ser. No. 15/204,900, filed Jul. 7, 2016, which is a continuation-in-part application of U.S. patent application Ser. No. 14/666,278, filed Mar. 23, 2015 (now U.S. Pat. No. 10,319,468), which is a non-provisional of U.S. Provisional Patent Application No. 61/968,693, filed Mar. 21, 2014. The present application is also a non-provisional of U.S. Provisional Patent Application No. 62/810,868, filed Feb. 26, 2019. The contents of these patent applications are hereby incorporated by reference in their entireties.

BACKGROUND

As technology advances, users of computer systems are asked to read and respond to an ever increasing amount of data. In complex systems, it is often difficult to present all of the data needed for decision-making in a way that facilitates quick decision-making that takes into account all of the relevant data. For example, physicians (interchangeable with "doctors" as used herein) are often called upon to make rapid life and death decisions based on a patient's conditions in the context of a medical history as presented in an Electronic Medical Record ("EMR"). However, the visual display systems for conventional EMRs are often difficult to understand and require the user to move through multiple screens, interfaces, and pop-up screens to obtain the disparate information needed to make a care decision. This is problematic when caring for multiple patients in a busy practice and is particularly problematic in a critical care setting.

Conventional EMR systems provide computerized interfaces between medical professionals and their staff and patients and are designed to facilitate and streamline the business of medical care. EMR systems allow a medical provider to track the delivery of medical care, access a patient's medical records, track billing for services provided, and follow a patient's progress. However, conventional EMR systems have mostly not met their promise because they typically include complex interfaces that require users to navigate through multiple layers, folders and/or windows to access even basic patient information. As a result, a HIMSS survey showed that 40% of physicians would not recommend their EMR to a colleague, 63.9% said note writing took longer with electronic health records, and 32% were slower to read other clinician's notes. A recent study by Medical Economics indicated that 67% of physicians are displeased with their EMR systems. Moreover, the complex interfaces are particularly problematic at the point of care as they slow physicians down and distract them from meaningful face time caring for patients. As a result, many physicians defer their interaction with the EMR systems until after the patients have been treated. A recent study reported in the Annals of Internal Medicine reported that physicians are spending almost half of their time in the office on EMR and desk work and spend just 27% on face time with patients, which is what the vast majority of physicians went into medicine to do. Once the physician gets home, they average another one to two hours completing health records. Thus, the complex interfaces of current EMR systems have led to diminished quality of the physician's practice of medicine, diminished patient quality of care, and negatively impacted physicians' job satisfaction. More user-friendly interfaces enabling physicians with ready access to the information accessible through EMR systems at the point of care would improve the physician-patient interactions and would be particularly useful in avoiding medical errors and missed diagnoses and increase compliance with insurance billing rules and regulations.

An underlying driver of physician's dissatisfaction with EMR systems is that medical knowledge is doubling every five years, diagnostic tests and procedures are exploding, and documentation requirements for payments are increasing. Physicians are becoming burdened with documentation and administrative tasks rather than spending their time as medical providers. As a result, the EMR system has created a barrier between the physician and patient, where physicians have to turn their back to the patient to input their findings, and have to navigate through multiple screens to do so rather than interact directly with the patient. The potential for medical errors, over ordering or under ordering of diagnostic tests, and other related mistakes generally, occurs because information is missed or buried in the electronic medical record and/or because information does not get transferred from the paper chart or copied from an earlier EMR entry. Important laboratory results or reports from other physicians can be lost or are difficult to access. Therefore, rather than reducing opportunities for potential medical errors, in many cases the electronic medical records systems themselves have created possibilities for error that did not exist with paper based medical files.

Communication of medical findings between physicians seeing patients treated by multiple health care providers has become more difficult. Now, rather than a phone call, simple fax or one page dictated medical summary, physicians are now sending voluminous amounts of information as the EMR gets stuffed with insurance documentation requirements and cut and paste options from "previous visits." Some medical conditions, such as diabetes, require multiple medical personnel to treat the patient. A single patient may have an eye doctor, family physician, endocrinologist, podiatrist, cardiologist, nephrologist, dietician/exercise physiologist, and diabetes education program coordinator. Primary care physicians can be audited and, if the annual report from a consultant is not in the chart, they can be financially penalized. The most important person in the team is the patient. A tool, such as the Command Center described herein, is needed that provides one summary page, with one entry per visit, that can be used by all of the care providers who can share care and see results. All can be alerted to a critical occurrence such as a hospital admission. Finally patients and their physicians can have a one page cliff note summary of the patients' visits with all of their physicians. Even a message can be sent to any or all who are sharing care. A tool is desired where physicians referring patients or sharing surgical and post-operative care (for instance a cataract surgeon co-managing with an optometrist) are able to share visits while looking at the entire patient's conditions.

A simplified method of sharing of pre- and post-operative care is desirable where a simple one page summary can be printed out and handed to the patient with future appointments on one line that can later be filled in. This will help with patient compliance and increase the likelihood that the patient will keep appointments. On this one page should include the results and the medications the patient is supposed to take, reminding a patient and the co-managing physician what was prescribed and for how long. A tool is also needed to stop duplication of diagnostic tests and to improve referring physician communication. If one physician (an optometrist, for instance) takes a photograph of an eye on a particular day and sends the patient to a physician (ophthalmologist) for a second opinion, it is desired that the exam of the referring physician be incorporated into a table whereby the consultant sees the results of the physician's (optometrist's) exam and diagnostic test (photos) on one line and does not need to repeat the photo. It is further desired that the findings of the consultant be shared with the referring physician whereby patients have one shared table for all of their physicians. This improves communication, reduces the likelihood of medical errors, and reduces the cost of healthcare, as fewer repetitive diagnostic tests are performed for physicians in different practices. Now, physicians can share information and patient histories in quick cliff note-like fashion. Through advancing technologies and telemedicine a shared diagnostic test can be looked at by multiple parties all instantly seeing previous examinations and the patient's medical history.

Another set of problems for users of EMR systems revolve around finance. Physicians are trained to treat disease and are typically not trained to manage their practices and be businesspeople. As a result, physicians increasingly rely on technicians, assistants, and other staff, often not qualified or properly trained to input information. Improper documentation or billing can occur, which the physician is held accountable for. Many current EMR systems require significant administrative overhead, and are prone to user error that can result in a discrepancy between billing, claims and payment for professional services and patient procedures. Physicians rarely know if what they had previously authorized to bill was in fact billed correctly, and rarely do physicians know if what they were paid was, in fact, correct.

In addition, there is a great demand for managing costs in the healthcare system. In recent years, health care networks have put in place systems for population health management and for revenue cycle management by providing software systems that enable healthcare providers to better track patient care and payment for healthcare services. However, it has been particularly difficult to involve the physicians directly into the revenue cycle management process. With so many priorities demanding the physicians' attention, few take the time to think about finances for an individual patient. Nine out of ten physicians cited shifting reimbursement models and the financial management of practices as their top challenges, according to a 2013 Wolters Kluwer Health Survey. Physicians typically make treatment decisions independent of cost factors and are unaware of the actual costs of the requested treatment. Providing such information to a physician at the point of care is desirable to enable the physicians to make informed decisions and is an excellent opportunity to get physicians involved on an individual patient basis in revenue cycle management. Unfortunately, providing such data to the physicians at the point of care would function to further clutter the EMR interfaces and require the physicians to spend more time interacting with the EMR system than interacting with the patient unless an efficient tool is designed.

To compound the physician's challenge, insurance companies and federal insurance programs such as Medicare and Medicaid hold physicians personally liable for what is billed, paid, and documented. Severe penalties and even criminal charges can occur when errors are made. The government has collected $2.5 billion for "wrongful under and over billing and inadequate documentation" (see https://www.justice.gov/opa/pr/departments-justice-and-health-and-human-services-announce-over-278-billion-returns-joint). Most physicians are not even aware that the government has written local coverage determinations (LCDs) (i.e. billing requirements) that are different across regions of the country and every insurance company has its own documentation frequency of tests and billing rules. Physicians, even if they are aware of the existence of LCDs, rarely have read the voluminous rules and regulations that without notice to a physician can change at any time, yet the physician is held liable. If a physician moves to another state, the rules and regulations can be entirely different. A tool is needed that at the point of care can briefly present to the physician, based on the patient's insurance, the rules and regulations for whatever a physician orders, and what needs to be documented or performed.

Overall, while EMRs were meant to reduce costs and improve quality of care, the opposite has occurred. Dr. Steven Stack, president of the American Medical Association, addressed this issue when he said: "Imagine, in a world where a 2-year-old can operate an iPhone, graduated physicians are brought to their knees by electronic health records. When you have more than a quarter million physicians being penalized by the Government by a single program, I think that most people will understand the math. It is not that 250,000 plus physicians are the problem, it is most likely the single program they are being punished by." The Government has collected substantial sums of money from physicians and hospitals annually for either under or over billing, or wrongful billing. Physicians need a tool that helps them meet all insurance regulations and make certain that charges are billed correctly.

The overarching problem is that data input and currently available user interfaces are not aligned with the way physicians practice medicine. As Gary Botstein, MD of Dekalb Medical Center in Decatur, Georgia, said at a Break the Red Tape Town Hall: "It's very easy to record large amounts of data and click-off boxes. So the emphasis is really on data collection, but what physicians ought to be doing is data synthesis. They ought to be taking that data, putting it together and coming up with a differential diagnosis and then figuring out what the best diagnosis is and then the best treatment . . . EMR was in front of me, I had 280 data points . . . to complete. To do this voluminous review of systems that was irrelevant to my patient's visit, it was like looking for a needle in a haystack. Once all this data was collected, you couldn't even find it." Dr. Puppula, of Alliance Pain and Spine Centers in Atlanta stated at the same Break the Red Tape Town Hall: "Most systems today are not (designed around clinical care). They are set to comply with the federal regulations with policy makers as opposed to actual physician care, and the concern is we're basically being turned into data miners in order to spend all of our time and effort on documentation as supposed to the key issue of medical decision-making." A simple, elegant solution is needed that helps the physician synthesize information and populate and document the chart when they see a patient on one screen, not on multiple tabs.

In current EMR systems numerous fields and data entry must occur on many different screens describing physician's findings. It takes a tremendous amount of time for data entry. A wrong click of a mouse can insert the wrong information. This is a difficult task for a busy physician and is often handed off to technicians to handle. A tool is needed that will help a physician modify and review a summary of the patient's history on one screen. Further, a tool is desired that would act like a switchboard and enable auto-population of data, where information is documented in a patient's chart when the patient is evaluated. Most EMR systems separate each patient visit by tabs representing each date of service. Critical historical information related to patient testing, diagnosis, surgical histories, and complications, are often dispersed on multiple pages, without any visual markers to identify which page houses the information that a clinician needs to review. These cumbersome formats in the EMR cause significant delay in evaluating a patient and can lead to medical mistakes, as information is lost in the confusing formatting. An improved system would provide a snapshot of the critical medical data along with the billing and clinical guidelines related to the patients' treatment, which is unique to existing EMR formats. In combining these critical data into one comprehensive format, the improved system would increase efficiency and accuracy of the patient evaluation process.

There is also a significant need for a tool that allows a physician to identify medical problems through data visualization, where data is presented and displayed in an intuitive, easy to read manner and which enables the rapid identification of billing and collections. Since physicians are typically time constrained, the tool should allow the physician to access information while examining a patient in order to quickly identify potential billing and or reimbursement problems, as well as medical problems, so that issues can be resolved with the patient in real time. The tool would thus enable the physician to be involved with revenue cycle management, while simultaneously double-checking documentation and reducing medical errors.

A tool is needed to help a physician order diagnostic tests, procedures and medications while seeing on one screen all of the patient medical situation and having a bird's eye overview of what has been ordered/performed in the past and the results and costs. Physicians can get distracted as they are forced to multi-task. A tool is needed that puts the pertinent information at the fingertips of the physician and that can be ordered directly from the screen including the patient's medical information. Yet, physicians often are blindfolded when it comes to knowing requirements of a particular patient's insurance that may require a patient to go to a particular location to obtain a diagnostic test or the cost of that test for the hospital, practice or patient. The same holds true in regards to ordering medication or a procedure. A tool is desired that will enable physicians to discuss options with the patient at the point of care and alter the plan if necessary.

Physicians also need a tool that will enable them to collect and evaluate their own clinical outcomes. This is important because pay for performance models are increasingly being implemented and compensation will be based on clinical and cost savings outcomes, rather than for services and procedures provided. At the heart of all pay for performance models is data analysis. Tinsley suggests "that tracking clinical data is essential in preparing for pay for performance models. Even if a small practice can participate in large scale, value-based model, it can surely implement measures that track and reward quality patient management. There is always more money behind knowing the clinical outcomes and data behind physicians' requests. A lot of physicians are saving payers money and not getting a piece of the pie." A tool is needed that can provide the physician with a summary of results of their medical care. This will then enable them to improve care and to negotiate rates with insurance carriers, and will help them in establishing cost saving methods for delivering care and determining if the care they provide meets set standards.

A tool is needed to help physicians document better and more quickly, identify errors and make suggestions by incorporating artificial intelligence and adaptive learning engine techniques into patient care to, for example, find discrepancies in payments, to alert physicians about inconsistent medical documentation or improper orders, to speed up the process of complying with regulations, or to alert the physician that a plan or order is inconsistent with a preferred practice plan for a patient.

A tool is also needed to alert the physician of important messages, letters and laboratory results that are not readily accessible in current EMRs, so they do not miss important findings and so that the physician may learn about important reports while they are examining a patient. In many cases, these reports may just have been received in the mail or by fax and a clerk just scans it and it becomes buried within the EMR without alerting the physician. Physicians rely on surrogates, like technicians or receptionists to document information on each visit such as a chief complaint. Important alerts that the staff wishes to send to a physician on the day the physician is examining the patient should be communicated on the same page so that everything relating to a patient can be seen at once and nothing important missed. Further, in some cases such alerts should be removed at the end of the day, because they are no longer relevant, thus reducing information clutter allowing the physician to focus on what is important and relevant.

A tool is further needed that allows a physician to make important notations, or that reminds the physician of changes or allows the physician to make a brief note that the physician understands and to help the physician rapidly guide decision making to care for the patient that is not just for chart documentation alone. The note should be able to be changed at any time if it is just for the physician to remind themselves of how to care for the patient. Insurance companies want complete, accurate and understandable notes to justify payment. Physicians are often forced to do meaningless documentation. A tool is needed just for the physician that allows shorthand reminders for the physician to best care for the patient without regard to what "the insurance company will police."

Most EMR systems are highly proprietary and do not communicate well with each other. This lack of interoperability presents a barrier to the transparent communication of health information. A tool is needed that can grab and summarize data from multiple sources and EMR systems. In particular, a tool is needed that will conform to new interoperability standards proposed and allow for a complete patient history, no matter what EMR system is used. The interface should also be flexible so that the information presented may be customized to the needs of the user.

Thus, there is a significant need for a data presentation tool that allows for the capture and presentation of large amounts of disparate data to a user such as a physician in a way that facilitates informed efficient decision-making. In the case of an EMR interface, the tool should allow physicians to rapidly detect potential problems, inconsistencies, medical changes, potential billing errors, review diagnostic tests and navigate through the entire patient chart history, and document within the chart with minimal navigation so that the data may be readily accessed at the point of patient care with minimal distraction from caring for the patient. The data command center described herein, is designed to address these and other needs in the art.

SUMMARY

The above and other needs in the art are addressed by a data command center visual display system and associated methods for displaying data on a display screen from multiple data sources and allowing navigation amongst the data without leaving the display screen of the visual display system. Numerous technical issues rooted in computer technology must be solved for the data to be presented to the visual display system so that the data may be displayed in the command center without leaving the display screen. For example, the visual display system must provide access to the requisite health information systems and third-party support services whereby the data may be accessed, processed, and presented without unacceptable delay. Also, the display data must be collected and ordered to facilitate the various combinations of the data into respective display panels that may be navigated on the display screen. For example, it is desirable for the data to be configured in a task-based or specialty-specific display configuration for use by physicians, for example. To do this, various features in prior art systems needed to be acquired and combined in a new way to facilitate access to the features without having to navigate away from the display screen. For example, conventional EMR systems provide interfaces to third party prescription ordering systems but require the user the navigate to another system and away from the EMR interface. Accessing ordering screens without leaving the display screen becomes particularly difficult where the display screen space is limited as is the case for many physicians who use portable display devices such a iPads™ and other mobile computers. The structural embodiments described herein address these technical issues to generate the command center visual display system embodiments described herein.

In exemplary embodiments, such a data command center visual display system includes a patient database that stores patient identification information, patient insurance information, patient medical history information, a computer readable storage medium having stored thereon instructions thereon, and a processor that executes the instructions to perform operations including creating a plurality of adjustable display panels configured to display predetermined combinations of the patient identification information, patient insurance information, patient medical history information, and creating a patient flowsheet that integrates the patient medical history information into a table that presents the patient's medical history by visit to at least one physician with respective procedures or actions performed during each visit represented as first icons identifying the procedure or action performed and second icons enabling selection of anew procedure or action, where the first and second icons provide links to associated patient medical information and ordering display panels that may be accessed without leaving the display screen. In response to selection of the second icon by a user of the visual display system, an ordering display panel is presented to the display screen in addition to the adjustable display panels and patient flowsheet. The desired procedures or actions may be ordered from the ordering display panels while relevant portions of the patient's medical history are still visible on the display screen. The scope of the claims also contemplates corresponding methods performed by the visual display system and users thereof.

In exemplary embodiments, the ordering display panel compromises an ePrescribing panel for ordering medication or a medical procedure ordering panel for ordering a medical procedure. By way of example, the medical procedure ordering panel for ordering a medical procedure may further provide a link to the quality reporting panel that displays quality reporting metrics and/or peer data related to the procedure that is being ordered. All of such ordering display panels are configured in the context of the screen display to save real estate so that the ordering display screen may be displayed while still being able to view the medical history data, for example.

In other exemplary embodiments, the ordering display panel comprises an imaging order panel for ordering a medical image of the patient or a lab order panel for ordering a lab test of the patient. In still other embodiments, instructions are provided that when executed create an image icon in an adjustable display panel and/or the patient flowsheet that, when selected by the user of the visual data system, opens a display window for viewing of one or more images without leaving the display screen.

In other exemplary embodiments, the visual display system incorporates financial data with the patient medical history data into the display panels. Such a visual display system includes a patient database that stores patient identification information, patient insurance information, patient medical history information, and patient payment information, a computer readable storage medium having stores thereon instructions thereon, and a processor that executes the instructions to perform operations including creating a plurality of adjustable display panels configured to display predetermined combinations of the patient identification information, patient insurance information, patient medical history information, and patient payment information, and creating a patient flowsheet that integrates the patient medical history information and patient payment information into a table that presents the patient's medical history by visit to at least one physician with respective procedures or actions performed during each visit represented as first icons identifying the procedure or action performed and second icons indicating whether the procedure or action has been paid for in part or in full, the first and second icons providing links to associated patient medical history information and/or patient payment information. In response to selection by a user of the visual display system, the adjustable display panels and patient flowsheet are moved into a task-based or specialty-specific display configuration such that the patient identification information, patient insurance information, patient medical history information, and patient payment information may be accessed without leaving the display screen. The task-based or specialty-specific display configuration is then presented to the display screen. In exemplary embodiments, selection of the first icons or second icons open display windows to associated medical history data and/or financial data and overlay a portion of the display screen with the display windows whereby the associated medical history data and/or financial data may be viewed by the user of the visual display system while the adjustable display panels and the patient flowsheet are displayed in a background on the display screen. Throughout this description, it will be appreciated that all financial data in the system, including costs to patient, is compartmentalized such that no user may see financial details for users or organizations not authorized in accordance with applicable policies and law. Also, the scope of the claims also contemplates corresponding methods performed by the visual display system and users thereof.

The visual display system includes a number of features that enable accessing information on the display screen. For example, third icons are provided in the patient flowsheet or display panels that include links to compliance information about compliance with insurance guidelines and/or good clinical practice guidelines for a procedure or action associated with each third icon. In exemplary embodiments, the compliance information includes aggregated medical treatment guidelines and an overview outlining similarities and differences amongst different medical treatment guidelines making up the aggregated medical treatment guidelines. The aggregated medical treatment guidelines may include information related to recommended follow-up with the patient, information related to procedures permitted or prevented by the patient's insurance or contra-indications, and information relating to proper billing for the procedure or action associated with a third icon selected from the patient flowsheet or display panels. In exemplary embodiments, the visual display system provides access to a clinical decision support system that uses a rules engine and/or natural language processing to aggregate the medical treatment guidelines and to generate the overview outlining similarities and differences amongst different medical treatment guidelines making up the aggregated medical treatment guidelines. The clinical decision support system and/or natural language processing system may further compare medical data to notice patterns, errors and anomalies in different entries or notes, find discrepancies in payments, alert the user of the visual display system about inconsistent medical documentation or improper orders, speed up the process of complying with regulations, alert the user of the visual display system that a plan or order is inconsistent with a preferred practice plan for a patient, or warn the user of the visual display system that billing certain procedures might not be covered. The natural language processing system may also be accessed parse notes in the patient flowsheet or display panels for potential ICD10 codes or alternative diagnosis.

The visual display system also includes a display configuration that enables users of the visual display system to order medications, diagnostic tests, images, procedures, and the like directly from the patient flowsheet or display panel. For example, an icon or link in the patient flowsheet or display panel may include an ePrescribing panel for ordering medication or a medical procedure ordering panel for ordering a medical procedure. The medical procedure ordering panel may further include a link to a quality reporting panel that displays quality reporting metrics and/or peer data related to the procedure that is being ordered. In other embodiments, an icon or link in the patient flowsheet or display panel may include an imaging order panel for ordering a medical image of the patient or a lab order panel for ordering a lab test of the patient. In still other embodiments, an image icon is provided in an adjustable display panel and/or the patient flowsheet that, when selected by the user of the visual data system, opens a display window for viewing of one or more images without leaving the display screen. In other embodiments, an alert icon is provided in an adjustable display panel and/or the patient flowsheet that, when selected by the user of the visual data system, opens an alert message without leaving the display screen. In still other embodiments, one of the display panels may be configured to accept today's visit notes from the user of the visual display system in connection with a patient visit for storage for access with other data of the one display panel.

Other novel features in exemplary embodiments include a moveable note icon for association with context information in a corresponding one of the adjustable display panels and/or the patient flowsheet. The note icon moves with the context information as the context information is moved on the display screen. When the note icon is selected, the user of the visual display system may enter a note relating to the context information.

In still other embodiments, data input by the user of the visual display system may trigger auto-population of information in the adjustable display panels and patient flowsheet and auto-population of the patient's medical record in an electronic medical record system. In the exemplary embodiments, the auto-population occurs without the user of the video display system leaving the display screen.

In other embodiments, new clinical information for the patient is provided to a diagnosis evaluation algorithm for comparison of the new clinical information with previous corresponding clinical information for the patient to determine whether the new clinical information is indicative of an improvement or worsening of the patient's medical condition. The visual display system further generates diagnosis indicators providing a visual representation of an improvement of a medical problem, disease, or symptom, or a worsening of a medical problem, disease, or symptom as a result of taking a particular medication or undergoing a particular medical procedure and displays the diagnosis indicators in the adjustable display panels and/or the patient flowsheet.

Other embodiments of the visual display system allow for increased speed of data presentation by a local database that stores a subset of patient identification information, patient insurance information, patient medical history information, and patient payment information, where the subset includes the patient identification information, patient insurance information, patient medical history information, and patient payment information for patients having an appointment within a predetermined time window.

The visual display system in exemplary embodiments includes interfaces to an external health information system and third party service systems. In exemplary embodiments, the external health information system includes at least one of an electronic medical records system, a practice management system, a health information exchange, a picture archive and communications system, a clearing house/billing system, and a laboratory system. On the other hand, the third party service systems may include one or more of an ePrescribing system, an insurance verification/referral/preauthorization system, a system for establishing medical necessity by verifying that a procedure or medication is associated with a correct ICD10 code supporting its use, a clinical services pricing and location system, a claim status checking system, services in support of the National Correct Coding Initiative, services to proactively ensure claims are coded correctly to prevent issues in billing, claims compliance services that evaluate claims against National Coverage Determination (NCD) and Local Coverage Determination (LCD) guidelines as well as local insurance regulations to establish and document medical necessity, a natural language processing system, and artificial intelligence/cognitive systems that provide clinical decision support.

In exemplary embodiments, the patient identification information, patient insurance information, patient medical history information, and patient payment information is stored in the patient database in transactional tables that capture clinical and billing data and reporting tables where data is aggregated for a particular physician, practice, health system or other entity. Each table uses a surrogate primary key that is a unique value within the table used to identify a row that is not directly tied to data in that row. In the exemplary embodiments, XML code moves and stores different display panel and flowsheet views. The XML code further identifies a collection of panels and tabs, wherein within each panel is a panel ID that links the panel to a tab, the panel's position, and whether or not the panel is stacked with another panel. The XML code may also set up the display panels and patient flowsheet on the display screen by, for example, identifying a collection of columns and, for each column, a name of the column along with a data source. The display panels so configured are presented to the display screen for selection and display panel frames on the display screen are manipulated for receiving selected display panels.

In other exemplary embodiments, the patient flowsheet is organized around patient medical information corresponding to a particular disease state and/or procedures and/or insurance coverage and/or actions for treating the particular disease state.

The patient database may also be adapted to include patient medical history information from a plurality of medical providers whereby the patient flowsheet may be adapted to include medical history information from more than one medical provider in order to provide shared treatment of the patient in the patient flowsheet. In other embodiments, a summary table may be provided that illustrates everything the user of the visual display system has done for each patient in a particular time frame or for each patient having a particular disease state in a particular time frame. The summary table may also include information from other medical providers who are providing shared treatment of the patient. If financial data, cost, charge, payment is on the summary table with the medical data, this data is compartmentalized such that no user may see financial details for users or organizations not authorized in accordance with applicable policies and law.

In yet other embodiments, a data command center visual display system is provided that presents dynamic data to a display screen. The command center visual display system includes a plurality of adjustable display panels configured to display predetermined combinations of patient identification information and patient medical information. A patient flowsheet is created that includes a table that presents the patient's medical information by medical service, medical procedure, diagnostic test, medication, and diagnosis that is prescribed, ordered, performed, or selected during respective encounters with at least one medical provider. In response to selection by a user, at least two adjustable display panels containing medical information relating to one or more patients in the patient flowsheet are presented to the display in a single view. The user may edit or move the medical information or the patient identification information within the display panels while the display panels are simultaneously open.

DESCRIPTION OF THE DRAWINGS

FIG. 12D illustrates a portion of a medical record dashboard for display as a function of patients seen by a gastrointestinal physician during a certain period of time with CPT codes performed on patients on a particular day in accordance with the first embodiment.

FIG. 36 presents a flowsheet for diabetes in accordance with the second embodiment.

FIG. 65 illustrates a Financial Analysis Algorithm for processing financial payment information in accordance with the tool described herein.

FIG. 75 illustrates the ViewLayout table that stores the panels and tabs that make up the view and how they are positioned in accordance with the tool described herein.

FIG. 76 illustrates the Panel table that stores references to the data displayed panel in accordance with the tool described herein.

FIG. 77 illustrates the view XML that provides means for moving and storing the different display panel and flowsheet views in exemplary embodiments.

FIG. 78 illustrates the panel XML that provides means for setting up the display panels and flowsheets in exemplary embodiments.

FIG. 83 illustrates an embodiment of a patient scheduler and triage system implemented in a flowsheet table.

FIGS. 84A-84C illustrate sample questions for a patient in a patient triage scheduler in a sample embodiment.

FIG. 84D illustrates sample formulas for urgency of appointments.

DETAILED DESCRIPTION

Figure 1:
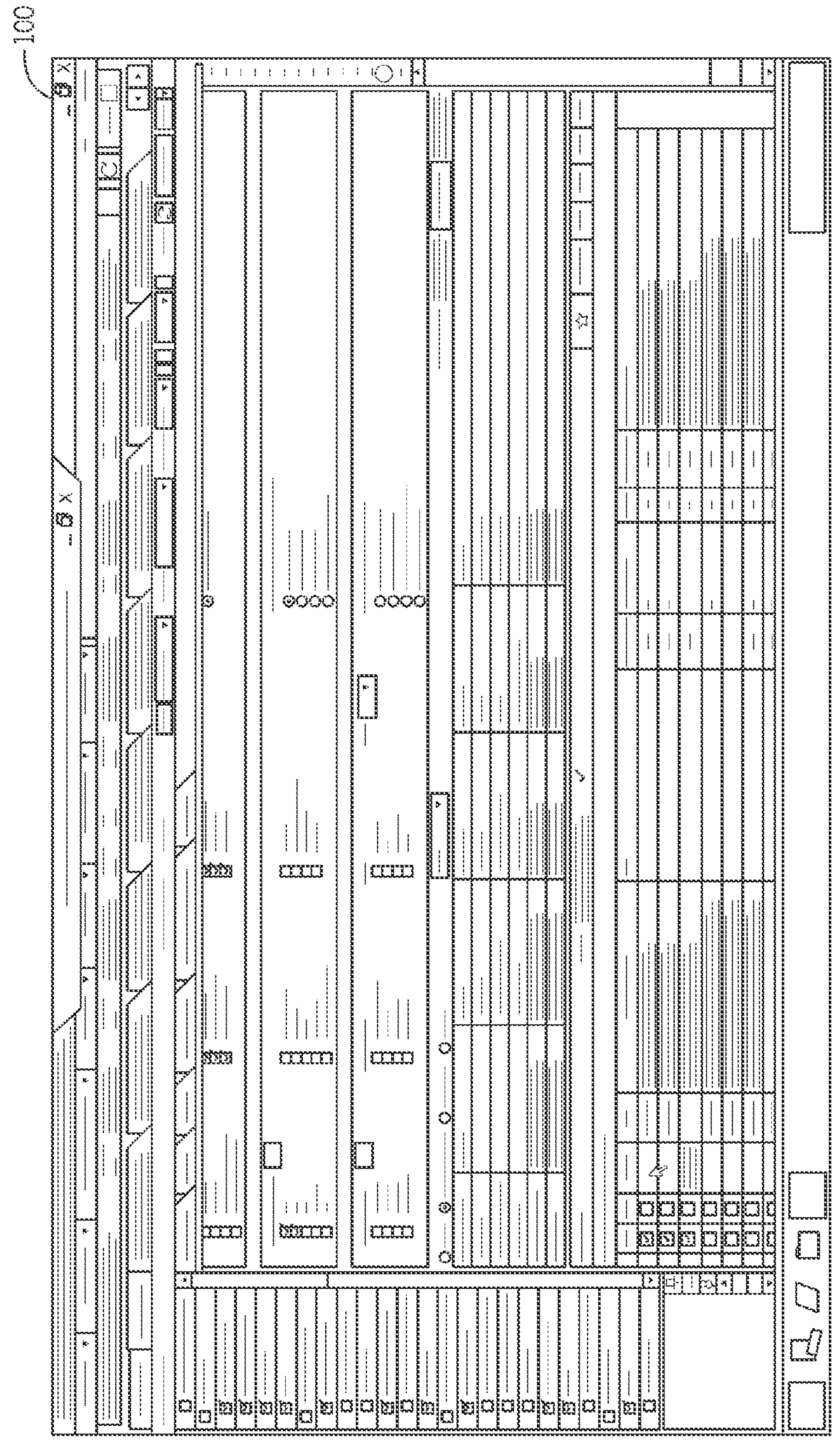
FIG. 1 illustrates an exemplary embodiment of a Data Command Center for use with art EMR system customized for a Retina Ophthalmology practice in accordance with a first embodiment.

Exemplary embodiments of a Data Command Center are described below with respect to FIGS. 1-85. Those skilled in the art will appreciate that the illustrated embodiments described are for exemplary purposes only and are not limited to the specific process and interfaces described.

Before any embodiments are explained in detail, it is to be understood that the tool is not limited in its application to the details of construction and the arrangement of components set forth in the following description or illustrated in the following drawings. The tool is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected," "supported," and "coupled" and variations thereof are used broadly and encompass both direct and indirect mountings, connections, supports, and couplings. Further, "connected" and "coupled" are not restricted to physical or mechanical connections or couplings.

As used herein, a "healthcare provider" may be any clinical professional such as a doctor, physician, podiatrist, chiropractor, dentist, veterinarian, ancillary staff, nurses, physician's assistant, medical provider, physical therapist, all allied health professionals, or hospital staff member. All such "healthcare providers" may use the tool as interchangeable users. Healthcare provider, doctor, and physician are used interchangeable herein.

A row, column, or line (even a diagonal line) may represent may provide sequencing or evaluation in either direction. Also, the time, date, date of service, visit and encounter are also interchangeable in this document. Similarly, "Electronic medical record (EMR)" is interchangeable with "Electronic Health Record (EHR)."

Practice management systems (PMs) are programs that perform the billing collection and reconciliation of payments as well as scheduling patients. This can also be termed Revenue Cycle Management (RCM) and associated with this are billing companies that use software to help practices and hospitals get the bills out and collect money from insurance companies. Also, all of these entities integrate with and work through clearing houses.

A screen, scrolling screen, view, or snapshot is interchangeable in some embodiments, but it is recognized that the doctor could grab different panels from a scrolling screen and converge them all into one view or snapshot. Some embodiments do have a scrolling screen which then could be made into a single view (snapshot) by the user or a combination of a scrolling screen with a single view overlaid so that different portions from the scrolling screen of other views could all be combined into one view that is always displayed on top of the scrolling screen. In other words, the tool allows the ability to look at the entire scrolling screen of information and to grab a panel from one screen and then move it to an overlaid single snapshot screen, thereby producing exactly what the doctor wants to see at any one point in time for that patient in one view—but with the doctor able to navigate to other portions of the EMR (could even be going into other tabs and not a scrolling screen) so that simultaneously the doctor can grab more information to create a personalized snapshot for that patient.

Medical tests as described herein is interchangeable and inclusive of image or imaging, diagnostic tests, radiological tests or procedures, laboratories, chemistry and hematological tests, photography, genetic testing, nuclear scans, ultrasounds, x-rays, optical coherent tomography photographs and angiographies and any medical testing or medical services that tests or screens patients for a medical condition. In addition, it is understood that terms like diagnosis can be reflected by ICD 9 or 10 or similar identifying factors, and medications may be interchangeable.

As used herein, an icon, symbol, or indicator are all interchangeable and are not just a means and conveyors of the ability to click what is underlying or a simple yes or no, but also such elements have the ability to convey much additional information. These elements enable an interaction to occur and even on a word or numbers can also have some interaction to convey and compress information such as blinking, flashing color change, italics, underline or any method that catches the attention of the user. When in a dashboard, the entire cell can have one color and the icon itself another or both can independently represent any of the intentions described, i.e. blinking.

As described herein, the "tool" may be referenced to herein alternatively as a "Data Command Center," a "Command Center," an "EHR Command Center," an "actionable Dashboard," "Dashboard," "table," "Visual Display System," "Flowsheet" and/or "Flowchart."

The following discussion is presented to enable a person skilled in the art to make and use embodiments. Various modifications to the illustrated embodiments will be readily apparent to those skilled in the art, and the generic principles herein can be applied to other embodiments and applications without departing from embodiments of the tool. For example, though the tool is described for use with an EMR system in an exemplary embodiment, those skilled in the art will appreciate that the systems and methods described herein may be used for numerous other applications where much data is presented to the viewer, including, for example, interfaces to stock tracking and purchasing software, industrial monitoring systems, and the like. Thus, embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments. Skilled artisans will recognize the examples provided herein have many useful alternatives that fall within the scope of embodiments.

Some embodiments herein provide one or more technological solutions in the realm of one or more of data assimilation and recordation with real-time communications across a network, computers, or the Internet to improve the performance of, and technology of, data assimilation and recordation, communication and messaging software, systems and servers by providing automated functionality that effectively and more efficiently manages data assimilation and recordation and related automatic triggering of new computing events in the network based on the data gathered during an actual event in ways that cannot effectively be done, or done at all, manually. For example, some embodiments herein provide one or more technological solutions to processing a user interface including a single page quick review "summary sheet" that is rendered by pulling key data points from EMR interactive notes allowing a physician to provide the best possible care. Further, the improved assimilation and recordation, communication and messaging software, and systems and servers enable centralized collection and review of information and two-way auto-population of the user interface from billing or other parts of local and remote electronic medical record systems that can reduce human error, and can cut down on medical errors. This technology can allow a physician or other healthcare worker to quickly access and review critical medical and procedure data using consistent data visualization field formats. This technology can automatically summarize each patient visit on one line on one page that can be seen and through pattern recognition, and rapidly visualized. This technology can allow a physician to instantly evaluate a patient's situation, and catch potential billing errors.

Some embodiments herein provide one or more technological solutions to providing a user interface that functions as a "command center" for the physician's decision-making. Using data collection, assimilation and recordation with real-time communications across a network, computers, or the Internet, some embodiments described herein provide an information hub where the lifetime of a patient's medical and surgical history, diagnostic tests results, and prescribed medications can be accessed. Further, the user interface can provide alerts regarding the reasons for the patient's visit, and can include messages from staff that can be programmed to self-delete and not be viewable after it has been removed.

Some embodiments provide a user interface that can function as an epicenter for physician care allowing medical synthesis of the problems confronting the patient. To make the best decisions, the physician needs to understand the entire picture of a patient's life, while being able to home in on any detail. Some embodiments can function as an EMR similar to how a ganglion cell is to the brain or the spinal cord to the body. Some embodiments provide the ability for the findings of a physician during "today's visit" to be rapidly entered into the relevant fields/tabs/screens within an EMR, streamlining data entry required for documentation and interpretation. Some embodiments can provide a starting point for caring for a patient, where new orders can be placed or messages can be sent. Using a summary review table, the physician can navigate and interact with the entire EMR for the patient without the need to access multiple screens, and can be interoperable to enable extraction of pertinent information from other sources.

Medical sub-specialization, information overload, and increased complexity of reimbursements for service all conspire to remove the physician from caring for a patient. Some embodiments can save the physician time that can be used for time with the patient rather than time used with a computer screen and a mouse. Finally, presented here is the new tool that makes the computer age successfully replace the paper age in properly caring for patients. Some embodiments can allow the physician and hospitals to comply with insurance companies and the government which demand that they comply and be responsible for their billing. Some embodiments can help transform the mindset of a physician from being a medical provider without any knowledge of business or finance, to a physician able to participate in revenue cycle management. Some embodiments can, therefore, insert the physician back into being the quarterback of the healthcare system. Some embodiments can give the physician the time to be a healer while at the same time rapidly synthesizing information that can cut costs and improve outcome quality. In an ever-expanding interoperable complex world, some embodiments can function as a physician's genie and magic carpet that seamlessly transports the physician though the maze of data entry and provides the overview needed for medical synthesis.

Some computerized or electronic medical record ("EMR") systems provide computerized interfaces between medical professionals and staff and one or more medical records databases. Some embodiments disclosed herein include a command center visual display system and method that can be linked to or otherwise accessed from a conventional EMR system. In some other embodiments, any conventional EMR system can be coupled or linked with the command center visual display system and method described herein.

Some embodiments of the command center visual display system and method can be interfaced with a variety of systems including but not limited to EMRs, Health Information Exchanges (HIEs), Billing Clearinghouses, Insurance Companies, Picture Archiving and Communication Systems (PACS) as well as third party services to provide information and services used in data presentation.

Some embodiments include a command center visual display system and method that can be included as an add-on software package to a conventional medical record system. In some embodiments, tasks associated with an add-on software program can be seamlessly linked and/or incorporated into one or more core software tasks or modules of the conventional medical record system. In some embodiments, a message-based interface can be used to connect and transmit data between one or more software modules of the command center visual display system and method, and one or more conventional medical records systems and/or one or more patient records and/or databases comprising patient records. In some embodiments, application programming interfaces (hereinafter "APIs") can be used to connect and transmit data between one or more software modules of the command center visual display system and method, and one or more conventional medical records systems and/or one or more patient records and/or databases comprising patient records. For example, in some embodiments, the command center visual display system and method can be configured to receive patient data from a health information exchange or a medical provider. In some further embodiments, the command center visual display system and method can auto-populate various data fields (including information fields, tables, or windows) from a variety of sources. The sources can include electronic, physical (paper records), and human input. In some embodiments, an electronic dataflow can be established between the command center visual display system and method and one or more computer systems of servers that comprise patient information (e.g., electronic medical records). In some embodiments, the dataflow comprises a one-way flow from the source to the command center visual display system and method. In some other embodiments, the dataflow comprises a two-way flow from the source to the command center visual display system and method, and from the command center visual display system and method to the source. This information can be any medical diagnosis information prepared by a medical practitioner, any medical procedures or services provided to the patient, including procedures or services by claims made, or billings or payments including billing signed off by a physician as detailed above, billings, payments, or other information from anywhere in the EMR chart not limited to treatment summaries, and/or diagnosis summaries, and/or patient feedback summaries, and/or other physician summaries, patient outcome summaries, and so on. For example, in some embodiments, the command center visual display system and method discussed below can display and/or auto-populate with at least one of a patient's prior medical procedures, diagnostic tests, surgeries, current medications, current illnesses, treated illnesses, and so on.

In some further embodiments, new software features of the command center visual display system and method can be added to an existing application without modifying the existing code of the existing application. In some other embodiments, the command center visual display system and method can function as an independent application, not linked, overlaid, or otherwise interfaced with any conventional medical record system.

First Embodiment of Data Command Center

Figure 2:
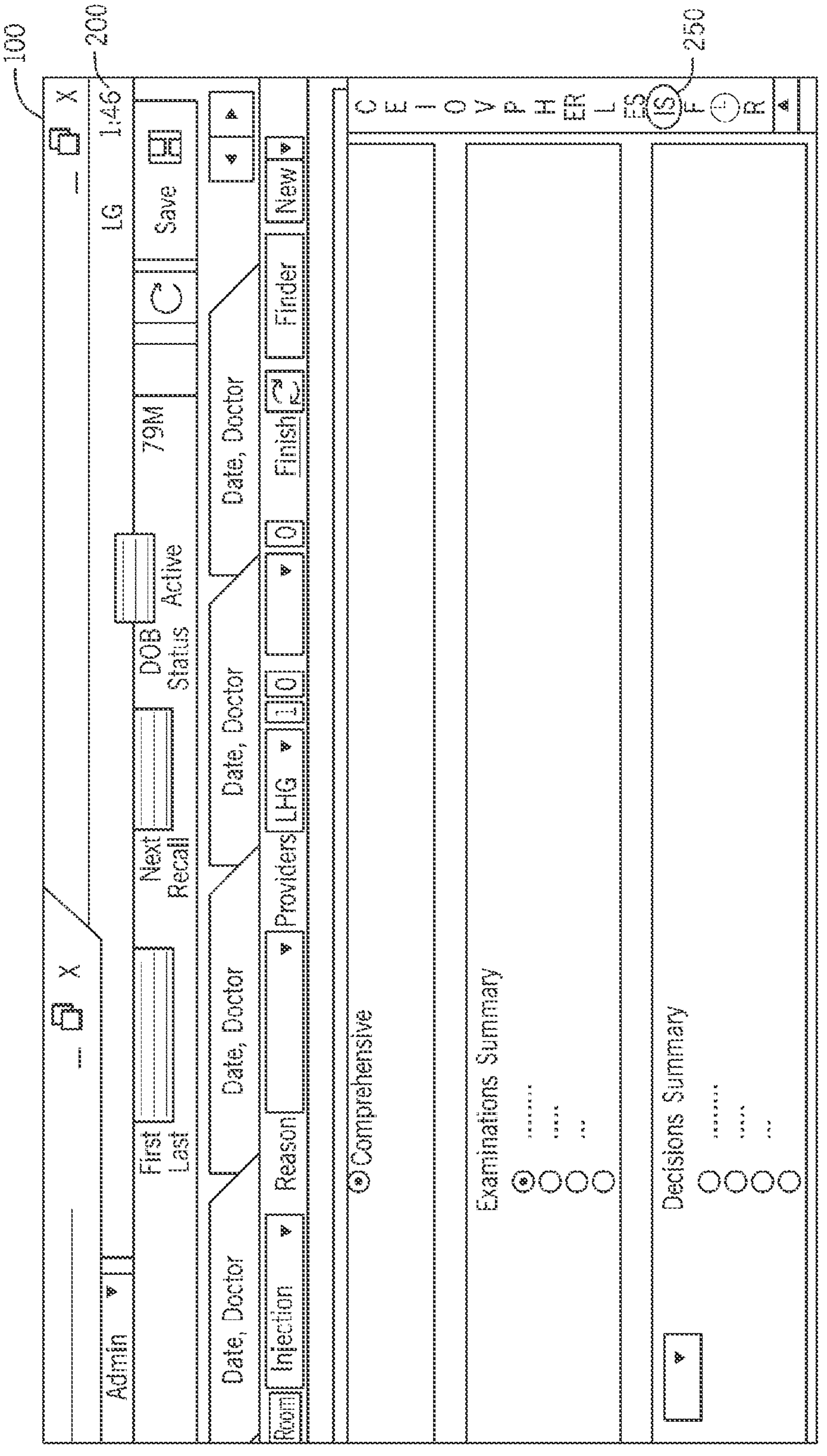
FIG. 2 illustrates a medical record window of the medical record system of FIG. 1 that is useful for deploying or launching embodiments in accordance with the first embodiment.

FIG. 1 illustrates an embodiment of a Data Command Center (CC) implemented as a data interface to a medical record system 100 in accordance with a first set of embodiments. In accordance with the first set of embodiments, a user, such a medical practitioner, can utilize a conventional medical record system to launch or enter a medical services tracking system that can display information dashboards, tables, charts, windows, as tailored by a user. FIG. 2 illustrates a medical record window 200 of the medical record system 100 in accordance with a first set embodiments described herein. In some embodiments, the medical record window 200 of a conventional medical record system can include a medical tracking system launch icon 250 to facilitate access to and/or launch of one or more embodiments of the medical service tracking system and method. It will be appreciated that the "icons" used herein are graphical elements with links to associated dynamic or static data in the same system or a remote system. Of course, the icons may simply be links. For the ease of description, whenever the text refers to "icons" such "icons" may be graphical elements with links or simply links to associated dynamic or static data.

In some embodiments, a user can use the command center visual display system launch icon 250 or other displayed icon or display element to access or launch the command center visual display system and method described herein. In some further embodiments, the launch icon 250 can be used to temporarily halt the medical record system 100 and access or launch the command center visual display system and method. In some other embodiments, the launch icon 250 can be used to access or launch the command center visual display system and method while the medical record system 100 continues to run in parallel, continues to run in a background mode, and/or is switched to an idle mode.

Figure 3:
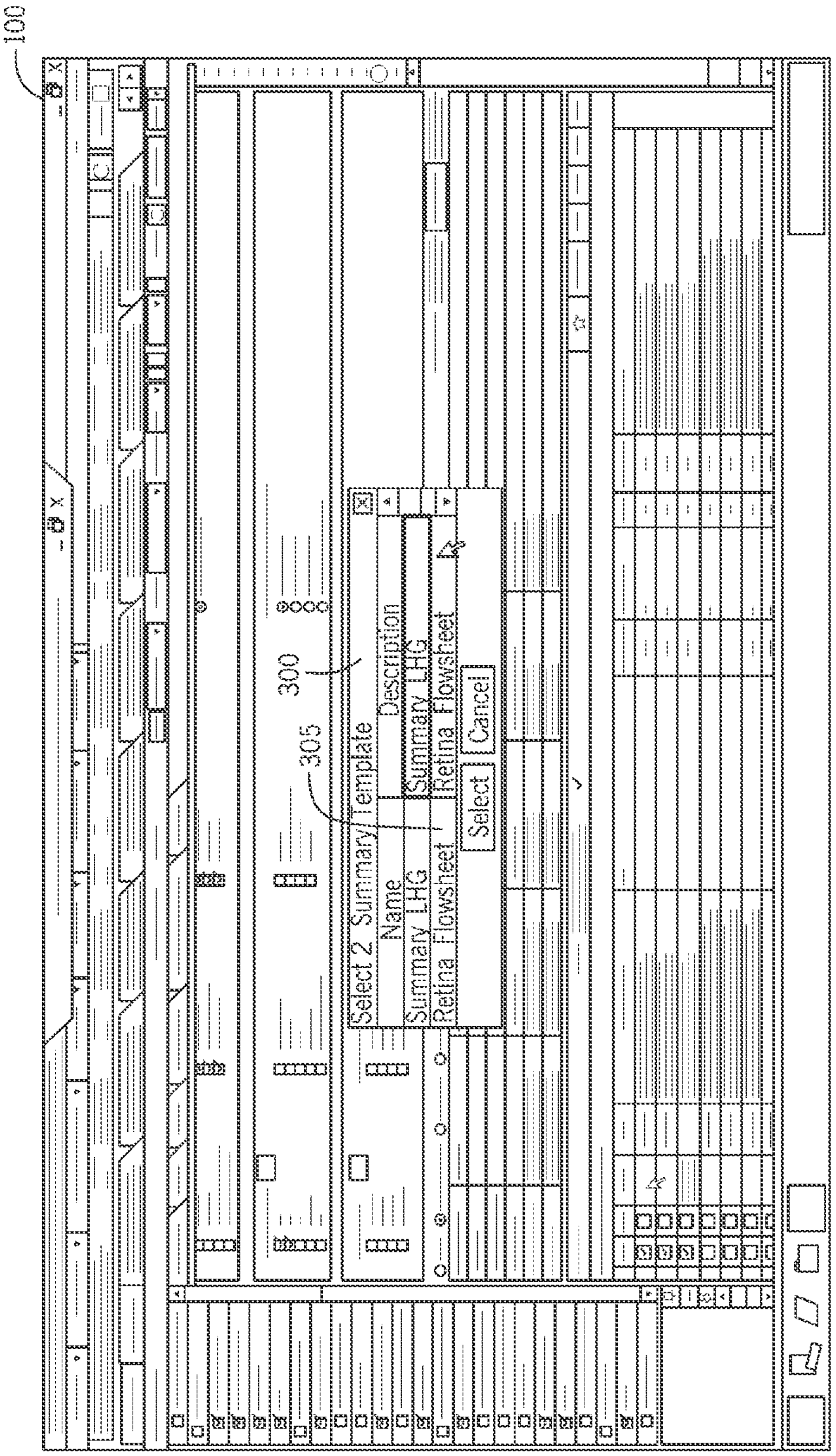
FIG. 3 illustrates a medical record dashboard selection window useful for selecting and launching embodiments in accordance with the first embodiment.

Referring to FIG. 3, illustrating a medical record dashboard selection window useful for selecting and launching embodiments described herein. In some embodiments, after a user selects or clicks the launch icon 250, a medical record dashboard selection window 300 can be displayed. The medical record dashboard selection window 300 can include one or more selectable medical record dashboards from which a user can select to access at least one medical record dashboard. For example, in one non-limiting example embodiment, the user can select "Retina Flowsheet" 305 to access and/or launch a medical record dashboard including a retina flowsheet. In some further embodiments, the at least one medical record dashboard can include any number of selectable medical records for any medical condition, and/or any medical diagnosis, and/or any medical treatment.

Figure 4A:
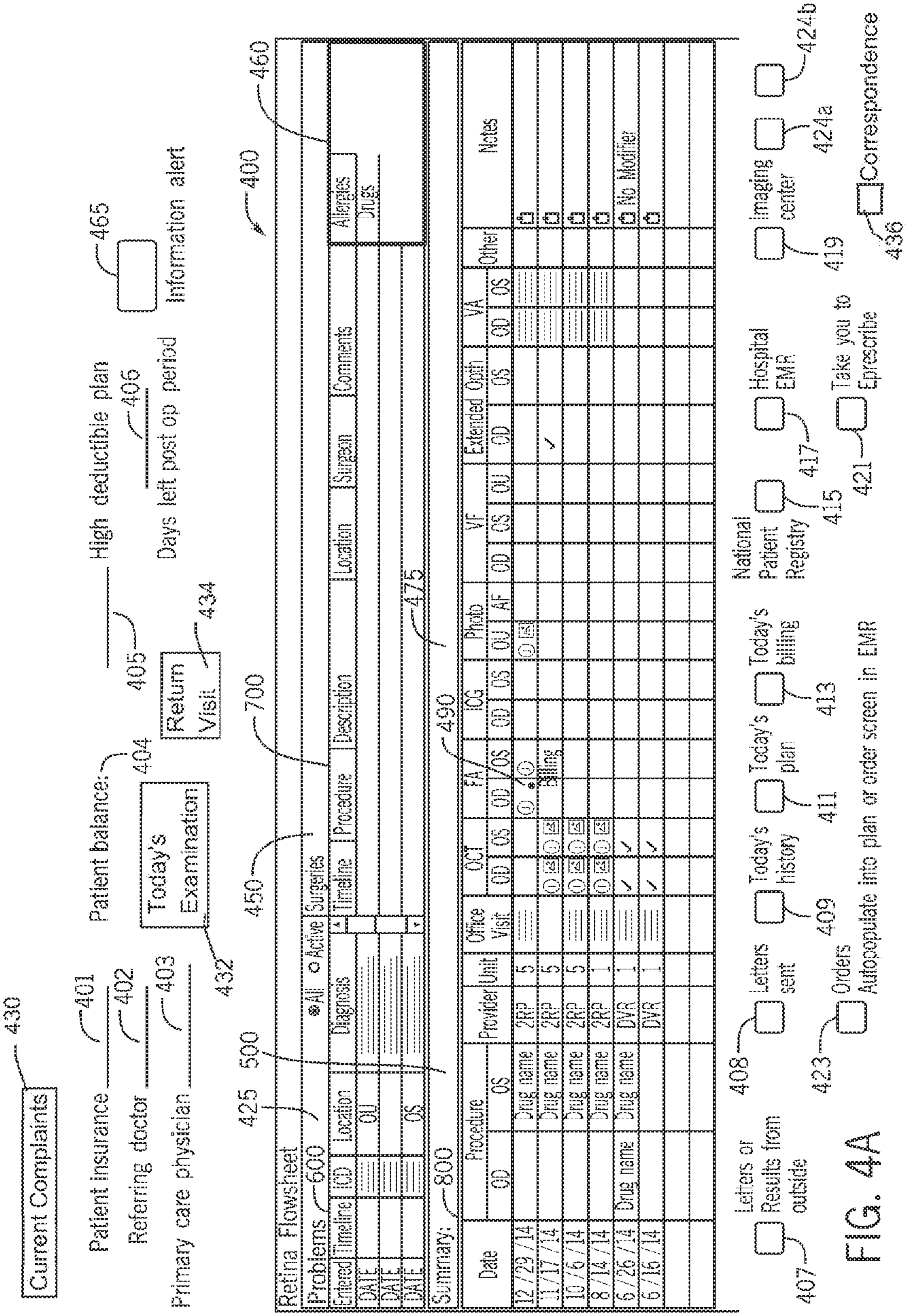
FIG. 4A illustrates a medical record dashboard in accordance with the first embodiment.

Some embodiments comprise one or more displayed tables and/or dashboards that function as a Data Command Center. The Data Command Center can enable a user to work with a single display that can be configured as a central medical record entry, access, update, recording, and archival site. For example, FIG. 4A illustrates a medical record dashboard 400 in accordance with a first embodiment. In some embodiments, the medical record dashboard 400 can be displayed by the user following the user's selection of at least one medical record dashboard from the medical record dashboard selection window 300. In some embodiments, the medical record dashboard 400 can display data from one or more medical records, and/or track medical procedures and services based on claims made or billing signed off by a physician for one or more delivered medical procedures or services. Some embodiments include a command center visual display system and method that can dynamically link to various external databases comprising patient information that can be displayed in the medical record dashboard 400. For example, in some embodiments, the command center visual display system and method can function as a portal to patient information prepared by the user or patient information from other sources. Further, in some embodiments, the medical record dashboard 400 can be auto-populated as a function of claims made or billing signed off by a physician. In this instance, any data displayed within the medical record dashboard 400 is derived from one or more claim records that have been billed for one or more procedures or services have previously been provided to the patient. In some other embodiments, auto-population can be enabled in both directions interacting as a switchboard between the entire EMR and the medical record dashboard 400 along with what is added to any window, sub-window, column or entry in the medical record dashboard 400 being automatically added to the appropriate part of the chart for documentation before finalizing the encounter.

In some embodiments, the medical record dashboard 400 can display information related to any medical procedures or services in relation to care of a patient. For example, in some embodiments, the medical record dashboard 400 can display information related to medical procedures or services in relation to retinal eye medical care of a patient. In some embodiments, the medical record dashboard 400 can display information including components where there is a summary of the patient's problem list that a user can input patient information and constantly update and change. Further, this information can be auto-populated with the touch of a button into a designated location such as the current plan documenting the patient's current visit (thus aiding documentation for the current visit). Further, whatever is important for a user to input into the day's visits for documentation can be initially inputted in the table, and then permanently into the day's patient visits. Further, the summary section of the medical record dashboard 400 can be constantly fluid, and can be changed at every visit rather than being written to an unchangeable document or file (e.g., such as a PDF). Further, any patient data that is inputted, received, analyzed, or created can be auto-populated into any portion of the dashboard 400, and/or can form a dataflow out of the medical record dashboard 400 to another electronic system or server, or another user, observer, or other 3$^{rd}$ party.

In some embodiments, the medical record dashboard 400 can display various windows and sub-windows based on a user preference and/or current or previous user interaction with the medical record dashboard 400. For example, in some embodiments, the medical record dashboard 400 can display a problems window 425 and/or a surgeries window 450 where information related to a patient's medical problems and surgeries can be displayed in information columns 600, 700 respectively. Further, in some embodiments, patient information related to allergies and drugs can be displayed within the allergies/drug section 460. This information can be auto-populated from a variety of sources, or inputted by a user.

In some embodiments, the medical record dashboard 400 can include a summary window 475 enabling a user to view and edit summary information related to the patient, any details of care provided to the patient, and/or and any medical diagnosis information prepared by a medical practitioner. Further, in some embodiments, the medical record dashboard 400 can also display detailed information related to any medical procedures or services provided to the patient, including procedures or services that are auto-populated by claims made, or billings or payments including billing signed off by a physician as detailed above. For example, in some embodiments, the medical record dashboard 400 can display a command center visual display window 500 including information columns 800 that can be auto-populated by claims made or billings signed off by a physician. The auto-population can include billings, payments, or other information from anywhere in the EMR chart. For example in some embodiments, the information that is auto-populated can include treatment summaries, and/or diagnosis summaries, and/or patient feedback summaries, and/or other physician summaries, and so on. For example, in some embodiments, the command center visual display system and method can display and/or auto-populate at least one field, table, or window with at least one of a patient's prior medical procedures, diagnostic tests, surgeries, current medications, current illnesses, treated illnesses, and so on. The command center visual display system and method can auto-populate various data fields via an electronic dataflow established between the command center visual display system and method and one or more computer systems of servers that comprise patient information (e.g., such as electronic medical records). The dataflow can comprise a two-way flow from the source of patient data to the command center visual display system and method, and from the command center visual display system and method to the source. In some embodiments, this information can be any medical diagnosis information, any medical procedures or services provided to the patient, procedures or services by claims made, or billings or payments including billing signed off by a physician as detailed earlier, any information from anywhere in the EMR chart including treatment summaries, and/or diagnosis summaries, the patient's prior medical procedures, diagnostic tests, surgeries, current medications, current illnesses, treated illnesses, and/or patient feedback summaries, and/or other physician summaries, patient outcome summaries, treatment summaries, and/or diagnosis summaries, and/or patient feedback summaries, and/or other physician summaries or treatments. Further, in some embodiments, the information that is auto-populated can include patient outcome summaries. For example, in some embodiments, the command center visual display system and method process a plurality of patient outcomes and display an analysis of patient outcomes based at least in part on patient information from treatment summaries, and/or diagnosis summaries, and/or patient feedback summaries, and/or other physician summaries or treatments. In some embodiments, the patient outcomes can include or comprise physician quality reporting system (PQRS) quality measures. In some embodiments, calculated or reported patient outcomes can include or comprise at least one PQRS measures code.

The medical record dashboard 400 can include miscellaneous information identifying the patient, information related to the patient's insurance plan, physicians and referring physicians, and the patient's current balance. Other information can relate to the patient's prior visit, prior diagnosis or procedure and any important information relevant to the next visit. Additional information can relate to the current visit, including history of illness and chief or current medical complaint, billing information, and retrievable medical information including pharmacy information. For example, in some embodiments, the medical record dashboard 400 can include a patient insurance entry 401, referring physician entry 402, and primary care physician entry 403. The medical record dashboard 400 can also include patient balance entry 404, and a high deductible plan entry 405. Important patient information related to a pending or current visit can include a "days left post op period" entry 406 and/or an information alert 465. In some embodiments, the information alert 465 can be auto-populated based on other information or entries in the medical record dashboard 400. In other embodiments, the information alert 465 can be set by any user to alert the user or other user of information relevant to the patient. In some embodiments, the information alert 465 can comprise a daily technician update, including information to medical information such as blood pressure, or whether the patient is pregnant, or any other urgent information with which a member of a health care team can alert another member. Further, this information can become permanent or can be deleted from the dashboard 400, and from any record or table accessible from the dashboard 400, including any medical record. Further, this information can serve as or be configured as a "sticky note" that can be removed from any of the above-mentioned records. For example, the "sticky note" can be an electronic sticky note riding on the dashboard or any record accessible from the dashboard. Further, the dashboard 400 can provide improvement as described where test interpretations and evaluation of patients, once documented and billed, usually become date stamped, and cannot be easily amended without applying a new date of amendment. In some embodiments, the command center visual display system and method can improve and follow care that not necessarily be used as part of a particular day's medical record. Therefore, months or years apart, physicians can add notes into the table when new findings, discoveries, or realizations warrant it without feeling encumbered that they are "changing past medical record" and a disclosure of such can be at the bottom of the dashboard 400. Allowing physicians and technicians to add and change notes within this dashboard 400 (rather than changing the patients EMR chart) can enable them to summarize critically important health/history/treatment data, which can then be used as a faster point of reference while examining the patient. Notes that sit on the table can flag or alert the physician to an important medical change, and can be used as an additional form of communication to strengthen lines of communication between technicians/clinic staff and physicians to better ensure that the physician is quickly directed to important medical information.

In some other embodiments, a daily technician update can be accessed or otherwise made visible to the user in at least one other portion of the dashboard 400. In some embodiments, the information alert 465 can be displayed in a specific color and/or with a specific graphic and/or animation. For example, in some embodiments, the information alert 465 can comprise a flashing red animation. To protect the physician during an audit, a statement on the dashboard 400 can be added that "notes on this table" are not necessarily added at the time listed as the date and not for documentation in a medical record, but as a rapid reminder medical decision making and cliff note reference tool. As another example, if this patient's records were ever sent to another physician or insurance company or were audited, this is critical information a physician is often not privy to and an icon on the table will alert the physician of this fact. By selecting this or another icon, the history of this audit or records release request or other occurrence can be seen. So, if an insurance company is requesting a medical necessity report or other information that is needed by a billing office or anyone else, the physician will be informed on the table so that the physician can instantly decide what is needed. A report can be dictated or chart information transmitted within or outside the practice in an expedited manner. Often just an office worker decides what to send in reply to an outside entity request. By using this tool at the point of care when a patient is being examined, the patient may be consulted by the physician to correct any information that needs clarification, and decisions and reports can most accurately be made. Additionally, physicians remotely can be alerted about requests and one summary table rapidly allows for more rapid and accurate communication.

Some embodiments include an alert or access to one or more letters or results from outside (icon 407) systems or third parties. Some further embodiments include an alert or access to letters sent 408. The letters can be written, typed, and/or one or more dictated letters from the user and/or another medical provider. Some embodiments include an entry or access to the current day's history, the current day's plan, and/or to the current day's billing. For example, some embodiments include a "Today's history" button or icon 409, a "Today's plan" button or icon 411, and a "Todays billing" button or icon 413. In some further embodiments, a correspondence button or icon 436 can be used to view, access, enter, and/or auto-populate correspondence related to a patient's care. This can include any medical record and/or any correspondence generated while the patient is under care by the user and/or any other physician or medical practitioner, medical services provider, and/or medical insurance company.

In some embodiments, the medical record dashboard 400 can display a summary of the patient's problem list that a user can input patient information and constantly update and change. For example, some embodiments include the ability to enter or access current complaints of the patient (button 430). In some embodiments, a user can add or update one or more entries of the patient's chief or current complaints, and/or a user can view one or more entries of the patient's chief or current complaints using the button 430. In some embodiments, if a user activates (e.g., by clicking using a cursor) the button 430, information related to the patient's current medical problems or complaints can be shown and/or displayed and/or updated by any user or user's assistant. In some embodiments, the information can be auto-populated into the medical record dashboard 400 and/or to any other accessible window displayed by the command center visual display system and method.

In some embodiments, the medical record dashboard 400 can display a today's examination access button 432 that a user can use to view and/or input patient information, patient examination results, tests, notes, or any information relevant to the medical care of the patient. In some embodiments, a user can add or update one or more entries of the today's examination, and/or a user can view one or more entries of the examination. In some embodiments, if a user activates (e.g., by clicking using a cursor) the button 432, information related to the patient's examination including medical problems or complaints patient information, patient examination results, tests, notes, etc., can be shown and/or displayed and/or updated by any user or user's assistant. In some embodiments, the information can be auto-populated into the medical record dashboard 400 and/or to any other accessible window displayed by the command center visual display system and method. In some embodiments, any stored or displayed patient's examination can be cleared from the medical record dashboard 400 following some time period once the patient visit is complete. In some embodiments, the medical record dashboard 400 can remove display or access to a previous patient's examination details once the patient visit has ended. In some other embodiments, the medical record dashboard 400 can remove display or access to a previous patient's examination details later in the day of the patient's visit, or before the following day, or at any time selectable by the user or user's assistant. In some embodiments, the information can be auto-populated into the medical record dashboard 400 and/or to any other accessible window displayed by the command center visual display system and method. In some embodiments, the information can be auto-populated into any EMR system for recordation into one or more EMR's of the patient. In some embodiments, for any auto-populated information that includes technical information without any associated professional interpretation, the command center visual display system and method can provide a visual and/or audible alert to enable a user to provide an update for auto-population to an EMR system.

In some embodiments, the medical record dashboard 400 can also include at least one link to information from external databases, providers, hospitals (e.g., such as a discharge summary), clinics and/or testing laboratories, etc., (e.g., where the information can include the overall diagnostic imaging center of the practice for certain pieces of equipment and into the machine to actually see all of the study). In the latter example, the medical record dashboard 400 can receive information from at least one database and/or server and/or controller coupled to receive data from the diagnostic equipment. Further, some embodiments may include an entry or access to the National Patient Registry or other kind of registry (link 415), hospital EMR (link 417), imaging center 419 (including accessing software imaging and diagnostic management systems to handle many diagnostic images and studies or specific diagnostic equipment), and ePrescribe link 421.

In some embodiments, the user can access at least one ePrescribe database, server, and/or website directly from the dashboard 400 using the ePrescribe link 421. Further, in some embodiments, orders can be auto-populated into the plan or order screen of EMR ("Orders" link 423). For example, in some embodiments, during or after completion of a patient examination, any medical service, medical test or diagnostic, or other medical service can be auto-populated into an order section of the chart. In some embodiments, any recommendation for a return visit can be viewed, accessed, and/or auto-populated using the return visit button or icon 434. For example, in some embodiments, the recommendations can be any advised next steps in the patient's care, any diagnosis, prescriptions, tests, etc. In some embodiments, the aforementioned "Today's plan" button or icon 411 can be used to view, access, and/or auto-populate details and systems including for a day's activities for the patient examination.

In some embodiments, a single button or icon entitled "Imaging Center" (button 424*a*) can take a user (e.g., a physician) instantly or immediately to the piece or pieces of diagnostic equipment that were used that or another day for testing so the physician can now measure and enter the findings. This can be internal in the user's practice so that any diagnostic equipment can be accessed. In some embodiments, the same or another button can provide a link in the major table to an image or diagnostic management software system. In this way, some embodiments can handle the tremendous amount of diagnostic equipment and images, and unlike prior art tables that just provide access to a PDF, these embodiments provide access to not just one single piece of diagnostic equipment but all of them and the complete study, not just a "slice", can be evaluated and comparison of changes over time made.

Once entered, the data can be auto-populated into the dashboard 400 (e.g., such as a retina flowsheet) under other column 1200 (FIG. 4C), where each clinical research study would have other factors followed such as central macular thickness ("CMT"), or ischemic index ("ISI"). Further, the second button (button 424*b*) can take the user to either the company sponsoring the clinical research website (sometimes a pharmaceutical company and other times a company that invented a device). The clinical researcher could immediately go to this website and input any data that was obtained from that visit from the diagnostic equipment button 424*a*, and/or to a research spreadsheet where the user (e.g., a clinical researcher in this example embodiments) can input the data, or where the data can be auto-populated (e.g., from the other column 1200 or into the other column 1200).

Figure 4B:
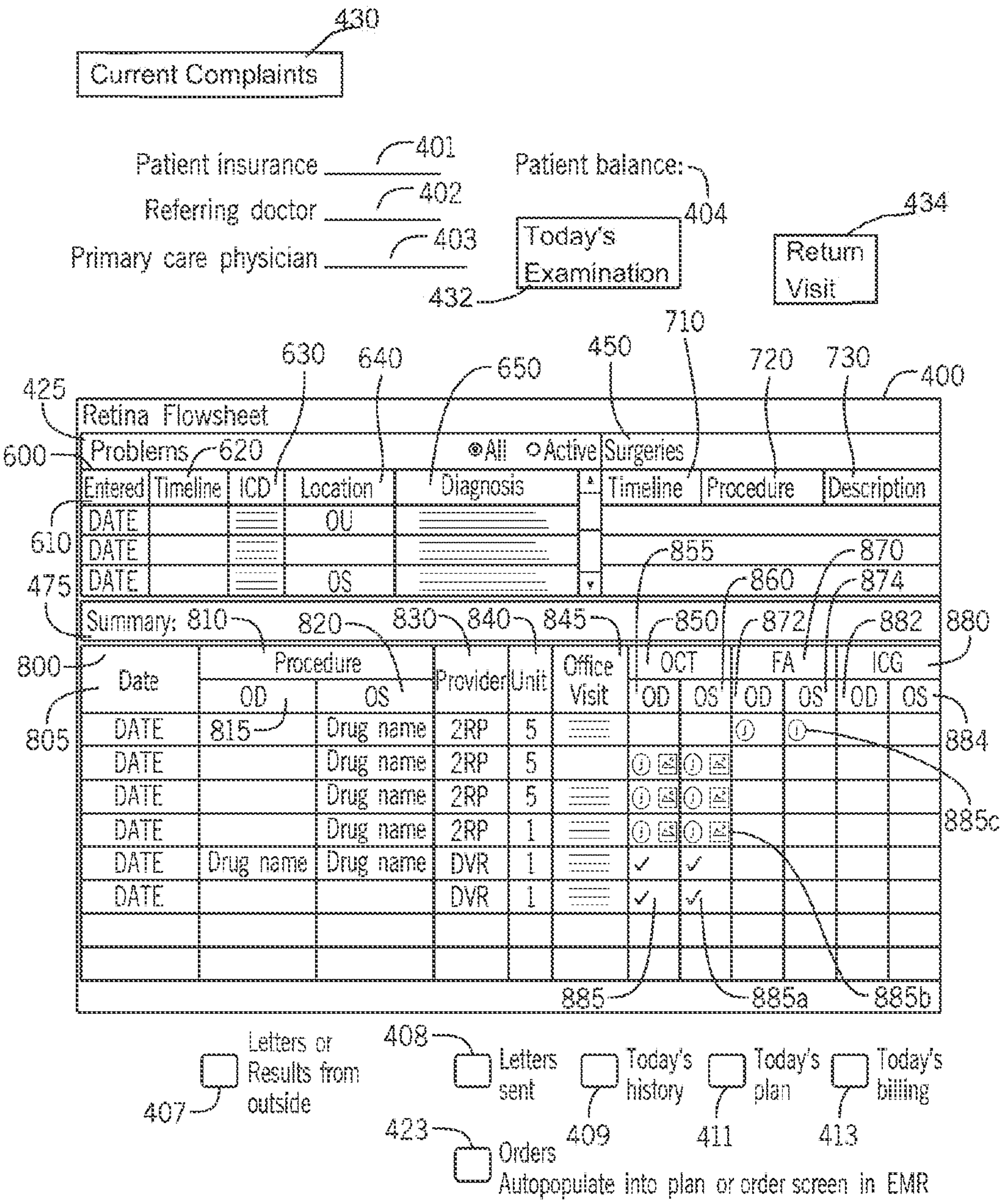
FIG. 4B illustrates a portion of the medical record dashboard of FIG. 4A in accordance with the first embodiment.
Figure 4C:
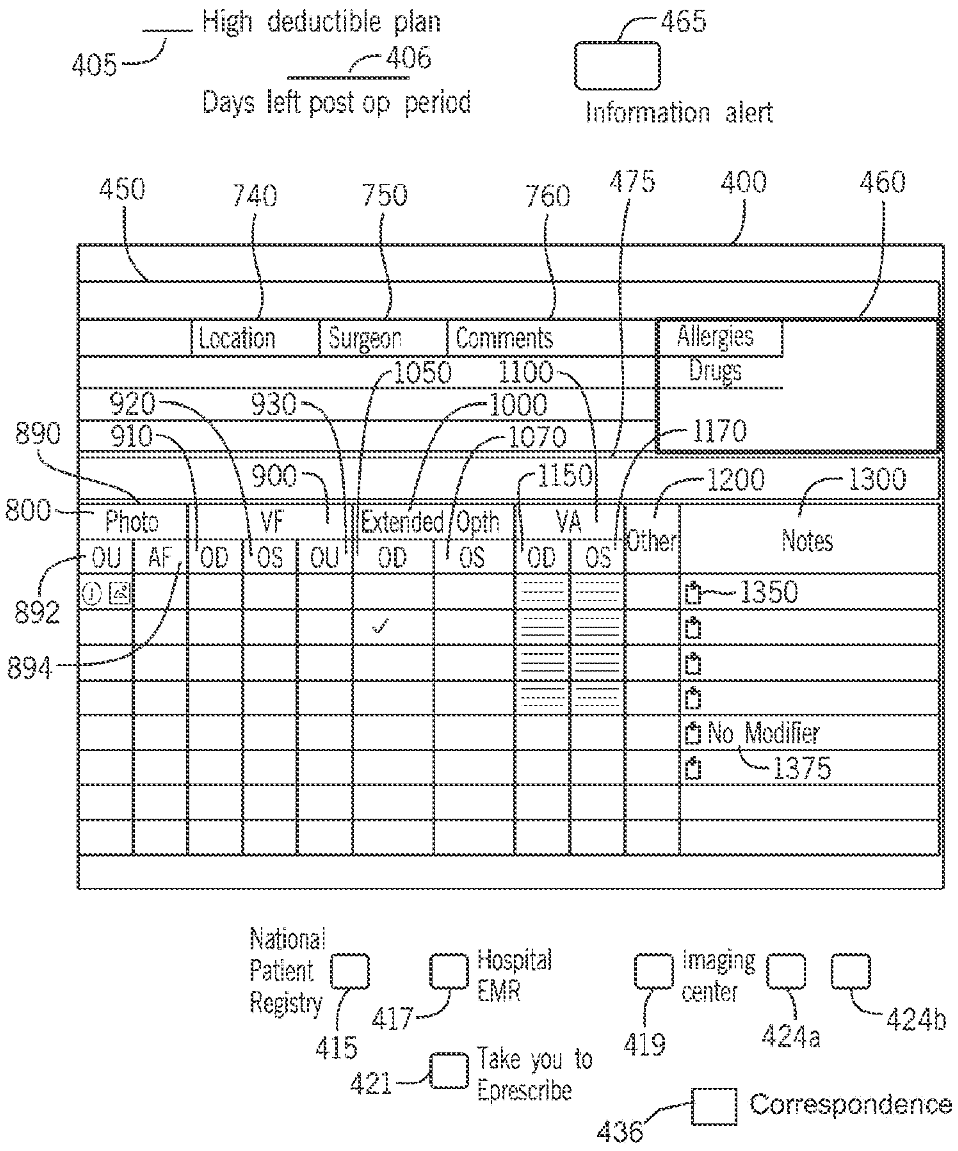
FIG. 4C illustrates a portion of the medical record dashboard of FIG. 4A in accordance with the first embodiment.
Figure 4D:
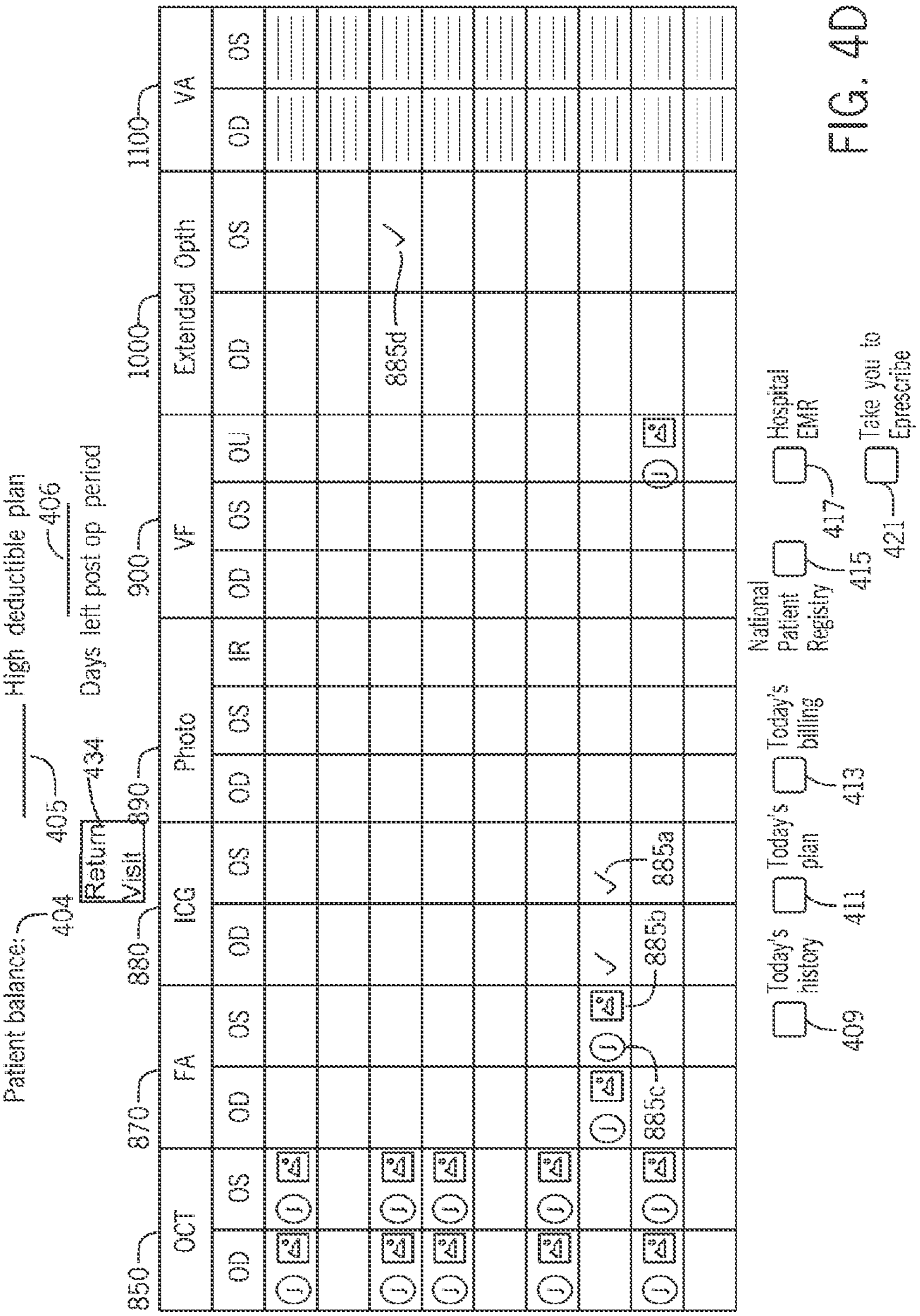
FIG. 4D illustrates a portion of the medical record dashboard of FIG. 4A in accordance with the first embodiment.

Further details of the problems window 425, surgeries window 450, and command center visual display window 500 and are provided in FIGS. 4B-4D illustrating enlarged views of portions of the medical record dashboard 400. For example, FIG. 4B illustrates a portion of the medical record dashboard of FIG. 4A in accordance with some embodiments. As illustrated, in some embodiments, the information columns 600 of the problems window 425 can include a date and time information in entered date column 610, a timeline column 620, an "ICD" column 630 for international classification of disease codes including international classification of disease codes version 9 or version 10 (hereinafter collectively referred to as "ICD code") information, location of the problem or disorder (shown as "OD", "OS", "OU" identifying right eye, left eye, both eyes), or from any part of the body, and a diagnosis column 650 for detailing information related to an initial diagnosis or final diagnosis of a patients problem or disorder that can be auto-populated or inputted. Further, in some embodiments, the information columns 700 of the surgeries window 450 can include information related to services or procedures that were provided to the patient (procedure columns 720), a description of the services or procedures performed (description columns 730), and when the services or procedures were provided (timeline columns 710). Referring to FIG. 4C, in some embodiments, the surgeries window 450 can include location information 740, surgeon or physician information 750, and a comments section 760.

Referring to the command center visual display window 500, the information columns 800 can include a date column 805, and a procedure column 810 illustrating or providing access to information detailing one or more procedures performed on the patient. Further, the procedure column 810 can include an "OD" column 815, and "OS" column 820 providing right and left eye procedure information, or could be a body part (i.e., orthopedic surgery limb versus spine). In some embodiments, information related to the medical provider, the location where the procedure was performed, and office visit information can be provided to the user in the provider column 830, and unit column 840, and office visit column 845.

In some embodiments, the user can view information related to tests and procedures performed on the patient. For example, in some embodiments, these can include information related to one or more medical imaging procedures such as an optical coherence tomography ("OCT"), or fluorescein angiography ("FA"), and/or indocyanine green chorioangiography ("ICG"), or any current procedural terminology code (hereinafter "CPT code"), including any CPT code found in the American Medical Association CPT 2015 professional edition or other edition, the entire contents of which is incorporated by reference. Moreover, the user can view information related to tests and procedures performed on the patient based on an ICD code. Other clinical vocabularies such as Systematized Nomenclature of Medicine (hereinafter "SNOMED codes") can be used in other embodiments as the system is not limited.

In some embodiments, the user can compare patient clinical information, such as labs and vitals, before and after a selected medication has been prescribed or a procedure has been performed to better understand the effect of the medication or procedure on the patient. Similarly in other embodiments, the user can examine how the current patient compares against other patients in the practice and population in general to better understand outcomes.

In some embodiments, medical procedures performed (including any of the aforementioned medical imaging procedures) that have been billed and claimed can be viewed or accessed by a user within any of the "OCT" column 850 (split as an "OD" column 855 and "OS" column 860), an "FA" column 870 (split as an "OD" column 872 and "OS" column 874), and/or "ICG" column 880 (split as "OD" column 882 and "OS" column 884).

Referring to FIG. 4C, illustrating a portion of the medical record dashboard of FIG. 4A in accordance with some embodiments, the information columns 800 can include a photo column 890 configured to enable a user to access any photographic images of the patients eyes including optical and auto-fluorescent images of the eyes ("OU" column 892 and "AF" column 894). In some embodiments, if visual function tests were performed, information can be viewed or accessed in the visual field "VF" column 900 (including an "OD" column 910, "OS" column 920, and/or "OU" column 930). Some embodiments also include an extended ophthalmology column 1000 (including "OD" column 1050 and "OS" column 1070), and a visual acuity column ("VA" column 1100, including "OD" column 1150, and "OS" column 1170). In some embodiments, as described earlier, other details of various tests, procedures or services can be viewed or accessed in the other column 1200. Further, information associated with any of the user-accessible tests, procedures or services or other notes provided by the user and/or medical provider can be viewed or accessed in the notes column 1300 using one or more notes access icon 1350 and/or by viewing a note entry 1375 (e.g., and/or any note entered using the note entry window 1305). The information can also be auto-populated into the EMR plan pages. The command center visual display system and method can auto-populate various data fields of the medical record dashboard of FIG. 4A via an electronic dataflow established between the command center visual display system and method and one or more computer systems of servers that comprise patient information (e.g., such as electronic medical records). The dataflow to and from the medical record dashboard of FIG. 4A can comprise a two-way flow from the source of patient data to the command center visual display system and method, and from the command center visual display system and method to the source.

Some embodiments include visual cues, icons, or markers representing and/or enabling access to detailed information related to medical services, procedures or tests provided to the patient. Further, by employing data visualization techniques to train the user's eye to quickly identify these icons or markers can increase the efficiency of user accessing key medical indicators such as test results and surgical histories. For example, in some embodiments, medical services, procedures or tests performed or provided can be assigned a visual code, icon, or graphical marker. For example, FIG. 4B at least shows visual cues, icons, or markers 885 representing medical services, procedures or tests performed or provided to the patient. In some embodiments, the information columns 800 within the command center visual display window 500 can include at least one "test done, no image attached" icon 885*a*, one or more "see image in order viewer" icon 885*b*, at least one "view order interpretation" icon 885*c*, and/or at least one "procedure billed or claims made" icon 885*d*, where an appearance in the medical record dashboard 400 represents a claim was made, and a change in color or other method (italics, bold, etc. can represent whether the bill was paid. Further, FIG. 4D illustrates another portion of the medical record dashboard 400 of FIG. 4A in accordance with some embodiments and shows example of "test done, no image attached" icon 885*a*, "see image in order viewer" icon 885*b*, "view order interpretation" icon 885*c*, and "procedure billed or claims made" icon 885*d*, where an appearance in the medical record dashboard 400 represents a claim was made, and a change in color or other notification method can represent whether the bill was paid. Data visualization icons and markers housed in the table can be used to quickly identify billing or coding errors, and thus can empower the physician to be proactive and thorough in areas of compliance with insurance guidelines. The use of these icons to identify potential errors in coding can provide an additional level of protection and proofing to reduce and prevent potential billing and/or malpractice errors.

Figure 5A:
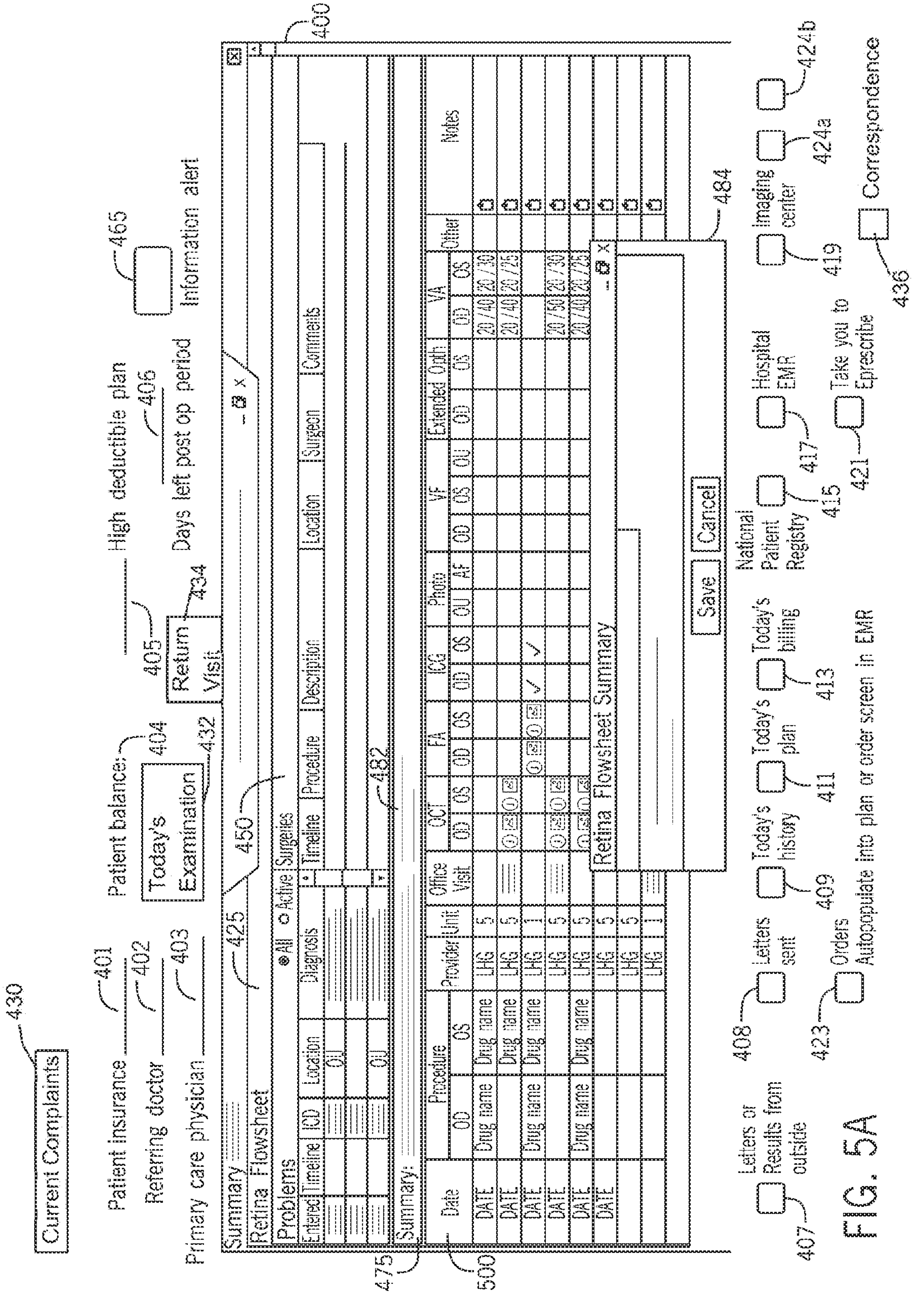
FIG. 5A depicts a medical summary update process in accordance with the first embodiment.

In some embodiments, the medical record dashboard 400 can provide a text summary of any aspect of the medical record dashboard 400. As described earlier, the summary window 475 can enable a user to view and edit summary information related to the patient, any details of care provided to the patient, and/or and any medical diagnosis information prepared by a medical practitioner. In some embodiments, the user can add and/or edit the summary information. For example, FIG. 5A depicts a medical summary update process in accordance with some embodiments. In some embodiments, the medical record dashboard 400 including the problems window 425, surgeries window 450, summary window 475, and command center visual display window 500 can include summary comments 482 that can be entered, updated, expanded using the summary input window 484. In some embodiments, a user can enter information within the summary input window 484 for entry into the summary window 475.

Figure 5B:
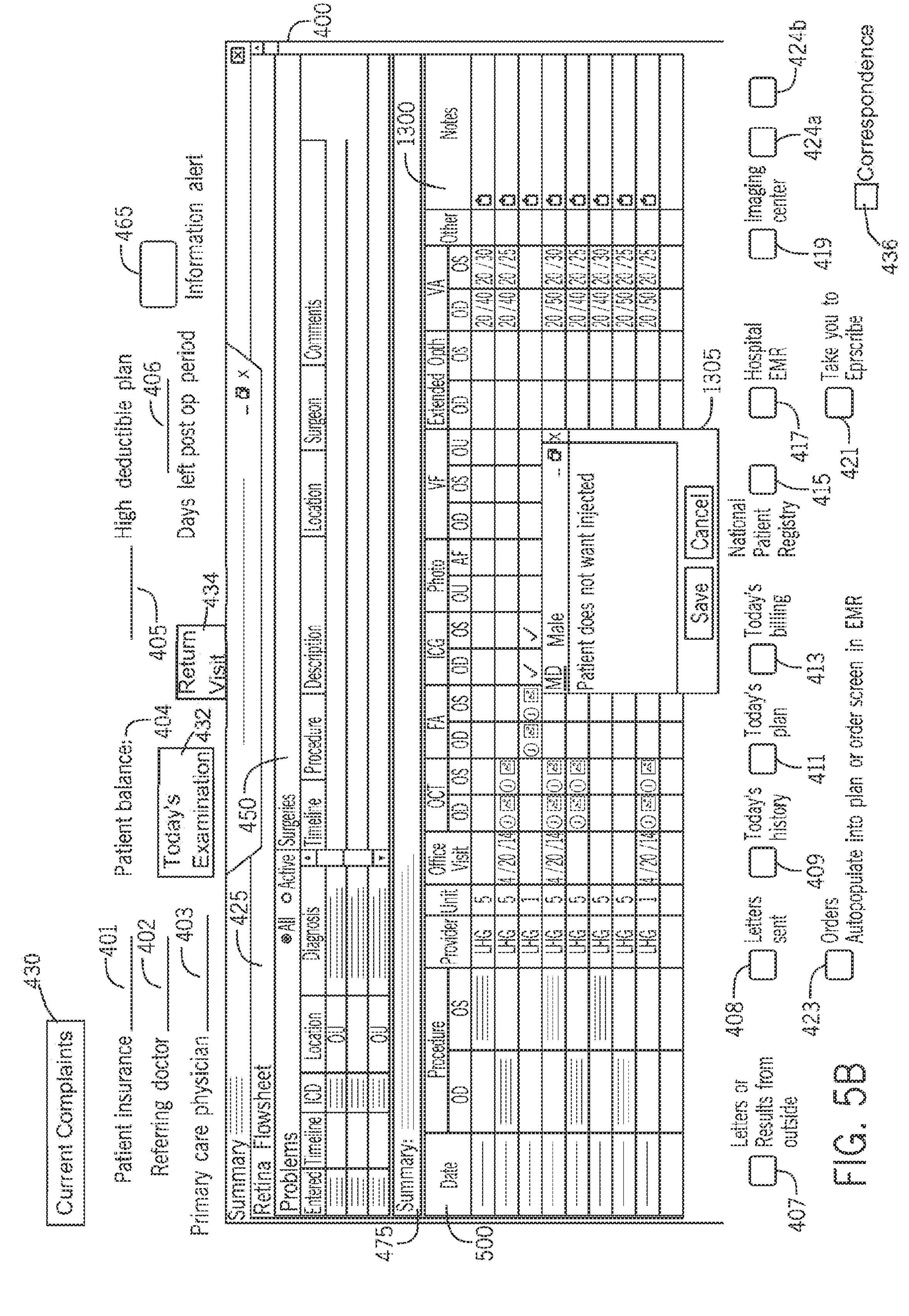
FIG. 5B illustrates a notes update process in accordance with the first embodiment.

In some embodiments, the user can add or update information associated with any of the user-accessible tests, procedures or services or other notes provided by the user and/or medical provider in the notes column 1300. For example, FIG. 5B illustrates a notes update process in accordance with some embodiments. In some embodiments, the medical record dashboard 400 comprising the problems window 425, surgeries window 450, summary window 475, and the command center visual display window 500 with notes column 1300 can be updated with one or more notes using the note entry window 1305. In some embodiments, placement or viewing functions can be toggled using a left or right mouse click function. For example, in some embodiments, following an initial impression or diagnosis, a right click can be updated or shown in a note (e.g., through note entry window 1305), and/or a left click can show in the summary (e.g., summary window 475 as summary comments 482). Further, a right-click for instance or other method can insert what is typed in the table into the corresponding area of the medical chart (e.g., the plan), whereas a left click would insert only into the table and not any other location within the EMR.

Figure 6:
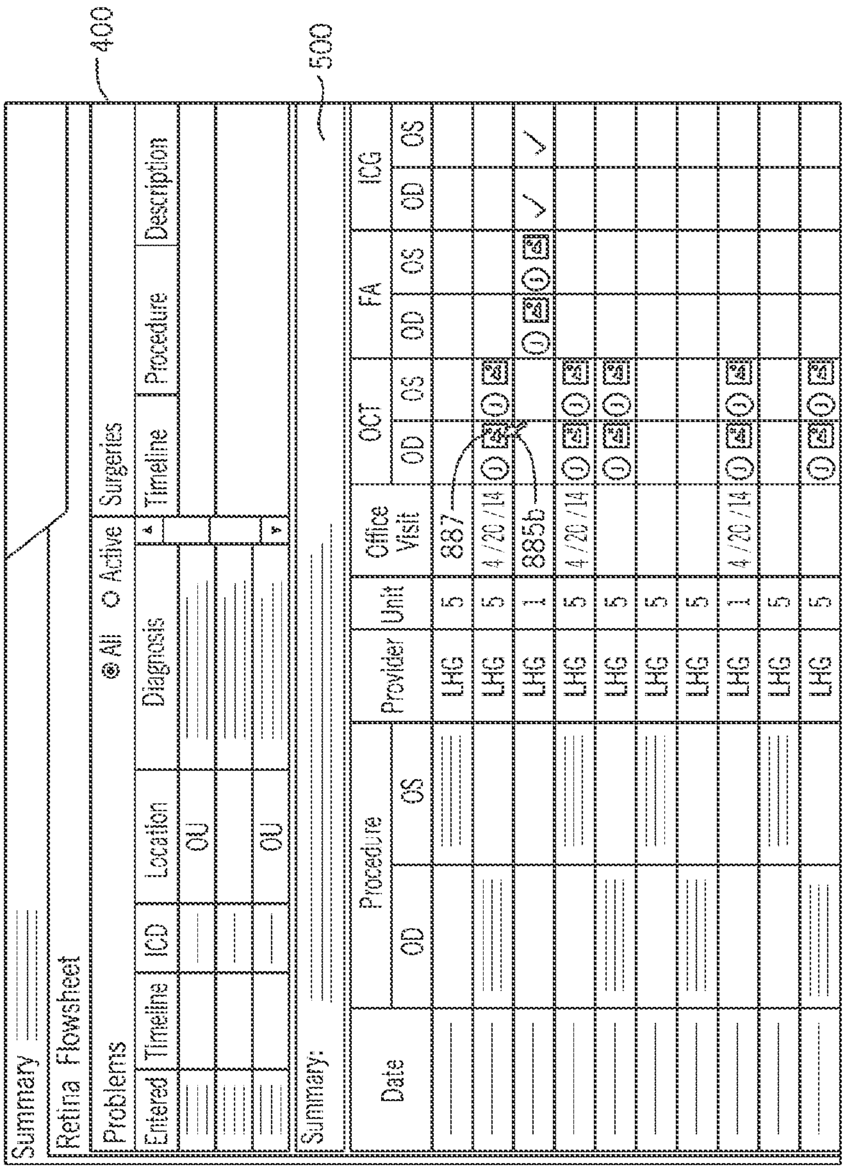
FIG. 6 illustrates a user action record access process in accordance with the first embodiment.

Regarding the visual cues, icons, or markers 885 (referred to above and shown at least in FIG. 4B), in some embodiments, a user can access underlying information linked to the visual cues, icons, or markers 885. For example, using a single click or mouse-over, a user can use the command center visual display window 500 of the medical record dashboard 400 to access and view any information auto-populated within the command center visual display window 500 and/or other windows or sub-windows of the medical record dashboard 400. For example, FIG. 6 illustrates a user action record access process in accordance with some embodiments. In some embodiments, a user action 887 (depicting a user click or mouse-over of a cursor) can enable a user to access and view information (in this example, information lined to "see image in order viewer" icon 885*b*). In some further embodiments, a user can use a single click or mouse-over to user can access and view any information within any portion of the medical record dashboard 400. Further, in some embodiments, a user can use left and right mouse clicks to navigate from one portion of the medical record dashboard 400 to another. Furthermore, in some embodiments, a right-click mouse function update the user and/or display any important information in the medical record dashboard 400, and a left-click can bring the user back to another portion of the medical record dashboard 400.

Figure 7:
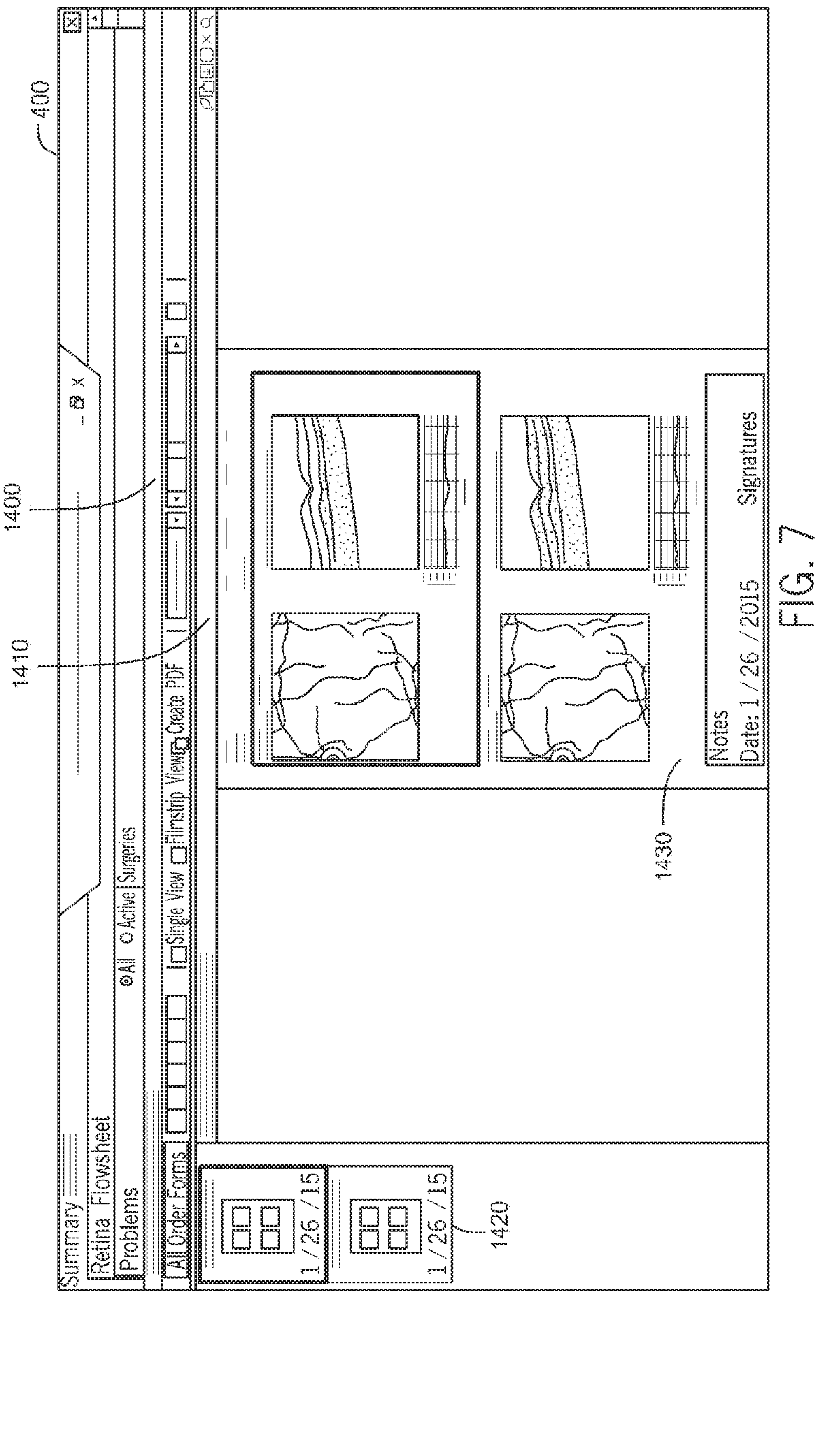
FIG. 7 illustrates a medical records access window in accordance with the first embodiment.

As an example embodiment, the command center visual display system and method can display at least one medical record as a result of the user action 887. For example, FIG. 7 illustrates a medical records access window 1400 in accordance with some embodiments. In some embodiments, the user's action (represented by user action 887) can direct the command center visual display system and method to display the medical record access window 1400 including a medical record display 1410. Further, in some embodiments, at least one medical record 1430 can be selected from the medical record list 1420 for viewing in the medical record display 1410. As illustrated in FIG. 7, in some embodiments, the at least one medical record 1430 can include an image or photograph such as an optical and/or fluorescein angiogram image. In other embodiments, the at least one medical record 1430 can comprise an X-ray image. In some further embodiments, the at least one medical record 1430 can include an MRI scan or any report or anything ordered or performed by the physicians. In some embodiments, the at least one medical record 1430 can comprise one or more dictated letters from the user or another medical provider. Further, in some embodiments, the at least one medical record 1430 can comprise a record or any portion of a correspondence from another medical provider.

In some embodiments, the command center visual display system and method can enable a user to access underlying information linked or related to diagnostic codes. In some other embodiments, the command center visual display system and method can enable a user to access underlying information linked or related billing codes. For example, in some embodiments, using a single click or mouse-over, a user can use the command center visual display window 500 of the medical record dashboard 400 to access and view any information related to diagnostic and/or billing codes. In some embodiments, the diagnostic and/or billing code information and payment history can be displayed in a separate document or window. In some other embodiments, diagnostic and/or billing code information can be display overlaid onto the medical record dashboard 400 (e.g., as a pop-up window or transient text and/or graphics).

In some embodiments, at least one medical record 1430 can comprise a transition of care document (hereinafter "CCD"). In some embodiments, the command center visual display system and method can be configured to receive one or more CCDs from one or more medical providers for display to the user. In some embodiments, command center visual display system and method can be configured to extract information from the CCD for display to the user. For example, in some embodiments, information from a received CCD can be extracted and used to populate one or more data columns or fields of the medical record dashboard 400 and/or one or more linked data columns or fields of the medical record dashboard 400. In some other embodiments, the command center visual display system and method, enabled by the system 30, can be configured to receive direct messaging information. The command center visual display system and method can be configured with standards and profiles required for interoperability and document-based health information exchange with other healthcare organizations. These can include IHE profiles, CDA and CCD, NwHIN Direct, HL7v2, HL7v3, DICOM, X12, ITK (UK), DMP (France), and NEHTA (Australia), etc. For example, in some embodiments, the system 30 can include an HL7 message router and schemas for exchange of direct messages including a graphical editor for transforming messages and data.

Figure 8:
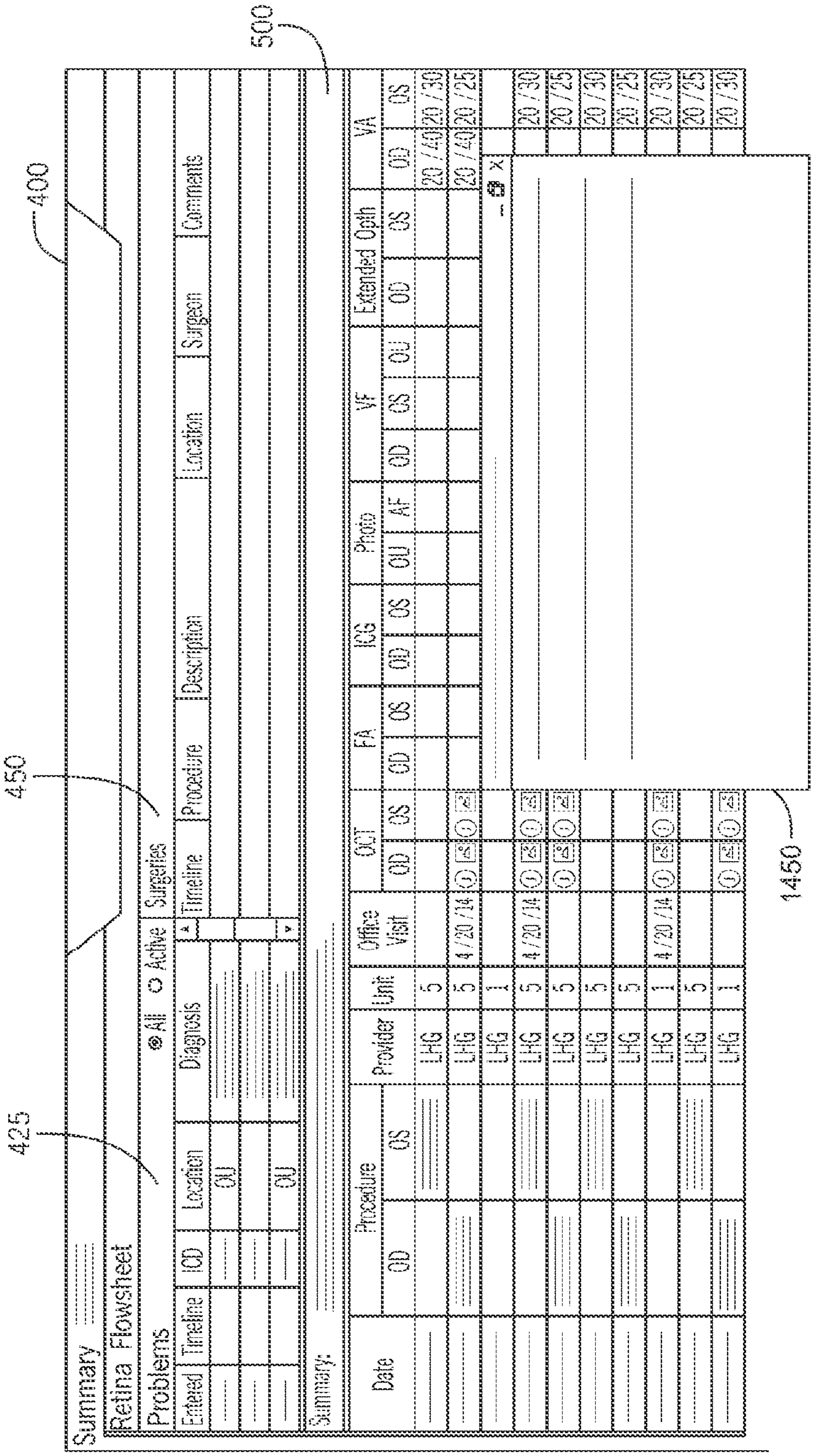
FIG. 8 illustrates a medical record and diagnosis update process in accordance with the first embodiment.

In some embodiments, the user can retrieve and/or update information related to a medical diagnosis. For example, FIG. 8 illustrates a medical record and diagnosis update process in accordance with some embodiments. In some embodiments, the medical record dashboard 400 including problems window 425, surgeries window 450, summary window 475, and command center visual display window 500 can include an option to enable a user to update or enter at least one medical diagnosis using a medical record/diagnosis window 1450. In some embodiments, multiple medical diagnoses can be provided or updated by a user. In some embodiments, the user providing the medical diagnosis can be any medical practitioner providing the service or procedure to the patient. In some other embodiments, the medical record/diagnosis window 1450 can be updated by a user other than the medical practitioner providing the service or procedure to the patient.

Further, in some embodiments, information can also be auto-populated into the EMR plan pages. The command center visual display system and method can auto-populate various data fields related to information in any one of the problems window 425, surgeries window 450, summary window 475, and record/diagnosis window 1450 via an electronic dataflow established between the command center visual display system and method and one or more computer systems of servers that comprise patient information (e.g., such as electronic medical records). The dataflow can comprise a two-way flow from the source of patient data to the command center visual display system and method, and from the command center visual display system and method to the source.

Figure 9:
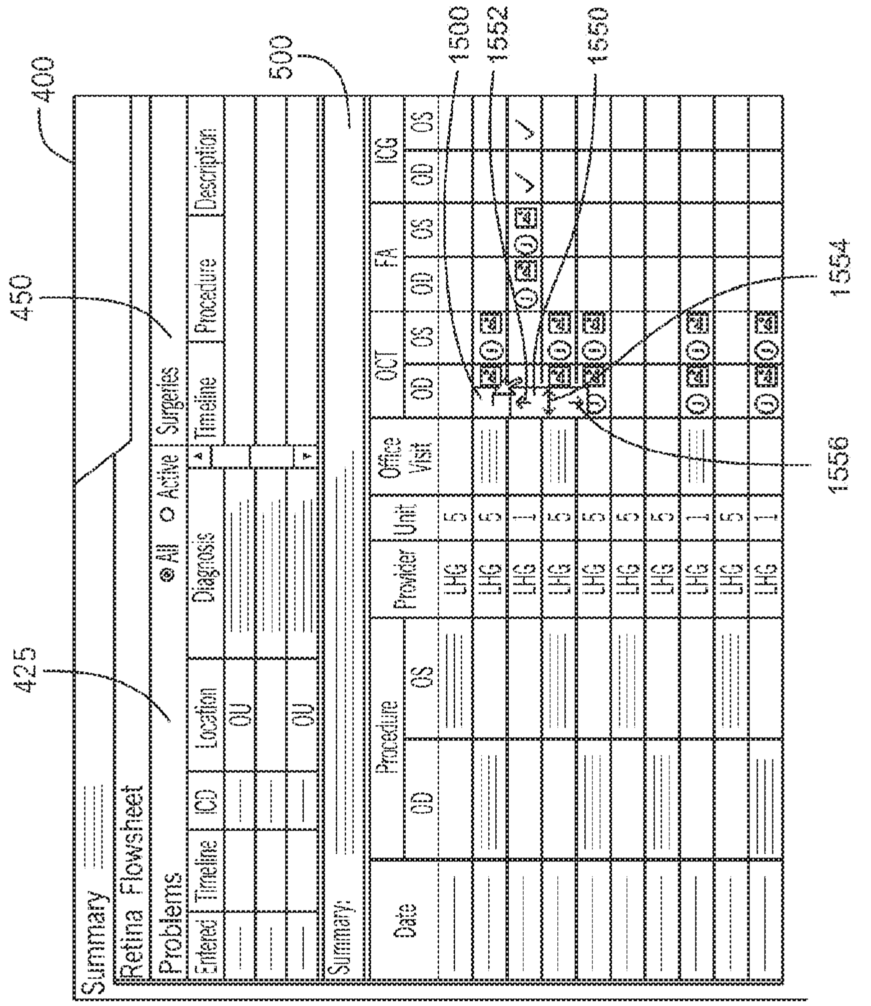
FIG. 9 illustrates a medical record update marker process in accordance with the first embodiment.

In some embodiments, the command center visual display system and method can enable a user to update information displayed in the command center visual display window 500. For example, in some embodiments, a user can update information related to a medical diagnosis and/or information related to a medical test or other service or procedure. For example, FIG. 9 illustrates a medical record update marker process in accordance with some embodiments. The medical record dashboard 400, including problems window 425, surgeries window 450, and summary window 475 is shown with a record update marker 1500 being accessed by a user and displaying a update marker selection tab 1550. In some embodiments, the update marker selection tab 1550 can include a user-selectable marker or icon. For example, in some embodiments, update marker selection tab 1550 can include a selectable diagnosis indicator 1552, a selectable diagnosis indicator 1554, and/or a selectable diagnosis indicator 1556. In some embodiments, the selectable diagnosis indicators 1552, 1554, 1556 can provide a graphical representation of a medical diagnosis, outcome, or test. For example, in some embodiments, the diagnosis indicators 1552, 1554, 1556 can provide a visual representation of an improvement of a medical problem, disease, or symptom, or a worsening of a medical problem, disease, or symptom. Further, in some embodiments, the diagnosis indicators 1552, 1554, 1556 can provide a visual representation of a medical problem, disease, or symptom that is stable or substantially unchanged. In some embodiments, the diagnosis indicators 1552, 1554, 1556 can provide a visual representation directly related to one or more variables of a physical test. For example, in the field of ophthalmology, some imaging tests can provide an analysis of the thickness of the retina related to an eye disease such as macular degeneration. In some embodiments, an increase in thickness can represent a worsening of the condition, whereas a decrease in thickness can represent an improvement. A stable or unchanged thickness can indicate the disease is responding to treatment or is in remission. Further, by using data visualization techniques such as by using a color change or other method (e.g., such as using italics, bold text, and/or underlined text), a particular important change in a test can be marked for internal reference alerting a physician to the tests or procedures that are important and to take note for future reference. Further, in some embodiments, the diagnosis indicators 1552, 1554, 1556 can comprise a color and/or graphical change providing a visual representation of items billed, items not billed, or tests needing reports or interpretations are required. A color change or data visualization method (e.g., such as using italics, bold text, and/or underlined text) can also tell a physician if a test or procedure was billed, rejected, or if an interpretation needs to be made.

As an example embodiment, the diagnosis indicators 1552, 1554, 1556 can provide a visual representation of the status of a patient with an eye disease such as macular degeneration. For example, in some embodiments, the diagnosis indicators 1552, 1554, 1556 can be selected from the update marker selection tab 1550 when the user intends to indicate a worsening of the condition (e.g., where the thickness of the retina is increasing). In some embodiments, any of the diagnosis indicators 1552, 1554, 1556 can be color-coded to represent a status or provide a visual indicator of a medical condition, test, or diagnosis linked to the diagnosis indicators 1550. For example, in some embodiments, the diagnosis indicator 1552 can be color coded red and the diagnosis indicator 1556 can be color-coded green. Further, the diagnosis indicator 1554 can be color-coded blue or black. In some other embodiments, the diagnosis indicator 1552 can be color coded green and the diagnosis indicator 1556 can be color-coded red. In other embodiments, other graphical markers or icons can be used, and/or other colors can be used to differentiate the diagnosis indicators 1552, 1554, 1556. Further, in some embodiments, in addition to or in place of using a color differentiation between the diagnosis indicators 1552, 1554, 1556, one or more of the diagnosis indicators 1552, 1554, 1556 can flash or pulsate.

Figure 10A:
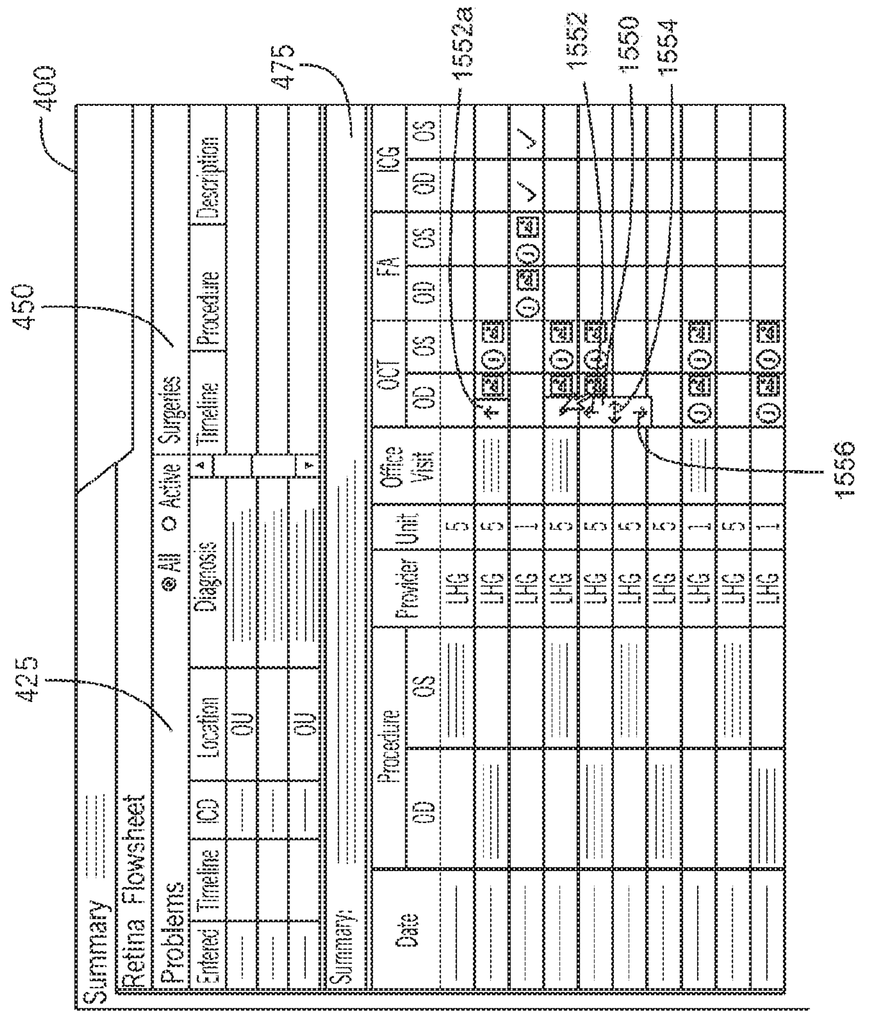
FIG. 10A illustrates a medical record update marker process in accordance with the first embodiment.

In some embodiments, the command center visual display system and method can enable a user to provide a plurality of updates to information displayed in the command center visual display window 500. For example, in some embodiments, a user can update information related to a medical diagnosis and/or information related to a medical test or other service or procedure, and subsequently provide further updates to the same information or to other information. For example, FIG. 10A illustrates a medical record update marker process in accordance with some embodiments including medical record dashboard 400, with problems window 425, surgeries window 450, summary window 475, and command center visual display window 500. The command center visual display window 500 depicts diagnosis indicator 1552*a* representing previously updated information. The command center visual display window 500 also illustrates a user updating information with a process described above using the update marker selection tab 1550 comprising a selection of diagnosis indicator 1552, diagnosis indicator 1554, or diagnosis indicator 1556.

Figure 10B:
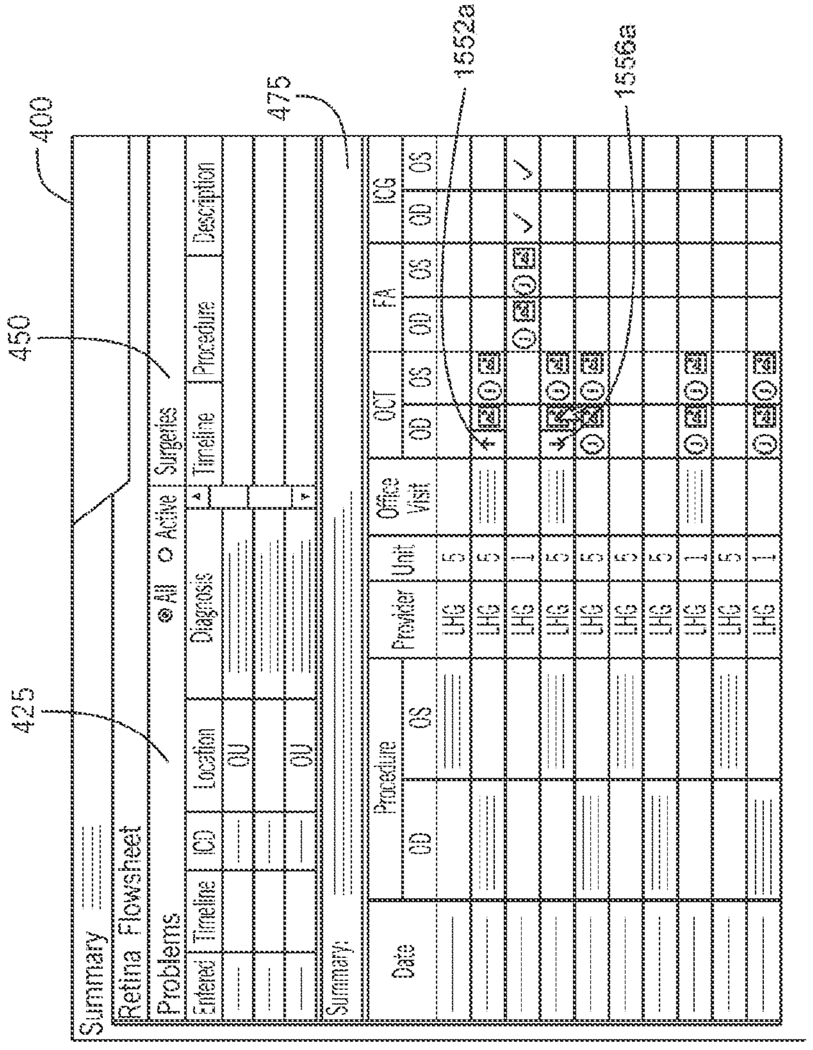
FIG. 10B illustrates a medical record update marker process in accordance with the first embodiment.

Further, FIG. 10B illustrates a medical record update marker process in accordance with some embodiments. Following the medical record update marker process shown in FIG. 10A, in some embodiments, the medical record dashboard 400 including medical record dashboard 400, with problems window 425, surgeries window 450, summary window 475, and command center visual display window 500 can display diagnosis indicator 1552*a* and diagnosis indicator 1556*a* indicative of updated information or status of a patient and/or a patient's disease, test, or medical condition. Further, any ICD, SNOMED or similar code can be inserted.

Figure 11:
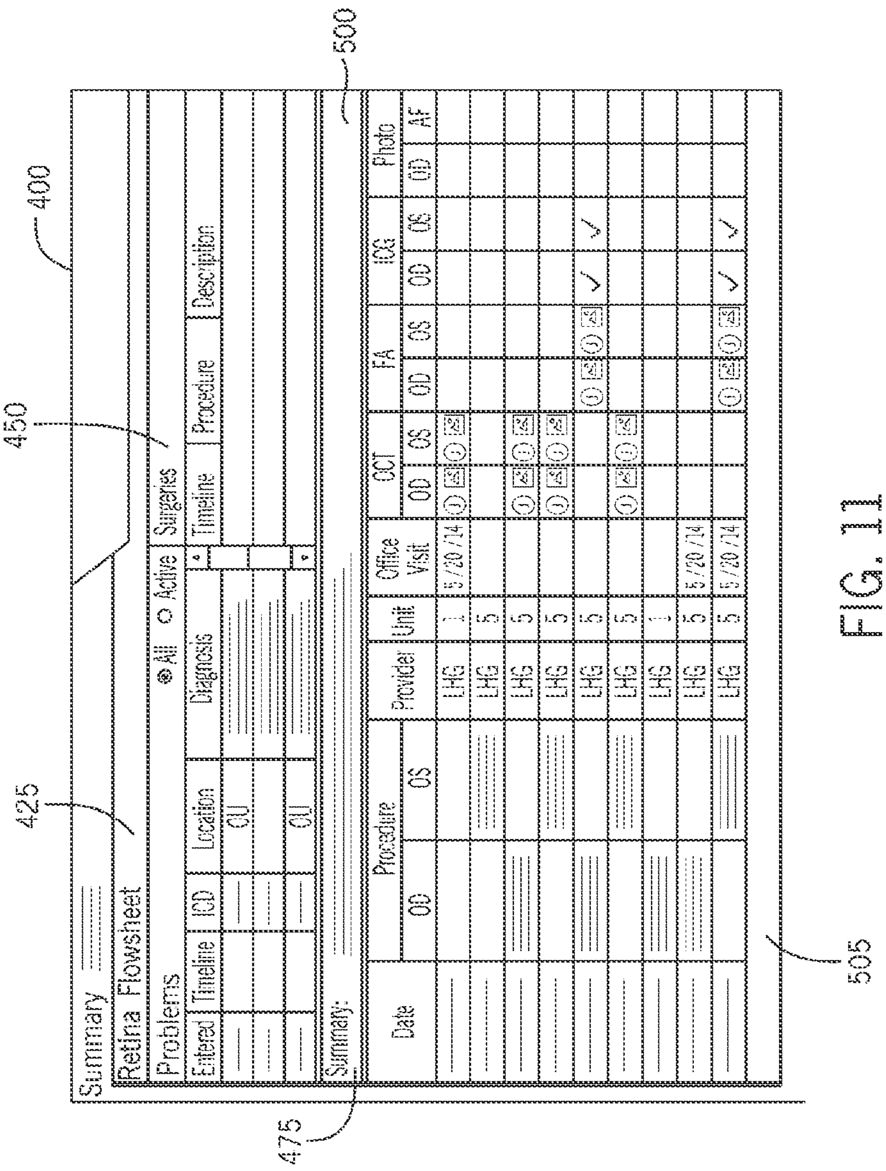
FIG. 11 illustrates a portion of the medical record dashboard of FIG. 4A including a scrolled display in accordance with the first embodiment.

FIG. 11 illustrates a portion of the medical record dashboard 400 of FIG. 4A including a scrolled display in accordance with some embodiments. In some embodiments, the medical record dashboard 400 including problems window 425, surgeries window 450, summary window 475 can include a command center visual display window 500 that comprises a scroll display 505. In some embodiments, any information displayed in the command center visual display window 500 can be scrolled by the user to bring non-visible portions of the command center visual display window 500 into view. This procedure can enable the user to view the entire history of the patient independent of the number of years of history that is on record.

Figure 12A:
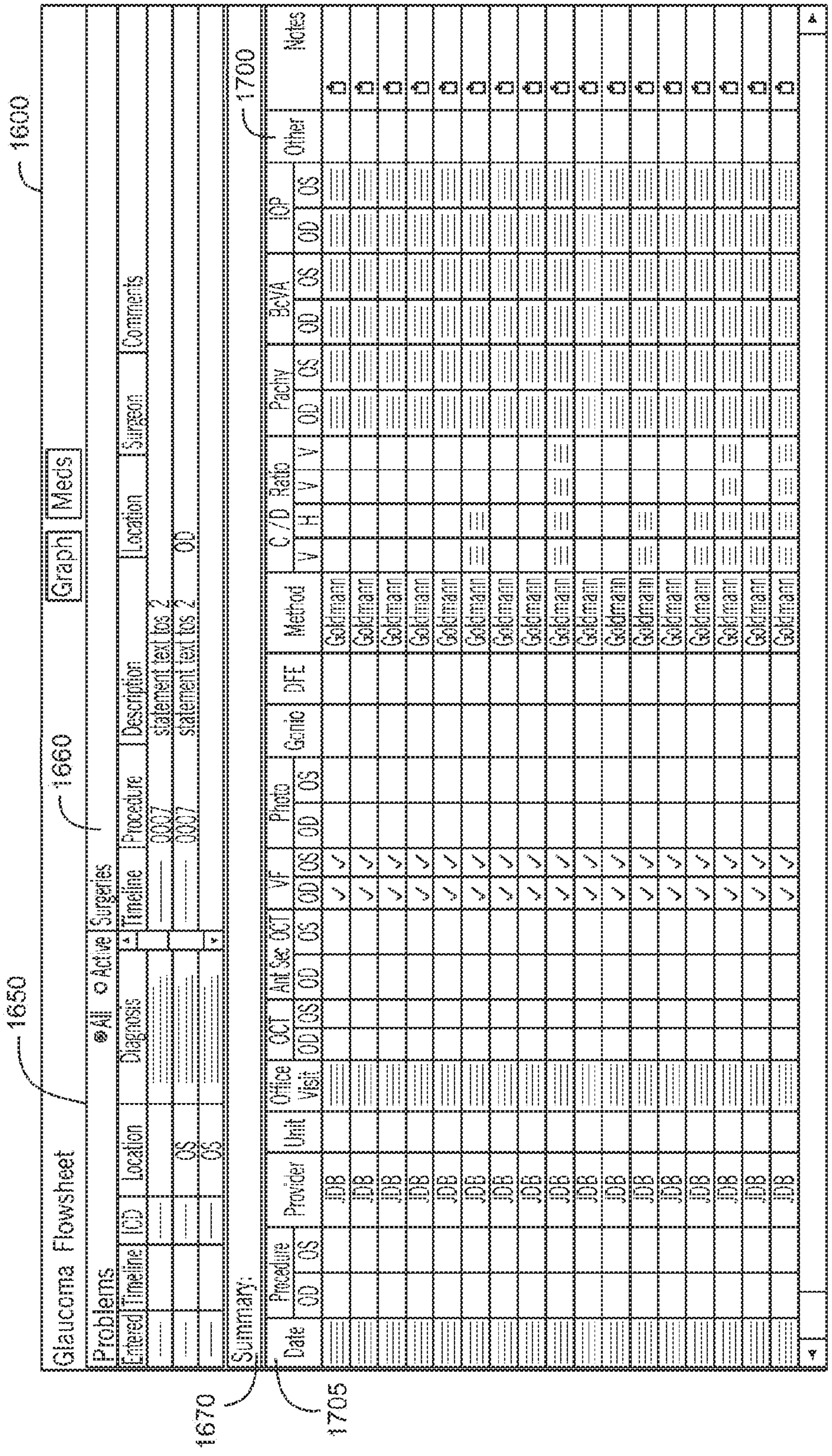
FIG. 12A illustrates a portion of the medical record dashboard for a glaucoma practice in accordance with the first embodiment.

FIG. 12A illustrates a portion of the medical record dashboard 1600 in accordance with another embodiment. In some embodiments, the medical record dashboard 1600 can display data from one or more medical records, and/or track medical procedures and services based on claims made or billing signed off by a physician for one or more delivered medical procedures or services. Further, in some embodiments, the medical record dashboard 1600 can be auto-populated as a function of claims made or billing signed off by a physician, auto-populated from any portion of a selected chart. In this instance, any data displayed within the medical record dashboard 1600 can be derived from one or more claim records that have been billed for one or more procedures or services have previously been provided to the patient. In reference to the medical record dashboard 1600 and/or the previously described medical record dashboard 400, in some embodiments, auto-populating visits by actual claims made or billings signed off by a physician, by definition occurs after the visit with the patient. In some embodiments, the command center visual display system and method can auto-populate the some information at the time the patient is seen, or shortly thereafter, or even before in preparation for a visit (i.e., lab results), so that even if a patient is not seen on a particular day, the user (e.g., medical provider) can view the displayed information in the table for information. For example, in some embodiments, information related to vision can be made with the current date at the time patient is seen. In some embodiments, a user or user's assistant can update the command center visual display system and method with medical tests or test results (e.g., a vision test) as they are performed or shortly thereafter (i.e., on the same day). In this example, this information can immediately trigger the current date and auto-populate the vision column. This information can then be immediately viewed by a user and/or medical provider, and can be updated with notes or comments or other information as the user and/or medical provider is attending to the patient. Further, after the claim has been made for any diagnostic tests or examinations or procedures that have not yet been billed, the date will then auto-populate in the future with the other related columns. In some embodiments, while examining a patient, important information and/or certain parameters that are critical to follow can be immediately updated to the command center visual display system and method. Using these procedures, the command center visual display system and method can enable the medical provider to review the patient's medical history, treatment history, and instantly see items of importance on the day they're examining a patient. For example, the user and/or medical provider can be enabled by the command center visual display system and method, on the day the patient is examined, to review information such as a vision or glaucoma table, intraocular pressure, blood pressure, blood sugar, etc. When billing claims are made, further information is filled to complete the billed claims record. As a further example, a patient may be seen a few days apart and the diagnostic tests etc. and claims have not yet been made, however the command center visual display system and method can be configured to show that the patient was seen that day (e.g., with a vision, pressure test, etc.), and the command center visual display system and method can enable a user (such as a physician) to interpret and/or add special notes on the day they see a patient or before they see the patient rather than waiting to make some notes when a claim is actually generated.

In some embodiments, a medical office wishes to communicate results or a test (e.g., a pathology result or test) a blinking cursor can appear to alert a lab physician to confirm done or other correspondence can be auto-populated into other portions of the EMR. Also any written or type correspondence or any links to dictated information using voice recognition coupled to or integrated with the command center visual display system and method. The display can include information including components where there is a summary of the patient's problem list that a user can input patient information and constantly update and change. Further, this information can be auto-populated with the touch of a button into a designated location such as the current plan documenting the patient's current visit (thus aiding documentation for the current visit). Further, whatever is important for a user to input into the day's visits for documentation can be initially inputted in the table, and then permanently into the day's patient visits. Further, the summary section of the medical record dashboard 2100 (FIG. 13A) can be constantly fluid, and can be changed at every visit rather than being written to an unchangeable document or file (e.g., such as a PDF). Any patient data that is inputted, received, analyzed, or created can be auto-populated into any portion of the dashboard 2100. The command center visual display system and method can auto-populate in a one-way or two-way direction in various data fields related to information in any patient information via an electronic dataflow established between the command center visual display system and method and one or more computer systems of servers that comprise patient information (e.g., such as electronic medical records). The dataflow can comprise a two-way flow from the source of patient data to the command center visual display system and method, and from the command center visual display system and method to the source including another electronic system or server, or another user, observer, or other 3rd party.

By following a patient on the day of delivery (e.g., for a vision intraocular pressure or anything else) The Data Command Center Visual Display system and method can enable the user and/or medical provider to see the diagnostic test on same day even though it has not been billed. Further, this procedure can enable the medical provider to optionally add a note (as described earlier) and allow free hand typing at the end of the line.

In some embodiments, medical information populated within the command center visual display system and method (e.g., shown as visual cues, icons, or markers 885 representing medical services, procedures or tests performed or provided to the patient) can include a visual marker such as a red dot. In some embodiments, the command center visual display system and method can display the red dot until a claim is actually made at which time the command center visual display system and method can display a green dot (i.e., the command center visual display system and method can convert the red dot to a green dot). In some embodiments, by clicking on the dot, the user can toggle between the payment screen and the command center visual display window 500, 1700. This can allow medical providers to improve patient care, to review the actual picture of a diagnostic test that is displayed within the command center visual display window 500, 1700, to review other diagnostic tests results, and to compare to what happened on other days. In some embodiments, at any time, a medical provider can click on the dot to access a display where the claim is billed, and any payment that was made can be displayed. This process can help to reduce medical errors enabling medical providers to quickly review the billings and claims made or billings signed off by a physician and payment portions of the command center visual display system and method. Further, this procedure serves as an additional tool to minimize coding, compliance with insurance guidelines, and medical treatment errors, as the command center visual display system can provide a quick reference tool that can pull all critical medical and procedure data from the patients EMR chart into a concise and clear table.

In some embodiments, the medical record dashboard 1600 can display information related to medical procedures or services in relation to care of a patient with glaucoma. In some embodiments, the medical record dashboard 1600 can display various windows and sub-windows based on a user preference and/or current or previous user interaction with the medical record dashboard 1600. Some embodiments include a medical record dashboard 1600 that comprises information columns 1640 including a problems window 1650 and/or a surgeries window 1660 where information related to a patient's medical problems and surgeries can be displayed. In some embodiments, the medical record dashboard 1600 can include a summary window 1670 enabling a user to view and edit summary information related to the patient, any details of care provided to the patient, and/or and any medical diagnosis information prepared by a medical practitioner. Further, the medical record dashboard 1600 can also display detailed information related to any medical procedures or services provided to the patient, including procedures or services that are auto-populated by claims made or billing signed off by a physician as detailed above or other method. For example, in some embodiments, the medical record dashboard 1600 can display a command center visual display window 1700 including a plurality of information columns 1705. In some embodiments, the command center visual display window 1700 can be scrolled by the user to display other portions of the command center visual display window 500.

In some embodiments, the medical record dashboards 400, 1600 can also display detailed information related to notification of payment of any medical procedures or services provided to the patient, including procedures or services that are auto-populated by claims made or billing signed off by a physician as detailed above or other method. Moreover, the medical record dashboards 400, 1600 can enable a user to access and/or track the status of the billing and payment process at any point in time. For example, in some embodiments, the medical record dashboards 400, 1600 can access and view any patient encounter form (i.e. a superbill), any claims made to a clearing house, any updates on accepted or rejected bills from the clearing house, any claims made to an insurance company, and/or any payments received for any claims made.

Figure 12B:
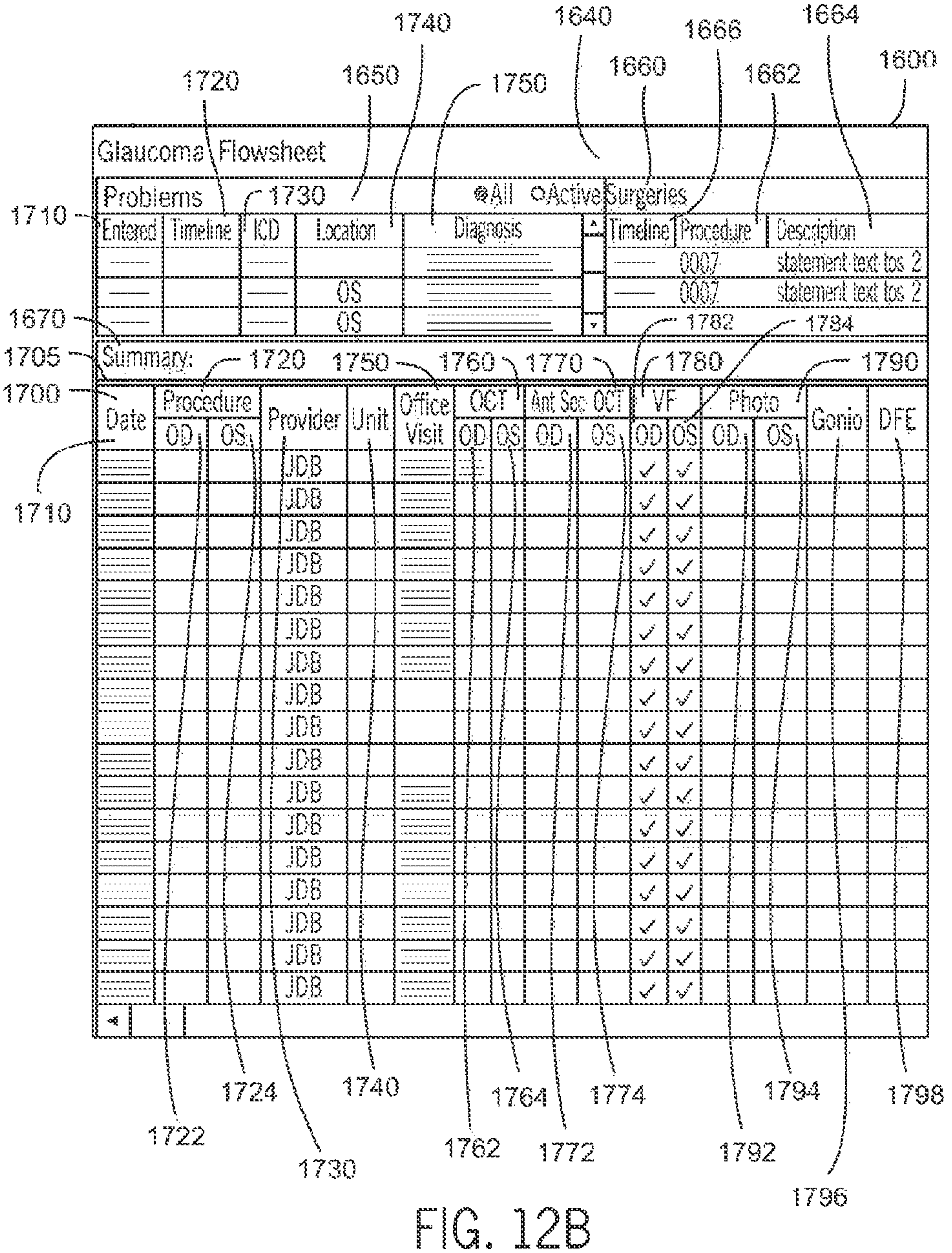
FIG. 12B illustrates a portion of the medical record dashboard of FIG. 12A in accordance with the first embodiment.

FIG. 12B illustrates a portion of the medical record dashboard 1600 of FIG. 12A in accordance with some embodiments. As shown, the problems window 1650 can include a date and time information in entered date column 1710, a timeline column 1720, an "ICD" column 1730 for ICD code information, location of the problem or disorder (shown as "OD", "OS", "OU" identifying right eye, left eye, both eyes) (column 1740), and a diagnosis column 1750 for detailing information related to an initial diagnosis or final diagnosis of a patients problem or disorder. Further, the surgeries window 1660 can include information related to services or procedures were provided to the patient (procedure columns 1662), a description of the services or procedures performed (description columns 1664), and when the services or procedures were provided to the patient (shown as timeline columns 1666), and can include a surgical report that can be brought up and viewed by the user.

Referring to the command center visual display window 1700 of dashboard 1600, the information columns 1705 can include a date column 1710, and a procedure column 1720 illustrating or providing access to information detailing one or more procedures performed on the patient. Further, the procedure column 1720 can include an "OD" column 1722, and "OS" column 1724 providing right and left eye procedure information. In some embodiments, information related to the medical provider, location where the procedure was performed, and office visit information can be provided to the user in the provider column 1730, and unit column 1740, and office visit column 1750.

In some embodiments, the command center visual display window 1700 can enable a user to view information related to tests and procedures performed on the patient including, but not limited to one or more medical imaging procedures such as an optical coherence tomography ("OCT"), or fluorescein angiography ("FA"), and/or indocyanine green chorioangiography ("ICG"). In some embodiments, medical procedures performed (including any of the aforementioned medical imaging procedures) that have been billed and claimed can be viewed or accessed by a user within any of the "OCT" column 1760 (shown split as an "OD" column 1762 and "OS" column 1764), an "Ant Seg OCT" column 1770 (split as an "OD" column 1772 and "OS" column 1774).

In some embodiments, if visual function tests were performed, information can be viewed or accessed in the "VF" column 1780 (including an "OD" column 1782, and/or an "OS" column 1784. Some embodiments include a photo column 1790 configured to enable a user to access any photographic images of the patient's eyes including optical and/or auto-fluorescent images of the eyes ("OD" column 1792 and "OS" column 1794). Further, some embodiments include a Gonio column 1796 providing access to gonioscopy data and/or information related to a dilated fundus examination ("DFE" column 1798). In some embodiments, the surgeries window 1660, can include location column 1642, surgeon column 1644, and a comments column 1646 (shown in FIG. 12C).

Figure 12C:
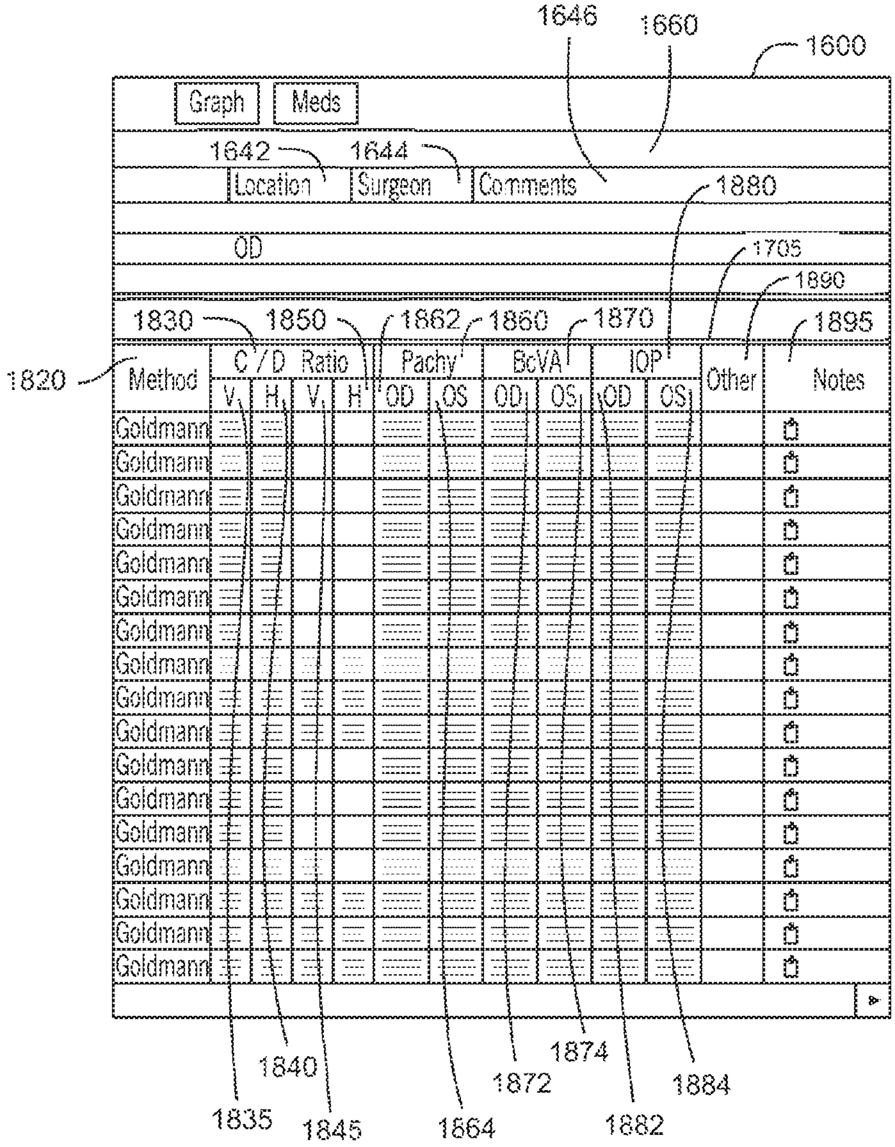
FIG. 12C illustrates a portion of the medical record dashboard of FIG. 12A in accordance with the first embodiment.

In some embodiments, the command center visual display window 1600 can enable a user to view information related to tests and procedures performed on the patient including a cup-to-disc ratio ("C/D") to assess the progression of glaucoma, Pachymetry data ("Pachy"), refraction test information such as best-corrected visual acuity ("BCVA"), and/or intraocular pressure (IOP) data. For example, FIG. 12C illustrates a portion of the medical record dashboard of FIG. 12A in accordance with some embodiments and shows method column 1820, "C/D ratio" column 1830, "Pachy" columns 1860, "BcVA" columns 1870, and "IOP" columns 1880. In some embodiments, the "C/D ratio" column 1830 includes "V" column 1835, "H" column 1840, "V" column 1850, and "H" column 1850. Further, in some embodiments, the "Pachy" columns 1860 includes "OD" column 1862, and "OS" column 1864. In some embodiments, the "BcVA" columns 1870 includes "OD" columns 1872, and "OS" columns 1874. Some embodiments include "IOP" columns 1880 including "OD" columns 1882, and "OS" columns 1884. In some embodiments, other columns 1890 can be used to add additional test information. Further, the command center visual display window 1700 can also include a notes column 1895 for accessing and updating notes related to tests and medical diagnosis. In some embodiments, the tracking display window 1700 can be updated with comments and notes as described earlier with respect to tracking display window 400.

In some embodiments, the command center visual display system and method can display and auto-populate the medical record dashboard 400 and/or the medical record dashboard 1600 with more than one patient information. For example, in some embodiments, any windows, sections, or columns of the medical record dashboard 400, 1600 can display information related to a plurality of patients. Any patient data that is inputted, received, analyzed, or created can be auto-populated into any portion of the dashboard 400, 1600, where the command center visual display system and method can auto-populate in either a one-way or a two-way direction. Thus, data fields related to information in any patient information can be communicated via an electronic dataflow established between the command center visual display system and method and one or more computer systems of servers comprising patient information (e.g., such as electronic medical records).

Further, in some embodiments, any information displayed by the command center visual display system and method can display and auto-populate the medical record dashboard 400 and/or the medical record dashboard 1600 as a function of patients seen during a specified time period. In some other embodiments, the command center visual display system and method can display and auto-populate the medical record dashboard 400 and/or the medical record dashboard 1600 as a function of a specified disease and/or diagnosis. For example, in some embodiments, the command center visual display system and method can display and auto-populate the medical record dashboard 400 and/or the medical record dashboard 1600 as a function of a diagnosis or procedure or prescribed medication or lab or imaging test from input received from a physician or other medical practitioner or provider. For instance, every patient who has the diagnosis of diabetes with their name and the date last scene is auto-populated. Certain parameters that may need to be followed by the user from all of their patients with this condition can be auto-populated. For example, in the case of patients with diabetes, parameters can include how often they've missed appointments, blood sugar, hemoglobin A1C, medications, major new medical complications such as heart attack, stroke, amputations, blindness, each of which can be auto-populated and followed to enable the user to see how all their patients are doing. In some embodiments, input and the ability to display data can be based on single values or on complex multi-variate input (i.e. patients with diabetes, taking metformin and seen by the practice in the last 30 days).

In some embodiments, the user can receive a daily report on all the patients they have seen, what the diagnosis codes are and what CPT, ICD, or office visit billing codes were done whether they have been billed or not. In some embodiments, the user can view a report of patients for a specific day or week based on appointments or other data such as referrals. With this functionality, at the end of the day physicians can see all of their activity or the practice's activity and using data visualization techniques can realize what activity still needs to be completed or was not entered properly. The user can then review the same information in a few days' time and weeks or months later to ensure that the proper billing and collections has occurred. In some embodiments, any report or diagnostic test can be sent to a patient portal, to an email server, and/or as a fax. Further, the user can be alerted when the claims go out and when they are actually paid. For example, in some embodiments, the above described methods of display can provide a mechanism for determining payments to the user, and if claims are being made for each patient seen in any particular day, week or month.

In some embodiments, any report, note, letter, referral or diagnostic test can be sent to an EMR, patient portal, a messaging platform to an email server, and/or as a fax. Messages can be transmitted to a patient or another practice focused on appointment reminders, medication prescriptions and/or refills, and good care management guidelines. It should be recognized the data interoperability and messaging are not limited to the examples provided but apply to any information within the Command Center.

Figure 12E:
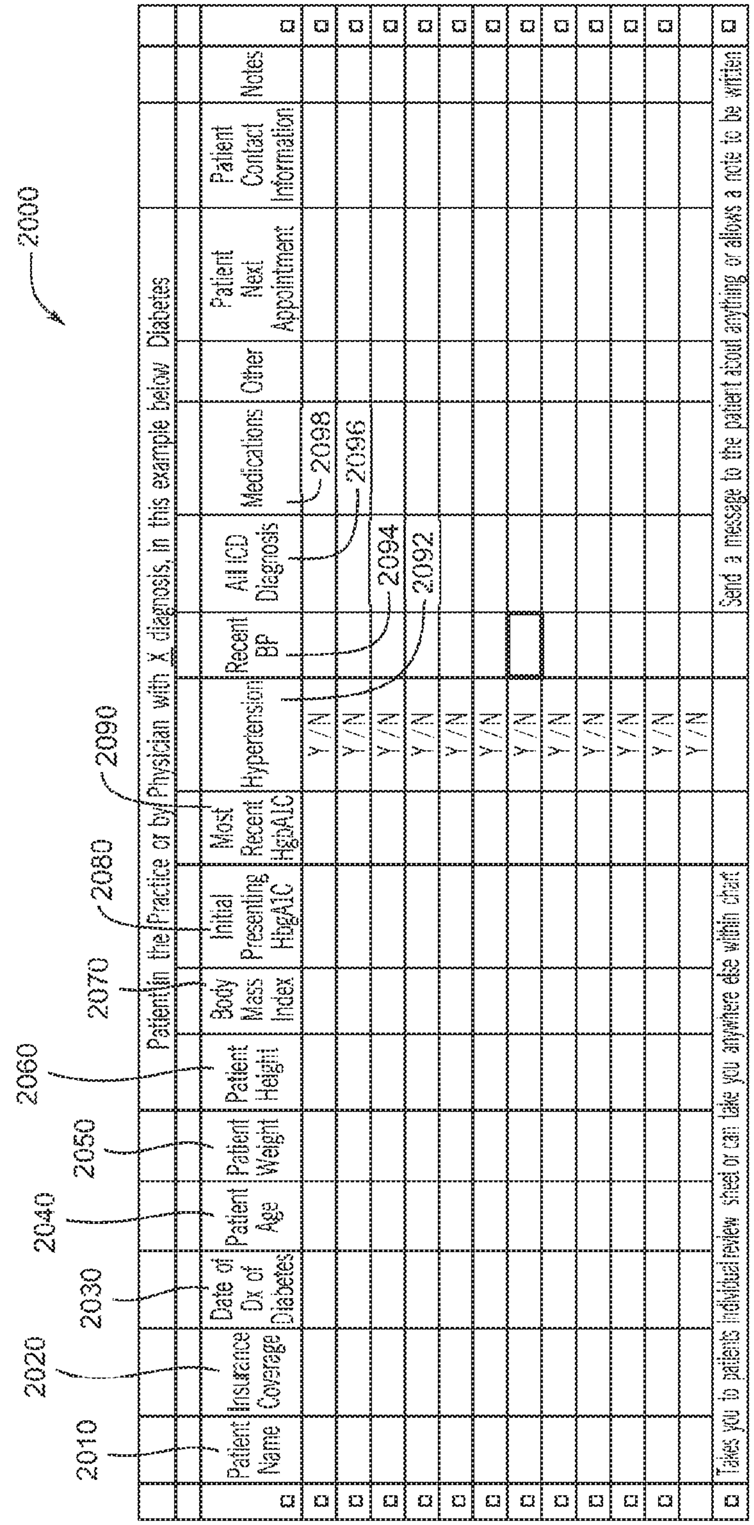
FIG. 12E illustrates a portion of a medical record dashboard for display as a function of patients with a specific disease ICD in accordance with the first embodiment such that many patients may be compared at the same time, which can be useful for clinical research or for tracking clinical outcomes.

Examples of the aforementioned examples of displayed data sorted and viewable by patient, disease time period, physician, etc., are shown in FIGS. 12D and 12E. For example, FIG. 12D illustrates a portion of a medical record dashboard 1900 for display as a function of disease or patient in accordance with some embodiments. Further, FIG. 12E illustrates a portion of a medical record dashboard 2000 for display as a function of patients or physician or disease state in accordance with some embodiments. In some embodiments, the medical record dashboards 1900, 2000 can be displayed overlaid on a previously viewed dashboard such as medical record dashboard 400, 1600. For example, in some embodiments, the medical record dashboards 1900, 2000 can be displayed in the command center visual display window 500. In other embodiments, the medical record dashboards 1900, 2000 can be displayed independently from the medical record dashboard 400, 1600, and the user can toggle a display of any of the medical record dashboards 400, 1600, 1900, 2000.

Referring to FIG. 12D, including providing a list of patients 1905, within column 1910, an entire day of patients listed by date or by insurance coverage can be provided or the list can comprise a single patient with multiple visits. For example, in some embodiments, within column 1920, an office visit and any items billed for a routine examination day and any other CPT codes billed that day can be displayed. Some specialties will have many CPT codes during an office visit (e.g. Ophthalmologists, whereas others (e.g., Gastroenterologists) may have four during an office visit. In some embodiments, column 1930 can include the procedures that a physician may perform, and are usually not on the same day as the exam (these are GI physicians examples). In some further embodiments, the column 1940 can include various important parameters that can be followed for a specific patient. Some embodiments include column 1950 that includes where a physician writes notes about patient care issues. In some embodiments, column 1960 can takes the user to that patient's personal EMR or review table and can also send a message to the patient. In some embodiments, the column 1970 can takes the physician to the charge payment history of the patient, and also a message can be sent to the billing department from this table. Columns can be reconfigured such that all patients with a particular insurance company that have a particular diagnosis on any given date or over a prolonged period of time can have tests and procedure results, as well as payments compared, allowing on one screen anyone to rapidly move through this visual display system to empower rapid comparison of results and potential payment anomalies for the same insurance company for the same CPT codes but perhaps different ICD9 or 10 diagnosis and to see if there is a mismatch (e.g., through the use of artificial intelligence systems discovering insurance payment irregularities). In some embodiments, columns 1920, 1930 can be colored 'black' when a claim is made, and can be colored 'green' if paid, and can be colored 'yellow' if a payment is pending, and can be colored 'red' if payment denied by one rendition, e.g., physician reconciliation report of messages sent individuals for follow up, and/or a report of all the message activity from any given day.

Referring to FIG. 12E, including example embodiments related to patients with diabetes, the display for patients 2010 can include a variety of medical, billing, and insurance related information. FIG. 12E illustrates a portion of a medical record dashboard for display as a function of patients with a specific disease ICD, such that many patients may be compared at the same time, which can be useful for clinical research or for tracking clinical outcomes. This embodiment tracks all patients in a practice or a subset of patients and can compare, for example, particular diagnostic test results in patients with a particular condition, the results of a particular medication, how all the patients did who received a particular intraocular lens into the eye, etc. The information is put into each individual patients table, but all patients with that issue can also be called up on a single table such at that illustrated in FIG. 12E. This feature can compile and compare all patients with a particular insurance company that have a particular diagnosis and compare tests and procedure results, as well as payments, allowing a doctor on one screen to rapidly see results, changes, patterns and payment anomalies. This feature also allows the extraction of patients with similar conditions for referrals and clinical research, batch generation for cross-referrals (e.g. optometry for an ophthalmologist), etc. This medical record dashboard 2000 can be displayed as shown, or can be sorted based on any of the data columns. For example, the patients 2010 can be shown including information displaying insurance coverage 2020, date of diagnosis of diabetes 2030, the patient's age 2040, the patient's weight 2050, the patient's height 2060, their body mass index 2070, their initial presenting HbgA1C 2080, their most recent HbgA1C 2090, their hypertension status 2092, their recent blood pressure 2094, their All ICD diagnosis 2096 and their current or past medications 2098. In some embodiments, the medical record dashboard 2000 can be reconfigured to shown patients 2010 sorted by any of the columns 2020, 2030, 2040, 2050, 2060, 2070, 2080, 2090, 2092, 2094, 2096, 2098.

Those skilled in the art will appreciate that a summary table of the type illustrated in FIG. 12E enables the physician to put into one dashboard 2000 everything the physician has done in a particular time frame, such as a day. For instance, a line of information for the information entered into the chart for every patient for today's visit, may be presented in the dashboard 2000. Whatever the technician records like the patient's vision and any diagnostic tests or laser procedures or injections in the eyes that were actually done that day, come up on the dashboard 2000 for interpretation. Dashboard 2000 thus shows on one page literally everything a physician will have done from laser surgeries to injections to photos is all summarized for inspection and confirmation. The physician may also refer to the notes section, such that physicians can write notes reminding themselves to do something like call the patient's family at night, check laboratories results, or remind doctors of items to do. Those type of messages can remain permanent or disappear if the physician chooses. The dashboard 2000 also serves as a double-check enabling the physician to check again (e.g. 48 hours later) when everything for that day should have already been billed or 60 days later when everything is paid and all dates queried can be compared. Also, the physician may call up all patient having a common insurance carrier to facilitate satisfaction payments from the insurance.

In some embodiments, the command center visual display system and method can enable a user to update a medical record dashboard 400 and/or the medical record dashboard 1600 to be mark personalized to the next treating physician or patient to follow progression changed outcomes. This will be used to access quality of care and prove effectiveness and results resolution, and can be used for negotiating with insurance carriers or for performance research. For example, anything can be tracked or personalized to the needs of the treating physician or patient to follow progression, changes, and outcomes. This can be used to assess quality of care and prove effectiveness and results of treatment. Quality outcome measures are important for all practices to start to follow as this improves patient care, and in the future, a physician's financial compensation from insurance companies, or any penalization will be determined based on the quality of care metric. Further, physicians who participate in clinical research must follow defined parameters over time as they learn whether a particular drug, or device, or other item being investigated actually improve changes or worsens particular parameters. As described earlier, in some embodiments, the information that is auto-populated can include patient outcome summaries. In some embodiments, the command center visual display system and method can process patient outcomes and display an analysis of patient outcomes based on patient information from treatment summaries, and/or diagnosis summaries, and/or patient feedback summaries, and/or other physician summaries or treatments. The patient outcomes can include or comprise physician quality reporting system (PQRS) quality measures, and calculated or reported patient outcomes can include or comprise PQRS measures codes.

By way of example in FIG. 4C, vision is followed in column 1100, and in the other column 1200, many different parameters that may change over time can be added. For example, as described earlier with respect to participation in clinical research studies, other factors followed such as central macular thickness ("CMT"), or ischemic index ("ISI") (% and a scan in millimeters) can be followed. Therefore, every time the patient comes in to be examined, the table can serve the multi-purpose of treating the patient, and for inputting research data from the office visit right into the table. This can then auto-populate into another portion of the EMR or derive these numerical values and place them into the research Excel spreadsheet. Also, it could go the other way, where if the Excel research spreadsheet can also have the data inputted into the review table.

In some embodiments, the command center visual display system and method can enable a date alert or self-destruction of any information or data entered or auto-populated in the medical record dashboard 400 and/or the medical record dashboard 1600. For example, in some embodiments, any message, or note, or summary, or any medical data can include a date alert and/or a self-destruct function that can instruct the command center visual display system and method to remove and/or delete information from the medical record dashboard 400 and/or the medical record dashboard 1600. In other embodiments, the historical date and/or an alert or warning can be provided with any auto-populated or user-summoned information to assist the user with an assignment of relevancy to any data being reviewed prior to, during, or after a patient visit or examination. In some embodiments, this feature can optimize the standard of care being delivered by the user. For instance, this feature can help monitor preferred practice patterns or serve as a reminder on information needed for clinical review.

Within the rows and columns of data displayed, the flowsheet view prioritizes relevant data, while masking less important values. This functionality allows the physician to focus on the most important data pertinent to the current use case, e.g., with a patient that has a certain diagnosis, several preferred diagnostic test results and data are germane. The display is also inclusive of data that originates from additional physicians/EHR visits deemed important which is rendered in chronological order. Utilizing Artificial Intelligence (AI), Natural Language Processing (NLP), and/or conventional business logic, the tool programmatically filters out unnecessary information and queries for display additional information which may consist of additional rows displaying external physician encounters, diagnostic test results, etc.

Flowsheet Configuration may be defined based on key events, results, date/time, and/or logical parameters which can include, but are not limited to:

Diagnoses
Medication Start/End Dates
Allergy Start/End Dates
Billing History
Demographic Data
Observations/Plans
Life Events Format and display of rendered data will make maximum usage of space by shrinking less relevant rows, auto-sizing of columns, and automatically collapsing less relevant data. The intention of this functionality is to provide the most efficient view of relevant data, while not overloading the provider with information not germane to the current Flowsheet Configuration. An example would be if a patient has glaucoma there are specific columns that are highly important to monitoring the chronic condition but some which have no relevance. In this example, the patient that has a diagnosis of glaucoma will have Intra-Ocular Pressure (IOP), Glaucoma medications, etc. displayed prominently while the other less relevant columns are masked. It is important to note that the masked columns can be expanded so that, in each case, the doctor may still want to view those data.

Involving several layers of business logic, correlated to predefined parameters, all data is parsed for relevance. Rules and logic compile a final dataset for the interface, while system or user-defined flow/sheet templates determine actual rows and columns for display. A Flowsheet Configuration Object is used to store configuration settings. The Flowsheet Configuration Object is a JSON object containing definitions and constraints outlining what parts of dataset should render on-screen. All configurations are then outputted to the Flowsheet Configuration Object.

The Flowsheet Editor Interface provides a method by which a provider can configure the formatting and display of Flowsheet data. This simplified interface editor embodies "What You See Is What You Get" (WYSIWYG) methodology, with drag and drop of Flowsheet elements. Upon completion of a Flowsheet Template, associated parameters must be defined. The Flowsheet Editor allows the user to define how columns and rows will display. While providers have the ability to only view predefined data, filtered data may trigger a rule to display in lieu of predefined filters. Preconditioned upon required contract/agreement between providers, data may display from multiple, disparate sources to display continuity of care.

The Flowsheet Editor Interface also allows the end-user to configure the way that summary rows are presented within the flowsheet. A provider may choose to discard certain edge-cases from the summary calculation, take the highest and lowest values, take an average, or some other logical calculation to determine how the individual columns summary row data presents itself.

In addition to allowing changes which reflect the display of the data, it is possible for the end-user to program the alerts and auto-tasks which are sent as a result of the rule threshold being exceeded. For example, if a provider determines that a new alert rule must be created, they are able to select the column, or columns, apply logical rules to the column or columns being analyzed, and set the task associated with rule which will be sent to the user-defined staff member or groups of staff members. As another example, a provider may choose to add a new alert for those patients which have a diagnosis of Glaucoma and have not had a required diagnostic test, a Visual Field, in 365 days. The provider is then able to set a task that will be sent to front-desk staff to schedule the diagnostic test will automatically be sent when the Auto Task Container processes both the system and user-defined auto task and alerts. The editor interface also allows for the end-user to configure the way the alert displays in the flowsheet. For example, the end-user can set the display of the alert to any of the following, but not limited to, headers, within the rows and columns of the flowsheet, on the patient demographic panel, etc.

Pre-defined display rules may override a user-defined flowsheet configuration when the rule is prioritized for patient safety reasons. These overrides will display the visit in question in a prominent color. An example of this would be if a patient had recently found out that she was pregnant, it becomes very important that she does not have certain diagnostic tests as they can endanger the viability/health of the fetus. For example, a Fluorescein Angiogram should not be performed on a patient to monitor the progress of a patient if she is pregnant. Due to the potential life altering consequences, the system, through the use of AI, is smart enough to override the flowsheet template, and display the visit from the OBGYN, where the patient was confirmed to be pregnant.

With regard to Co-Management and/or Multi-Specialty Practices, external provider data may be included subject to necessary contracts/agreements. When this is the case, external provider rows may be collapsed, truncated, or expanded dependent upon system or user preference. The data will only be available in the case of explicit acceptance of liability for viewing patient health information.

Figure 13A:
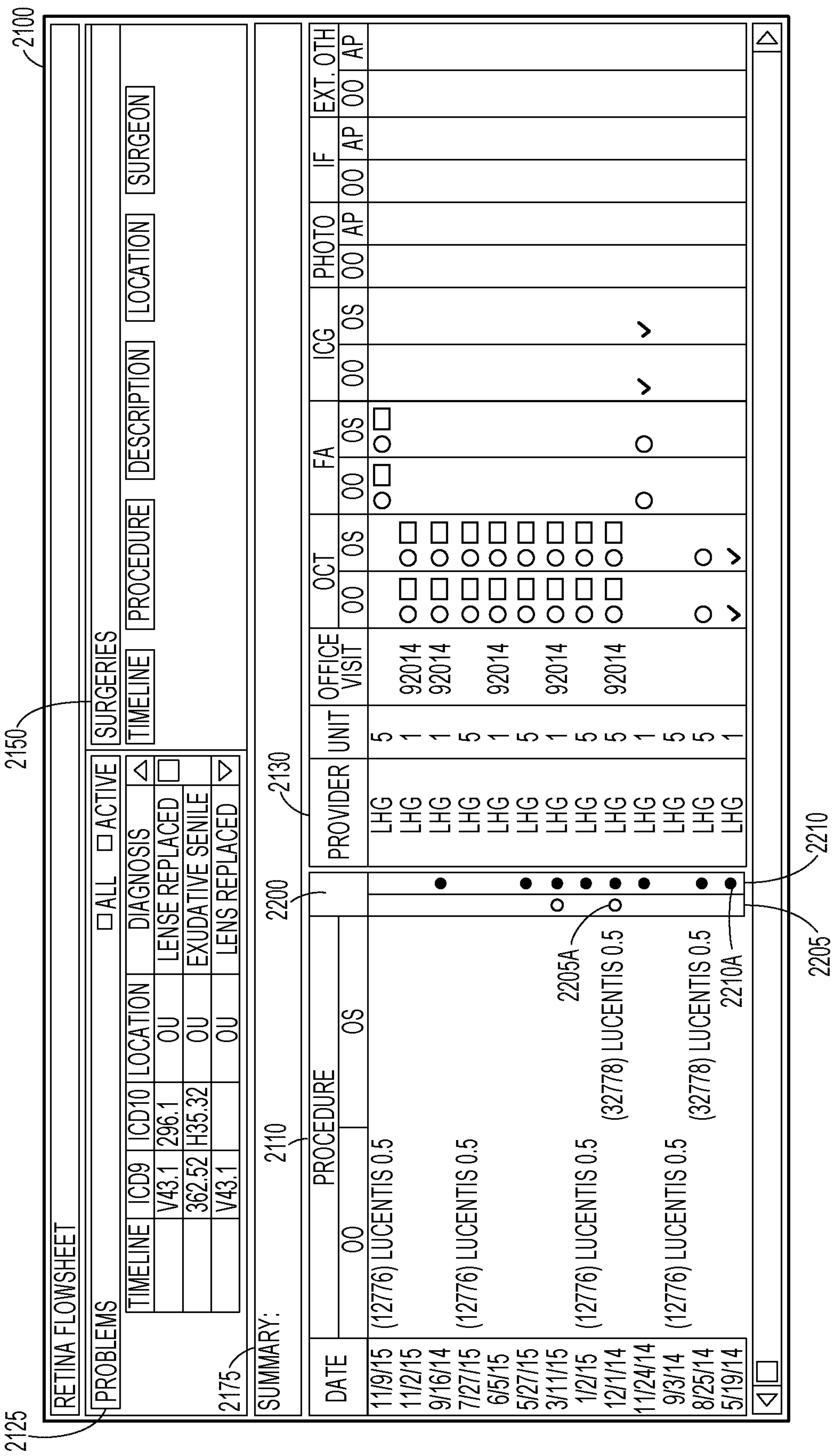
FIG. 13A illustrates a medical record dashboard in accordance with the first embodiment.

In some embodiments of the inventor, the command center visual display system and method also can enable a user to access a detailed ledger comprising financial information related to one or more procedures. In some embodiments, the ledger can be accessed from a medical record dashboard. Further, in some embodiments, the dashboard can include at least one visual indication of a payment for services provided, where detailed information of the charges, payments, write-offs, adjustments, and balances can be accessed and displayed. For example, FIG. 13A illustrates a medical record dashboard 2100 in accordance with some embodiments. In some embodiments, the medical record dashboard 400 illustrated in FIG. 4A can comprise, include, or be replaced by the medical record dashboard 2100. In some embodiments, the medical record dashboard 2100 can be accessed as described for the medical record dashboard selection window of FIG. 3. In some embodiments, the medical record dashboard 400 can be displayed by the user following the user's selection of at least one medical record dashboard from the medical record dashboard selection window 300. For example, in some embodiments, the user can select "Retina Flowsheet" 305 to access and/or launch the medical record dashboard 2100.

In some embodiments, the command center visual display system and method display a medical record dashboard 2100 including a display of data from one or more medical records, and/or track medical procedures and services based on claims made or billing signed off by a physician for one or more delivered medical procedures or services. Some embodiments include a command center visual display system and method that can dynamically link to various external databases comprising patient information that can be displayed in the medical record dashboard 2100. For example, in some embodiments, the command center visual display system and method can function as a portal to patient information prepared by the user or patient information from other sources. Further, in some embodiments, the medical record dashboard 2100 can be auto-populated as a function of claims made or billing signed off by a physician. In this instance, any data displayed within the medical record dashboard 2100 is derived from one or more claim records that have been billed for one or more procedures or services have previously been provided to the patient. In some other embodiments, auto-population can be enabled in both directions interacting as a switchboard between the entire EMR and the medical record dashboard 2100 along with what is added to any window, sub-window, column or entry in the medical record dashboard 2100 being automatically added to the appropriate part of the chart for documentation. In some embodiments, the medical record dashboard 2100 can display information related to medical procedures or services in relation to retinal eye care of a patient. In other embodiments, the medical record dashboard 400 can display information related to medical procedures or services in relation to any kind of medical care of a patient.

In some embodiments, the medical record dashboard 2100 can display various windows and sub-windows based on a user preference and/or current or previous user interaction with the medical record dashboard 2100. For example, in some embodiments, the medical record dashboard 2100 can display a problems window 2125 and/or a surgeries window 2150 where information related to a patient's medical problems and surgeries can be displayed.

In some embodiments, the medical record dashboard 2100 can display information including components where there is a summary of the patient's problem list that a user can input patient information and constantly update and change. Further, this information can be auto-populated with the touch of a button into a designated location such as the current plan documenting the patient's current visit (thus aiding documentation for the current visit). Further, whatever is important for a user to input into the day's visits for documentation can be initially inputted in the table, and then permanently into the day's patient visits. Further, the summary section of the medical record dashboard 2100 can be constantly fluid, and can be changed at every visit rather than being written to an unchangeable document or file (e.g., such as a PDF). For example, in some further embodiments, the medical record dashboard 2100 can include a summary window 1670 enabling a user to view and edit summary information related to the patient, any details of care provided to the patient, and/or and any medical diagnosis information prepared by a medical practitioner. Further, the medical record dashboard 2100 can also display detailed information related to any medical procedures or services provided to the patient, including procedures or services that are auto-populated by claims made, or billings or payments including billing signed off by a physician as detailed above. All of the features of the medical record dashboard 400 as described earlier can be provided in the medical record dashboard 2100.

Some additional features include the dashboard 2100 displaying at least one visual indication of a payment for services provided on the dashboard 2100. Further, the user can be provided with access to a detailed ledger comprising financial information related to one or more procedures. For example, in some embodiments, the dashboard can comprise a payment indicator column 2200 including one or more indicator and/or access icons. For example, in some embodiments, the payment indicator column 2200 can comprise a column 2205_a_ that can be populated with one or more indicator icons. In other embodiments, the column 2205_b_ can be provided with one or more indicator or access icons. In some embodiments, the one or more indicator or access icons can comprise icons of color such as yellow or green.

The payment indicator column 2200 can be positioned anywhere on the dashboard 2100. In the example embodiments of FIG. 13A, the payment indicator column 2200 can be positioned between the procedure column 2110 illustrating or providing access to information detailing one or more procedures performed on the patient, and information related to the medical provider, provider column 2130, that can display the location where the procedure was performed, and office visit information.

Figure 13B:
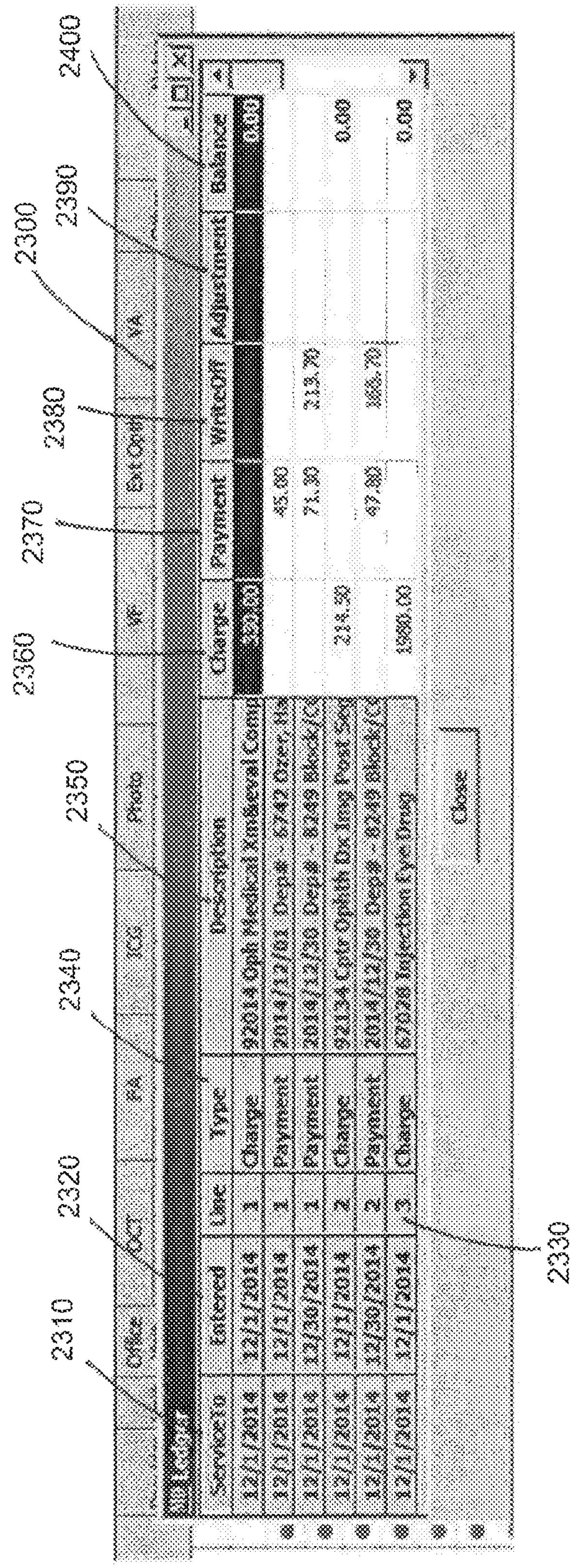
FIG. 13B illustrates a ledger window accessible from the medical record dashboard of FIG. 13A in accordance with the first embodiment.

In some embodiments, one or more of the icons of the payment indicator column 2200 can be accessed by the user to initiate the command center visual display system and method displaying more detailed financial information. An example embodiments is illustrated in FIG. 13B illustrating a ledger window 2300 accessible from the medical record dashboard 2100 of FIG. 13A. In some embodiments, the command center visual display system and method can display the ledger window 2300 overlaid onto the medical record dashboard 2100. In other embodiments, the ledger window 2300 can be displayed in place of the medical record dashboard 2100. In other embodiments, the ledger window 2300 can be displayed with the medical record dashboard 2100.

In some embodiments, the ledger window 2300 can include information processed by the command center visual display system and method including information related to the date of procedure, description of the procedure, dates entered, a charge type, etc. For example, in some embodiments, ledger window 2300 can include the service to column 2310, entered column 2320, line column 2330, type column 2340, and description column 2350. Further, in some embodiments, the ledger window 2300 can include information related to payments and billing. For example, in some embodiments, the ledger window 2300 can include a display of a charge column 2360, payment column 2370, write-off column 2380, adjustment column 2390, and a balance column 2400. In some embodiments, the user can close the ledger window 2300 and return to the medical record dashboard 2100 at any time. In other embodiments, more than one ledger window 2300 can be displayed based on selections made by the user in the medical record dashboard 2100.

Figure 14:
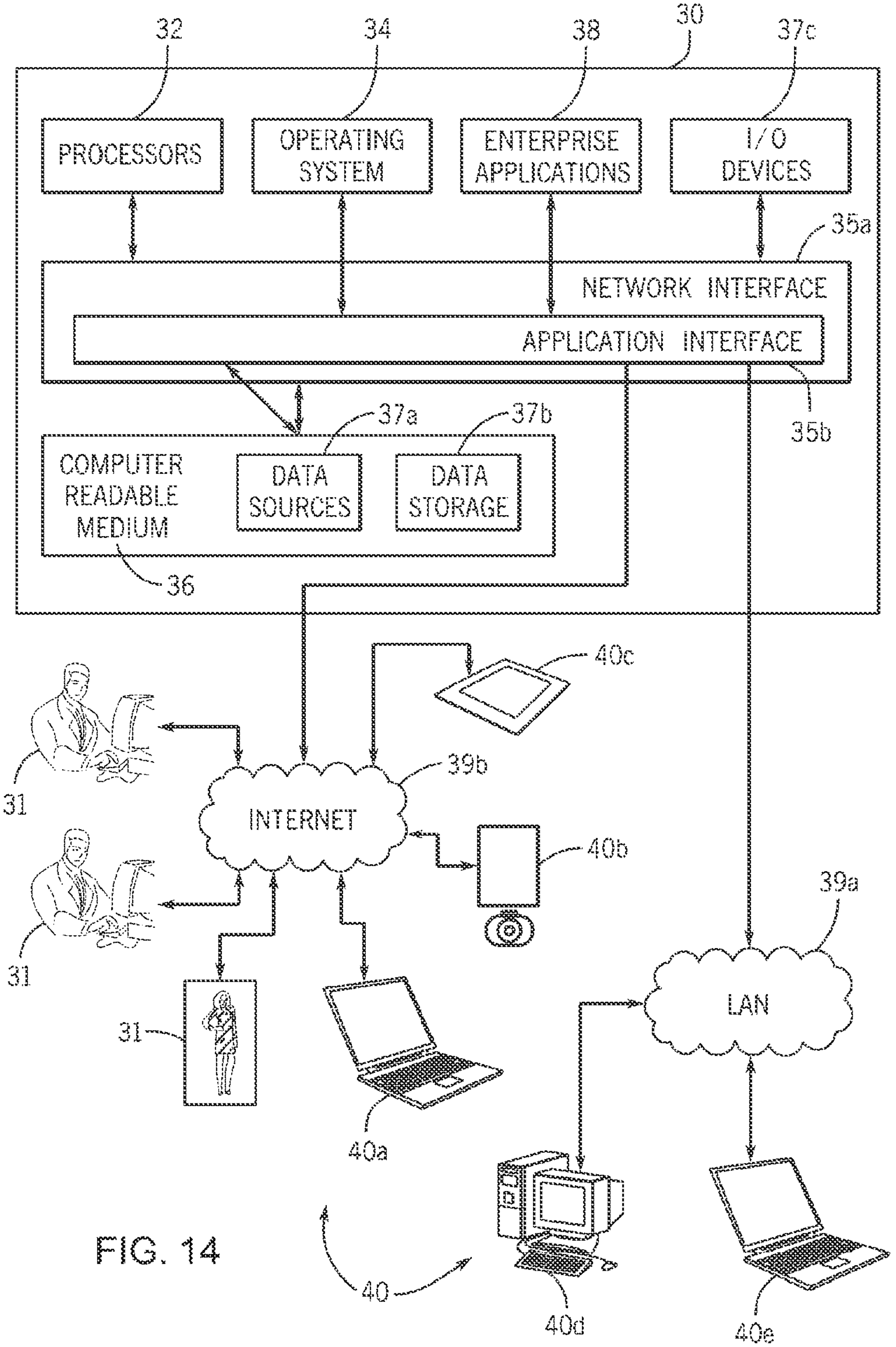
FIG. 14 illustrates a computer server system configured for operating and processing components of the command center visual display system and method in accordance with the first embodiment.

FIG. 14 illustrates a computer system 30 configured for operating and processing components of the command center visual display system and method in accordance with some embodiments. In some embodiments, the computer system 30 can process one or more software modules of the aforementioned command center visual display system and method and display information related to medical services within at least one graphical user interface. Further, in some embodiments, using the computer system 30, the command center visual display system and method can manage the organization of data and data flow between the various components of the command center visual display system and method. For example, in some embodiments, the computer system 30 can be configured to process and display the medical record dashboard 400 and/or the medical record dashboard 1600. Further, in some embodiments, the computer system 30 can be configured to process and display auto-populated data within any portion of the medical record dashboards 400, 1600, including, but not limited to the command center visual display window 500 and/or the command center visual display window 1700.

In some embodiments, the system 30 can include at least one computing device, including one or more processors 32. Some processors 32 can include processors 32 residing in one or more conventional server platforms. The system 30 can include a network interface 35*a* and an application interface 35*b* coupled to at least one processors 32 capable of running at least one operating system 34. Further, the system 30 can include a network interface 35*a* and an application interface 35*b* coupled to at least one processor 32 capable of running one or more of the software modules (e.g., enterprise applications 38). Some embodiments also relate to a device or an apparatus for performing these operations. The apparatus can be specially constructed for the required purpose, such as a special purpose computer. When defined as a special purpose computer, the computer can also perform other processing, program execution or routines that are not part of the special purpose, while still being capable of operating for the special purpose. Alternatively, the operations can be processed by a general purpose computer selectively activated or configured by one or more computer programs stored in the computer memory, cache, or obtained over a network. When data are obtained over a network the data can be processed by other computers on the network, e.g. a cloud of computing resources.

With the above embodiments in mind, it should be understood that the tool described herein can employ various computer-implemented operations involving command center visual display data stores in computer systems. Moreover, the above-described databases and models can store analytical models and other data on computer-readable storage media within the system 30 and on computer-readable storage media coupled to the system 30. In addition, the above-described applications of the command center visual display system can be stored on computer-readable storage media within the system 30 and on computer-readable storage media coupled to the system 30. These operations are those requiring physical manipulation of physical quantities. Usually, though not necessarily, these quantities take the form of electrical, electromagnetic, or magnetic signals, optical or magneto-optical form capable of being stored, transferred, combined, compared and otherwise manipulated.

Some embodiments include the system 30 comprising at least one computer readable medium 36 coupled to at least one data storage device 37*b*, and/or at least one data source 37*a*, and/or at least one input/output device 37*c*. In some embodiments, the command center visual display system can also be embodied as computer readable code on a computer readable medium 36. The computer readable medium 36 can be any data storage device excluding a modulated electrical signal that can store data, which can thereafter be read by a computer system (such as the system 30). Examples of the computer readable medium 36 can include hard drives, network attached storage (NAS), read-only memory, random-access memory, FLASH based memory, CD-ROMs, CD-Rs, CD-RWs, DVDs, magnetic tapes, other optical and non-optical data storage devices, or any other physical or material medium which can be used to tangibly store the desired information or data or instructions and which can be accessed by a computer or processor (including processors 32).

In some embodiments, the computer readable medium 36 can also be distributed over a conventional computer network via the network interface 35*a* so that the command center visual display system embodied by the computer readable code can be stored and executed in a distributed fashion. For example, in some embodiments, one or more components of the system 30 can be tethered to send and/or receive data through a local area network ("LAN") 39*a*. In some further embodiments, one or more components of the system 30 can be untethered to send or receive data through an internet 39*b* (e.g., a wireless internet). In some embodiments, at least one software application 38 running on one or more processors 32 can be configured to be coupled for communication over a network 39*a*, 39*b*. In some embodiments, one or more components of the network 39*a*, 39*b* can include one or more resources for data storage, including any other form of computer readable media beyond the media 36 for storing information and including any form of computer readable media for communicating information from one electronic device to another electronic device.

In some embodiments, the network 39*a*, 39*b* can include wide area networks ("WAN"), direct connections (e.g., through a universal serial bus port) or other forms of computer-readable media 36, or any combination thereof.

Further, in some embodiments, one or more components of the network 39*a*, 39*b* can include a number of client devices which can be personal computers 40 including for example desktop computers 40*d*, laptop computers 40*a*, 40*e*, digital assistants and/or personal digital assistants (shown as 40*c*), cellular phones or mobile phones or smart phones (shown as 40*b*), or smart watch, pagers, digital tablets, internet appliances, and other processor-based devices. In general, a client device can be any type of external or internal devices such as a mouse, a CD-ROM, DVD, a keyboard, a display, or other input or output devices 37*c*. In some embodiments the display can be a heads-up or virtual display, such as a HoloLens available from Microsoft, that can only be seen by the user. In some embodiments, various other forms of computer-readable media 36 can transmit or carry instructions to a computer 40, including a router, private or public network, or other transmission device or channel, both wired and wireless. The software modules 38 can be configured to send and receive data from a database (e.g., from a computer readable medium 36 including data sources 37*a* and data storage 37*b* that can comprise a database), and data can be received by the software modules 38 from at least one other source. For example, as described earlier, in some embodiments, using the system 30, the command center visual display system and method can be configured to receive one or more CCD from one or more medical providers for display to the user 31. In some embodiments, the command center visual display system and method can be configured to receive HL7 messages and or use Application Programming Interfaces (APIs) to send and receive data. Further, in some embodiments, patient data can be retrieved from one or more master patient index databases (e.g. a master patient database managed by a government entity and/or a third party provider such as insurance company or collective of insurance companies). In some further embodiments, data can be retrieved from the national register of drugs and pharmaceuticals. In some further embodiments, data can be retrieved from health information exchanges.

In some embodiments, at least one of the software modules 38 can be configured within the system 30 to output data to at least one user 31 via at least one digital display (e.g., to a computer 40 comprising a digital display). In some embodiments, the system 30 as described can enable one or more users 31 to receive, analyze, input, modify, create and send data to and from the system 30, including to and from one or more enterprise applications 38 running on the system 30. Some embodiments include at least one user 31 coupled to a computer 40 accessing one or more modules of the command center visual display system including at least one enterprise applications 38 via a stationary I/O device 37*c* through a LAN 39*a* or via a wireless connection. In some other embodiments, the system 30 can enable at least one user 31 (through computer 40) accessing enterprise applications 38 via a stationary or mobile I/O device 37*c* through an internet 39*a*.

In some embodiments, the software modules 38 can include a server-based software platform that can include medical services tracking software modules suitable for hosting at least one user 31 account and at least one patient account or record. Further, some embodiments include the software modules 38 that can include at least one server-based software platform that can include medical services tracking software modules suitable for hosting at least at least one patient account or record. In some embodiments, using the system 30, the command center visual display system and method can manage multiple user accounts and/or multiple patient accounts. In some embodiments, the software modules 38 can include a server-based software platform that can include medical services tracking software modules suitable for hosting a plurality of user accounts accessible by multiple medical practitioners (e.g., physicians, surgeons, optometrists, ophthalmologists, podiatrists, dentists, etc.) In some embodiments, patient accounts can be accessible by the patient's medical practitioner and not shared with other medical practitioners holding one or more user accounts within the command center visual display system and method. In some further embodiments, one or more patient accounts can be accessible and shared by a user 31 associated with the patient account. For example, in some embodiments, a user 31 can grant access to at least one other user of the command center visual display system and method. In some embodiments, shared access can be at least partially restricted. For example, in some embodiments, shared access can be restricted to viewing at least a portion of the shared patient's account or record.

Second Embodiment of Data Command Center

Figure 15:
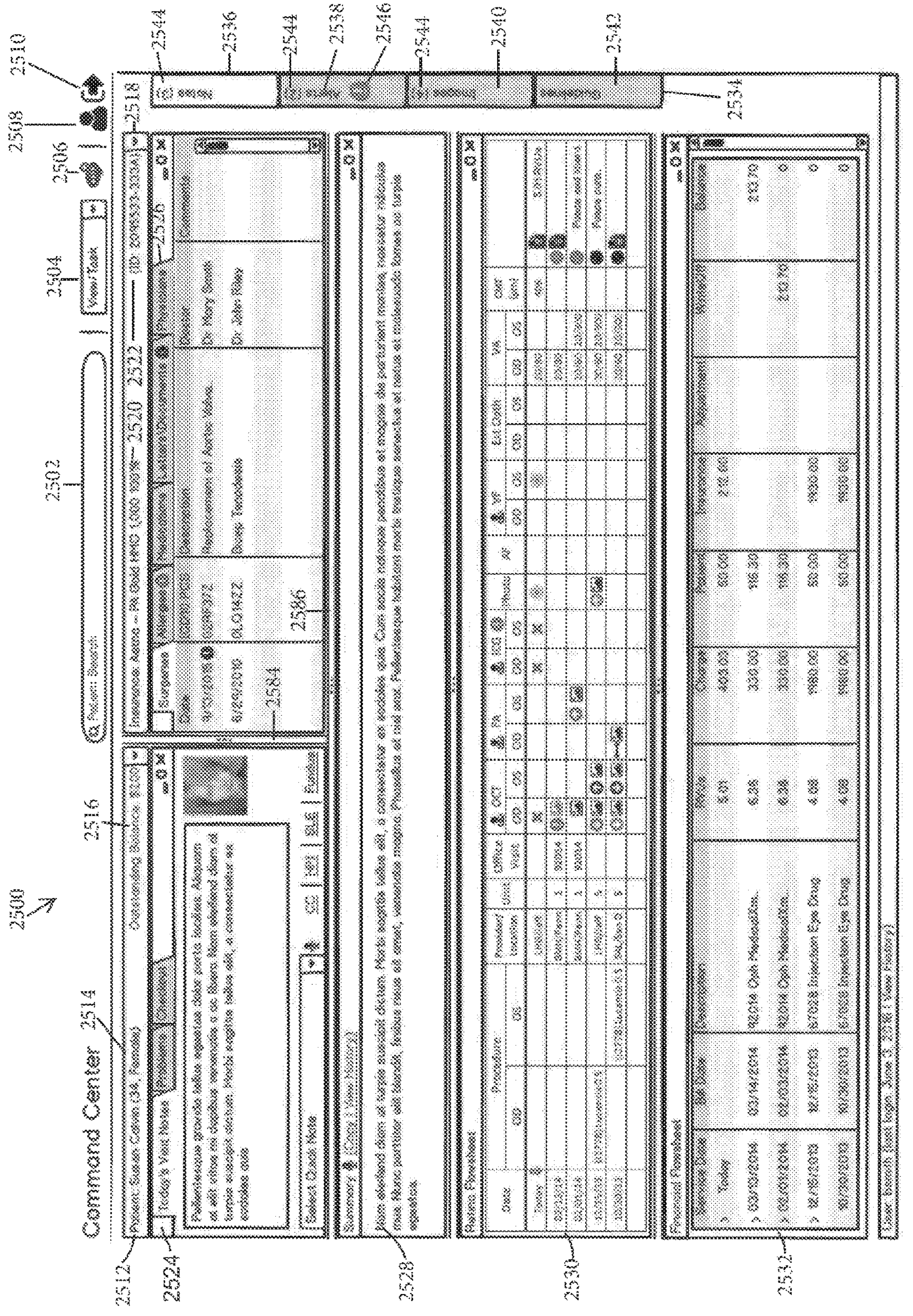
FIG. 15 illustrates an exemplary embodiment of a Data Command Center for use with an EMR system customized for an Ophthalmology Retina practice in accordance with a second embodiment.

FIG. 15 illustrates another embodiment of a Data Command Center (CC) 2500 implemented as a data interface to a medical record system useful for deploying or launching a second set of embodiments. The CC 2500 in the exemplary embodiment is designed to interact with a conventional EMR system although, as noted above, the CC 2500 may be used with other large data systems to present data to users in a meaningful way. In addition, the exemplary embodiment illustrates a CC 2500 for implementation in an Ophthalmology practice. Those skilled in the art will appreciate that the interface may be readily configured for other medical specialties. Indeed, one of the key features of the CC 2500 described herein is its flexibility to display data from multiple data sources in multiple different panels on a single interface. In the exemplary embodiment, the CC 2500 provides a comprehensive overview of the patient's clinical and financial history as well as providing a means to quickly order tests while retaining the ability to see previous medical history. Clinical and insurance guidelines as well as preferred practices are quickly accessible based on the patient's conditions, medications and procedures so that the physician may readily provide optimal care and be compliant with medical and billing requirements. The physician thus becomes a part of revenue cycle management for each patient in the physician's practice.

It will be appreciated by those skilled in the art that specific features of the first embodiment described above may also be included in the second embodiment, and vice-versa, and the descriptions of the features of the first embodiment above are incorporated into the following description by reference. For example, like the first embodiment described above, the Data Command Center 2500 described with respect to FIGS. 15-56 may incorporate self-deleting staff messages that are presented to the Command Center 2500. For example, a staff person can send a message about a patient to the physician that appears in a display window in the Command Center 2500 with a message such as "the patient has been waiting over an hour and is upset" or the "patient has previously filed a malpractice complaint" that do not become part of the patient's medical record. The message may be programmed to be deleted once the patient's visit is billed.

FIG. 15 illustrates an exemplary embodiment of a Data Command Center (CC) 2500 for use with an EMR system customized for an Ophthalmology practice. As illustrated, across the top of the page the user has the ability to search for patients at 2502, select different views of the data at 2504, add sticky notes at 2506, access user information at 2508, and logout at 2510. Immediately below that on the upper left-hand side of the CC 2500 is the Patient Information Bar 2512, which contains the patient's identifying information 2514 so the user knows they are looking at the correct patient record. The Patient Information Bar 2512 also notifies the user of patient's outstanding balance 2516. To the right of the Patient Information Bar 2512 is the Patient Insurance Bar 2518, which provides the patient's insurance information 2520, including the ID number 2522 for the patient's primary insurance. Below the Patient Information Bar 2512 is a collection of tabs 2524 displaying different sets of information about the selected patient. A different collection of tabs 2526 is found underneath the Patient Insurance Bar 2518. Under tabs 2524 is the Summary panel 2528 where the user can enter notes about the patient (e.g. patient did not show up for missed appointments). The next section, the Retina Flowsheet 2530, is an encounter driven panel that summarizes key clinical and financial information in chronological or reverse chronological order at a glance, allows the user to order new Procedures and Imaging tests, and provides assistance complying with insurance regulations, as will be described in more detail below. Below the Retina Flowsheet 2530 is the Financial Flowsheet 2532 providing a summary of the financial information related to the patient and this is adapted to provide the user with the ability to drill down into individual transactions. On the right side of the CC 2500 are a series of vertical tabs 2534 that when individually clicked slide out to provide more information to the user. The Notes Tab 2536 expands to display patient notes, while the Alerts Tab 2538 expands to display patient alerts (e.g. patient's chart was requested by insurance company or sent for a second opinion). The Images Tab 2540 expands to display images for the patient and the Guidelines Tab 2542 expands to display clinical practice and insurance guidelines along with preferred practice patterns where applicable. On each tab, displayed next to the tab title is the count of the new items 2544 since the last time the user accessed the patient record. Once the tab is expanded, the new count will be removed because the user has seen the information. If important or critical data exists within the tab, a special alert icon 2546 is displayed on the tab. Once viewed, the alert icon 2546 is removed. As will become apparent from the following description, the layout of the CC 2500 permits access by the user to all of the relevant information within one click of the mouse and without having to steer to other screens that would take the user away from the CC 2500. For example, the information is either available in a display window, behind a tab, or available via a pop-up window; accordingly, the user does not have to leave the display screen to access the information.

Figure 16:
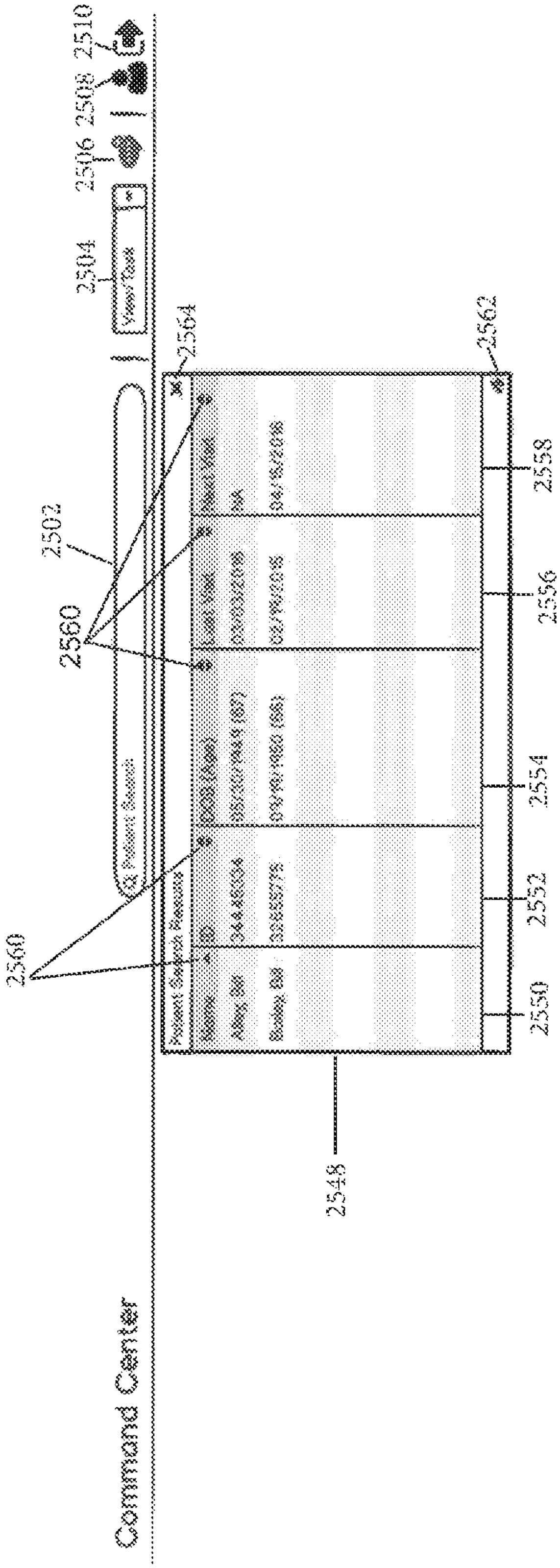
FIG. 16 illustrates the search results of a patient search input into the patient search field in accordance with the second embodiment.

FIG. 16 illustrates the search results 2548 of a patient search input into the patient search field 2502. To search for a patient, the user types in the Patient Search field 2502. After the user types the third character in the field, the search results 2548 appear matching the criteria. As the user enters additional characters, the search results are refreshed. The search criteria looks for any patients where the sequential string of characters entered matches the same sequential string of characters in either the patient's first or last name. For example, entering 'sam' matches Sammy Smith, Isamra Turek, Bill Samson, Michelle Bosam, but not Silas Amhearst. In an exemplary embodiment, the results 2548 display the following fields: Name 2550 (Last, First), Patient ID 2552, Date of Birth and age 2554, Last Visit (Date) 2556, and Next Visit (Date) 2558 if scheduled. The results are sorted alphabetically by last name, then first name, followed by date of birth, but the user can change the search order by clicking the sort icons 2560 at the top of each column. This sorting capability is available through the Command Center 2500 when viewing lists. The user may select a patient by clicking on the row in the results list 2548. When a patient is selected, the results panel 2548 closes and the patient record is retrieved. The user may control the size of the panel by clicking and holding the icon 2562 in the bottom right of the panel 2548. The user can close the results panel 2548 by clicking the close icon 2564.

Figure 17:
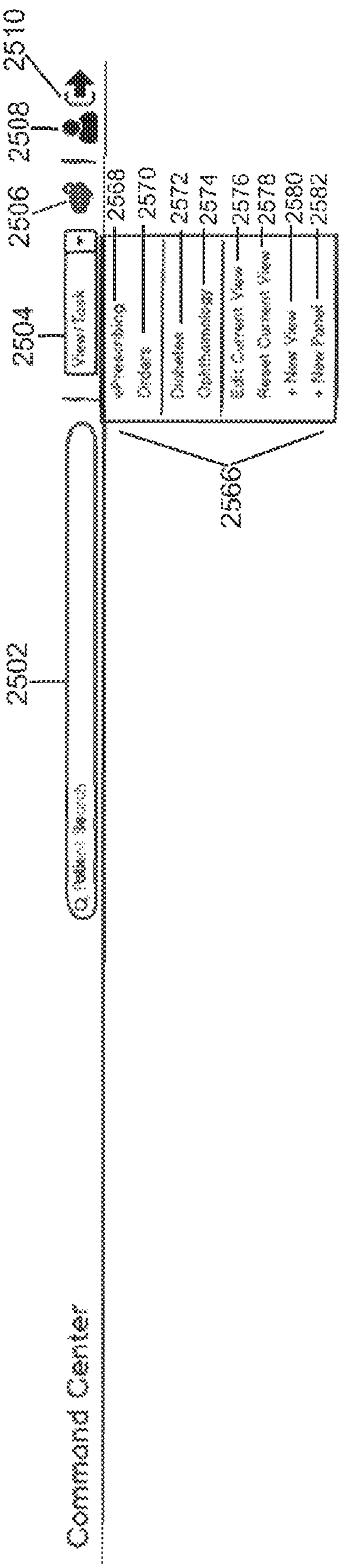
FIG. 17 illustrates a user control panel that displays views for selection by the user in accordance with the second embodiment.

A key feature of the Command Center 2500 is that it allows the user to control the layout of the screen and to create different views or layouts of the information based on their needs. FIG. 17 illustrates a user View control panel 2566 that displays views for selection by the user. As illustrated, the user may select one of several Views 2568-2574. Views ePrescribing 2568 and Orders 2570 are examples of task based views, while Diabetes 2572 and Ophthalmology 2574 are examples of condition or specialty specific views. In an exemplary embodiment, the system has several pre-configured views but more can be added over time by deploying new versions of the system or by user modification. The user may edit the Current View 2576, Reset the Current View 2578 to its default configuration, create a new View 2580, or create a new Panel 2582. If the user selects a new view from options 2568-2574, the screen layout is changed to reflect the selected view for the current patient. Referring back to FIG. 15, it should be noted the dimensions of the different panels can be resized by changing the location of the vertical sliders 2584 and horizontal sliders 2586. This allows the user to control how much real estate (space/area) on the screen is used for each panel. As the user adjusts the sliders 2584 and 2586, the dimensions are remembered so when the user returns to the view at a later time the system remembers the dimensions. The user also can reset the view to its default dimensions by clicking the Reset Current View 2578 option in the view control panel 2566. The entire view also resizes based on the dimensions of the user's monitor and the size of the browser displaying the CC 2500.

Figure 18:
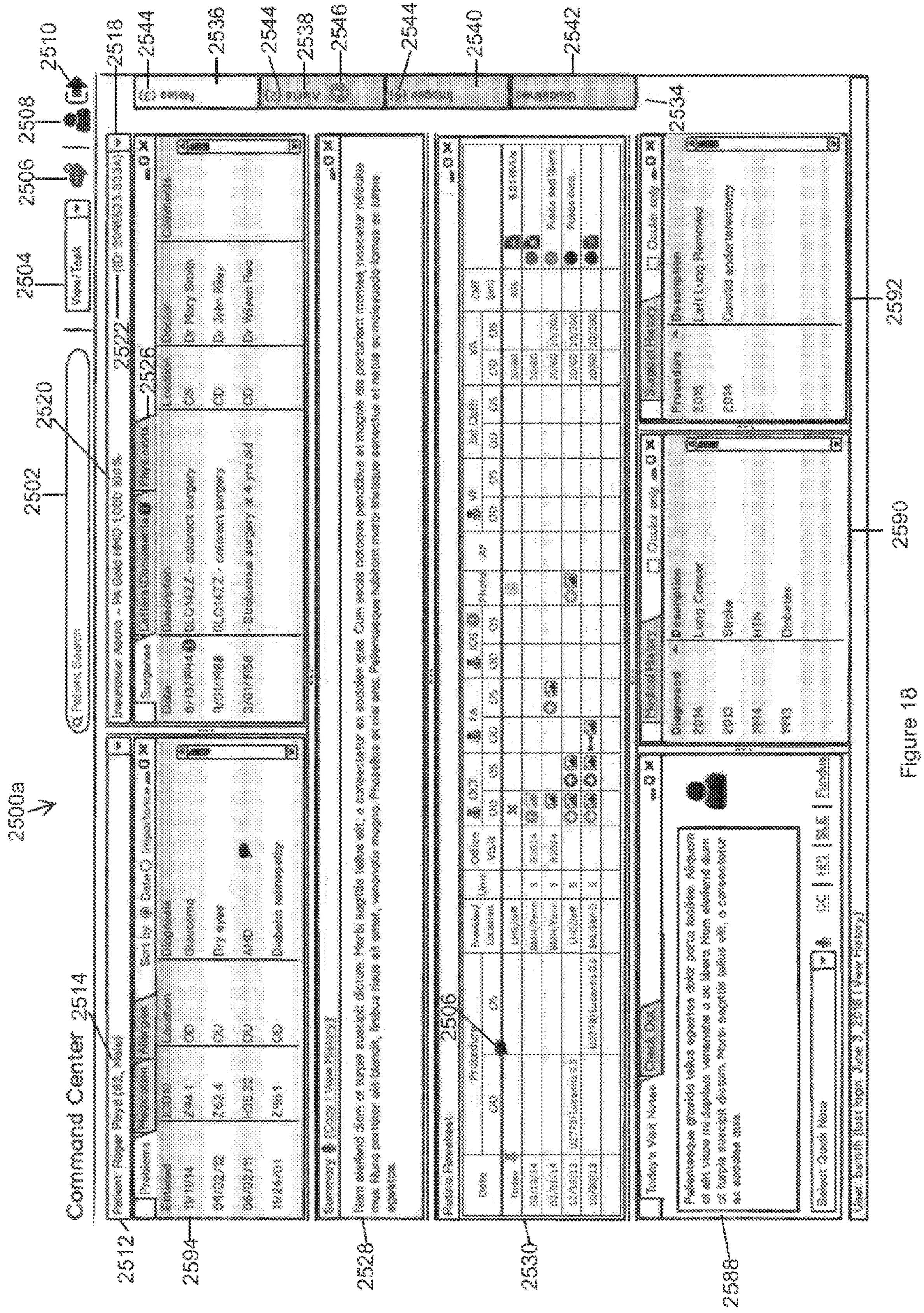
FIG. 18 is an example of a new view created by the user for their personal use in accordance with the second embodiment.

FIG. 18 is an example of a new View 2500*a* created by the user for their personal use. In this View 2500*a*, the financial flowsheet 2532 of FIG. 1 is replaced by panel 2588 for receiving today's visit notes (moved from the top left-hand side of CC 2500 in FIG. 15), a panel 2590 for illustrating the patient's medical history, and a panel 2592 for illustrating the patient's surgical history. Also, a medication panel 2594 is inserted in place of the panel for today's visit notes illustrated in FIG. 15. As described above, the user can change views by using the View Selection control 2504 at the top of the FIGS. 15 and 18.

Figure 19:
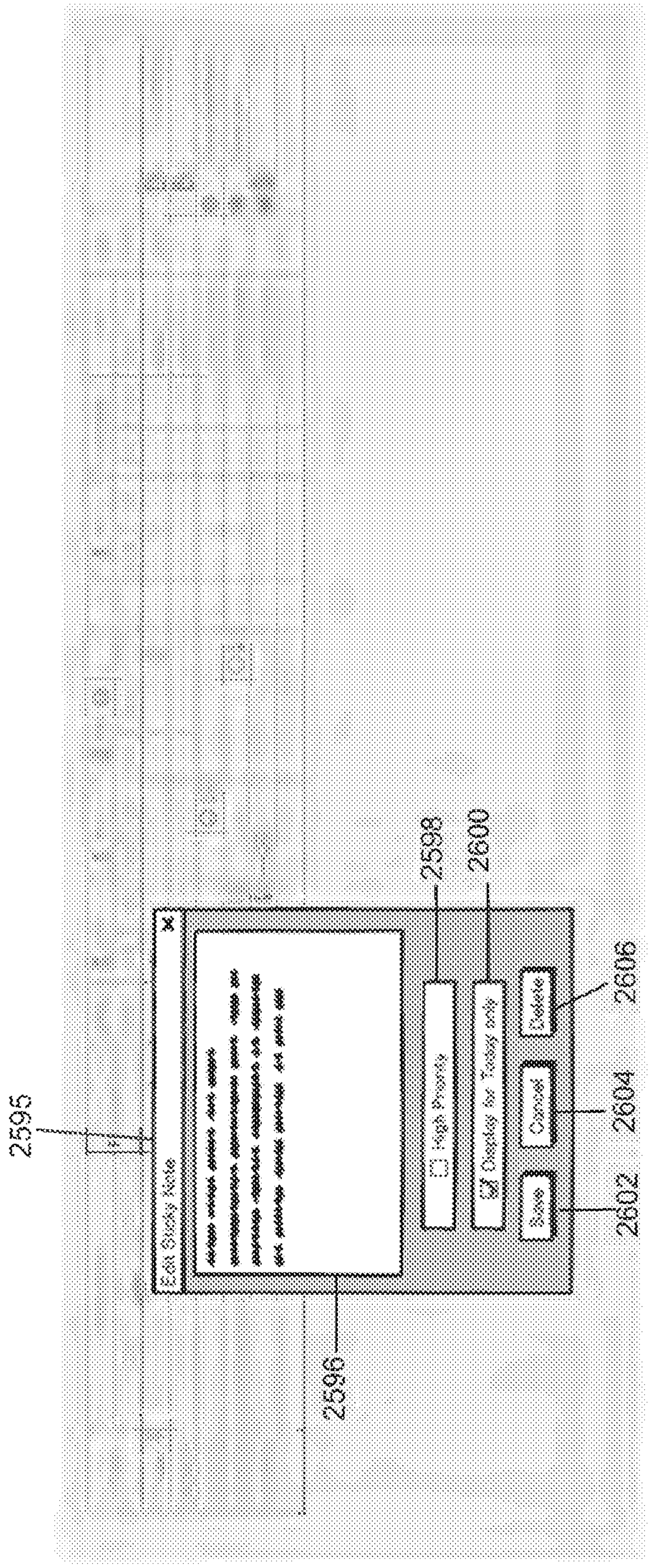
FIG. 19 illustrates the panel presented when the add sticky notes icon in FIG. 15 is selected.

FIG. 19 illustrates the panel 2595 presented when the add sticky notes icon 2506 in FIG. 15 or FIG. 18 is selected. As illustrated, the user may click and drag the icon 2506 to any location on the page and drop it where they want it placed. This allows the user to place the note in context of the information to which it refers. The icon 2506 then stays in place and is associated with dynamic data until deleted by a user or it expires based on the note settings. When the icon 2506 is placed, the Edit Sticky Note control panel 2595 is displayed. The Edit Sticky Note control panel 2595 can also be displayed if a user selects the icon 2506. Once the Edit Sticky Note control panel 2595 is opened, the user can enter a note in field 2596, select if the note is high priority 2598, select if the note should only be displayed today 2600, in which case after the date it is entered the note will no longer display. The user can save the note by clicking the Save Button 2602 or cancel the action by clicking the Cancel Button 2604. The user can delete the note by clicking the Delete button 2606 at which point the action is confirmed before deleting. When a user moves the mouse over the note icon 2506, the note text is displayed next to it in a tooltip. The note icon is colored, e.g., black if it is not high priority and, e.g., red if it is high priority or can flash or be highlighted in any other manner. A note icon 2506 is shown in context in the retina flowsheet 2530 in FIG. 18. If the note is deleted or expires, the note icon 2506 displayed on the page is removed. All deleted or expired Sticky Notes along with the location and duration where they are displayed are preserved for purposes of legal discovery but not accessible to the user as a general practice.

With reference back to FIG. 15, when the user selects the user profile icon 2508, a panel (not shown) is presented to allow the user to edit typical user information including their name, address, phone numbers, email address and password. The user can also select their preferred email or phone number or other method for communications sent by the Command Center.

When the user selects the Logout icon 2510, if any data is not saved, the user shall be prompted to save data before closing the system. If the user answers positively that they want to save unsaved data, the user is not logged out. Once all data is saved, the user is prompted to confirm their desire to logout. If confirmed, the user is logged out.

Figure 20:
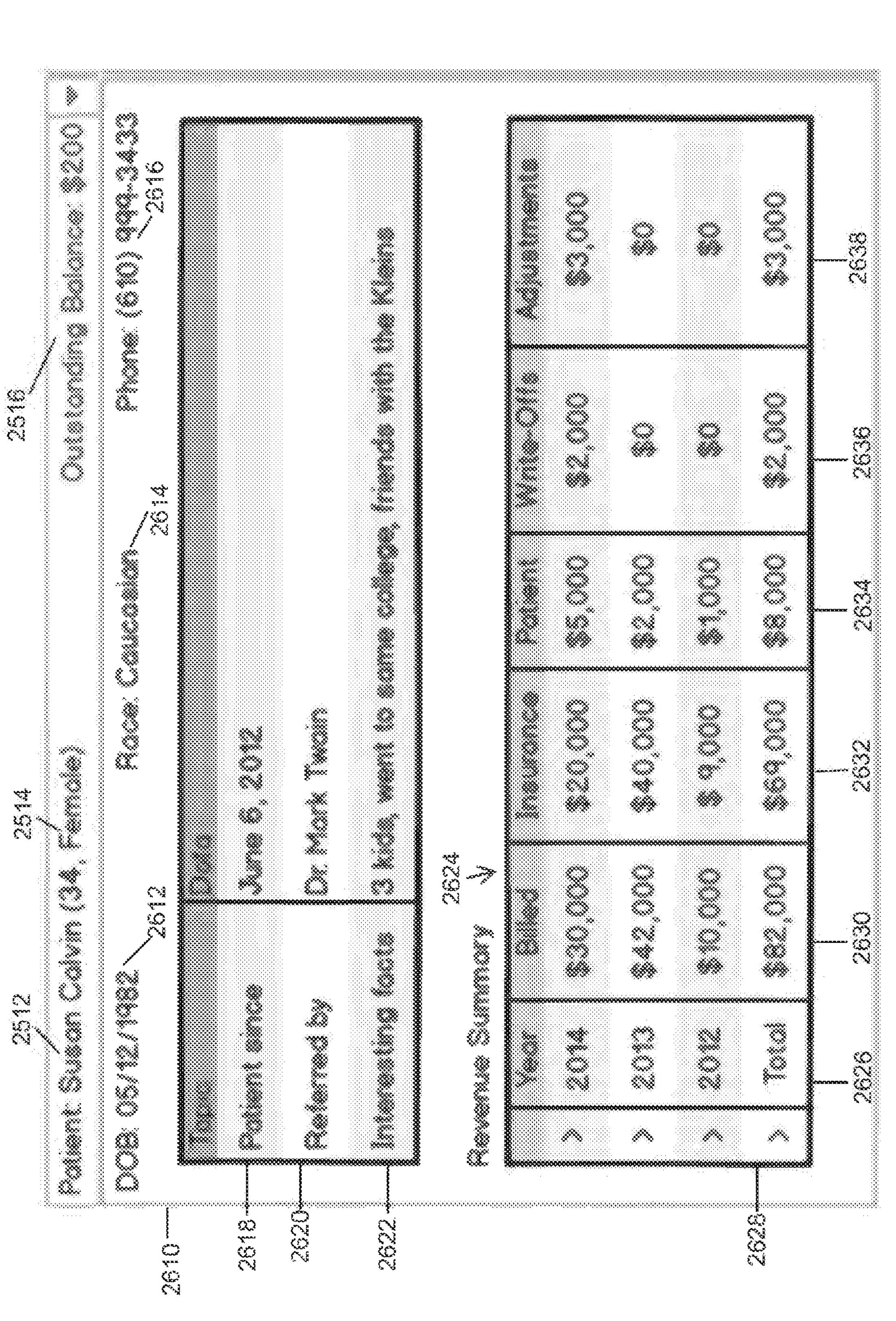
FIG. 20 illustrates the Patient Information panel for displaying high level information about the patient in accordance with the second embodiment.

The Patient Information Bar 2512 illustrated in FIG. 15 displays high level information about the patient. The user can click on the Patient Information Bar 2512 and the Patient Information Panel 2610 shown in FIG. 20 is displayed underneath the Patient Information Bar 2512. Clicking the bar a second time or anywhere else on the page will close the Patient Information Panel 2610. The Patient Information Panel 2610 contains the patient's date of birth 2612, race 2614, phone number 2616, the date when the patient was first seen 2618, the referring physician 2620, and interesting facts to remember 2622. Information in the Patient information Panel 2610 can be edited in place by clicking on the item to be changed. When clicked, the field will change to a text field allowing the value to be changed with a Save button displayed next to it (not depicted). Clicking Save will save the data. Clicking a Cancel button (not shown) will not save the data leaving the value unchanged and the control will revert to static text. Below these fields is a Revenue Summary 2624 for the patient. The Revenue Summary 2624 displays patient totals for each year 2626 as well as grand totals 2628 for the total amount billed 2630, amount paid by insurance 2632, amount paid by the patient 2634, amount written off 2636, and the adjustments 2638 for each year.

Figure 21:
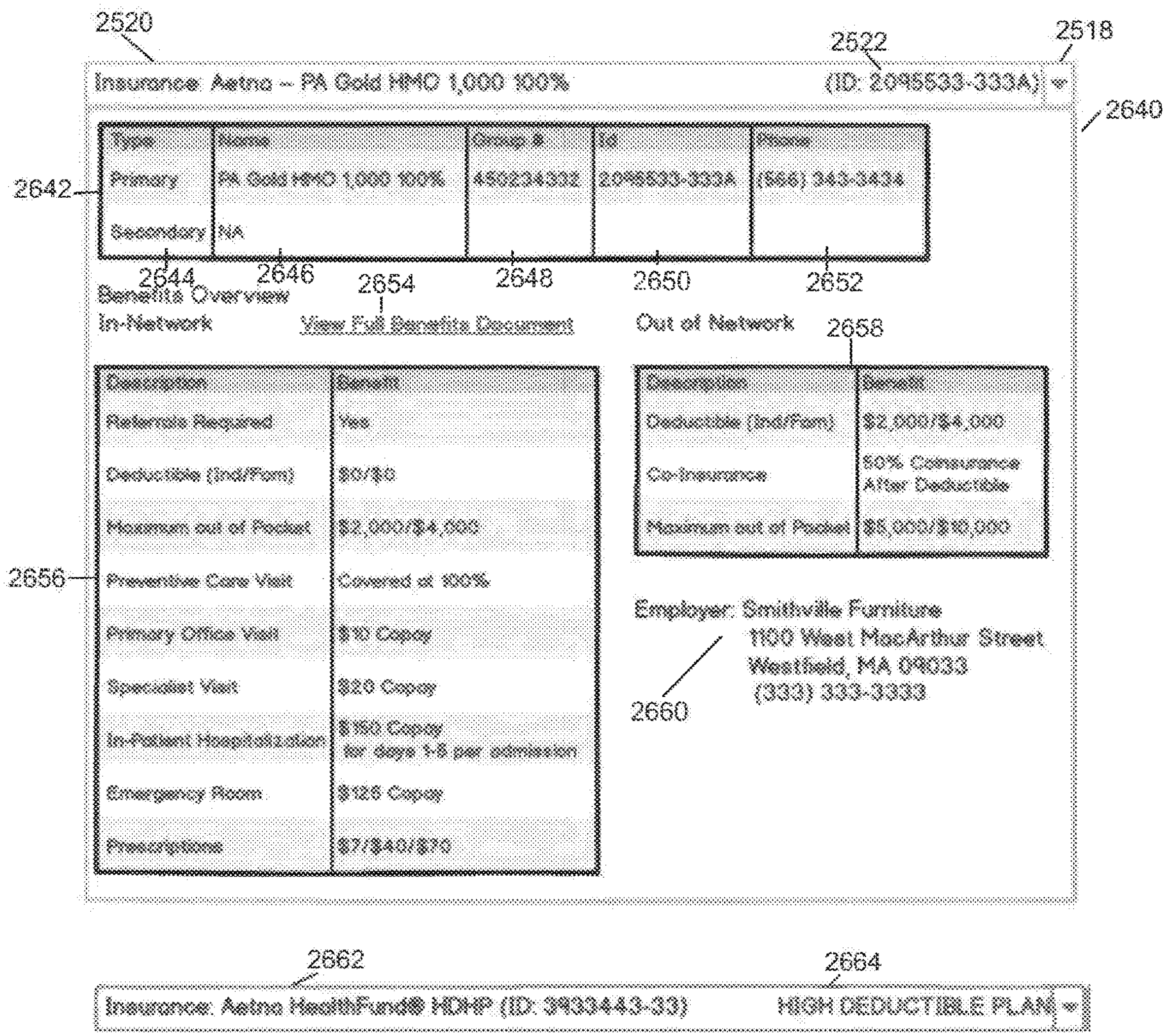
FIG. 21 illustrates the Patient Insurance panel for displaying the patient's insurance information in accordance with the second embodiment.

To the right of the Patient Information Bar 2512 in FIG. 15 is the Patient Insurance Bar 2518. The user can click on the bar and the Patient Insurance Panel 2640 illustrated FIG. 21 is displayed underneath the Patient Insurance Bar 2518. Clicking the Patient Insurance Bar 2518 a second time or anywhere else on the page will close the Patient Insurance Panel 2640. The Patient Insurance Panel 2640 contains information about the patient's insurance 2642 including the type 2644, name 2646, group number 2648, insurance ID number 2650, and phone number 2652 for each insurance company. A link to the patient's benefit document 2654 is provided as well as an overview of the patient's in-network benefits 2656 and out of network benefits 2658 as provided by the patient's insurance company. The values illustrated as 2656 and 2658 are provided for example purposes and will vary based on the data provided by insurance companies. The patient's employer's address and contact information 2660 is also displayed for convenience. Item 2662 displays an alternative embodiment of the Patient Insurance Bar 2520. In this case, the patient has a high deductible plan and this fact is displayed at 2664 in red in the Patient Insurance Bar 2520 to be sure the physician is aware that, in this case, the patient has a high deductible plan.

Figure 22:
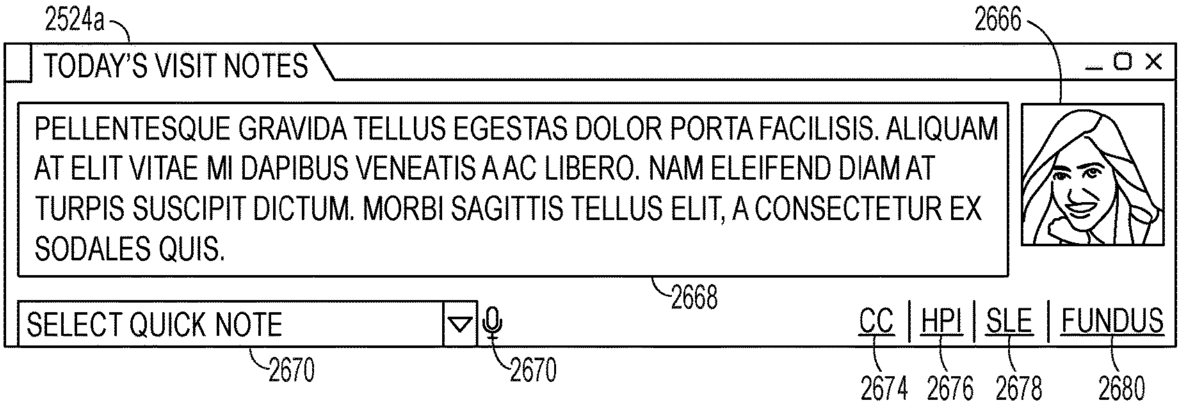
FIG. 22 illustrates Today's Visit Notes tab containing elements related to capturing information about notes specific to today's visit in accordance with the second embodiment.

Today's Visit Notes tab **2524*a* as illustrated in FIG. 22 contains elements related to capturing information about notes specific to today's visit. The tab 2524 contains a photo 2666 of the patient, free form text notes 2668, a control allowing the user to select pre-configured notes 2670, an icon 2672 that triggers a dictation feature allowing text entry into free form text notes 2668 via voice recognition, and a set of links 2674-2680 that are reminders to complete important aspects of an encounter in the EMR. The patient image 2666 is imported from the EMR and text notes 2668 can also be imported from the EMR through the Command Center CCOW Implementation described below. Items 2674-2680 display the status of the chief compliant (CC) 2674, history of present illness (HPI) 2676, slit lamp exam (SLE) 2678, and Fundus photograph 2680. This status is also provided to the Command Center via the CCOW implementation. Items 2674-2680 are displayed in red until complete at which time they are displayed in black. Based on EMR access and functionality, items 2674-2680 are links back to the specific area in the EMR. In an exemplary embodiment, the physician may dictate or type notes into the Today's Visit Notes tab 2524*a*** that automatically generates a letter to a referring physician or another physician alerting that physician about something important in the patient's medical history. Beneficially, the referring letter may be generated while the patient's medical history is on the display screen in the Command Center interface.

Figure 23:
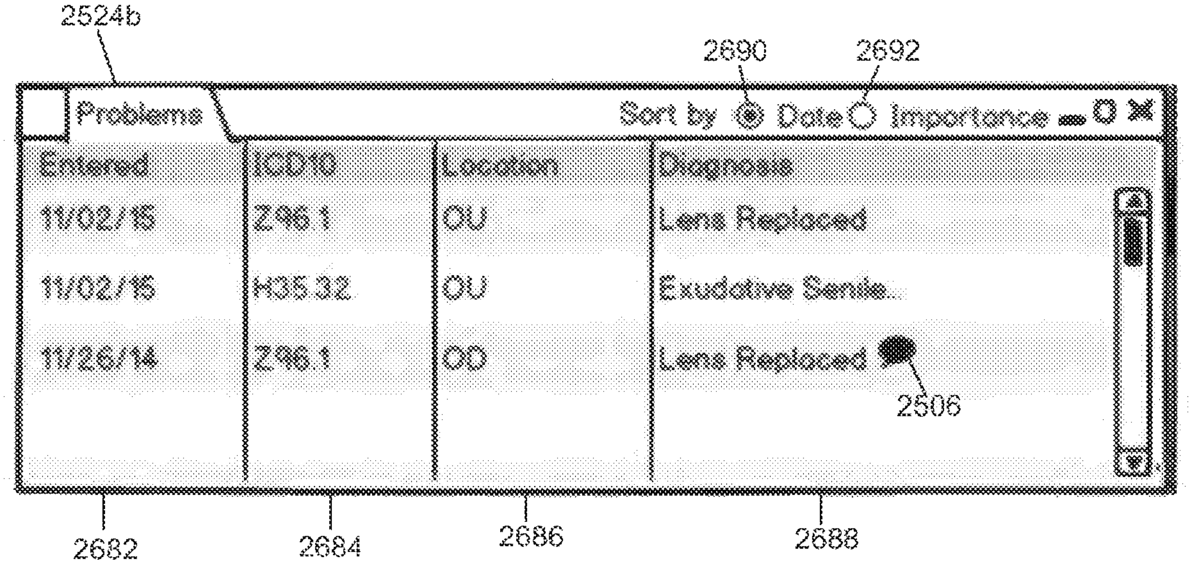
FIG. 23 illustrates the Problems tab displaying a patient's problem list as imported from the EMR in accordance with the second embodiment.

The Problems tab **2524*b* as illustrated in FIG. 23 displays a patient's problem list as imported from the EMR. The following fields are displayed in this embodiment but can be configured to display other fields: date entered 2682, associated ICD10 code 2684, body location 2686, and diagnosis 2688. The user can manually order the list in order of severity or importance by clicking and dragging the rows. Sort by Date 2690 sorts the list in reverse chronological order and Sort by Importance 2692 sorts the list using the user's manual ordering. If the user has not adjusted the order of Problems, it will display in reverse chronological order. The default sort order is by Date 2690, but the user's last selection is remembered and automatically selected when the user returns to the application. The Sticky Note icon 2506 is another example of how a Sticky Note can be dropped anywhere on the page as previously seen in FIG. 18**.

Figure 24:
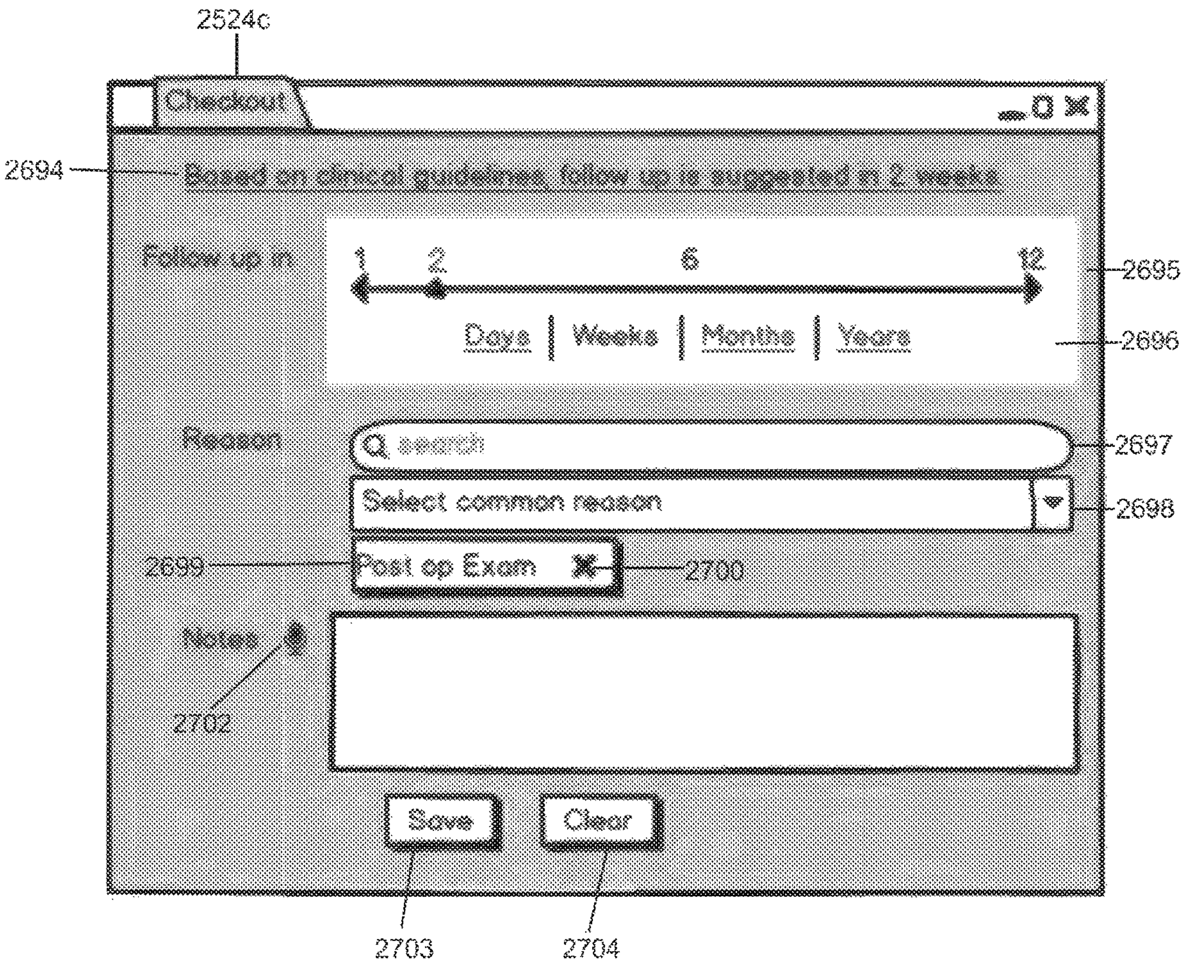
FIG. 24 illustrates the Checkout tab that is used to determine when a patient should return to the practice in accordance with the second embodiment.

The Checkout tab **2524*c* as illustrated in FIG. 24 is used to determine when a patient should return to the practice. This can also be used for a return visit to a shared physician's office which would then also in some embodiments populate a shared care medical table (FIG. 25A) that can be given to a patient for a future reminder of appointment. The Checkout tab 2524*c* displays the recommended clinical guideline 2694 based on the Command Center's Clinical Decision Support algorithms. The follow up timeframe 2695, 2696 is defaulted to the recommendation but can be overridden by the user. The user selects a count 2695 and a period 2696 to generate a time period in which the patient should return. The user can search for a reason using the search field 2697 or select a common reason 2698 from the control. The search feature 2697 implements basic type-ahead, search and results listing allowing the user to select an item. In the case of either the search 2697 or drop down 2698 the selected item is listed underneath at 2699. The user has the ability to delete the item by clicking the associated delete icon 2700. The user can also enter a free form text note 2701 or use dictation by selecting icon 2702. When complete, the user may click the Save button 2703 to save the Checkout information and send it to the EMR or clear the information by clicking the Clear button 2704**.

Figure 25:
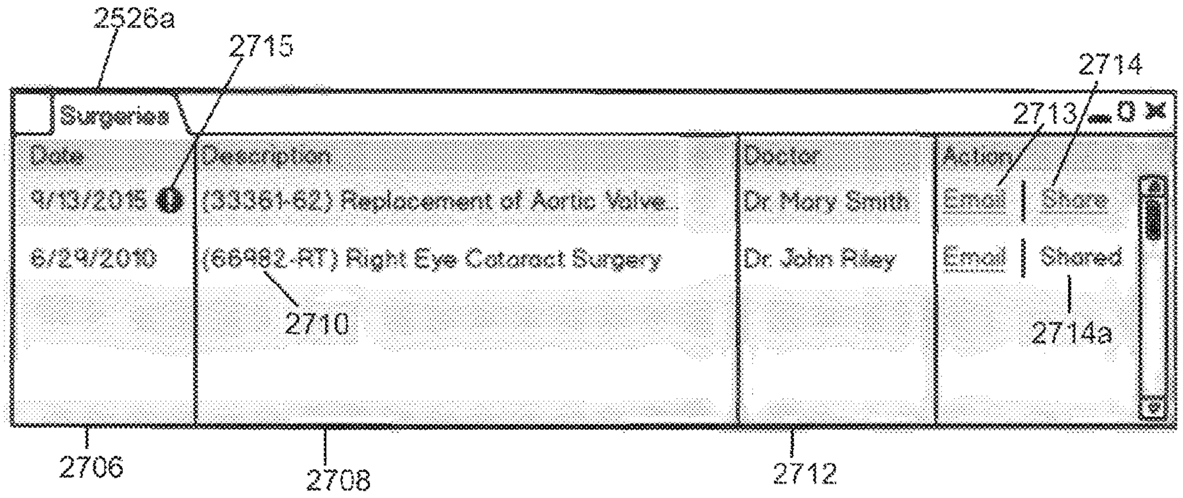
FIG. 25 illustrates the Surgeries tab that displays information about the patient's surgeries in accordance with the second embodiment.

The Surgeries tab 2526*a* as illustrated in FIG. 25 displays information about the patient's surgeries. The Surgeries tab 2526*a* displays the date of surgery 2706, the description 2708 including the billing (ICD10) code 2710, the primary physician 2712, and several actions including the ability to email 2713 or share 2714 the patient record with another physician. The shared notation 2714*a* signifies that the patient record has already been shared with the other physician. A notes column (not shown) displays the first few characters or words based on available space of an associated note. Moving the mouse over the specific note displays it in a pop up. In the case of some surgeries, a hospital or physician will not be paid if readmitted in 30 days. In these cases, if a surgery has been performed in the last 30 days a black circle with an exclamation point 2715 shall be displayed next to the date. Moving the mouse over the icon displays a message stating how many days are left until the patient can be readmitted. An associated note 2506 (FIG. 18) may also indicate that the patient is participating in a capitated plan where anything the physician orders for the patient will not be reimbursed.

When a patient record is shared with another medical professional, if the professional does not have access to the Command Center 2500, the other medical professional will receive an email to register for access to the Command Center 2500 (not depicted). If the professional does have an account but a new patient is being shared, the physician will receive an email notification. The new external user will only have access to the specific patients that are shared. Such sharing of patient medical records amongst the patient's physicians better enables the physicians to work together to follow preferred practice patterns for patient treatment as may be required by insurance companies and/or the government. This process is particularly helpful for managing patients with certain chronic diseases like diabetes where a nephrologist, podiatrist, ophthalmologist, endocrinologist, and family physician need to see each other's results. Another example is shared care before and after cataract surgery where optometrists and ophthalmologist need to see each other's results. Another example is shared care before and after cataract surgery where optometrists and ophthalmologist need to see each other's results.

Figure 25A:
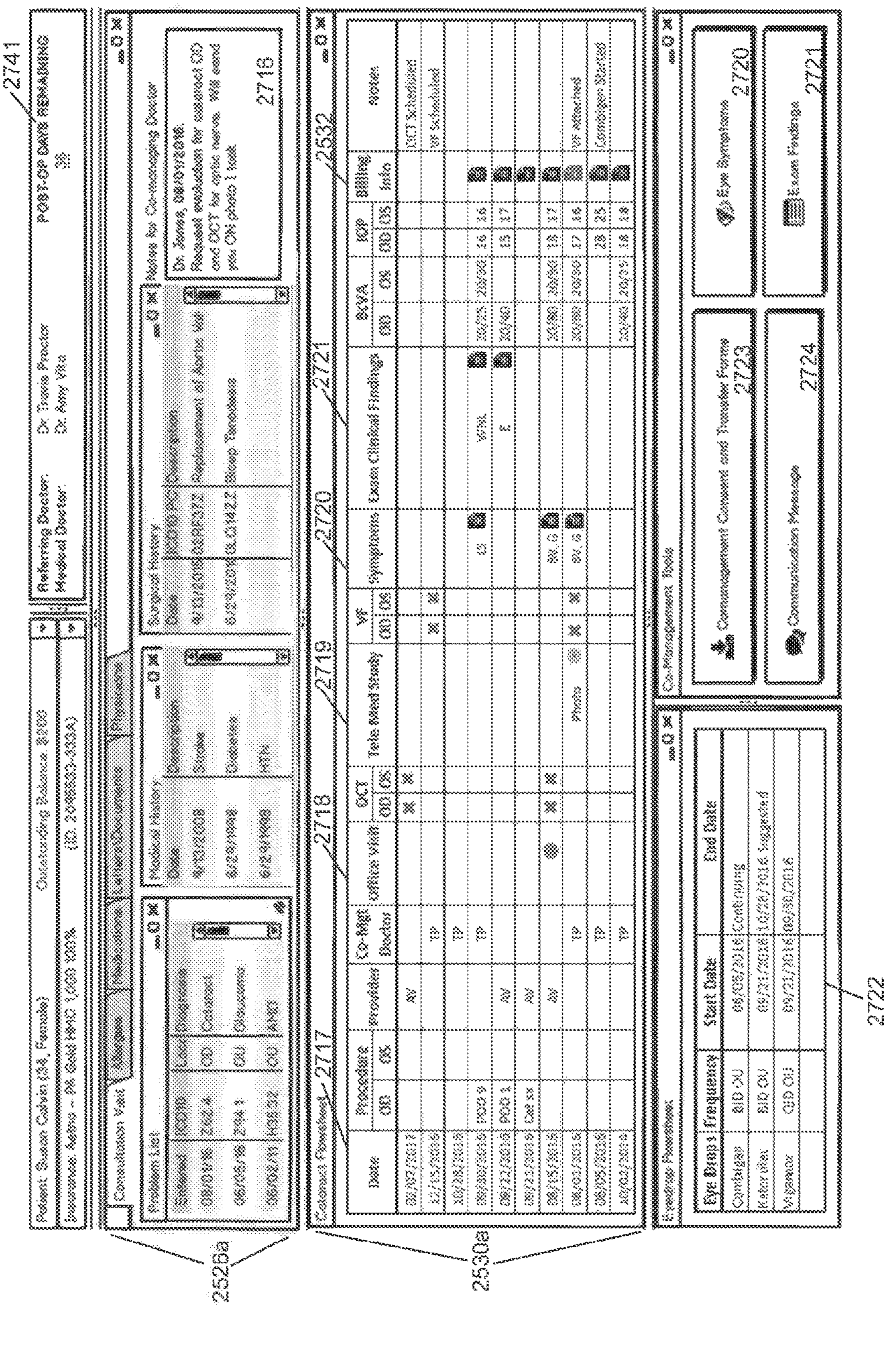
FIG. 25A illustrates an exemplary embodiment of a Data Command Center for use with an EMR system customized for shared care between an optometrist and an ophthalmologist.
Figure 25B:
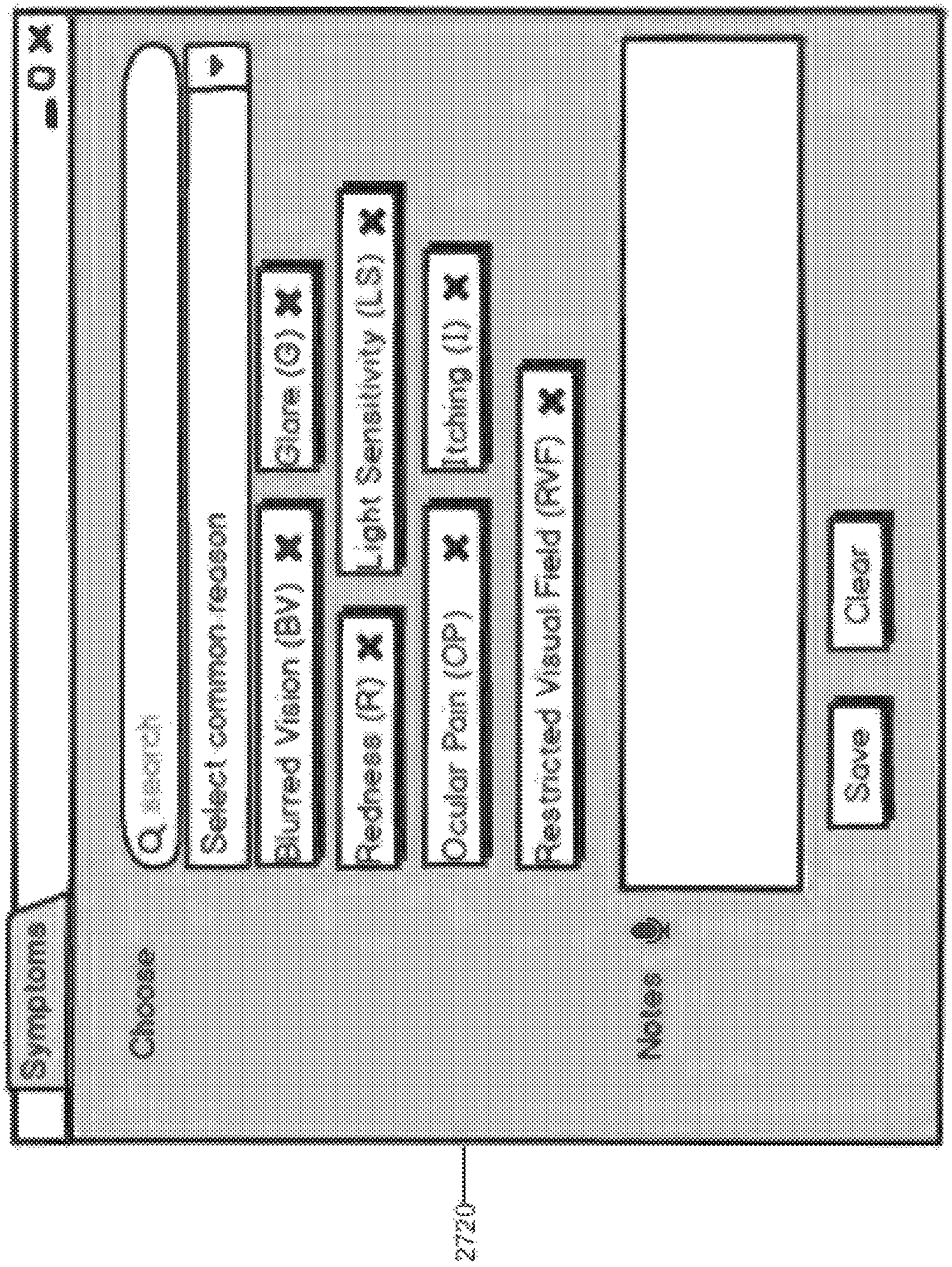
FIG. 25B illustrates a summary of symptoms selected from the Data Command Center of FIG. 25A.

FIG. 25A presents an embodiment of a co-managed patient record in the Data Command Center (CC). In this instance, an optometrist and an ophthalmologist share (co-manage) a patient's cataract surgery then share treatment of the patient's glaucoma. A notes field 2716 in the Consultation Visit 2526*a* panel presents a mechanism to facilitate contextual content surrounding the co-managed procedure (s). A Cataract Flowsheet 2530*a* (purpose optimized dynamic panel) is presented with structured data elements designed to facilitate the identified procedure as conducted by multiple care givers. The Cataract Flowsheet 2530*a* (purpose optimized dynamic panel) is presented with structured data elements designed to facilitate the identified procedure as conducted by multiple care givers. The Cataract Flowsheet 2530*a* is arranged by interaction dates 2717 and tracks office visits 2718 (both scheduled and realized) including sending reminders to patients and alerts when an appointment is missed (not shown), provides means to review and issue concurrence or dissent with diagnostic tests 2719, a summary of symptoms 2720 (clicking opens FIG. 25B), and a summary of exam findings 2721 (clicking opens FIG. 25C). Where available, billing summaries 2532 are presented in the Cataract Flowsheet 2530*a* as well. Clicking the billing summary 2532 may open a new billing window such as that illustrated in FIG. 25D to show billing details and the correct modifier at 2532. Eye drops after cataract surgery and/or glaucoma treatment is tracked on the Eye Drop Flowsheet 2722 (another purpose optimized dynamic panel). There is panel of co-management tools that provide the user with a means to download relevant forms 2723, and to send direct messages to the co-managing physician using button 2724 to access a co-management message center. An indication of the number of postop days remaining 2741 may also be provided. All financial data in the system, including costs to patient, is compartmentalized such that no user may see financial details for users or organizations not authorized in accordance with applicable policies and law.

To co-manage a patient using the interface embodiment illustrated in FIG. 25A, when a referring physician outside the practice wants a consultation, he or she can connect to the practice they are referring to and send information by opening the Cataract Flowsheet 2530*a*. The referring physician may manually insert or auto-populate information from any previous visit of the patient, and provide an annotation 2717 giving the reason for the consultation. When the receiving consultation physician examines the patient, the Cataract Flowsheet 2530*a* is auto-populated with the physician's findings. Co-management forms can be downloaded from the table at 2718 either at the time of the referral or after the consulting physician fills out the paperwork and the patient signs a consent form by selecting co-management forms or by visiting the referring physicians website. A message is sent to the referring physician to open the Cataract Flowsheet 2530*a* and the consent or other forms can be clicked upon and the referring physician can read or sign any forms needed. The "co-management consent" can change color or be distinguished in some other fashion when received back from the referring physician. Every time the surgeon sees the patient, the Cataract Flowsheet 2530*a* automatically includes the date and findings. Then, post-operatively the co-managing physician, or consultation physician or optometrist, when they see the patient in their office, auto-populates or fills out on the Cataract Flowsheet 2530*a* and shares any results.

Figure 25C:
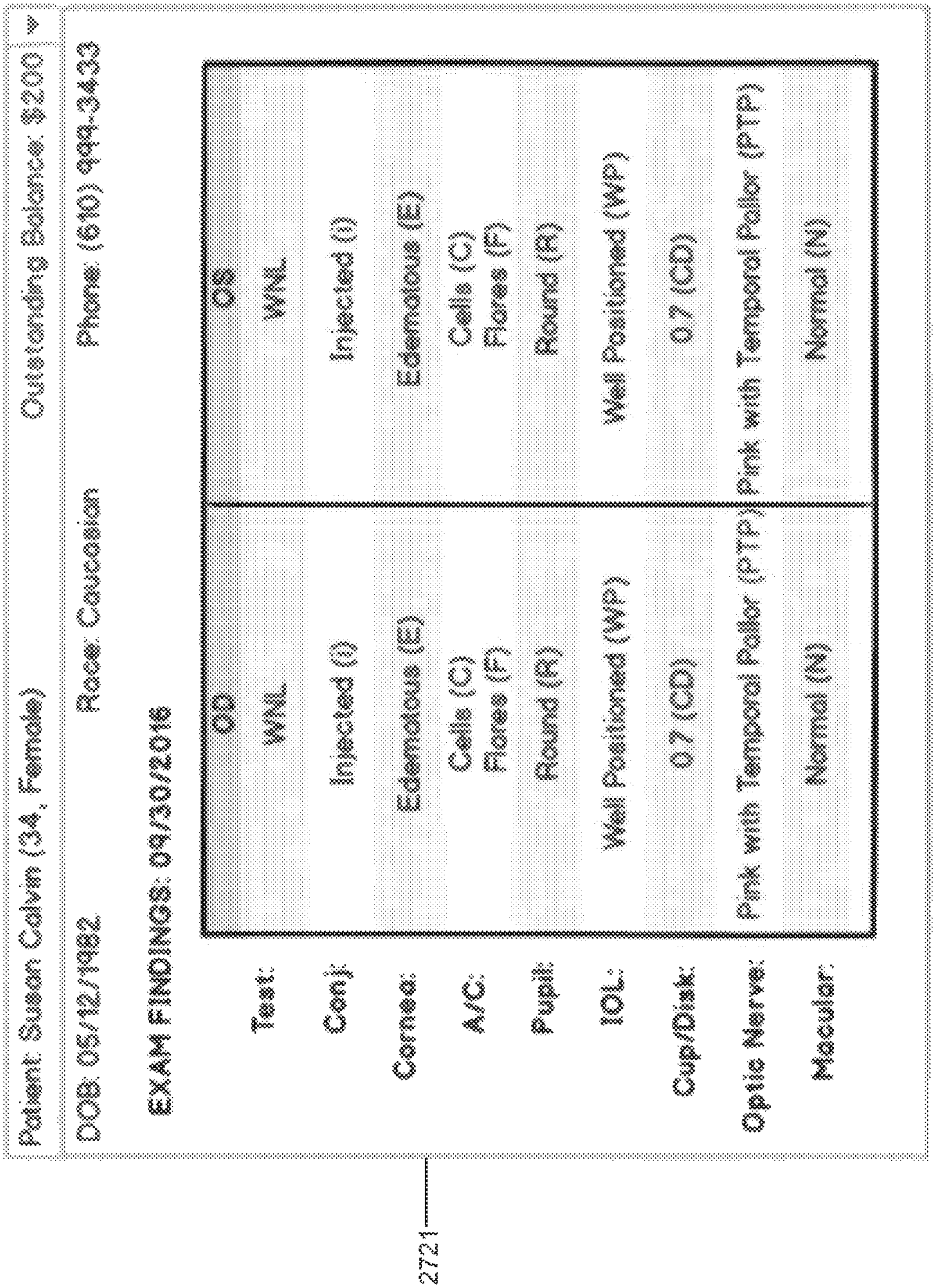
FIG. 25C illustrates a summary of exam findings selected from the Data Command Center of FIG. 25A.
Figure 25D:
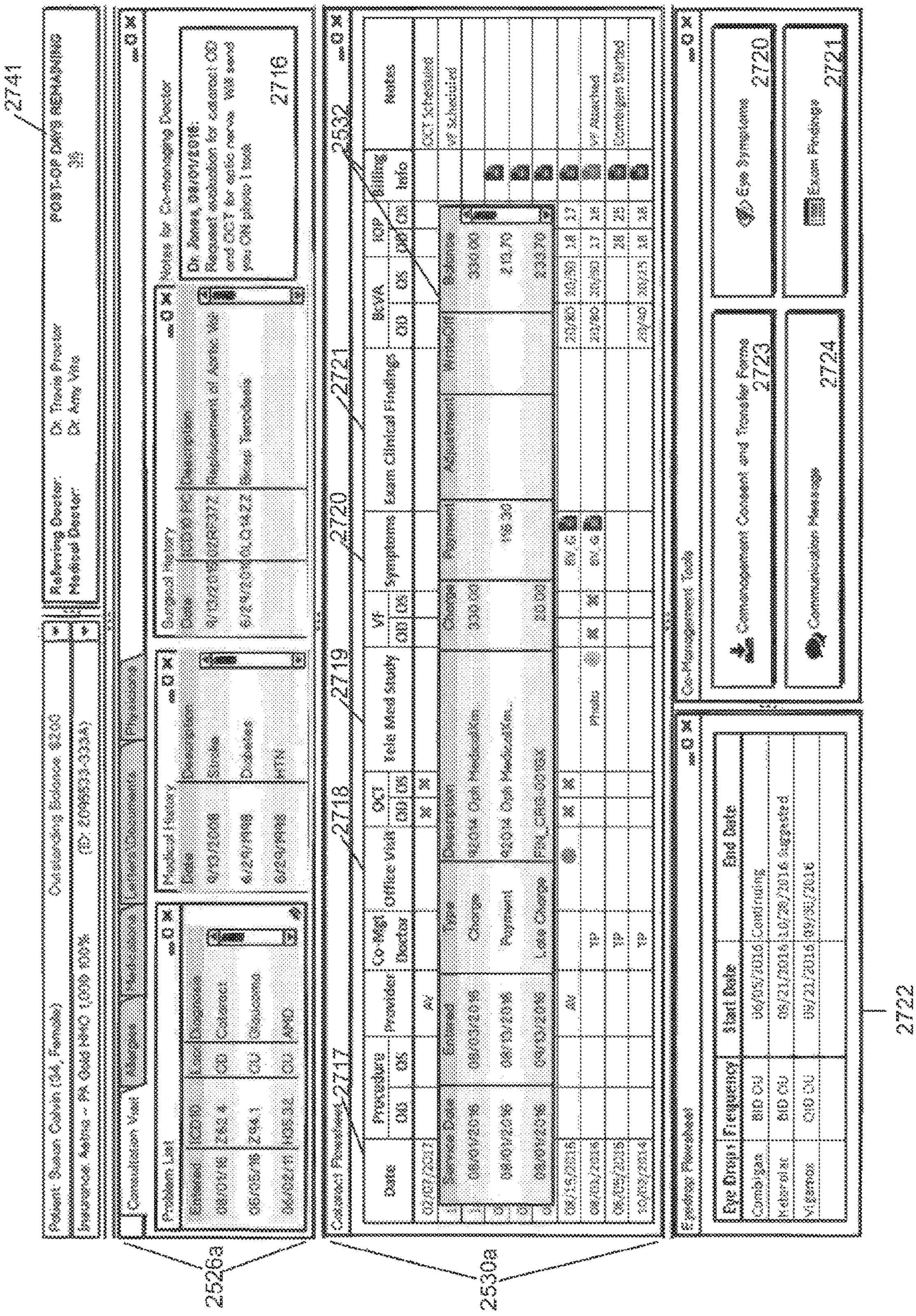
FIG. 25D illustrates the billing summaries selected from the Data Command Center of FIG. 25A.

The headers in the table in FIG. 25A may be selected to generate drop down menus for communicating results between symptoms 2722 may be selected so that the surgeon can determine if there are new symptoms (FIG. 25B) or exam clinical findings 2723 may be selected so that the surgeon can determine if there are any new exam findings (FIG. 25C). In co-managing situations where one office does a diagnostic test but wants to share it with another office, instantly through telemedicine or other methods, including the physician wants to fax the report or scan it to the EMR or the other physician, a report (e.g., "telemedicine study") 2721 maybe selected for a demonstration of the diagnostic tests performed elsewhere. By selecting telemedicine study 2721, the surgeon/consulting physician can review the diagnostic test and then send a message if he or she agrees with the interpretation of the physician who performed the diagnostic test.

Notes may be communicated between the physicians by selecting "communication message" 2724 to determine if there is any information that needs to be shared for office visits. The date column 2719 and office visit column 2720 are tied together. Some of the columns are left blank until the patient actually shows up for a future visit. For instance, after a surgery or consultation, the consulting physician, just as they would normally give an appointment card to a patient can actually give a co-management medical summary table where it shows the date of the future appointment at the referring or sharing physician's office, and when that date arrives the patient is seen and everything is auto-populated so the surgeon can see the results that the co-managing physician found. The findings are auto-populated by the optometrist/referring physician/co-managing sharing physician. If the appointment date is missed, the table can link up with the missing ticket report or send an alert to the patient themselves, the surgeon, the referring physician, business managers or anyone else as appropriate.

Figure 35:
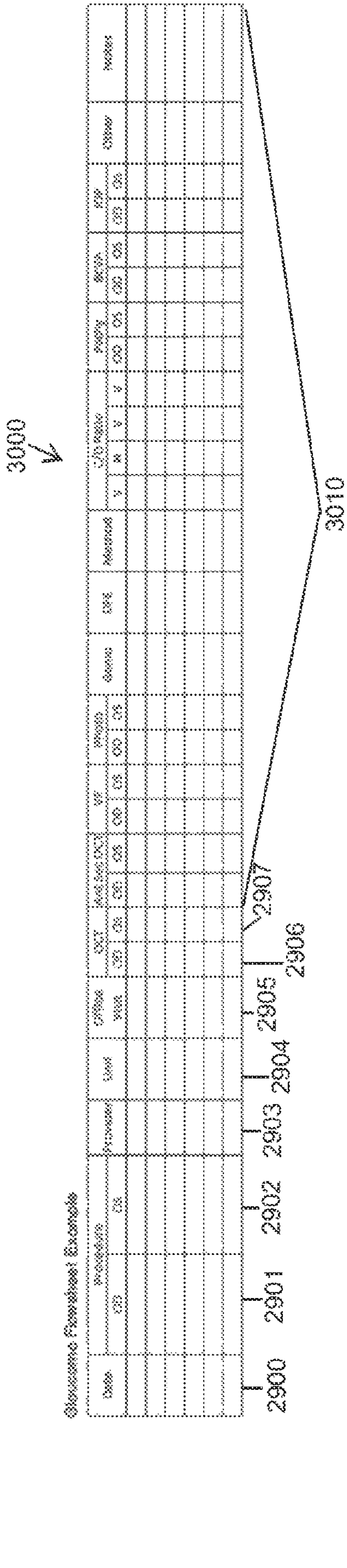
FIG. 35 illustrates a possible flowsheet for glaucoma in accordance with the second embodiment, which is similar to that presented above in FIG. 12A with respect to the first embodiment.

The FIG. 25A is an example also of how shared medical care may be provided in management of common eye conditions besides cataracts, such as glaucoma. An optometrist/general ophthalmologist can manage interval visits after the glaucoma specialist establishes a plan of care. For example, after initial consultation, the plan is shared with the referring or co-managing provider. At a subsequent examination, the referring provider accesses patient data, executes plan and enters the data into Cataract Flowsheet 2530*a* and/or a Glaucoma Flowsheet 3000 as illustrated in FIG. 35. An alert is sent to the glaucoma specialist confirming that the action plan is being carried out. This facilitates care of the patient by the plan. The glaucoma specialist can follow up every year or two while sharing interval visits with the referring optometrist/general ophthalmologist. Multiple benefits of such an arrangement include excellent care, appropriate supervision, reduced cost, improved quality of care of the patient without undue distance traveled. At any point of execution of the treatment plan, treatment can be altered based on clinical data available to the patient, glaucoma specialist as well as referring provider at all times.

Of course, other fields of medicine and industry have similar examples. For example, orthopedic surgeons share care with podiatrists and family physicians share care with all medical specialists. A prime example is shared care with multiple healthcare providers caring for a patient with a chronic disease, state such as diabetes. One patient can have an eye doctor, podiatrist, primary care doctor, endocrinologist, nephrologist, dietician, exercise physiologist, all who need to share care. Different providers may order the same or different tests. If they are in separate health systems, they may not know each other's diagnostic tests, but through this shared medical care table they can avoid duplication of ordering tests, thereby, reducing costs and delivering better care. They can share important data. FIG. 36 demonstrates parameters that could be shared among providers (in this case, participating in the care of diabetes patients) and, if so, the doctors sharing care would have a column next to perhaps the date listing the name of the physician and the healthcare provider office or medical practice/hospital they work. As previously noted, all financial data in the system, including costs to patient, is compartmentalized such that no user may see financial details for users of organizations not authorized in accordance with applicable policies and law.

Figure 26:
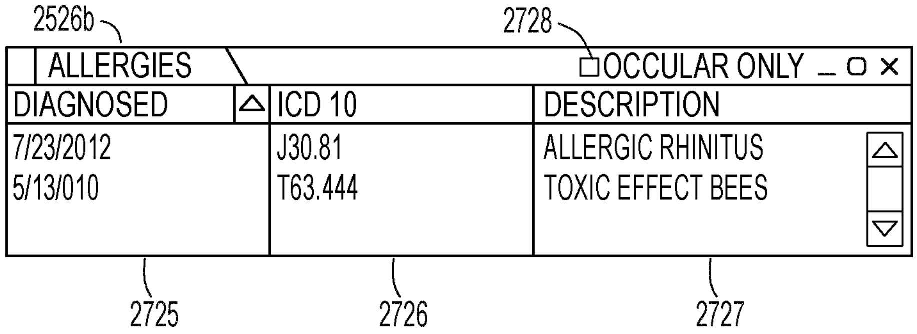
FIG. 26 illustrates the Allergies tab that displays a patient's allergy information in accordance with the second embodiment.

Referring now to FIG. 26, the Allergies tab 2526*b* from display panel 2526 in FIG. 15 displays allergy information. The Allergies tab 2526*b* displays the date of diagnosis 2725, the ICD10 code 2726, and the description of the allergy 2727. This Allergies tab 2526*b* also has an option 2728 to show only Ocular related allergies. In other embodiments, different filters may be applied.

Figure 27:
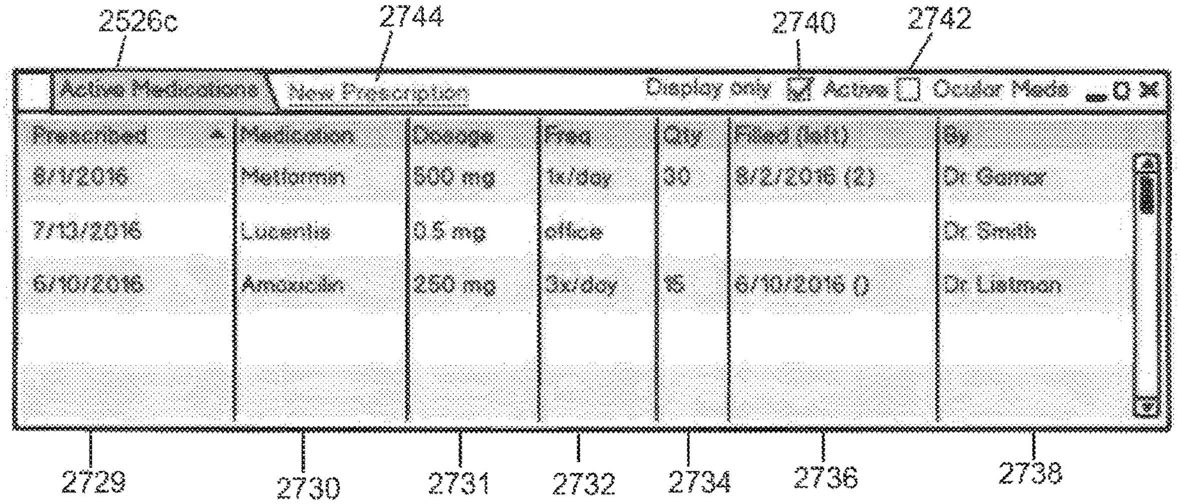
FIG. 27 illustrates the Medications tab that displays medication information in accordance with the second embodiment.

The Medications tab 2526*c* as illustrated in FIG. 27 displays medication information. The Medications tab 2527*c* displays the prescription date 2729, the medication name 2730, the dosage 2731, the frequency 2732, quantity 2734, last time it was filled and the number of refills remaining 2736, and who prescribed the medication 2738. The medications may be filtered by active medications 2740 and/or ocular medications 2742. The tab also includes a link to order new medications 2744. When the new medication link 2744 is clicked it opens the New Prescription overlay (FIG. 44) so that the existing medications can be seen when prescribing any new ones.

Figure 28:
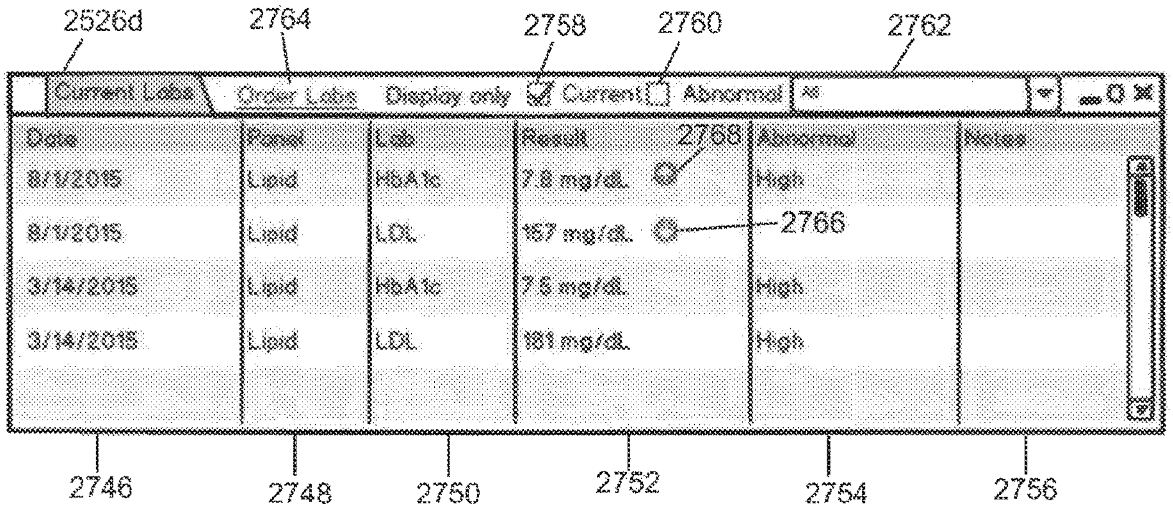
FIG. 28 illustrates the Labs tab that displays lab information in accordance with the second embodiment.

The Labs tab 2526*d* (not shown in FIG. 15) as illustrated in FIG. 28 displays lab information. The Labs tab 2526*d* displays the lab date 2746, the lab panel 2748, the lab name 2750, the result and unit of measure 2752, whether or not it is an abnormal lab result 2754, and any associated notes 2756. The notes column only displays the first few characters or words based on available space. Moving the mouse over the specific note displays it in a pop up. The tab includes filters for displaying only current labs 2758, only abnormal labs 2760, and the ability to select any individual lab 2762. The Labs tab 2526*d* also includes a link to order new Labs 2764. When the Order Lab link 2764 is clicked it opens the Order Lab overlay (FIG. 46) so that the existing labs can be seen when ordering new ones. The declining health icon 2766 and improving health icon 2768 are indicators so the user can quickly see how the patient is progressing or not progressing. These icons are determined on data import by Clinical Decision Support features of the Command Center as described below with respect to FIG. 63.

Figure 29A:
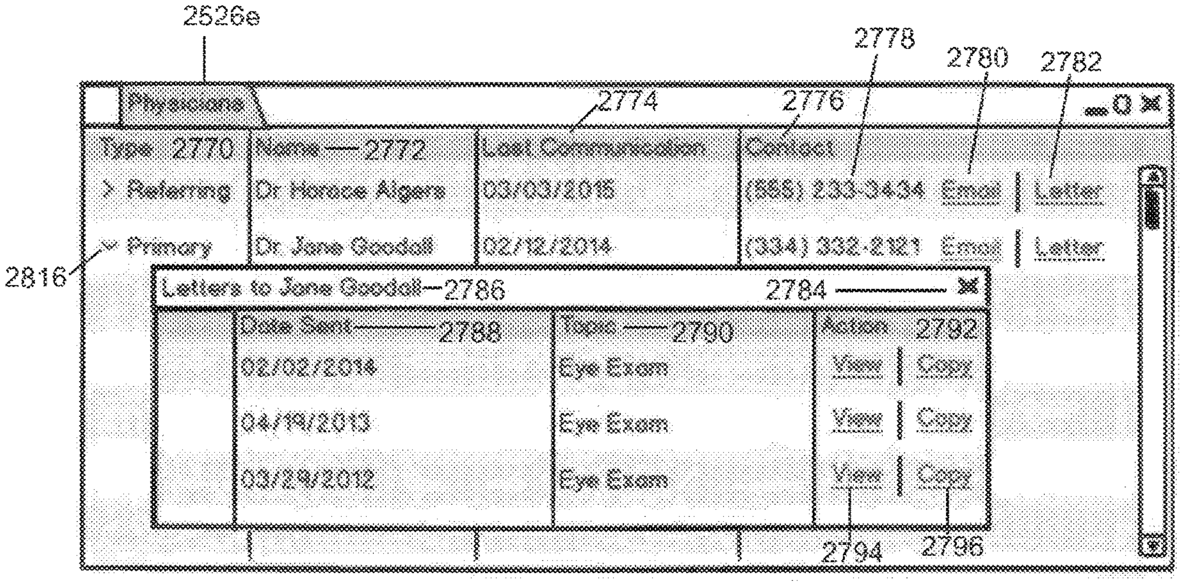
FIG. 29A illustrates the Physician tab that displays information about the patient's other physicians and provides a listing of letters sent to the patient's other physicians in accordance with the second embodiment.
Figure 29B:
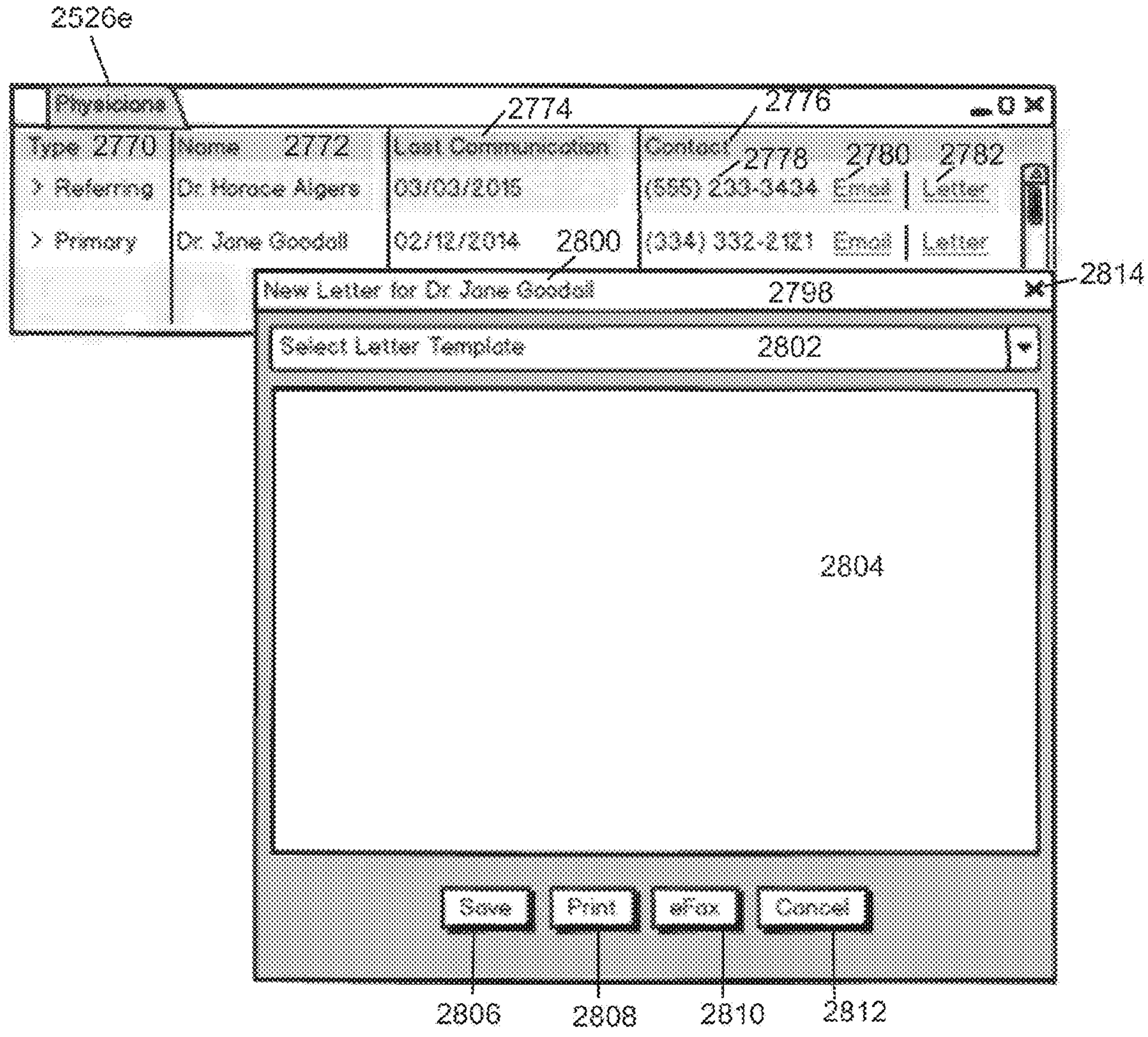
FIG. 29B illustrates the New Letter Popup when the letter link in FIG. 29A is selected in accordance with the second embodiment.

The Physician tab 2526*e* as illustrated in FIG. 29A displays information about the patient's other physicians and provides a listing of letters sent to the patient's other physicians. The Physician tab 2526*e* displays the type of physician 2770, the physician's full name 2772, the last time communication was officially recorded 2774, and the physician's contact information 2776 with the phone number 2778, link to email 2780, and a link to create a new letter 2782. Clicking the email link 2780 opens a window to email the physician using a secure email client on the local computer used to access the Command Center 2500. Clicking the Letter link 2782 opens the New Letter Popup 2798 shown in FIG. 29B. The New Letter Popup 2798 displays the title including the name of the physician 2800 to whom the letter is being addressed, a list of letter templates 2802, a text area to draft the letter 2804, a Save button 2806, a Print button 2808, an eFax button 2810, a Cancel button 2812, and a Close Icon 2814. The user can select a letter template from the list of templates 2802 and the contents are populated in the text area 2804 where the user can edit the letter. Once complete, the user can save the letter by clicking the Save button 2806 in which case it is sent to the EMR. The letter can be printed by clicking the Print button 2808 and can be faxed electronically by clicking the eFax button 2810 in which case the letter is transmitted by an integrated $3^{rd}$ party fax service. If the user does not want to complete a letter, the user can close the New Letter Popup 2798 by clicking the Cancel button 2812 or clicking the Close Icon 2814. For each physician, selecting the icon 2816 displays a list of letters 2784 sent to that physician. Clicking the icon 2816 a subsequent time closes the list of letters 2784. The list of letters 2784 displays the title including the name of the physician for the list 2786 to ensure context, and a list of letters including the date sent 2788, the topic 2790, and action column 2792 including View link 2794 and Copy link

2796. Clicking the View link 2794 displays the letter in a read-only format in a popup (not displayed) and clicking the Copy line 2796 opens the New Letter Popup 2798 of FIG. 29B with the copied letter content displayed in the text area 2804 for editing or printing by selecting Print button 2808.

Figure 30:
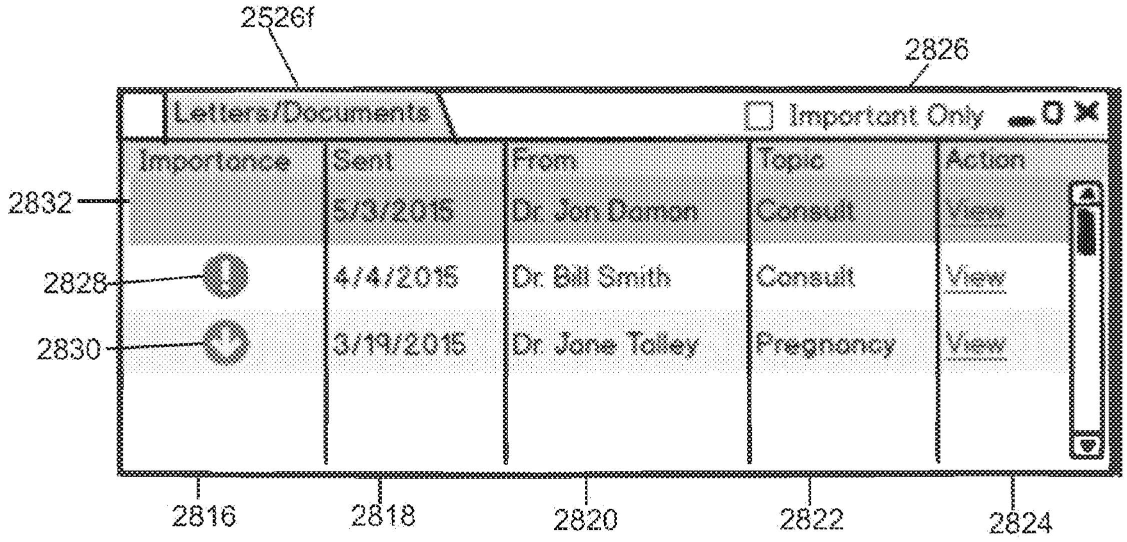
FIG. 30 illustrates the Letters/Document tab that displays letters and documents transferred from the EMR system in accordance with the second embodiment.

The Letters/Document tab **2526*f* as illustrated in FIG. 30 displays letters and documents transferred from the EMR system. The list of Letters and Documents displays a tabular list of items. The list includes a Level of Importance icon 2816, the date the letter was sent 2818, who the letter was from 2820, the topic of the letter 2822, and a link 2824 to View each document. Documents can also be filtered at 2826 so that only the important ones are displayed. The importance icon 2816 may either be blank, a red circle with an exclamation point 2828 if it is important (ex. cancer diagnosis letter the physician does not want to misplace) or a blue circle with a down arrow 2830 if it is low priority. If the user clicks the View icon 2824 for a document, the document is displayed in a popup (not displayed). The user can adjust the priority of a document by clicking on the importance column and selecting a Level of Importance (not displayed). Letters that have not been viewed since the last appointment are also highlighted at 2832** to focus the user's attention on new items and after viewing the items they are no longer highlighted.

Figure 31:
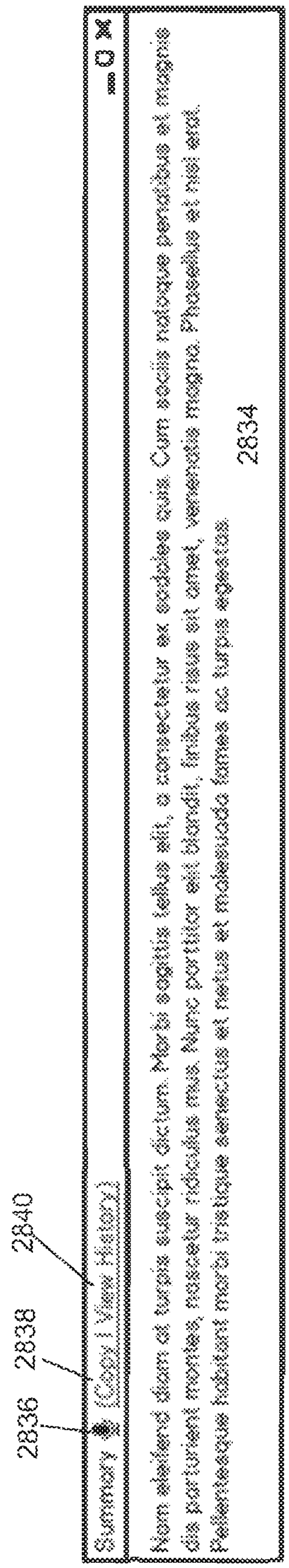
FIG. 31 illustrates the Summary panel that is a permanent note feature allowing the user to save and change the same note that is always visible when viewing the patient in accordance with the second embodiment.

The Summary Panel 2528 as illustrated in FIG. 31 is a permanent note feature allowing the user to save notes that are always visible when viewing the patient, so they do not get "lost" within general encounter notes. The Summary Panel 2528 includes a text area 2834 that when clicked enables in place editing (not displayed) and when complete the notes are saved. A dictation icon 2836 allows for note dictation, and the user can copy the notes at 2838 onto the operating systems copy area and by clicking the View History link 2840 the user can see a past history of edits and recover any of those previous edits (not depicted).

Figure 32A:
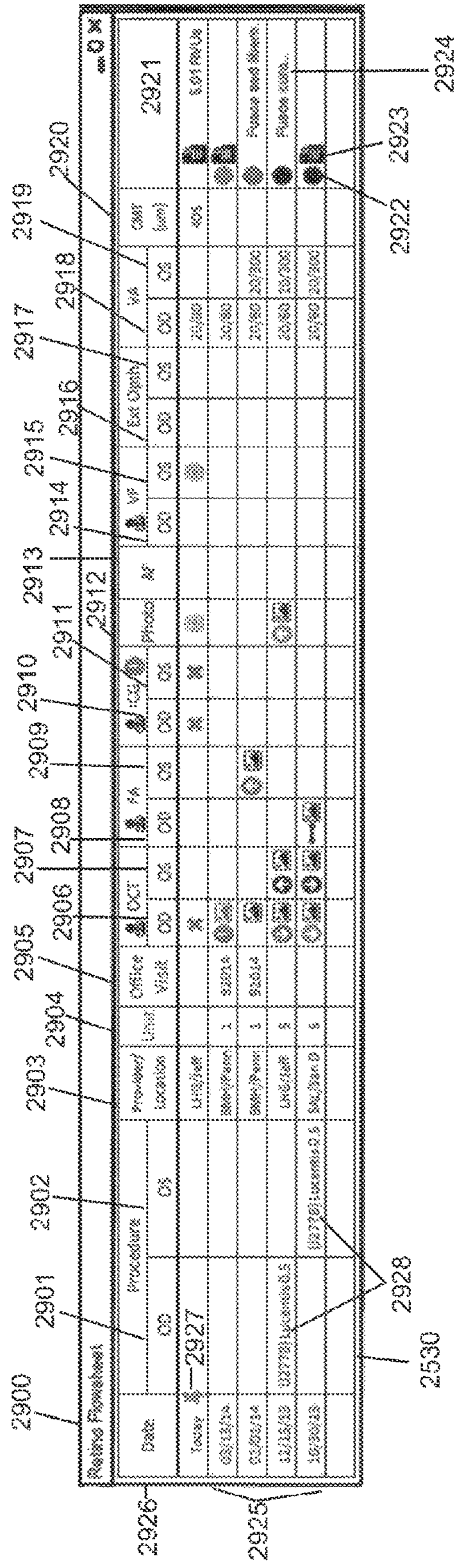
FIG. 32A illustrates an exemplary embodiment of the Retina Flowsheet illustrated in FIG. 15 in accordance with the second embodiment.
Figure 32B:
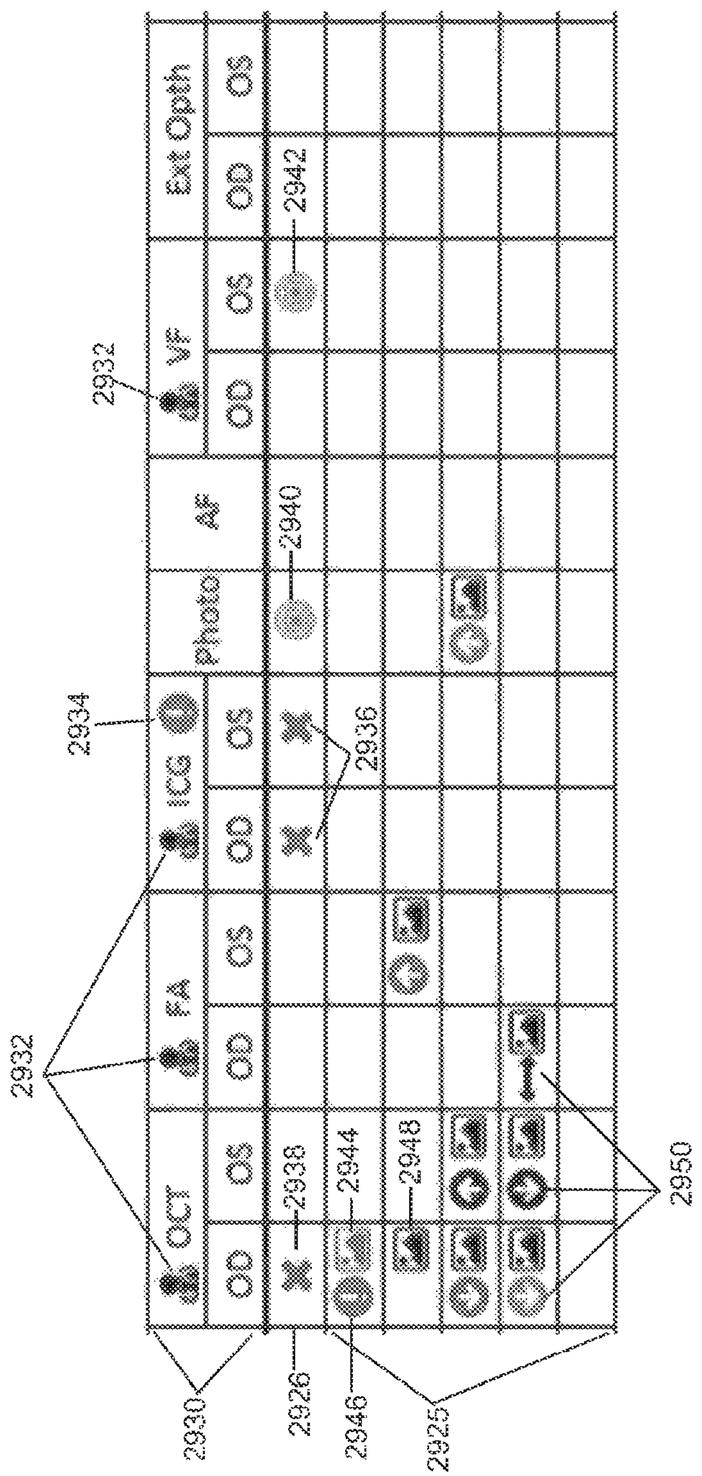
FIG. 32B illustrates the medical treatment information of the Retina Flowsheet of FIG. 32A in more detail.

The Retina Flowsheet 2530 illustrated in FIGS. 32A and 32B is the central focus of the Command Center. The Retinal Flow/sheet 2530 is an embodiment of one implementation of how the Table can be configured. Like the embodiment illustrated in FIG. 4A, the Retina Flowsheet 2530 is based on implementation in an Ophthalmology practice, but can be easily configured for other medical specialties. The Retina Flowsheet 2530 provides a comprehensive overview of the patient's clinical 2900-2920 and financial 2922 history as well as providing a means to quickly order tests 2926 while retaining the ability to see past medical history as illustrated in FIGS. 23 and 25-29. As will be explained in more detail below with respect to FIG. 42, clinical, insurance guidelines and preferred practices are quickly accessible for each imaging modality.

The Retina Flowsheet 2530 displays the following columns in the illustrated exemplary embodiment: Encounter Date 2900, Procedure OD 2901, Procedure OS 2902, Provider and Location 2903, Unit 2904, Office Visit 2905, Optical coherence tomography (OCT) OD 2906, OCT OS 2907, fluorescein angiography (FA) OD 2908, FA OS 2909, indocyanine green (ICG) angiography OD 2910, ICG OS 2911, Retinal Photo 2912, Fundus auto fluorescence (AF) 2913, Visual Field (VF) OD 2914, VF OS 2915, Extended ophthalmoscopy (Ext Opth) OD 2916, Ext Opth OS 2917, Visual Acuity (VA) OD 2918, VA OS 2919, Central Macular Thickness (CMT) 2920, and Other 2921. The Other column 2921 includes a financial status icon 2922, a notes icon 2923 and note text 2924, if available.

The first row in the Retina Flowsheet 2530 represents the current visit 2926 and orders placed. The subsequent rows correspond to past encounters 2925. In the first row, if a pre-authorization is required for a procedure during today's visit, a tack icon 2927 is displayed. If a precertification is required and not available, the icon is red. If it is required and available it is green. If a precertification is not required, no tack is displayed.

The Procedure columns 2901, 2902 contain the procedures) performed 2928 on that date 2900. The full text may not fit in the field, so the data is truncated and when the user moves the mouse over the displayed text the full text is displayed in a tooltip (not depicted). Multiple procedures may be done on a single day and these would be visible in the tooltip. These will be concatenated into a single string and displayed as appropriate (not depicted). The Provider 2903 column contains the initials of the provider associated with the claim for that day and the location of the provider (as when the practice has more than one office). The Unit 2904 column contains the units of medication delivered, if applicable. The Office Visit 2905 column contains the office visit code, if one was billed for that day. In the VA columns 2918 and 2919 the Visual Acuity is entered either manually or through the CCOW interface (described below with respect to FIG. 60). The CMT 2920 column also is entered manually or through the CCOW interface. The user clicks on the appropriate row and it becomes a text field allowing entry of the data following standard browser editing data in place conventions. Hitting enter saves the data. Clicking on the value allows it to be edited (not depicted). The data is saved immediately and does not require a Save action. In the Other 2921 column the financial status 2922 icon is displayed. It is black if the claim is finalized, red if rejected or denied, and blue if it is in process. Clicking on a financial status icon 2922 will highlight the corresponding row in the Financial Flowsheet 2532 (FIG. 15) or if the Financial Flowsheet 2532 is not visible based on the user's configuration, it will open a popup (not depicted) that displays the Financial Flowsheet 2532 with the row highlighted. The notes 2923 icon may be clicked to enter a note (FIG. 32A) and if a note exists the text that fits in the field will display and when the user moves the mouse over the field it will display in a tooltip (not depicted).

FIG. 32B shows the medical treatment information of the Retina Flowsheet 2530 in more detail. As illustrated, a header 2930 embodies several unique features. For example, the header 2930 provides icons for easy access to clinical and insurance guidelines as well as preferred practices for each image modality (OCT, FA, ICG, and VF). Next to each image modality is a Physician icon 2932 and it links to the appropriate clinical and insurance guidelines as well as preferred practice guidelines for that imaging modality and the patient being viewed. The information is displayed on the Guidelines tab 2542 shown in FIG. 15, for example. In an exemplary embodiment, in addition to making the guidelines available, the Command Center 2500 provides an overview of the guideline to make information relevant to the patient condition more easily located and provides clinical decision support (CDS). These features help optimize the physicians' time with the patient and help them comply with insurance guidelines. An example of the CDS in this embodiment is the Alert icon 2934 and highlighted (e.g. red) X icons 2936. The alerts may be generated through data analysis (e.g. FIG. 63) or the alerts may be entered by technicians based on observations during the patient evaluation. For example, these icons may be used by a technician to tell the physician that the patient is allergic to the chemical compound used in performing the ICG imaging test, so the imaging test should not be performed. As another example of CDS, the X icon 2938 for the OCT image test in the right eye (OD) is highlighted (e.g. red). Insurance guidelines do not typically pay for repeat tests within 30 days, so this test cannot be ordered unless the physician overrides the process. Customized to the patient's insurance, this alert assists the physician in meeting insurance guidelines and helps the practice insure they will be paid for procedures they perform, but allow the provider to exercise clinical judgement and perform the test if medically necessary. Once a test is ordered, it appears as a blue bullseye 2940, 2942 icon until it is completed. Because of the placement of the bullseye icon 2940, 2942 the user can easily see which tests have been ordered for which eye.

In each imaging test column 2906-2919 in FIG. 32A, if an image was taken for a date, an image icon is displayed. If the image needs to be interpreted, it is colored red 2944 and an alert icon 2946—red circle with an exclamation point is displayed next to it. Clicking on the image icon 2944 or the alert icon 2946 displays the image on the Image Tab 2540 (FIG. 15). Once the image has been interpreted, it is displayed as a black image icon 2948 and the user can move the mouse over the image to see the interpretation (not depicted). The user also may select a Change in Status icon 2950 to signify if the patient is improving, declining or staying the same for each completed image by clicking on the space to the left of each image icon or, once selected, the Change in Status icon 2950. The available Change in Status icons 2950 in an exemplary embodiment are as follows:

- Horizontal arrows (black)—no change.
- Circle with Up arrow (red)—Negative increasing trend
- Circle with Down arrow (red)—Negative decreasing trend.
- Circle with Up arrow (green)—Positive increasing trend
- Circle with Down arrow (green)—Positive decreasing trend
- Circle with Up arrow (black)—Increasing trend without comment on outcome
- Circle with Down arrow (black)—Decreasing trend without comment on outcome.

Figure 33A:
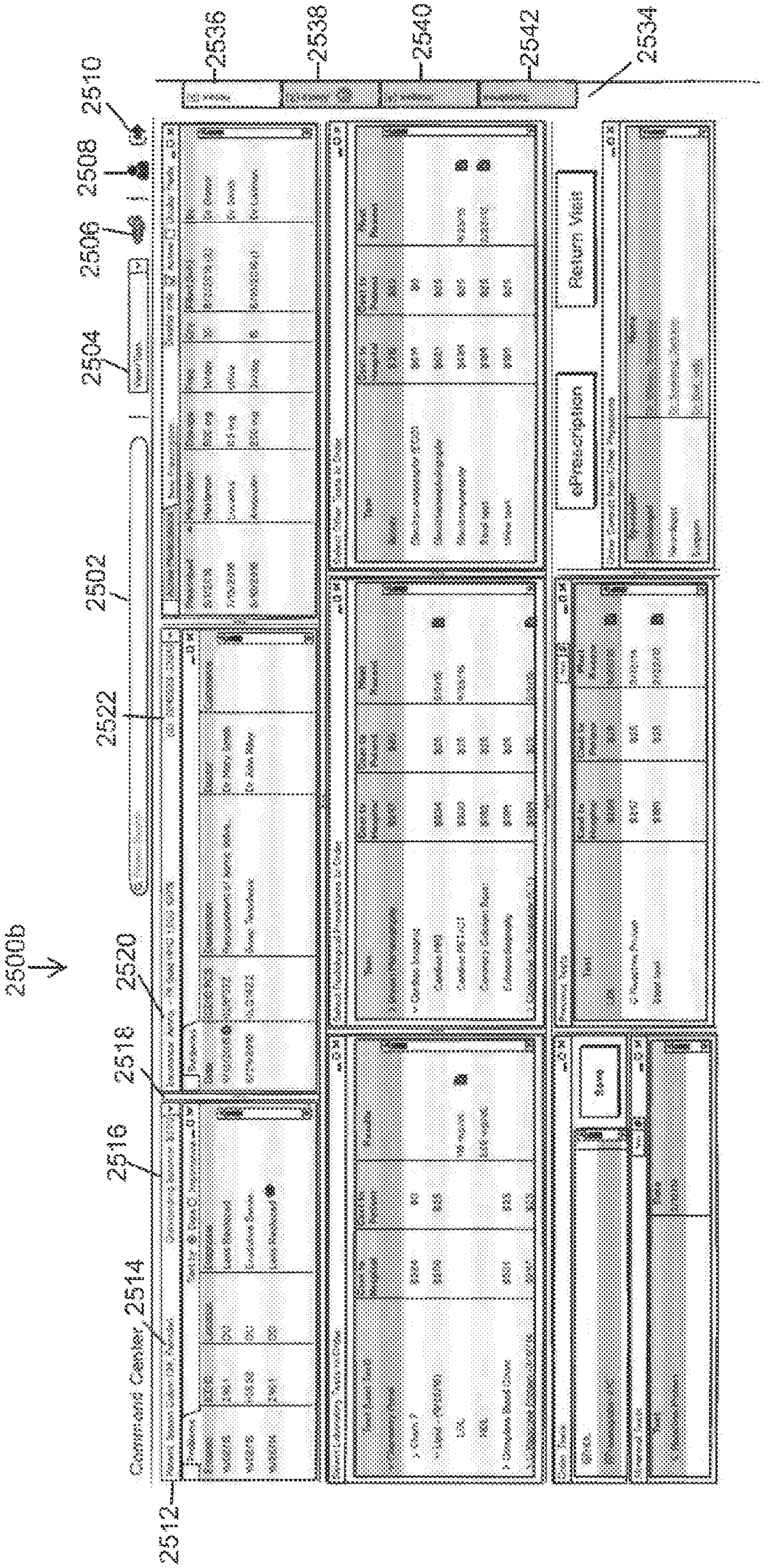
FIG. 33A illustrates a modified Command Center in which the display panels are replaced by panels for ordering clinical tests and procedures, diagnostic images, and medications in accordance with the second embodiment.

Several methods have been discussed by which the Command Center uniquely provides CDS to guide the physician to make better clinical and financial decisions. Physicians can also order tests and procedures directly from the Retina Flowsheet or via display panels in other embodiments of the Command Center 2500 without leaving the Command Center 2500 on the display screen. For example, the embodiment in FIG. 33A illustrates a modified Command Center 2500*b* in which the display panels are replaced by panels for ordering clinical tests and procedures, diagnostic images, and medications. This allows the user to see relevant tests, while further assisting the user in the decision-making process and reducing the cognitive burden imposed by other systems where the user must switch between results and order screens. In the exemplary embodiment, these tests are either ordered directly from the relevant portion of the Retina Flowsheet 2530 or the display panels are replaced by new tab or window popup display panels for ordering clinical tests and procedures, diagnostic images, and medications—all without leaving the display screen of the Command Center 2500, 2500*a*, or 2500*b*. As explained below with respect to FIGS. 56A and 56B, the configuration of display panels is flexible and may be set up and rearranged as desired by the user.

Figure 33B:
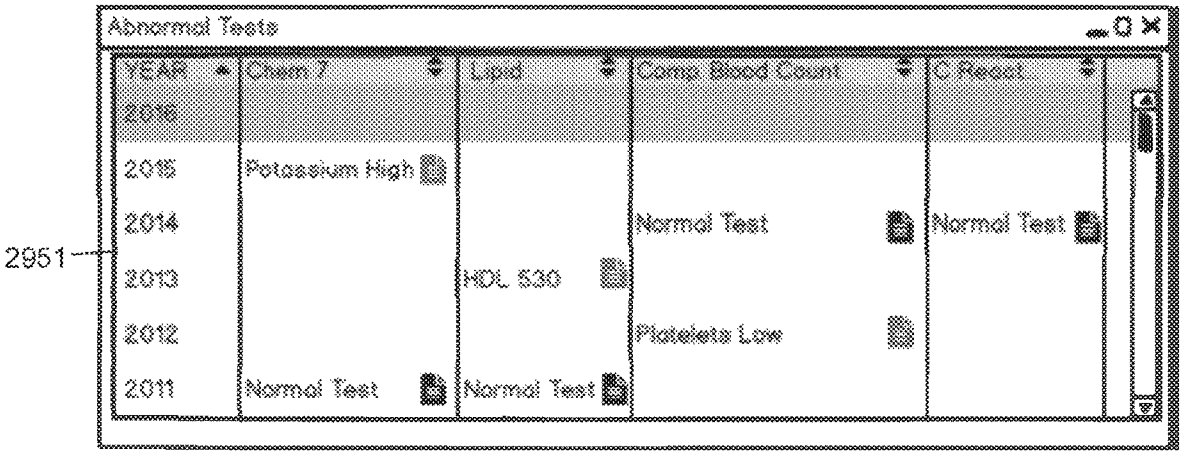
FIG. 33B illustrates an example popup display window illustrating abnormal test results over time.

By way of example, one or more of the display panels in FIG. 33A may be adapted to present an overview of every laboratory test performed and display just the abnormal results. Such an additional panel 2951 is shown in FIG. 33B and may be adapted to enable a physician who is ordering a test to see in overview all that had been ordered in the past thereby tailoring what is needed to be ordered today, all without leaving the Command Center 2500*b*. Such display panels in the Command Center 2500*b* not just allows the physician to see the test that could be ordered while simultaneously knowing the medical conditions, but simultaneously on one screen shows all of the relevant tests ever ordered for this patient whether at the physician's particular practice or their institution or other institutions and in particular abnormal results and even trends the physician wants to track and can be highlighted automatically or that the physician can highlight for their own future reference. Over time, the display panel of FIG. 339 may permit the physician to see everything that was ordered, look for a trend of improvement or decline, and help guide the physician establish what really is medically indicated to now order to help diagnose, manage and treat a patient's condition.

Figure 34A:
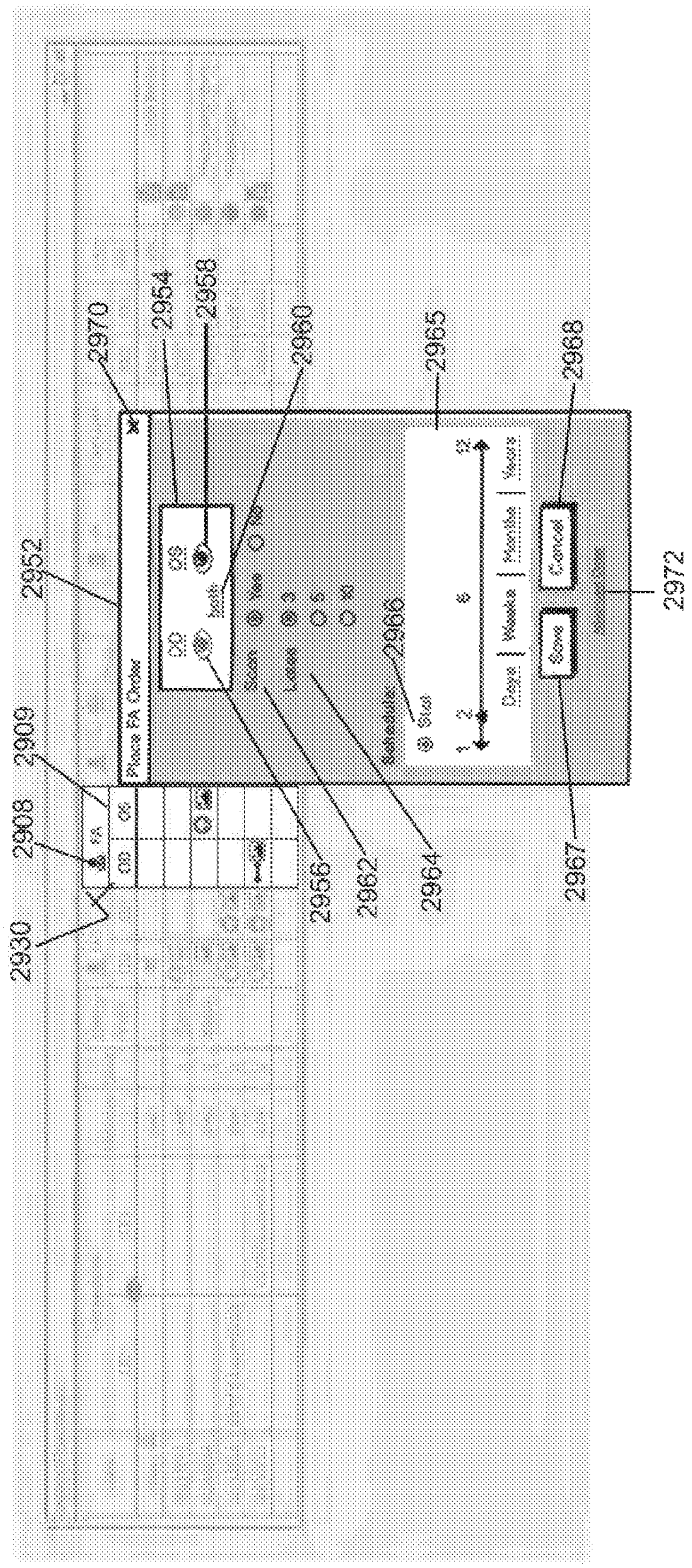
FIG. 34A illustrates the Place FA order dialog box that pops up when the user clicks the column header for the FA exam in accordance with the second embodiment.
Figure 34B:
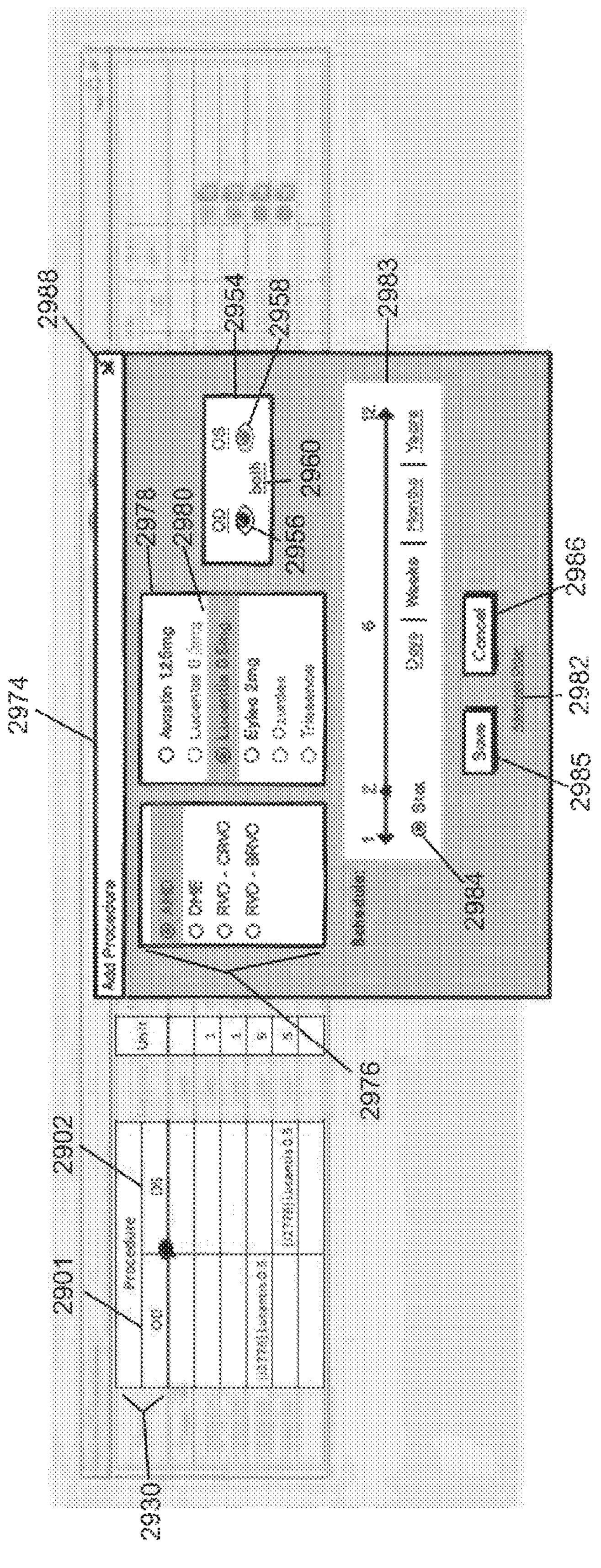
FIG. 34B illustrates another example of in situ ordering for the Procedure columns OD and OS in accordance with the second embodiment.
Figure 48:
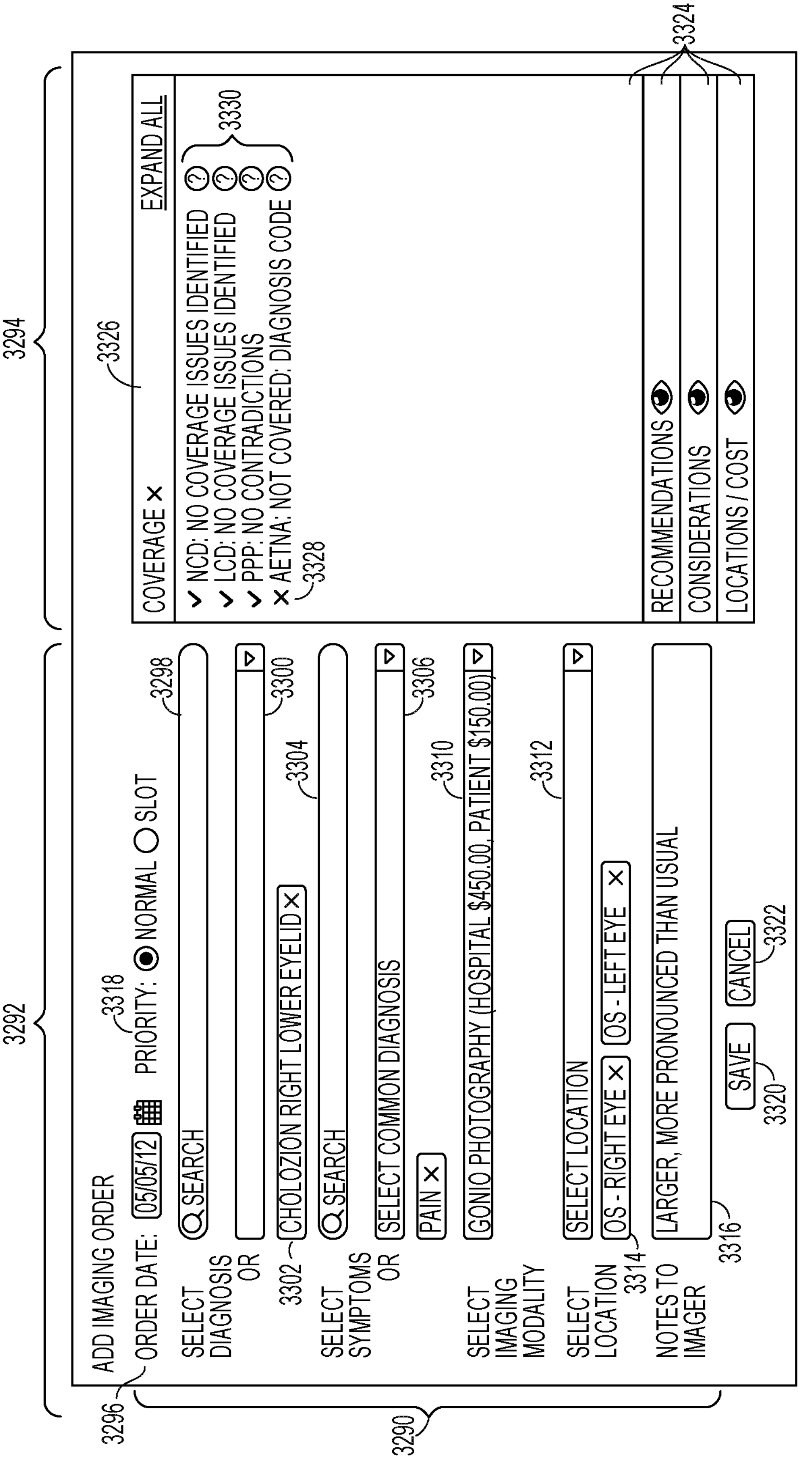
FIG. 48 illustrates a view of the Imaging Order panel in accordance with the second embodiment.

FIGS. 34A and 34B provide an example embodiment of the in situ ordering process using the Command Center of the exemplary embodiments. As illustrated in FIG. 34A, the user clicks the column header 2930 for the FA exam 2908, 2909 and the Place FA Order 2952 dialog box is displayed. At this time, the portions of the page not including the FA columns 2908, 2909 are greyed out to focus the user's attention. The dialog box contains a visual representation of the eyes 2954 allowing the user to visually select either the right OD 2956 or the left OS 2958 or both eyes 2960 by clicking the appropriate link. The user can select Scan 2962 and Lates 2964, schedule using the variable time frame slider 2965 or select stat 2966, and then click the Save button 2967 to save the order, which will place a blue bullseye in the field based on the user's selections. The user can in the same dialog box 2952 or in an added dialog box specify the timing of the diagnostic test, e.g., now, ASAP, 2 weeks, x months, etc. The user can also cancel the order by clicking the Cancel button 2968 or the Close icon 2970. If a more complex order needs to be placed, the user may click the Advanced Order link 2972 to open the Advanced Order Display (FIG. 48). If a CPT code (required for billing and medical necessity testing) has not been provided, the Advanced Order Display (FIG. 48) is automatically displayed.

FIG. 34B illustrates another example of in situ ordering for the Procedure columns OD 2901 and OS 2902. As in FIG. 34A, the areas of the screen not associated with the order are greyed out and the Add Procedure dialog box 2974 is displayed. The dialog box 2974 allows the user to select a Condition 2976 to treat, a medication and dosage 2978 and the eyes upon which the procedure is to be performed. The Medication and Dosage control 2978 only allows the user to select the appropriate medications for the selected condition. For example, for treating AMD (Age-related Macular Edema) Lucentis 0.3 mg (2980) is not appropriate, so it is greyed out and not available for selection. If a more complex procedure needs to be performed, the user may click the Advanced Order link 2982 to open the Advanced Order Display (FIG. 48). The user may schedule the procedure using the variable time frame slider 2983 or select stat 2984. If a CPT code (required for billing and medical necessity testing) has not been provided, the Advanced Order Display is automatically displayed (FIG. 48). When finished, the user may click the Save button 2985 to save the order, which will place a blue bullseye in the field based on the user's selections. The user can in the same dialog box 2974 or in an added dialog box specify the timing of the procedure, e.g., now, ASAP, 2 weeks, x months, etc. The user can also cancel the order by clicking the Cancel button 2986 or the Close icon 2988. The in situ ordering is designed to provide a quick and easy method in context for a provider to order an exam, but allows flexibility for more complex needs.

While the above embodiments of the flowsheet have focused on managing Retina-related issues, other embodiments addressing other specially practices can be easily created. Sticking with embodiments for ophthalmologists, FIG. 35 presents a possible flowsheet for Glaucoma, which is similar to that presented above in FIGS. 12A-12C. The Glaucoma Flowsheet 3000 shares columns 2900-2907 in common with the Retina Flowsheet 2530, but the group of columns 3010 is unique to this presentation. FIG. 36 presents a flowsheet for Diabetes. FIG. 36 shares the first column Date 2900 with the other flowsheets, but the remaining group of columns 3020 is unique to this presentation. The Meds column 3022 represents an example of further clinical decision support. With limited space, it is not possible to list all of the patient's medication, nor is it necessary in an overview. In this column 3022, the patient's diabetes medications may instead be categorized into an overall treatment approach. This could be Diet and Exercise (D&E), oral meds only (oral) or insulin therapy (insulin). At a quick glance the user can understand the progression of the patient's condition. This table of important results, tests, exams can also include cost of the labs, tests or procedures, as well as payments. In addition, this information is vitally important to all the healthcare providers caring for patients with chronic disease, in this case diabetes. Sharing care, as shown in FIG. 25A-D, allows all the patients providers to share information and to notify each other of changes. A column can be added next to the date listing each of the healthcare providers and their locations. As noted above, all financial data in the system, including costs to patients, is compartmentalized such that no user may see financial details for user or organizations not authorized in accordance with applicable policies and law.

Figure 37:
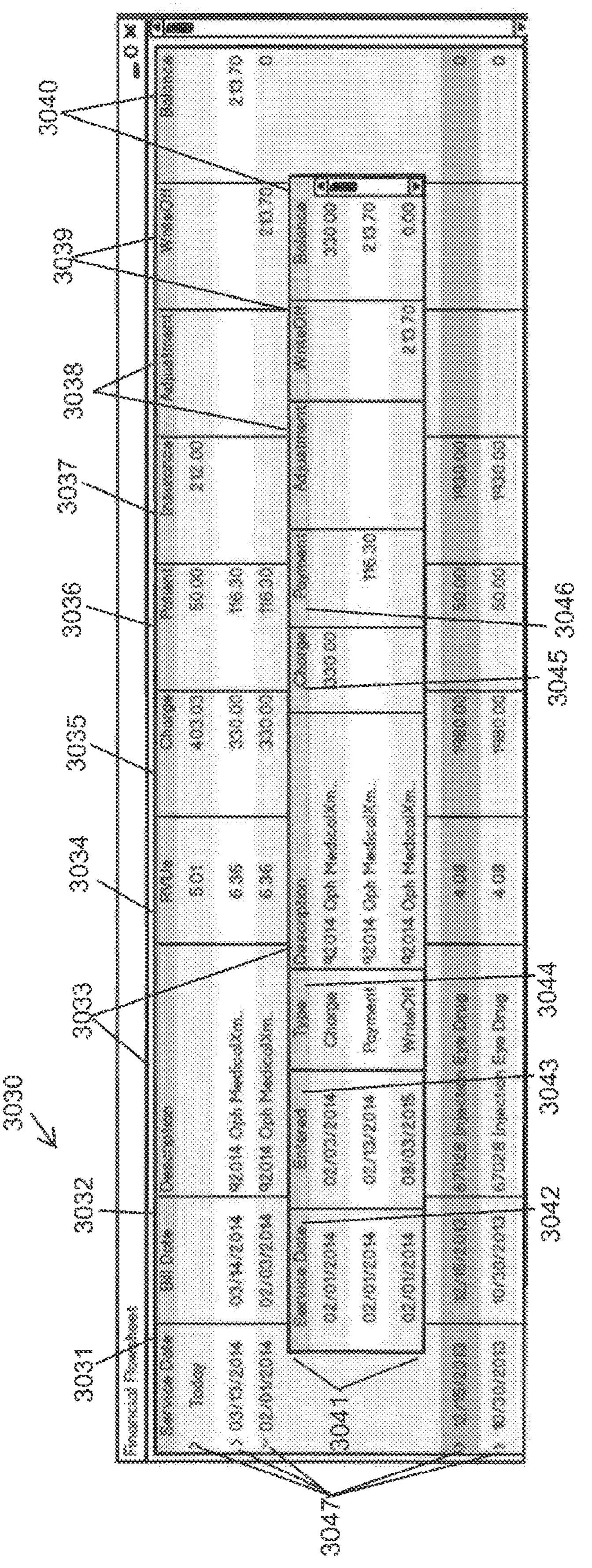
FIG. 37 illustrates an exemplary Financial Flowsheet in accordance with the second embodiment.

The Financial Flowsheet 2532 is illustrated in FIG. 37. The Financial Flowsheet 2532 contains a dynamic table 3030 of financial activity for the patient, as opposed to the physician's practice, as is usually the case with conventional EMR systems. As illustrated, an exemplary embodiment of the Financial Flowsheet 2532 includes the following fields: the Service Date 3031, Bill Date 3032, Service Description 3033, Relative Value Units (RVUs) 3034 that determine how a physician is paid in accordance with work effort, Gross Charges 3035, the Amount Due from the Patient 3036, the Amount Due from Insurance 3037, any Adjustments 3038, Write Offs 3039, and the outstanding balance 3040. Selection of the Encounter expansion control 3047 produces a second dynamic table 3041 within the first dynamic table 3030. The second table 3041 presents individual financial transactions associated with the encounter. In an exemplary embodiment, the second dynamic table 3041 contains: the Service Date 3042, Date Entered 3043, the Type of financial activity entered 3044, the Service Description 3033, the Charge or Amount Billed 3045, Payments 3046, Adjustments 3038, Write Offs 3039, and the outstanding balance 3040.

Figure 38:
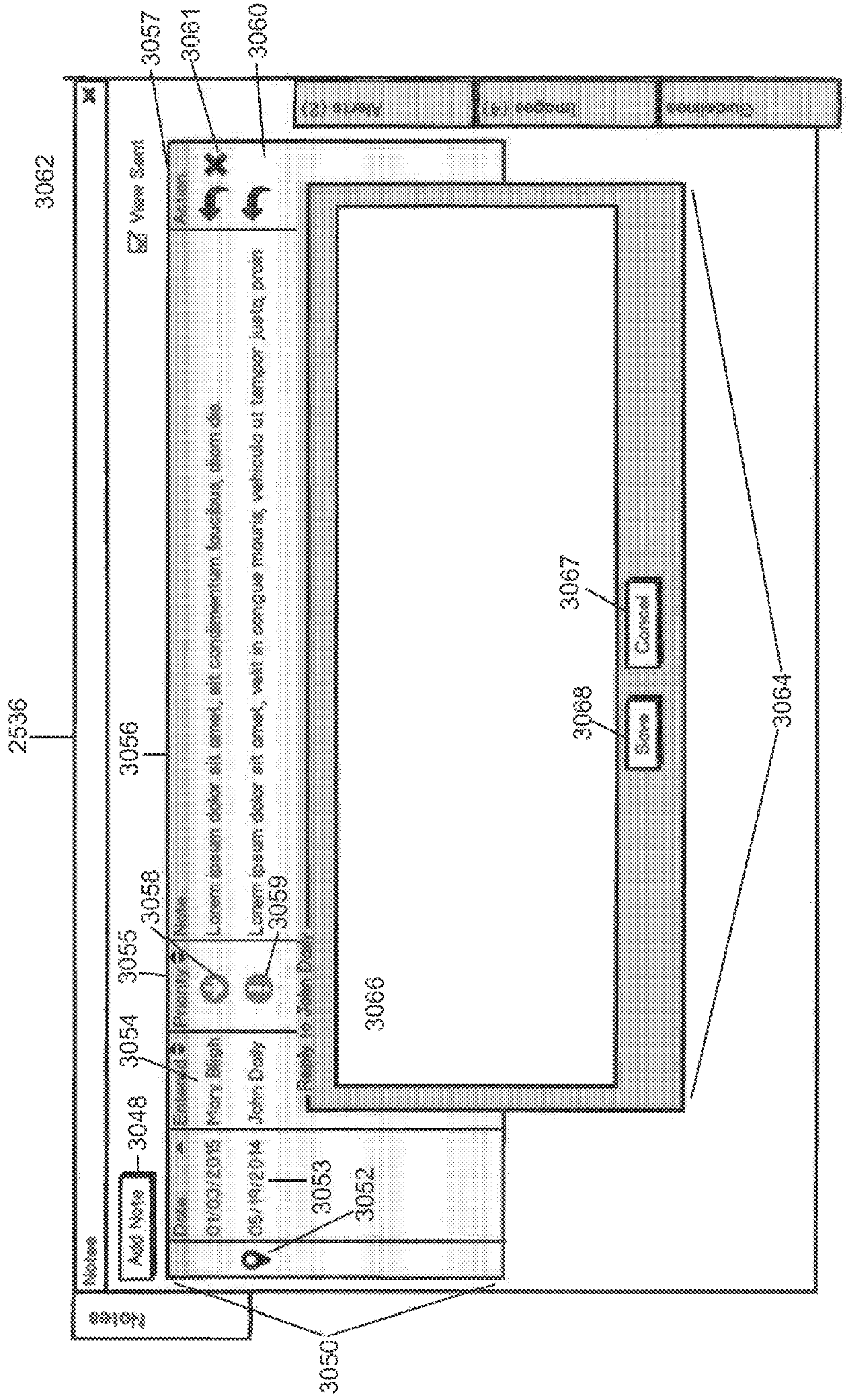
FIG. 38 illustrates a view of the Notes tab in accordance with the second embodiment.
Figure 39:
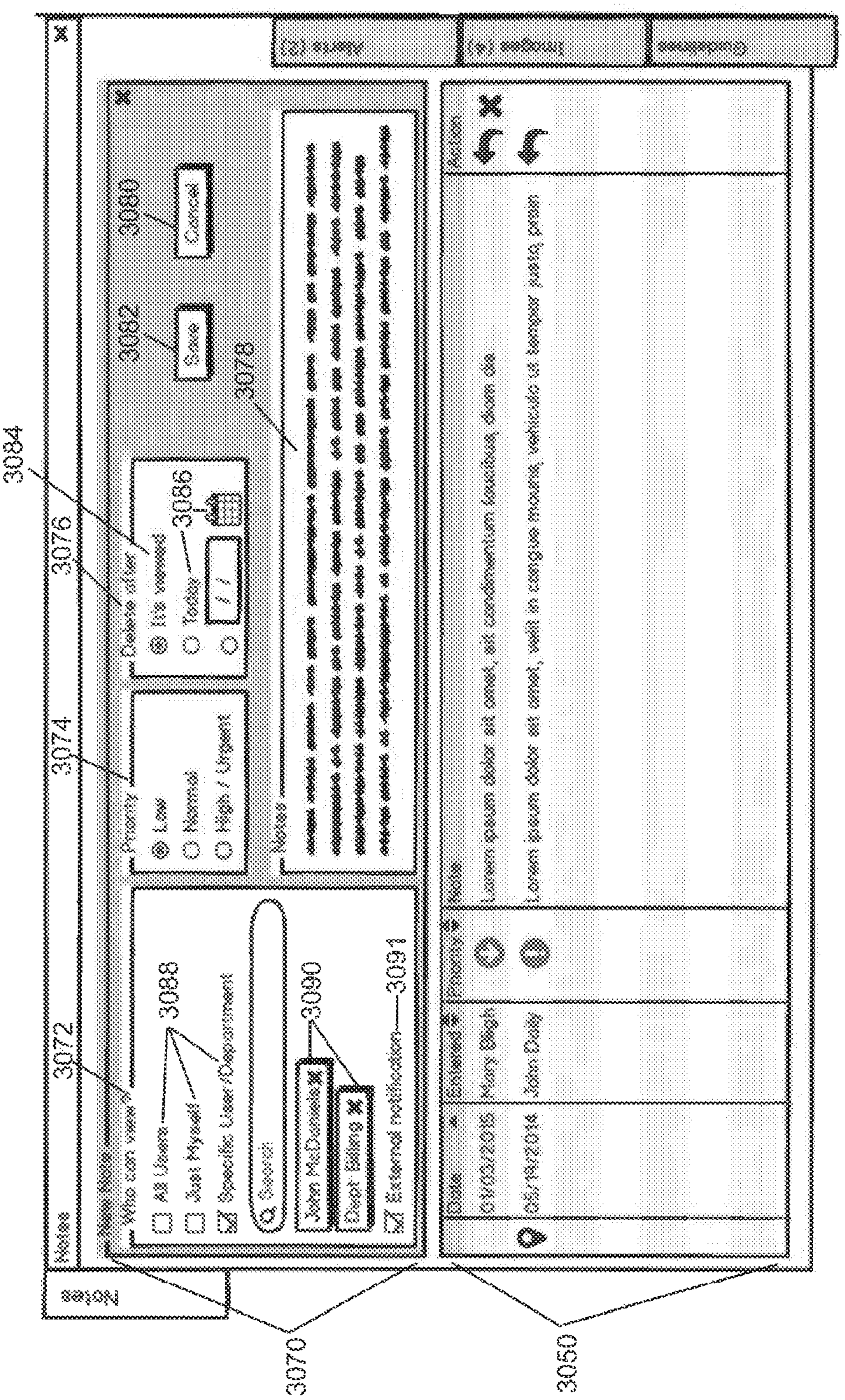
FIG. 39 illustrates how the Command Center enables the user to add notes in accordance with the second embodiment.

FIG. 38 presents a view of the Notes tab 2536. The Notes tab 2536 displays notes associated to the patient and may be used to create new notes. An Add Note button 3048 allows a user to create anew Note record (FIG. 39). A table 3050 presents the Note records previously created for this patient. The table contains several unique items, including: a map placement icon 3052 linking the record to a specified location in the system, the date the Note was created 3053, the user who created the Note 3054, the user specified priority of the note 3055, a preview of the note 3056, and the actions that the current user may perform 3057. The available priorities 3055 are low (3058), Normal (not shown), or High/Urgent (3059). Available actions may include the ability to reply to the Note (3060) or delete the Note (3061). The View Sent checkbox 3062 allows the user to select if the table filters records sent by the user from the list displayed in the table 3050. Selecting the reply object 3060 opens a new window 3064, which includes a free text entry field 3066, a Cancel button 3067, and a Save button 3068. Selection of the Cancel button 3067 causes the window to close without saving the text 3066. Selection of the Save button 3068 creates a new note.

FIG. 39 illustrates how the CC 2500 enables the user to add notes. The bottom of the page contains the table 3050 described in detail above with respect to FIG. 38. The top of the page displays the Add Note panel 3070 for creating a new note. The panel 3070 collects data for the note, including: the intended viewership 3072, the note's priority 3074, and the intended retention period of the note (3076). The panel 3070 also contains a free text entry field 3078, a Cancel button 3080, and a Save button 3082. The note's priority 3074 may be set to Low, Normal, or High/Urgent. The retention period 3076 of the note may be set to once It's viewed 3084 or after a given date 3086. The intended viewership 3072 may be restricted by the controls 3088. The list of approved viewers is presented as tags 3090. Selecting the External notifications checkbox 3091 will cause Command Center to send the note to the user's EMR. Selection of the Cancel button 3080 causes the panel to close without saving the text 3078. Selection of the Save button 3082 creates a new note.

Figure 40:
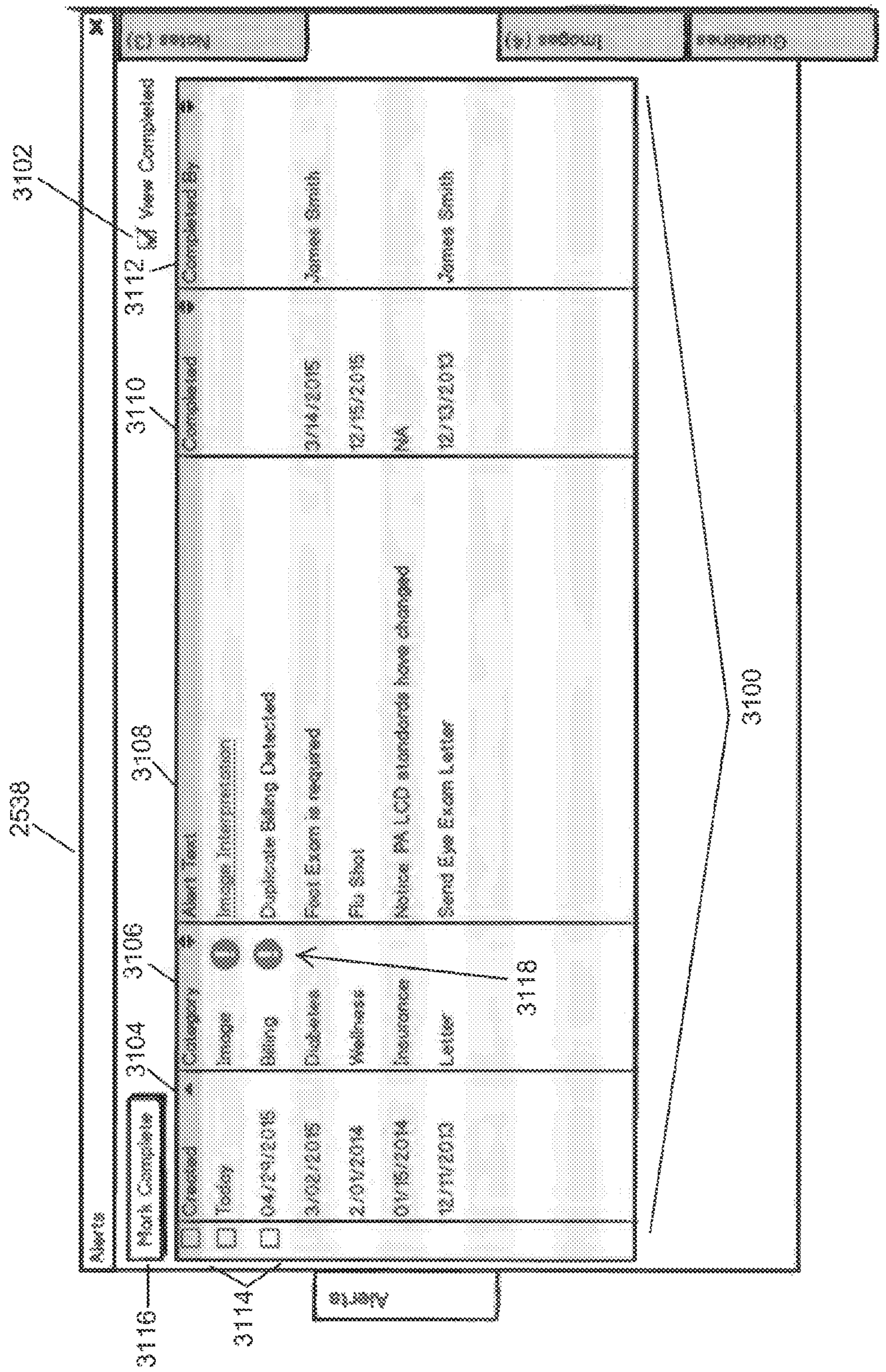
FIG. 40 illustrates a view of the Alerts tab notes in accordance with the second embodiment.
Figure 63:
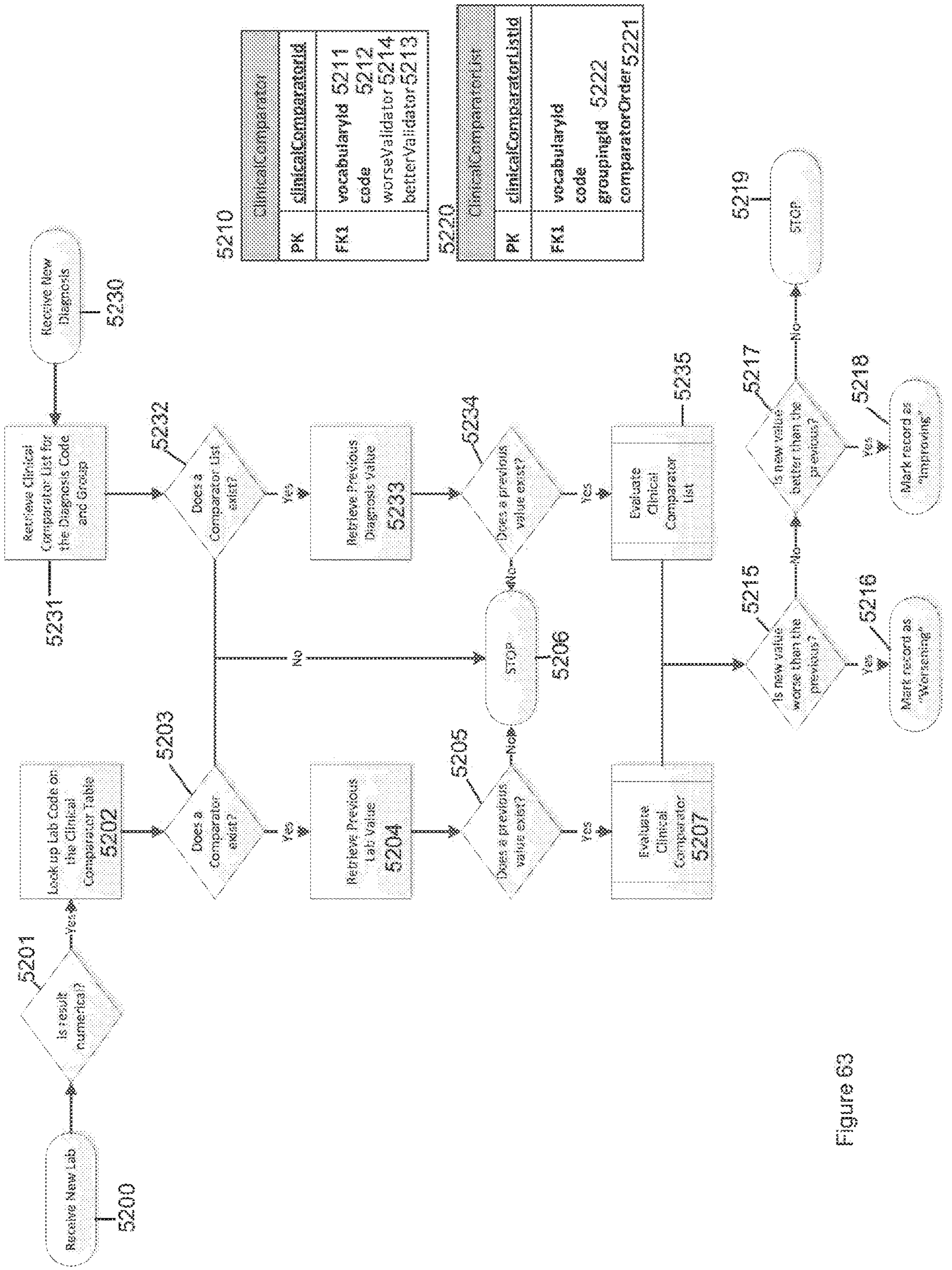
FIG. 63 illustrates a flowchart of the Clinical Evaluation Algorithm in accordance with the tool described herein.

FIG. 40 illustrates a view of the Alerts tab 2538. The Alerts tab 2538 displays a table 3100 of Alerts created for this patient. The View Complete checkbox 3102 allows the user to select if the table filters completed records 3100. In an exemplary embodiment, the table 3100 contains: the date created 3104, the Alert category 3106, Alert subject 3108, date completed 3110 (if applicable), and the user who completed the alert (3112) (if applicable). Alerts are marked as complete by selecting the appropriate checkbox 3114 and the Mark Complete button 3116. Priority Alerts are designated by an icon 3118 in the Category 3106 column. Categories 3106 are driven by conditions, medications, procedures, or other process management algorithms. FIG. 63 described below details the Clinical Decision Support used to create the alerts.

Figure 41A:
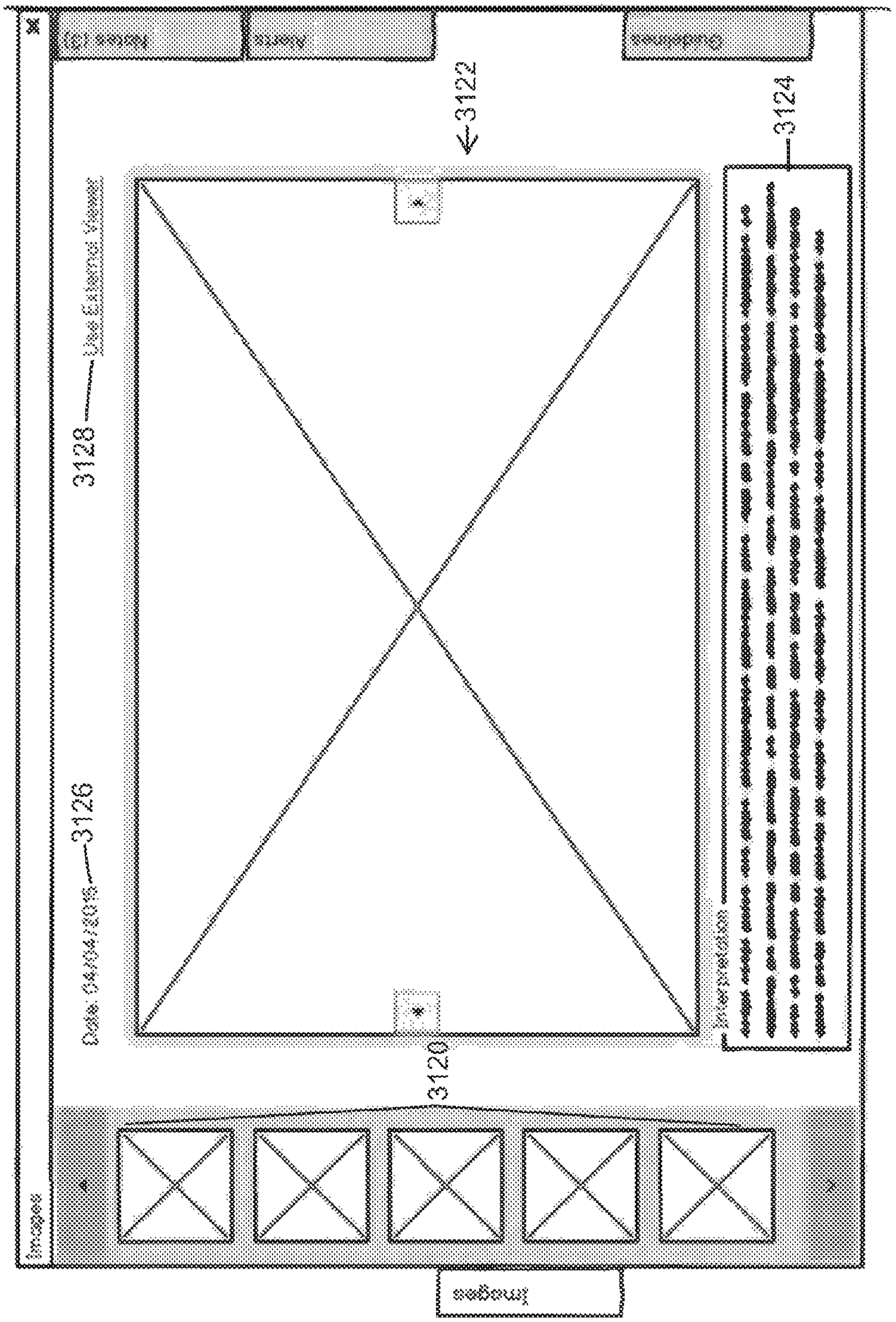
FIG. 41A illustrates a view of the Image tab in accordance with the second embodiment.

FIG. 41A illustrates a view of the image tab 2540. A ribbon 3120 of patient images is displayed along the left side of the interface with a selected image 3122 enlarged for more detailed examination. Interpretation text 3124 associated with the image is presented along with the date 3126 the image was captured. A link 3128 opens the image with an external viewer.

Figure 41B:
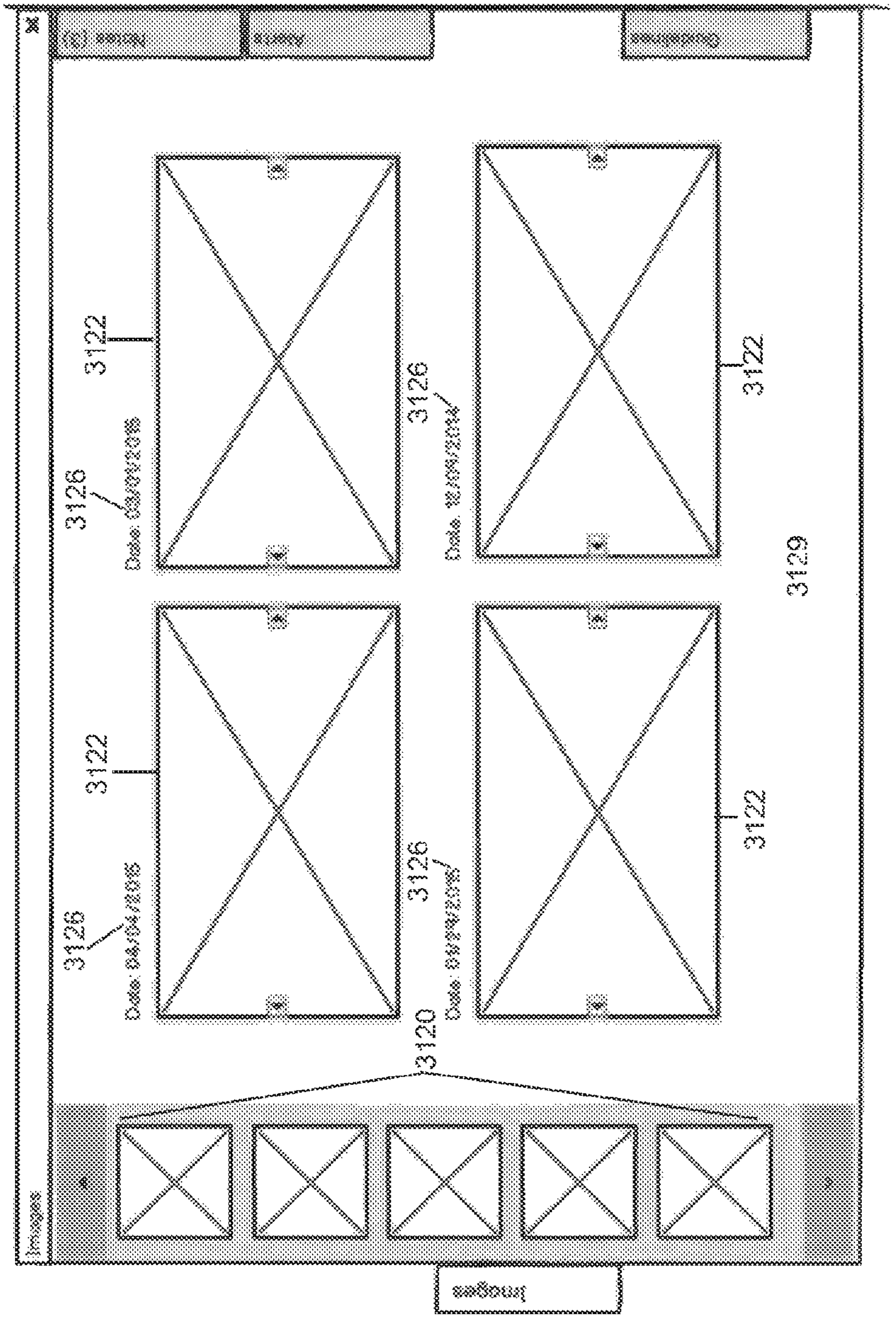
FIG. 41B illustrates an alternative presentation of the Image tab in accordance with the second embodiment.

In an alternative presentation of image tab 2540 in FIG. 41B, users may drag multiple images onto the viewing area 3129 allowing the user to compare similar images to see changes over time or different image types for a more complete understanding of the body part imaged. The images 3122 will snap or be fixed to a grid layout by default but may also be specifically placed in the viewing area to improve the user's ability to interpret the images (not depicted). Images may be acquired through connectivity with a variety of diagnostic equipment and/or a PACS (Picture Archiving and Communication System) and the images displayed are either PDF representations or the DICOM (Digital imaging and Communication in Medicine) images themselves allowing for complex image manipulation. As noted herein, such images may be ordered directly from the Retina Flowsheet 2530 by selecting an image icon within the flowsheet (FIG. 34A) or by opening the Add Imaging Order panel (FIG. 48 described below). It is noted that use of a third-party imaging vendor may require the user to navigate to a separate screen where the software of the third-party vendor would look at all diagnostic tests.

Figure 42A:
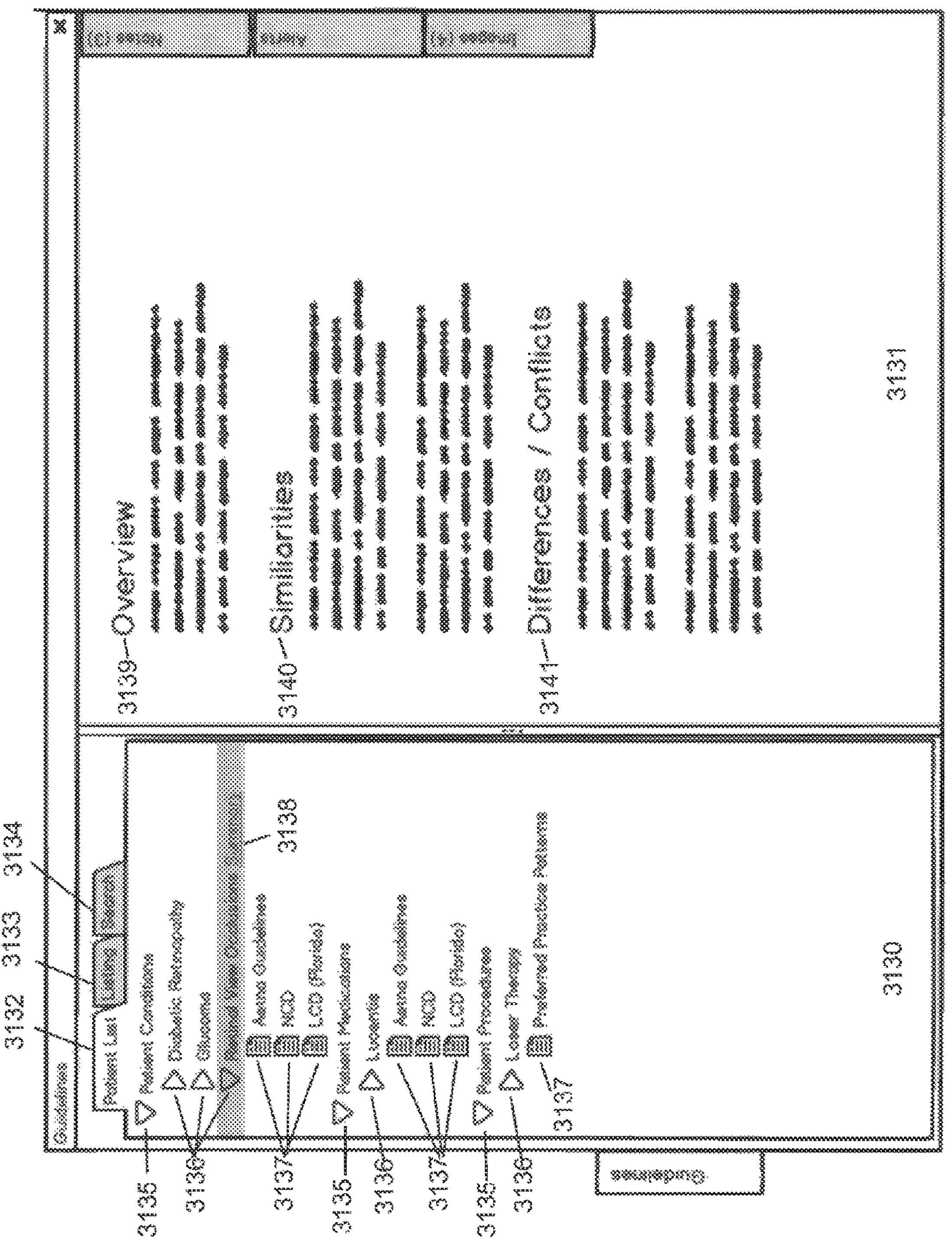
FIG. 42A illustrates a view of the Guidelines Summary tab in accordance to second embodiment.

FIG. 42A illustrates a view of the Guidelines Summary tab 2542. There are two panels on this tab: a tabbed navigation panel 3130 and a content panel 3131. The navigation panel 3130 has three tabs, the Patient List tab 3132 which presents a patient-specific list based on the patient's identified insurance, conditions, procedures and medications, the Listing tab 3133 presents an indexed view of all available guidelines, and a Search tab 3134. The Patient List tab 3132 options are categorized into three lists 3135: conditions, medications, and procedures. Each list 3135 contains unique items 3136 and presents applicable guidelines 3137 for each item 3136. The content panel 3131 presents an amalgamated Summary 3138 of associated guidelines when an item 3136 is selected. The summary 3138 provides an Overview 3139 of the guidelines, presents areas where the guidelines agree as Similarities 3140, and areas where there is not agreement in the guidelines as Differences/Conflicts 3141. This allows a user to quickly understand complex insurance billing guidelines and clinical practices and optimizes their ability to make sound clinical judgements and accurately bill.

Figure 42B:
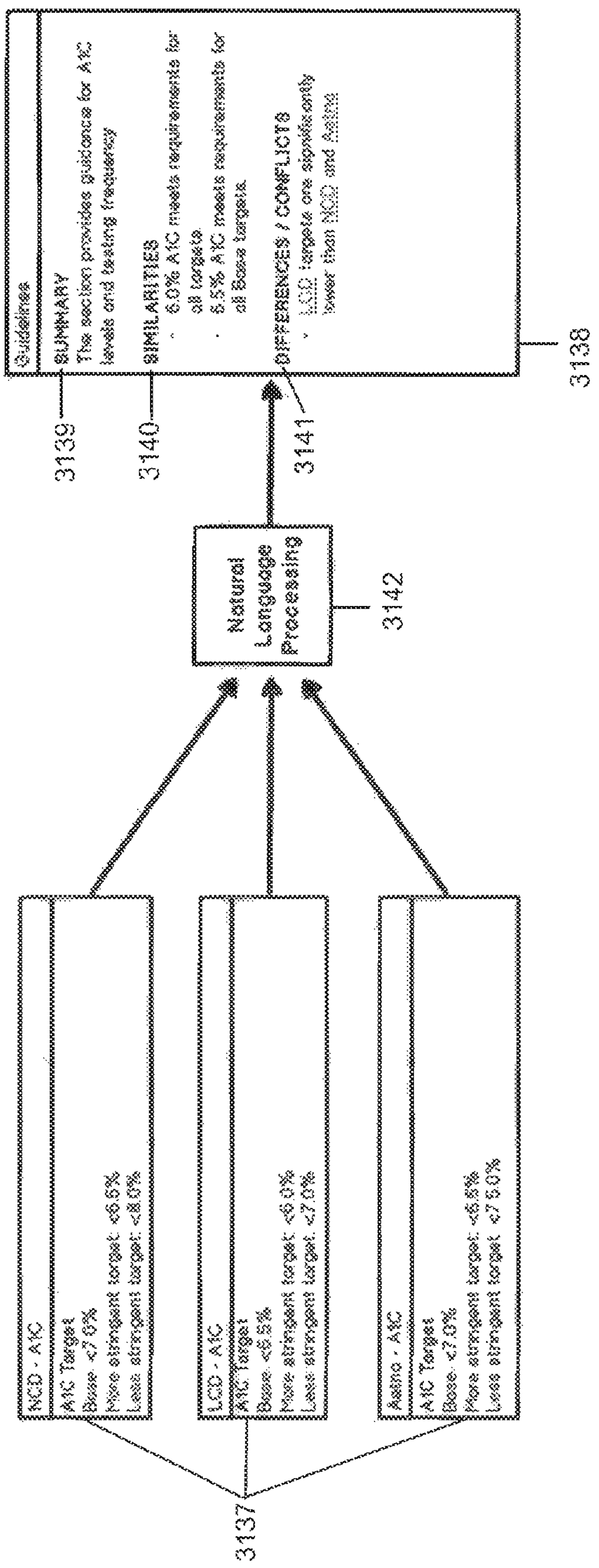
FIG. 42B illustrates an exemplary cognitive system enhanced clinical decision support system for providing cognitive enhanced guidance analysis and summary.

The Guidelines Summary may be enhanced using a cognitive system enhanced Clinical Decision Support ("CDS") system of type described below with respect to FIG. 72B to provide the summary 3138 shown in the content panel 3131 of associated guidelines illustrated in FIG. 42A. FIG. 42B presents a population process with disparate content encountered from various guideline jurisdictions 3137. Commercially available Natural Language Processing 3142 is used to contextually parse the language of the guidelines 3137 and to present the user with a unified summary 3138 including overview 3139, similarities 3140, and differences/conflicts 3141 described above. The cognitive system enhanced CDS thus augments the practitioner's judgement by representing a holistic view of relevant guidance.

Figure 43:
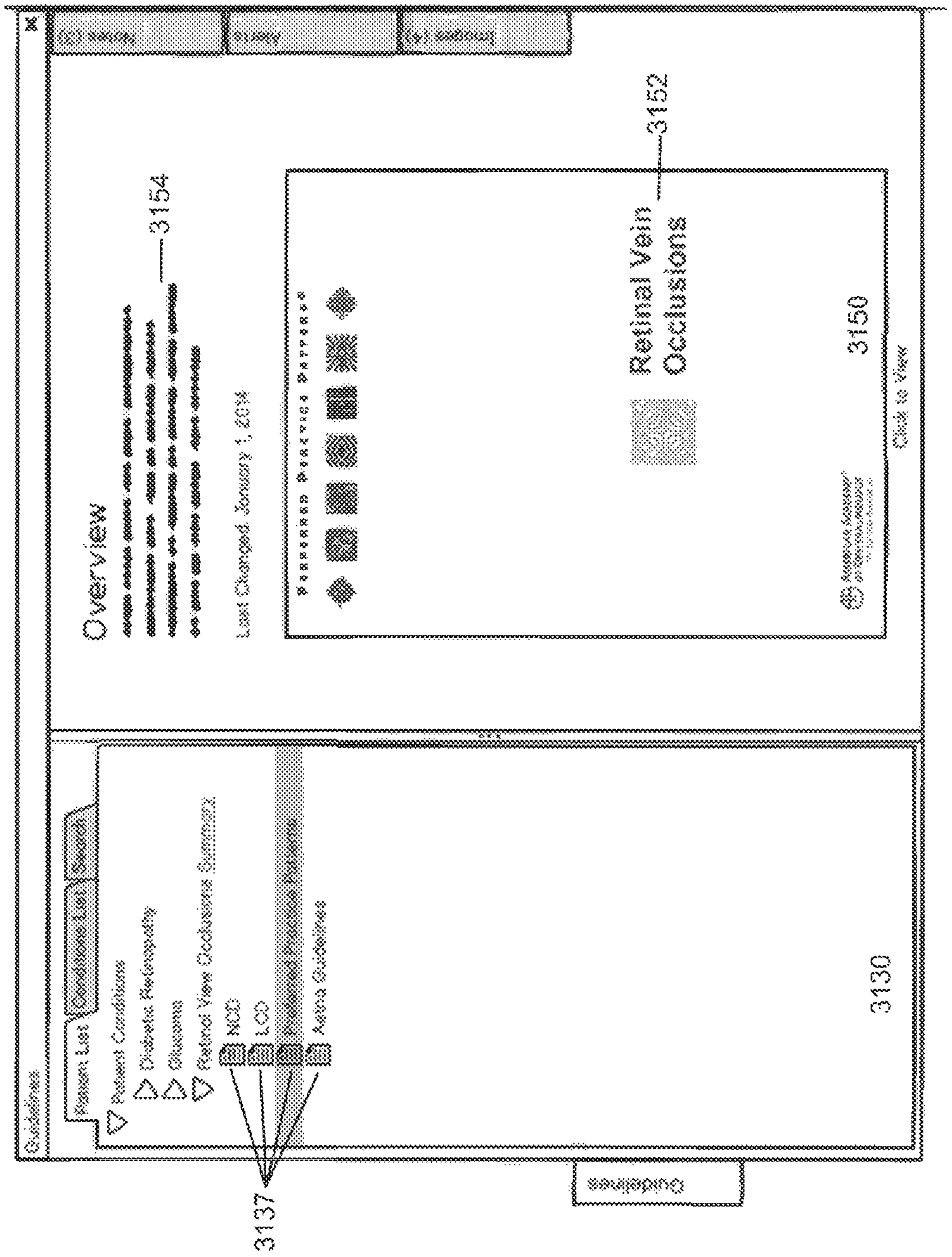
FIG. 43 illustrates a view of the Published Guidelines in accordance with the second embodiment.

FIG. 43 illustrates a view of the Published Guidelines, which may include Preferred Practice Patterns, and which may be accessed by selecting the physician icon 2932 in the header of the flowsheet (FIG. 32B), the guidelines tab 2542 (FIG. 15), and in each of the ordering panels for labs (FIG. 46), medications (FIG. 44), procedures (FIG. 51), and imaging (FIG. 48). The Smart Evaluation Panel in each of the order screens reference the Preferred Practice Patterns which may be used to track the physicians' activities. In FIG. 43, there are two panels: the tabbed navigation panel 3130 and a content panel 3150. The content panel 3150 presents a copy of the published guideline 3152 and an Overview 3154 of the guideline when that guideline 3137 is selected in navigation panel 3130. Clicking on the guideline 3152 opens the actual guideline.

The next few sections describe methods for ordering medications, labs, procedures, and imaging tests. Each unique panel has the ability to order the relevant items but also provides information about compliance with insurance guidelines, good clinical practice recommendations, provides cost-effective medically equivalent alternatives along with costs and pricing either in a hospital or outpatient selling allowing the clinical and patient may decisions that are both clinically and financially sound. These panels are presented as overlays or pop-up windows on the page allowing the user to easily see relevant medical information, critical notes, alerts and recommendations without leaving the ordering functions in the Command Center 2500. The user thus can understand the patient's complete medical history across institutions while placing a new order without having to switch contexts like within the typical EMR. By visualizing patterns and trends at the point of care, the user can better tailor the medications, labs, procedures, and imaging test they order to what is medically indicated.

Figure 44:
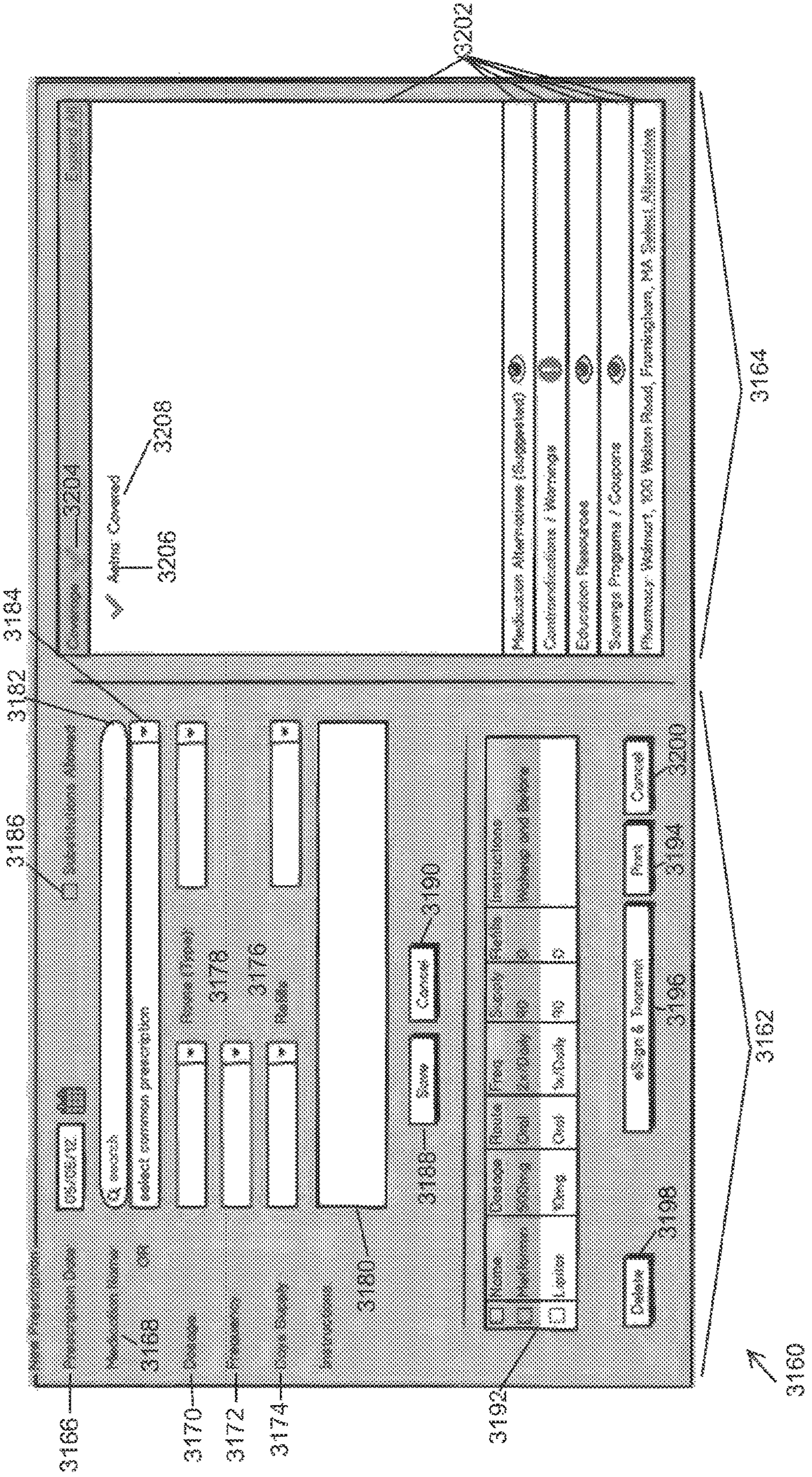
FIG. 44 illustrates a view of the Medication Order panel in accordance with the second embodiment.

FIG. 44 illustrates a view of the Medication Order panel 3160, which may be accessed from the Retina Flowsheet 2530 or may be provided as a separate display panel in the Command Center 2500. The Medication Order panel 3160 allows authorized users to order prescriptions for patients. There are two sections to the Medication Order panel 3160, a prescription section 3162 and a Smart Evaluation control section 3164. The prescription section 3162 allows the user to enter a prescription including: the prescription date 3166, medication name 3168, dosage 3170, frequency 3172, days' supply 3174, refills 3176, Route (Type) 3178, and text instructions 3180. The user can search for a medication using the search dialog 3182 or quickly select common prescriptions from the dropdown menu 3184. Allowing the pharmacist to make substitutions can be indicated with the checkbox 3186. The prescription can be saved 3188 or canceled 3190. Saved prescriptions are listed 3192 and they may be printed 3194, electronically transmitted 3196 to a selected pharmacy, or deleted using the associated checkboxes and Delete button 3198. The Cancel button 3200 will close the Medication Order panel 3160 and discard any unsaved work.

The Smart Evaluation control section 3164 contains six sub panels 3202 which may be toggled open and closed by the user. The Coverage subpanel 3204 presents the patient's insurer(s) 3206 and the coverage status 3208 of the selected prescription(s) 3192. In exemplary embodiments, the coverage status is determined by using third party services. The Smart Evaluation control section 3164 is a core aspect of combining clinical, financial, and insurance guidelines together into one display. The Smart Evaluation control section displays information related to insurance compliance, clinical guideline recommendations, recommendations for cheaper alternatives (drug cost advisor), pricing data from a hospital, practice and a patient's perspective all in the same display panel and all in the context of the patient's past medical history.

Figure 45:
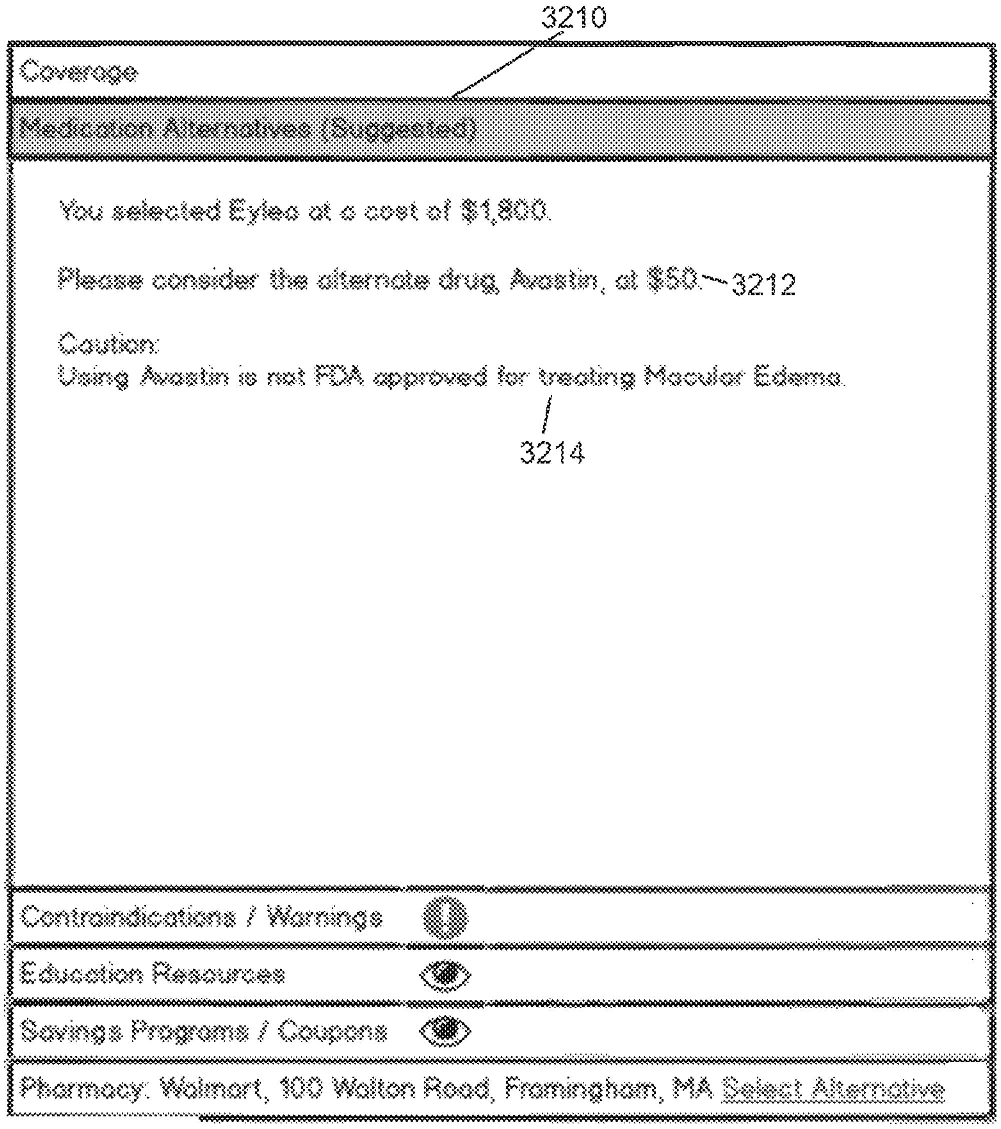
FIG. 45 illustrates the Medication Alternatives (Suggested) sub panel of the six sub panels illustrated in FIG. 44.

FIG. 45 illustrates the Medication Alternatives (Suggested) sub panel 3210 of the six sub panels 3202 illustrated in FIG. 44. The Medication Alternatives (Suggested) sub panel 3210 suggests alternative medications 3212 along with cautionary statements 3214 about its use. In exemplary embodiments, the alternative medication and pricing information are determined by using third party services.

Figure 46:
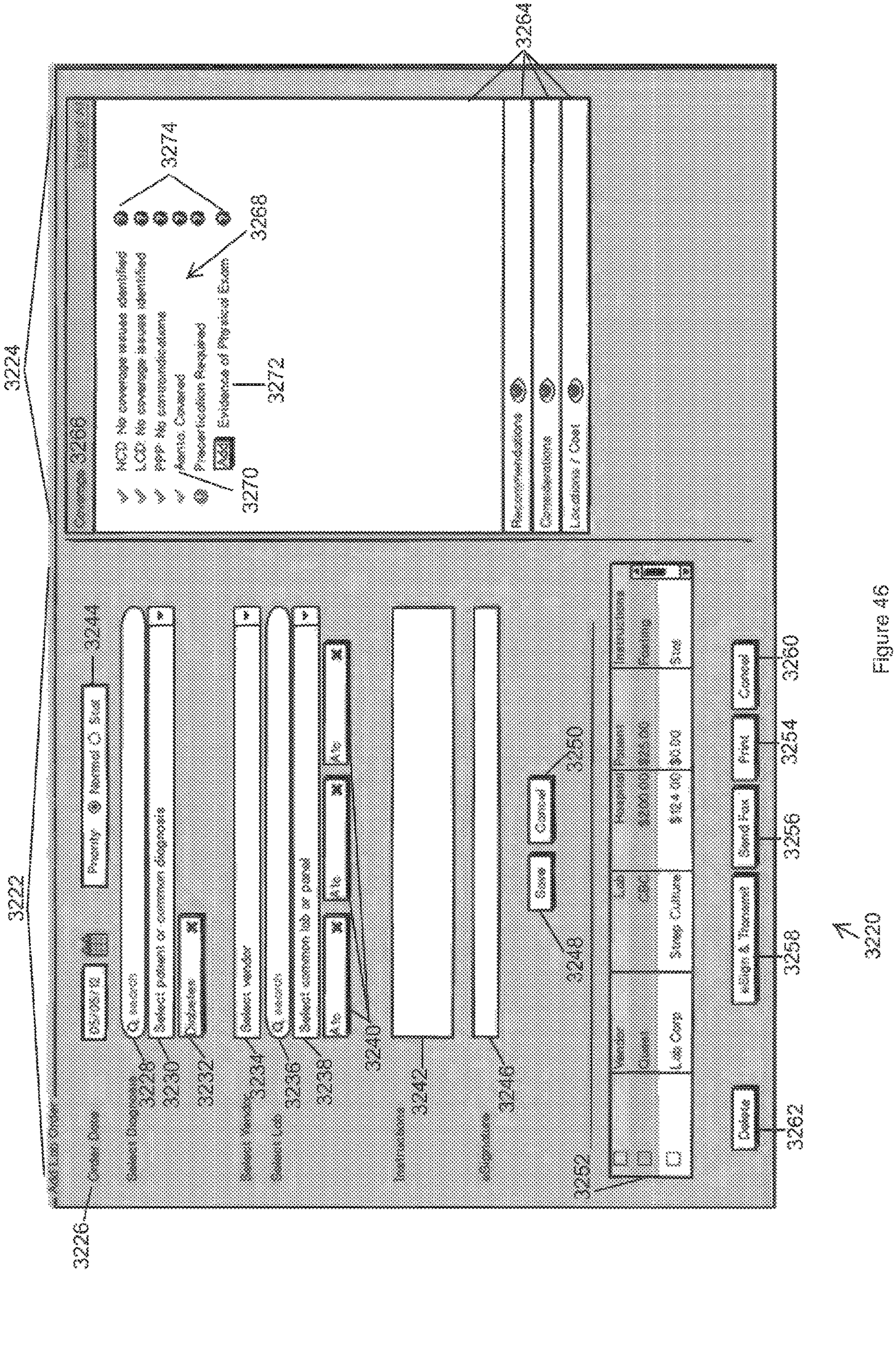
FIG. 46 illustrates a view of the Lab Order panel in accordance with the second embodiment.

FIG. 46 illustrates a view of the Lab Order panel 3220, which may be accessed from the Retina Flowsheet 2530 or may be provided as a separate display panel in the Command Center 2500. The Lab Order panel 3220 allows authorized users to order labs for patients. There are two sections to the panel, a Lab Activity section 3222 and the Smart Evaluation control section 3224. The Lab Activity section 3222 allows the user to enter a lab order including the order date 3226, associated diagnosis supporting the lab testing using either a search box 3228 or a drop down menu 3230, selected diagnosis as tags 3232, vendor selection 3234, and to search using a search box 3236 or to select commonly ordered labs from a drop down menu 3238, and a list of test ordered as tags 3240, along with instructions 3242. The priority is indicated with the checkbox 3244. An e-signature box 3246 is present for completing the lab order. Lab tests may be saved 3248 or canceled 3250 using the proper buttons. Selected lab tests 3252 may be printed 3254, electronically faxed 3256, electronically transmitted 3258 to a selected vendor, canceled 3260, or deleted 3262 with the associated buttons. The Cancel button 3260 will close the panel and discard any unsaved work.

The Smart Evaluation control panel 3224 contains four sub panels 3264 that may be toggled open and closed by the user. The Coverage subpanel 3266 presents an evaluation of whether or not the patient's insurance 3268 will cover 3270 the ordered tests 3252. Coverage subpanel 3266 also presents any precertification requirement 3272 and if a specific action is required. In the example demonstrated here, the patient primary insurance is Aetna and secondary insurance is Medicare. The Preferred Practice Guidelines are also evaluated. The question marks 3274 may also be activated to see more detail. In an exemplary embodiment, this evaluation is determined by using third party services.

Figure 47:
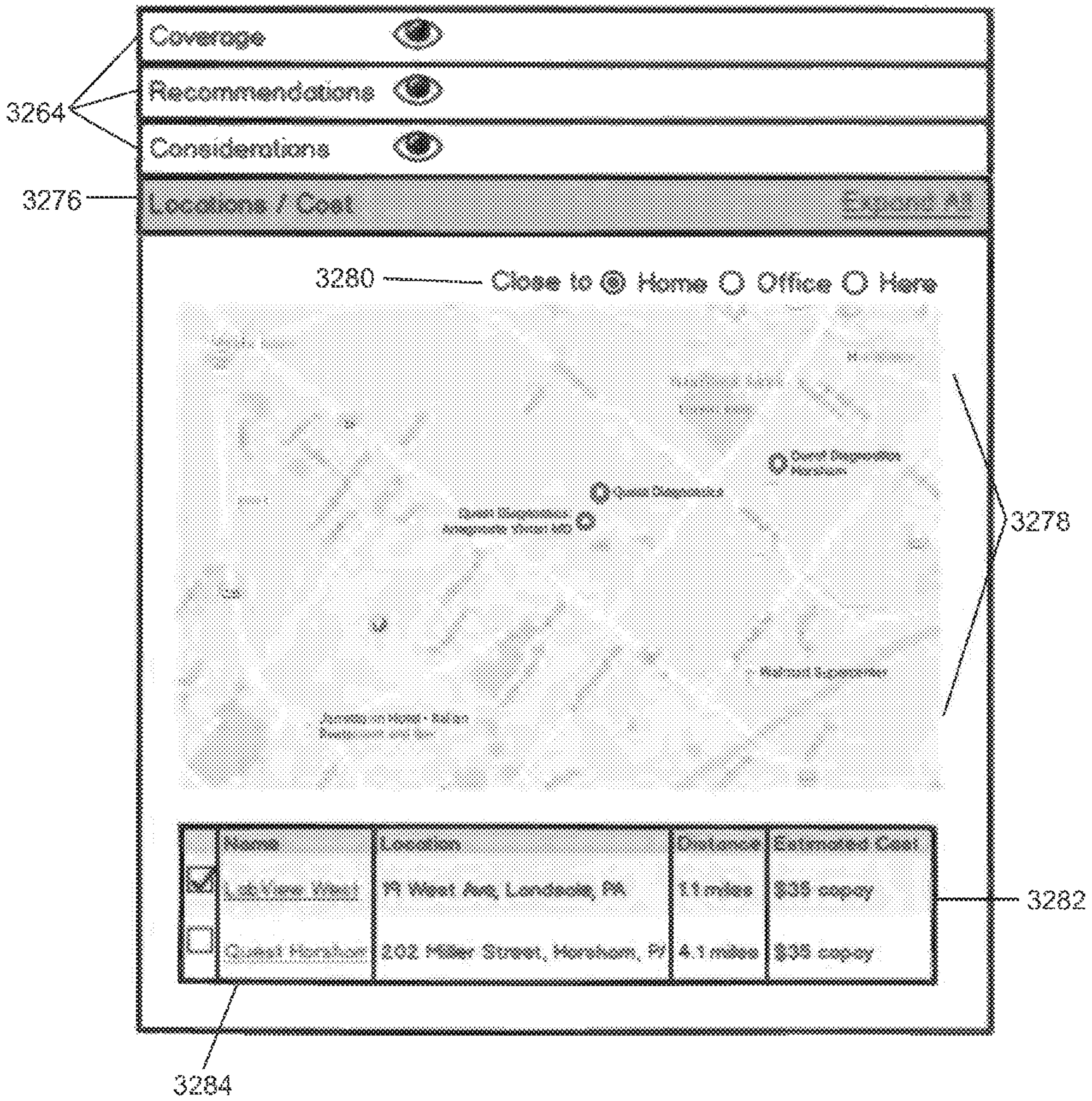
FIG. 47 illustrates the Locations/Costs sub panel of the sub panels of FIG. 46.

FIG. 47 illustrates the Locations/Costs sub panel 3276 of the sub panels 3264 of FIG. 46. The Locations/Costs sub panel 3276 provides a map 3278 with locations of vendors relative to selected locations 3280 (such as the patient's home, work, or provider's office). The Locations/Costs sub panel 3276 also displays the patient's costs (3282) for each vendor and address information in a map legend 3284. In an exemplary embodiment, this information is provided through a third party service.

FIG. 48 illustrates a view of the Imaging Order panel 3290. The Imaging Order panel 3290 allows authorized users to order Imaging for patients. There are two sections to the Imaging Order panel 3290, an Imaging activity section 3292 and the Smart Evaluation control section 3294. The Imaging activity section 3292 allows the user to enter an imaging order including the order date 3296, search using a search box 3298 or select a common associated diagnosis using drop down menu 3300 to supporting the imaging testing, select a diagnosis presented as tags 3302, search using search box 3304 or select common symptoms reported by the patient from a drop down menu 3306, select symptoms displayed as tags 3308, select the imaging modality 3310 with costs to the hospital and patient for each modality, select the location of the body to be imaged 3312 with supporting tags 3314, along with instructions 3316. The priority is indicated with the checkbox 3318. Imaging tests may be saved 3320 or canceled 3322 using the proper buttons.

The Smart Evaluation control panel 3294 contains four sub panels 3324 that may be toggled open and closed by the user. The Coverage subpanel 3326 is an evaluation of whether or not the patient's insurance will cover 3328 the ordered images 3310 and check medical necessity 3330 (per the relevant governmental and/or insurance guidelines).

Figure 49:
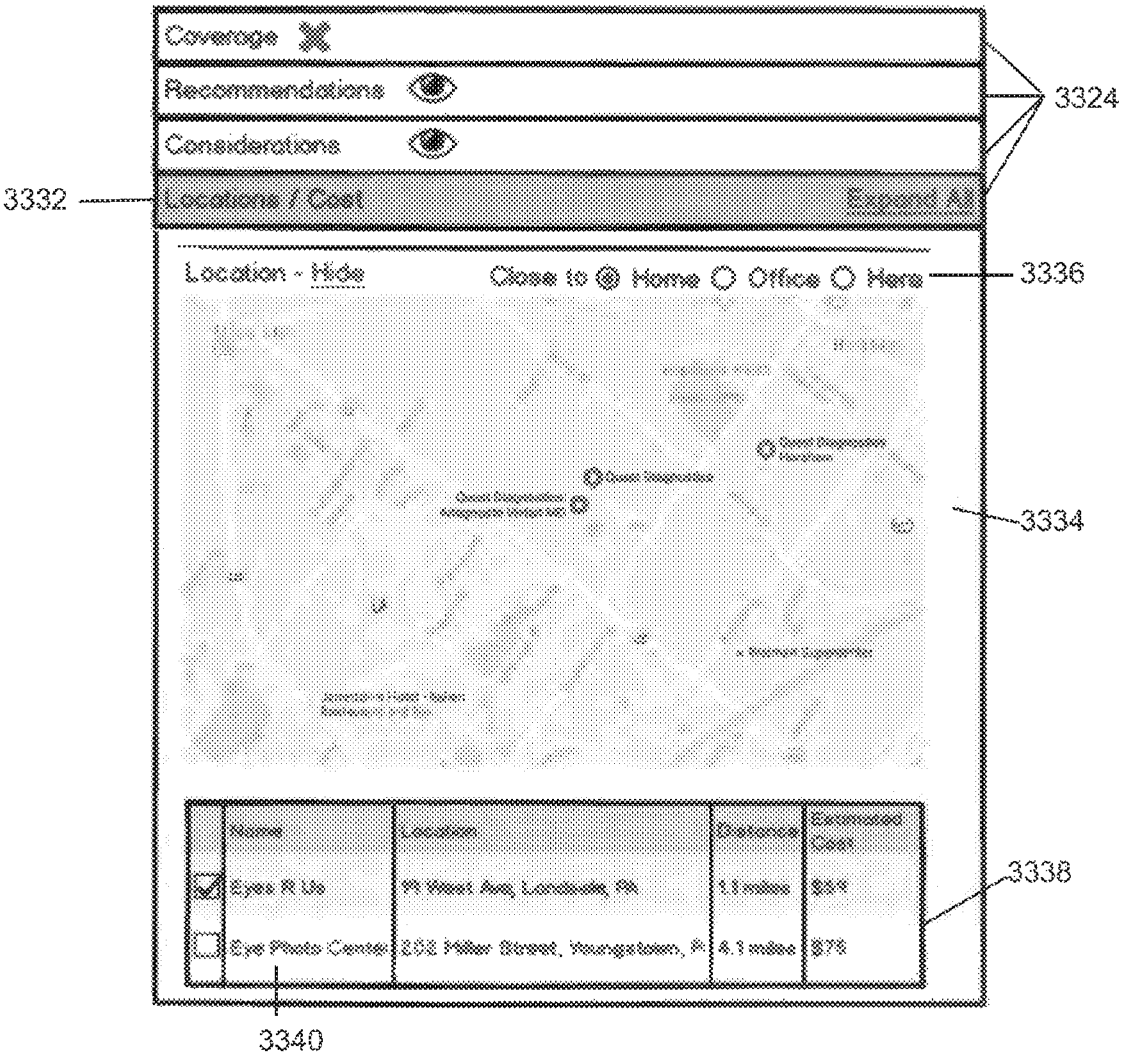
FIG. 49 illustrates the Locations/Cost sub panel of the sub panels illustrated in FIG. 48.

FIG. 49 illustrates the Locations/Cost sub panel 3332 of the sub panels 3324 illustrated in FIG. 48. The Locations/Cost sub panel 3332 provides a map 3334 with locations of vendors relative to selected locations 3336 (such as the patient's home, work, or provider's office). The Locations/Cost sub panel 3332 also presents the patient's costs (3338) for each vendor and address information in a map legend 3340. In an exemplary embodiment, this information will be provided through a third party service.

Figure 50:
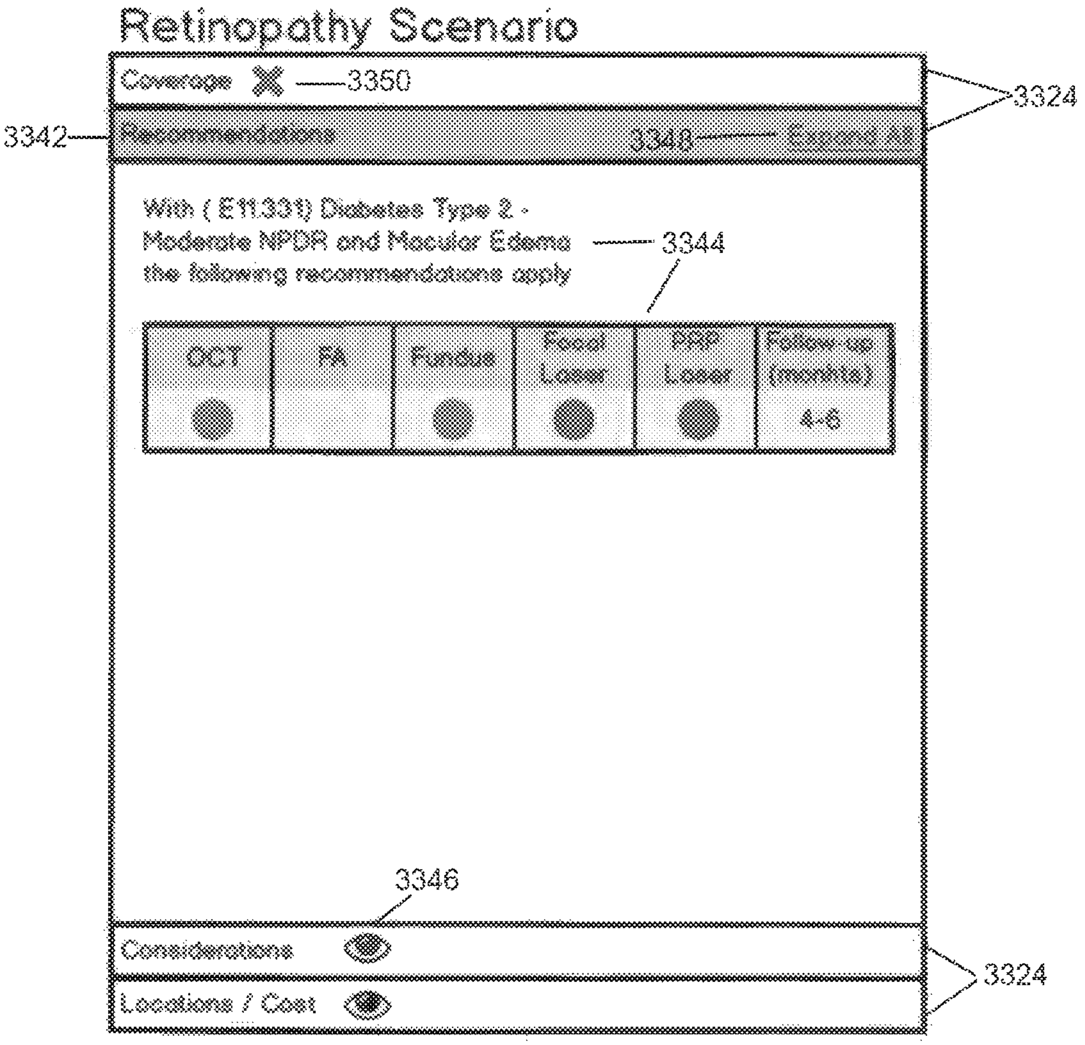
FIG. 50 illustrates the Recommendations sub panel of the sub panels illustrated in FIG. 48.

FIG. 50 illustrates the Recommendations sub panel 3342 of the sub panels 3324 illustrated in FIG. 48. In this example embodiment, the patient has Type 2 Diabetes, Moderate Non-Proliferative Diabetic Retinopathy and Macular Edema. The Recommendations sub panel 3342 provides recommendations for the proper imaging 3344 based on the patient's specified conditions and preferred practice guidelines. The eye icon 3346 on each of these panel headers signifies there is something on the tab. This prevents the user from having to click on each tab to see if anything exists. The user may expand all panels at the same time by clicking the Expand All link 3348 which is always displayed on the active tab. Once all panels are expanded, the active panel header displays a link to Close Other Panels (not depicted). The Coverage panel also displays a green checkmark or a red X icon 3350 to signify whether the selected diagnosis and imaging modality are covered under the patient's insurance.

Figure 51:
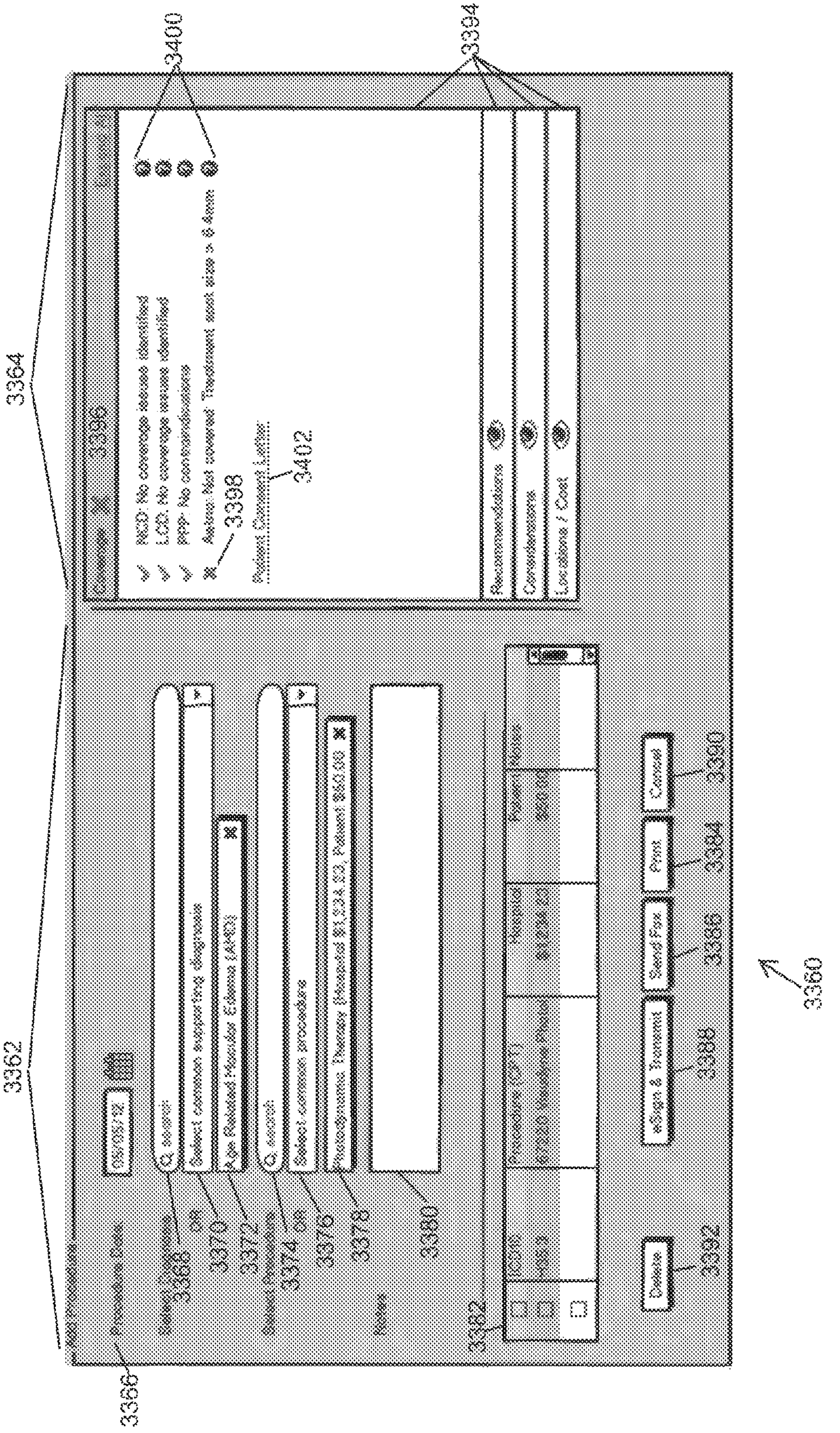
FIG. 51 illustrates a view of the Procedure panel in accordance with the second embodiment.

FIG. 51 illustrates a view of the Procedure panel 3360. The Procedure panel 3360 allows authorized users to order Procedures for patients. There are two sections to the Procedure panel 3360, a Procedure activity section 3362 and the Smart Evaluation control section 3364. The Procedure activity section 3362 allows the user to enter a Procedure including the order date 3366, search using a search box 3368 or select a common associated diagnosis using drop down menu 3370 to supporting the Procedure testing, select diagnoses presented as tags 3372, search using search box 3374 or select a common procedure using a drop down menu 3376, or select procedures displayed as tags 3378, along with notes 3380. The priority may be indicated with a checkbox (not shown). Selected Procedure(s) 3382 may be printed 3384, electronically faxed 3386, electronically transmitted 3388, canceled 3390, or deleted 3392 with the associated buttons. The Cancel button 3390 will close the panel and discard any unsaved work.

The Smart Evaluation control section 3364 contains four sub panels 3394 that may be toggled open and closed by the user. The Coverage subpanel 3396 presents an evaluation of whether or not the patient's insurance will cover 3398 the ordered procedures 3382 and check for medical necessity at 3400. Links 3402 are also presented to any documents that must be completed by the patient like a consent form. In an exemplary use, if a physician decided to schedule a laser treatment for a patient, the physician would input a plan of treatment by selecting the desired procedures from Procedure activity section 3362 and bring in all of the relevant cost data, effectivity, insurance restrictions, ability for the patient to choose care, etc. into Smart Evaluation control section 3364 for review before proceeding. Peer data (FIG. 55) may also be displayed to assist the physician in the decision-making process.

Figure 52:
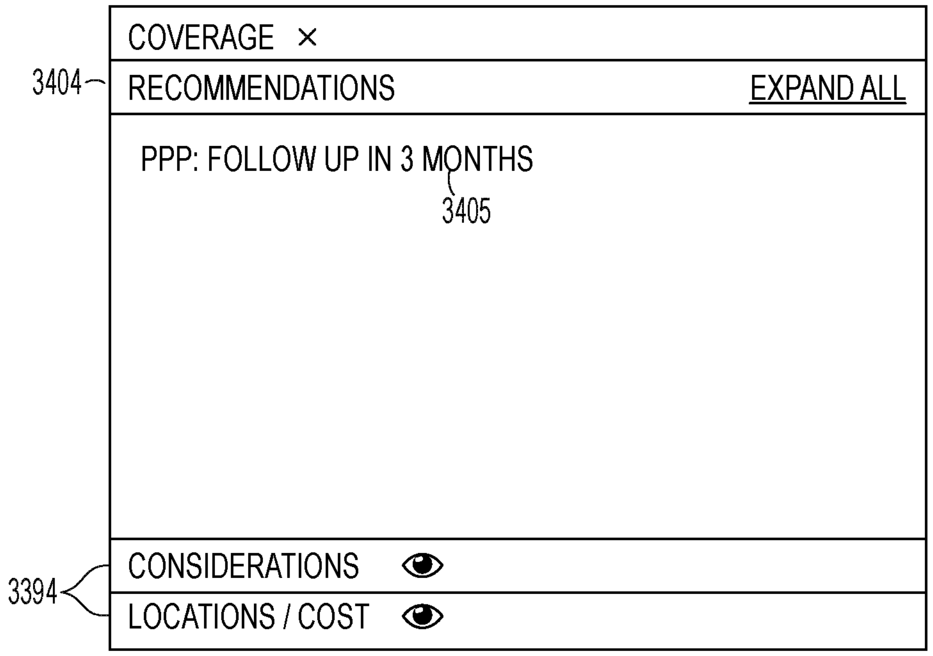
FIG. 52 illustrates the Recommendations sub panel of the sub panels illustrated in FIG. 51.

FIG. 52 illustrates the Recommendations sub panel 3404 of the sub panels 3394 illustrated in FIG. 51. The Recommendations sub panel 3404 provides recommendations 3405 based on the patient's specified conditions, selected procedures and clinical and insurance guidelines. Recommendations may be for alternative procedures based on the patient's condition, insurance regulations and or good clinical practice. Recommendations an also reflect necessary consults, for example rheumatology consult for uveitis. Alternatively, an automated consult request generator may generate prompts showing needed medical referrals based on various database inputs (e.g., rheumatology consult for uveitis). If the patient is already under the care of a rheumatologist, the system will alert the physician of the next scheduled appointment with a rheumatologist, who may, in turn, provide shared care as described with respect to FIG. 25A. In exemplary embodiments, this information is provided through a third party service.

Figure 53:
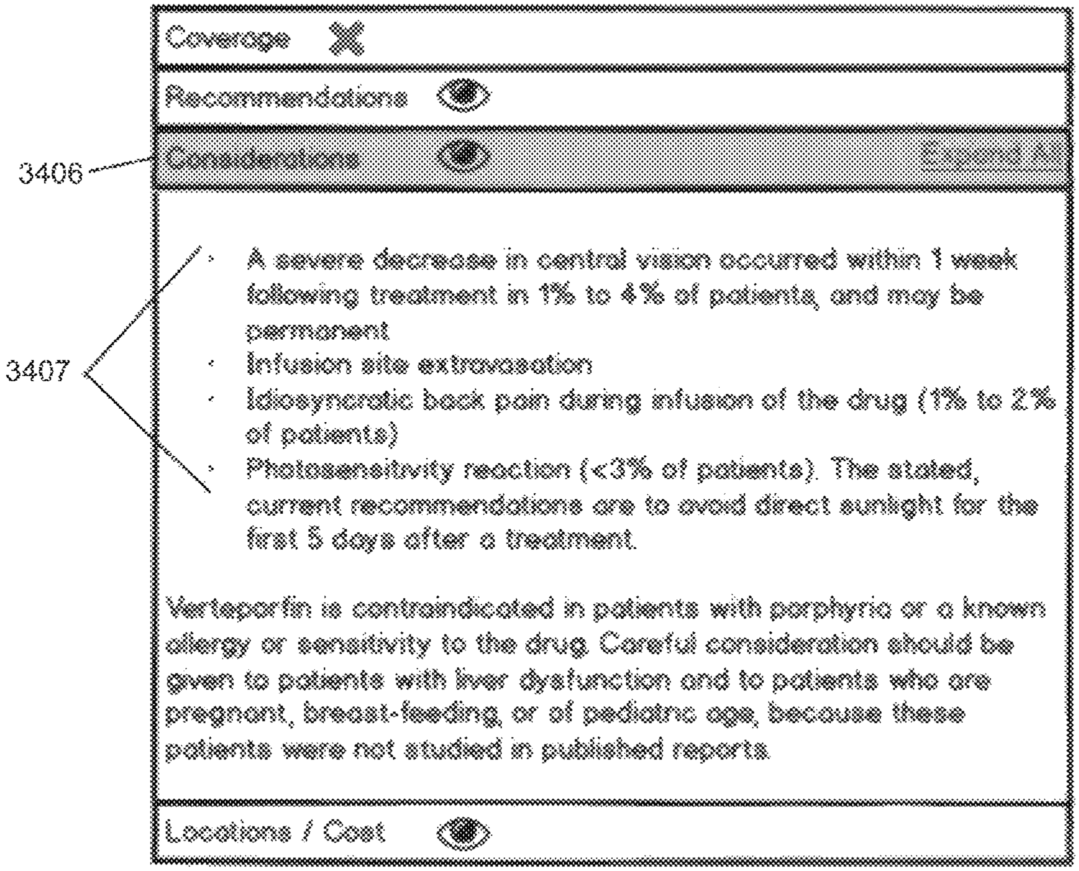
FIG. 53 illustrates the Considerations sub panel of the sub panels illustrated in FIG. 51.

FIG. 53 illustrates the Considerations sub panel 3406 of the sub panels 3394 illustrated in FIG. 51. The Considerations sub panel 3406 provides additional considerations 3407 a user may want to consider when evaluating procedures based on the patient's specified conditions and clinical and insurance guidelines. In exemplary embodiments, this information is provided through a third party service.

Figure 54:
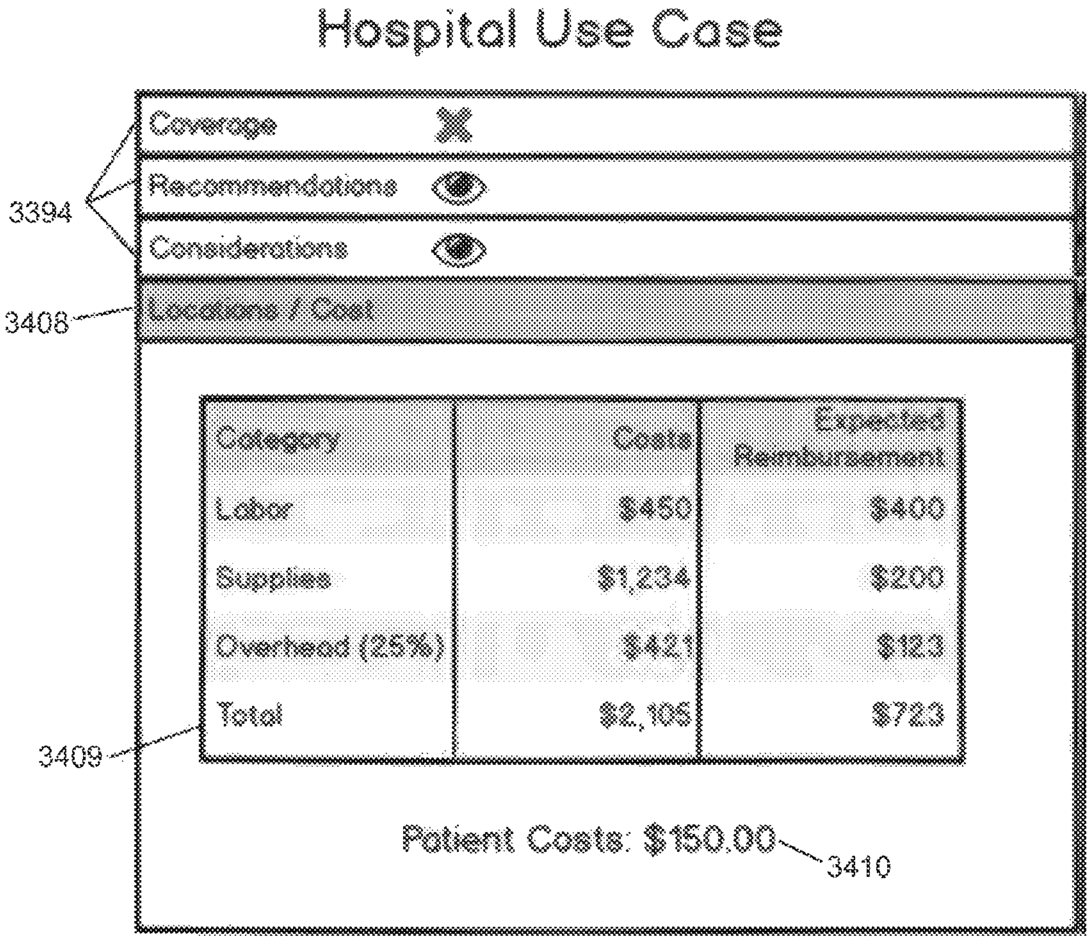
FIG. 54 illustrates the Locations/Costs sub panel of the sub panels illustrated in FIG. 51.

FIG. 54 illustrates the Locations/Costs sub panel 3408 of the sub panels 3394 illustrated in FIG. 51. The Locations/Costs sub panel 3408 is an embodiment of the panel as used in a hospital setting. The Locations/Costs sub panel 3408 provides a table 3409 with the associated costs and estimated reimbursement for the selected procedure to help the physician better understand the financial implications of providing the service. The Locations/Costs sub panel 3406 also presents the patient's estimated costs 3410. Where a medically equivalent but less costly alternative is available, it will be presented to the user (not depicted). In exemplary embodiments, this information is provided by the hospital itself from their charge sheet and accounting system and the patient costs from 3$^{rd}$ party services.

Figure 55A:
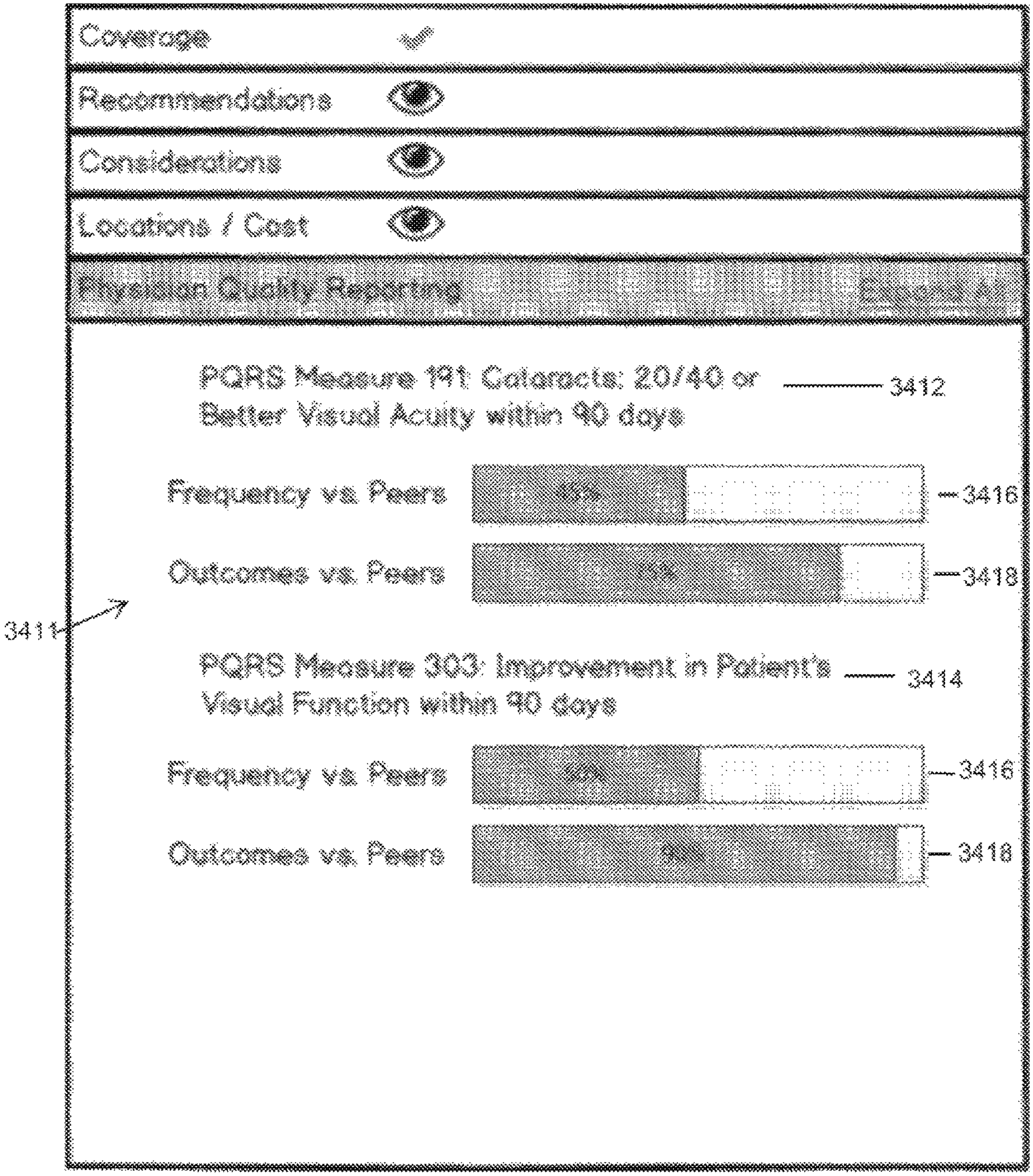
FIG. 55A illustrates a Physician Quality Reporting panel within the Smart Evaluation control panel.

FIG. 55A illustrates a Physician Quality Reporting panel 3411 within the Smart Evaluation control panel. The Physician Quality Reporting panel 3411 displays Physician Quality reporting metrics 3412, 3414 related to the procedure that is being ordered. Other quality reporting or peer data may be displayed. For each relevant metric, the Physician Quality Reporting panel 3411 displays the physician's frequency of performing the procedure in comparison to their peers 3416 as well as outcomes 3418.

Figure 55B:
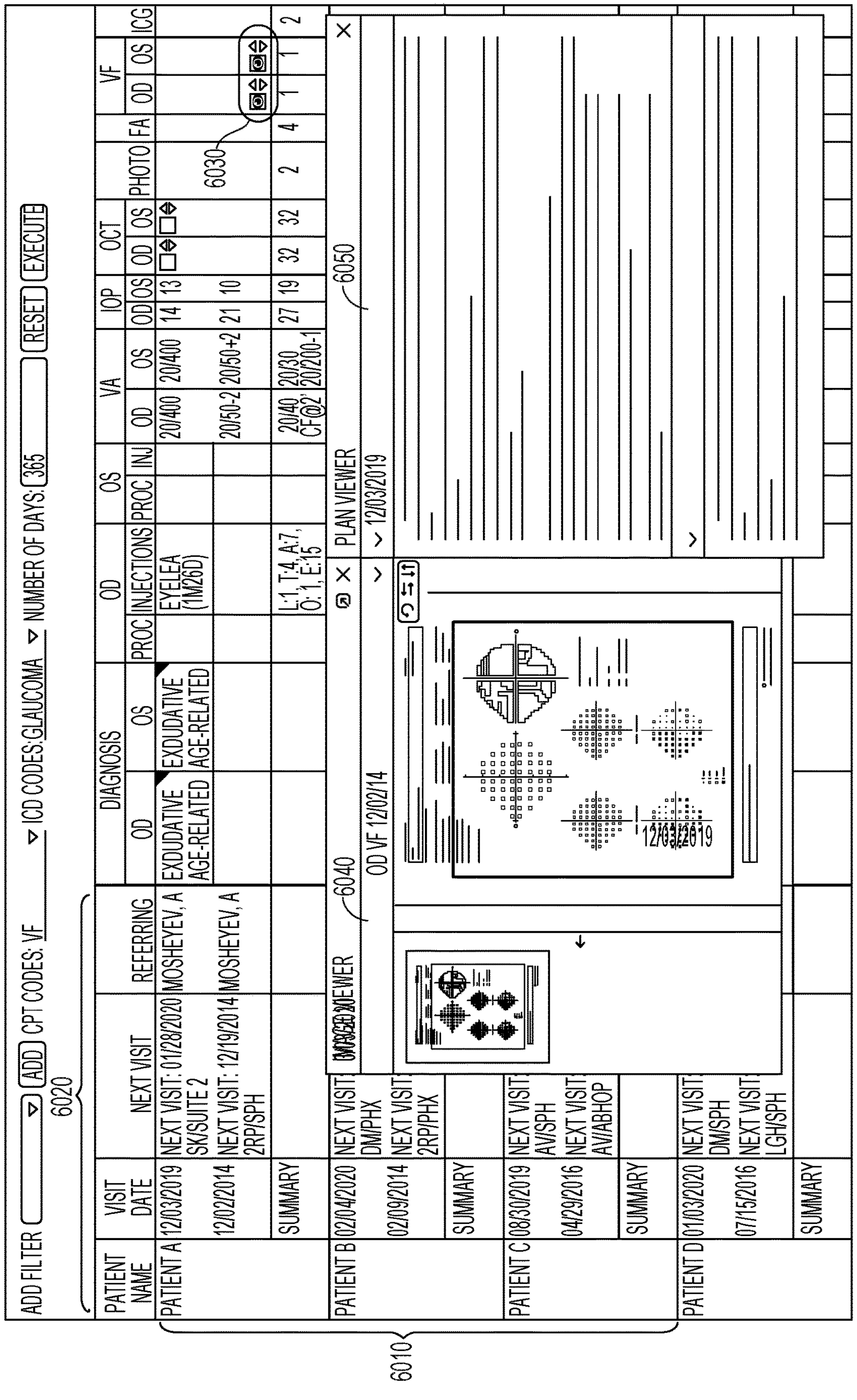
FIG. 55B illustrates an Evaluative Clinical Reporting (ECR) interface that provides an organized view derived from disparate data sources in accordance with user-defined parameters, of a specific report type, executable on a single or group of patients.

FIG. 55B illustrates an Evaluative Clinical Reporting (ECR) interface 6000 that provides an organized view derived from disparate data sources in accordance with user-defined parameters, of a specific report type, executable on a single or group of patients. The ECR interface 6000 displays only necessary and relevant data based on individual patient information in rows 6010 and columns 6020 that allows Clinical Professionals the ability to evaluate many data points and make informed clinical decisions, which would not otherwise be possible in a single display. While reviewing the data, the Clinical Professional can execute multiple actions, including but not limited to the following:

First, the Clinical Professional can, with a single click, view additional relevant data by clicking on icons 6030. An example of this would be viewing diagnostic imaging in a separate, overlaid panel 6040, from the relevant visit date. It is important to note that while viewing the diagnostic imaging, the Clinical Professional can manipulate the underlying flowsheet while manipulating the diagnostic image.

An additional example of this functionality would be viewing the plan 6050 that was used for that specified visit. As with the previous example, the underlying flowsheet can still be manipulated when viewing the plan 6050. It is important to note that N number of additional data panels can be simultaneously opened and overlaid on the reporting results.

A clinical professional can also use a single click on an icon 6030 to load a specified letter for viewing in a separate, overlaid panel, while still able to view the flowsheet in context. As with the previous examples, the Clinical Professional is able to manipulate the flowsheet and also view additional relevant data panels by clicking an icon on the flowsheet while viewing the letter.

After the Clinical Professional has reviewed the patient, there may be some action to take in order to rectify whatever is causing the patient to be included in the report. The Clinical Professional may choose to create a task for a support staff member to take some action. The Clinical Professional may also choose to create an order for a patient while viewing the report results. An ordering panel may be launched within context by clicking an icon. The panel is overlaid with the reporting results flowsheet. As described above with respect to FIGS. 33A, 34A, 34B, 44, 46, and 48, the panel provides a mechanism by which the Clinical Professional can select the type of order, input the relevant parameters and then create the order. A Clinical Professional may also choose to create a letter to a Referring Provider in order to satisfy regulatory requirements or provide guidance to the referring provider in a co-management situation. The Clinical Professional would launch the create letters interface over the top of reporting results flowsheet allowing them to write a letter in context of the flowsheet data on screen. However, it is possible that the Clinical Professional does not need to take any action and simply chooses to evaluate the many data points in a concise view of rows and columns of relevant data.

Figure 55C:
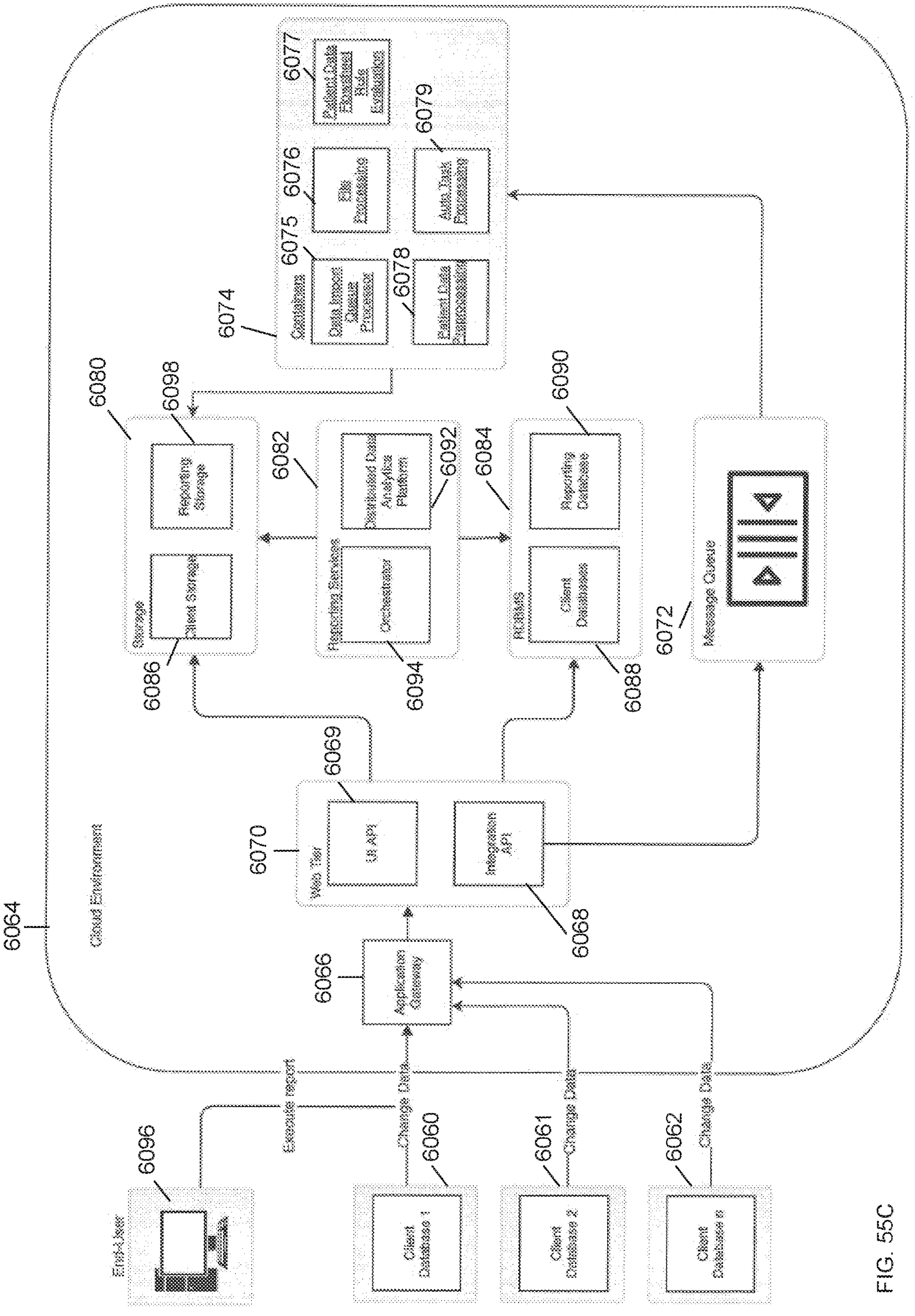
FIG. 55C illustrates a reporting architecture in a sample embodiment.
Figure 55D:
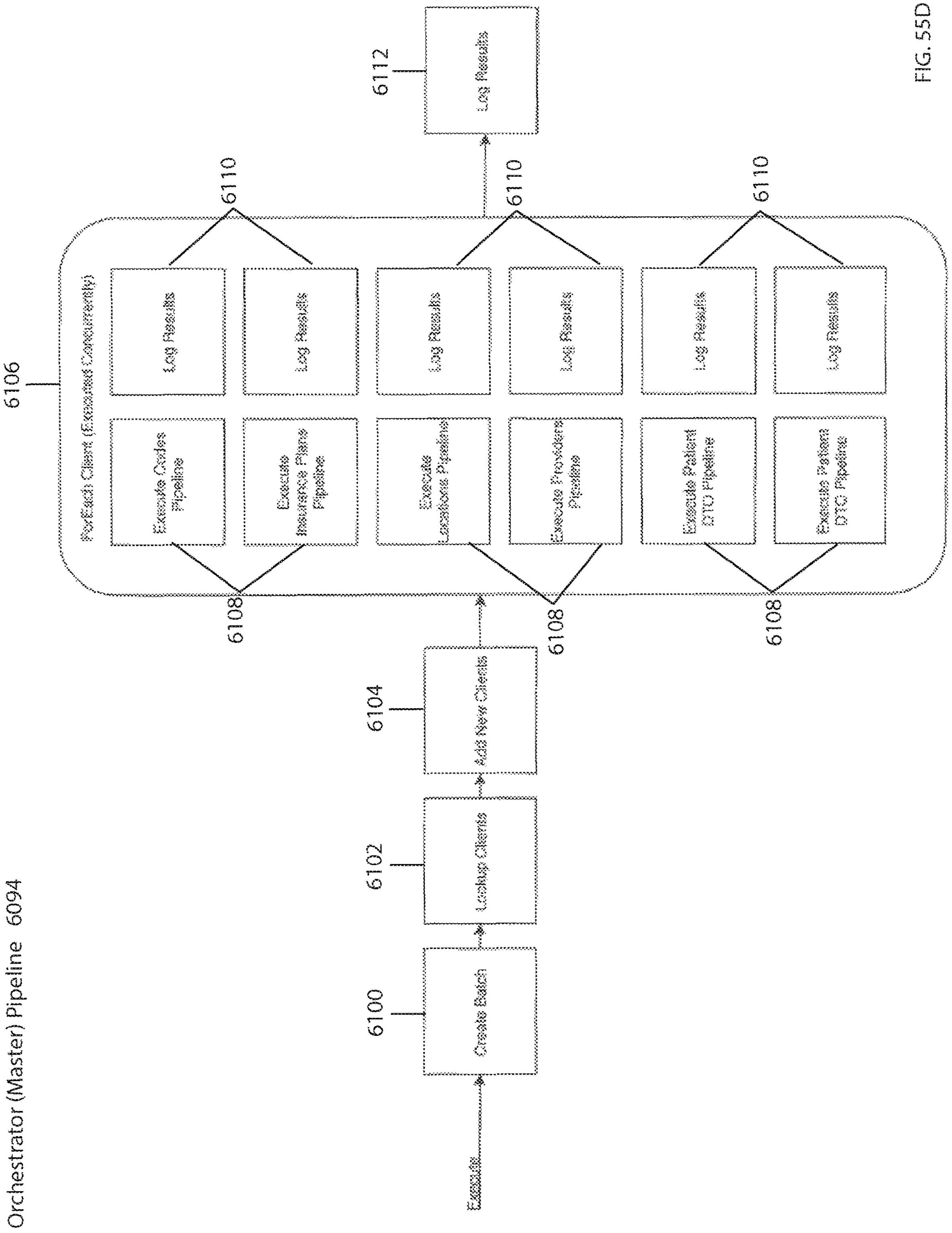
FIG. 55D illustrates the Orchestrator Master Pipeline of FIG. 55C in a sample embodiment.

FIG. 55C illustrates a reporting architecture in a sample embodiment. As data changes on a remote client's EHR 6060, Practice Management 6061, Diagnostic Equipment 6062, or other system, it is pushed to the cloud environment 6064 via an application gateway 6066 to an Integration API server 6068 in web tier 6070. Once the Integration API server 6068 receives the HTTP request with the updated data, it will then insert a message into the appropriate message queue 6072. Five separate application containers 6074 are connected to the message queue 6072 waiting to process information as it is received. A container is defined as a method to package an application, all its dependencies, and runs in isolation from other processes.

The first application container, Data Import Queue Processor 6075, processes changed data and loads it into the appropriate client database 6080. During the processing, the data is mapped to the correct database entities by reporting services 6082 and inserted into the Client Relational Database Management System (RDBMS) 6084. Once the entities are inserted into the client database 6086, a message is added to a Patient Data Preprocessing queue. Placing this message into the queue will cause the Patient Data Preprocessing Queue to begin processing for the patients whose records were updated.

The second application container, File Processing 6076, loads all new diagnostic imaging into Client Storage 6086. Additionally, a record will be added to the Client Database 6088 which contains a pointer that allows for the UI API 6069 to retrieve the correct image for the patient.

The third application container, Patient Data Flowsheet Rule Evaluation 6077, queries the client database 6086 for the latest snapshot information, including, but not limited to, Demographic information, Billing History, Diagnostic Imaging, and Medical Data. Once the relevant information has been loaded into memory, a series of rules are executed in order to transform those data into a JSON object optimized for displaying Medical information, Diagnostic Testing results, etc. in rows and columns of the flowsheet. Once all rules have been run, the Flowsheet Encounter Data is then written to the Client Storage File System 6086.

The fourth application container, Patient Data Preprocessing 6078, will generate an object that contains a historical snapshot of everything that has happened to the patient including, but not limited to, Demographic Information, Billing History, Diagnostic Imaging, and Medical Data. This snapshot, Patient Data Transfer Object (Patient DTO), is stored in a JSON object and written to the Reporting File System 6090 which will be used during the Extract, Transform, and Load (ETL) process to insert rows into the Reporting Database. The ETL process consists of multiple steps to Extract the data from the client RDBMS 6084, Transform it with logical commands executed by the Data-Analytics platform 6092 which is distributed to multiple worker nodes by Orchestrator 6094, and Load the data into the Reporting Database 6090.

The Reporting Database 6090 includes a series of Facts and Dimensions tables which can be extended to include new tables as new use-cases are encountered. Those skilled in the art will appreciate that the data may be architected to use a Star Schema in order to ensure that data is able to be returned in an acceptable time. All the data is stored in a single database. In order to ensure that data is kept appropriately segregated per client, all tables contain a Customer Id Unique Identifier column. The defined process to generate new reports mandates that Report Developers write all queries to include a Customer ID parameter in the WHERE clause, ensuring that data will only be returned for the customer that is specified. In order to be able to view the report execution interface, the user must complete the login, or authentication, process. The authentication process requires a practice identifier, a user, and a password be passed as parameters to the authentication controller. Once authentication has completed, a Secure, HTTP Only, Same Site cookie is generated by the Integration API server 6068 which contains a claim that ties the current authenticated user, to a customer ID. When the report execution HTTP request is made, the cookie is passed in the request, the customer ID is extracted from the cookie and passed automatically as a parameter to the stored procedure execution.

Finally, the Auto Task processing container 6079 runs a set of defined rules to evaluate for certain conditions and to generate a task for a patient once certain conditions are met. If it is found that a certain condition has exceeded a threshold, a task will automatically be sent to the appropriate user to handle the task. For example, if a patient has a diagnosis that requires a certain diagnostic test every 365 days and has exceeded that threshold of 365 days, a task will be sent to the computer 6096 of the Front Desk Staff to schedule that diagnostic test. Once the patient has the required diagnostic test, change data will trigger the reprocessing of the auto task rules, and will automatically resolve the task for the relevant patient.

In order to move the newly generated files from Client Storage 6086 to Reporting Storage 6098, a time-based job executes on a scheduled interval (cron job) on the order of minutes, to find all new and/or modified Patient DTOs in the Client File System since the last time the job was run, and then places a replica of the newly modified file in the Reporting File System of the Reporting Storage 6098. These jobs will continually copy new or modified files to the Reporting File System as the Patient DTOs are generated.

During the day, Patient DTOs will be moved from Client Storage 6086 to Reporting Storage 6098, waiting for its data to be loaded into the reporting database 6090. In order to start the ETL process, another cron job starts the execution of the Orchestrator Master Pipeline 6094 (FIG. 55D) which contains all its child pipelines. The interval for execution is generally set to each night. The master pipelines specify the order in which the child pipelines should execute, error handling, and other logical functions. The pipelines will load the base changed data from the clients' database to create a batch at 6100. Base changed data consists of, but is not limited to, patient demographics, patient insurances, customers, providers, practice locations, etc. The orchestrator pipeline allows the addition, or removal, of pipelines at 6102, 6104 to extend the ability to transform and load new facts and dimensions. While the base data is loaded, an additional pipeline 6106 executes concurrently which will process the Patient DTO data. Each child pipeline 6108 is processed by calling separate transformation jobs which contain the necessary logic to transform the Patient DTO data for insertion to the relevant Facts and Dimensions tables at 6110. The transformation logic is applied using the distributed data-analytics platform 6092. After the Orchestrator Pipeline 6094 has finished processing, the data is logged at 6112 and is available to be reported on.

Once the ETL process begins, the Patient DTO data is staged to be transformed and loaded to the reporting database. To begin the Transformation process, the most recent JSON schema for the Patient DTO object is loaded into memory. The schema is then used to read the DTO object from reporting storage into a proprietary table common for the data-analytics platform 6092. This object allows, but is not limited to, filtering out certain values, adding new columns, dropping unnecessary columns, and flattening child arrays. Due to the nature of the data coming from various source systems, with their own constraints for data-integrity, it is expected that some of the data will not be in a state where it can be loaded into the reporting storage. These data, dirty data, must be scrubbed and cleaned, or be discarded for later analysis. If the data has been discarded, an alert is sent, within the reporting system that data has been dropped and inserted into the dropped data table and requires investigation for the reporting developers. If the data can be scrubbed, then it is transformed in order to meet the minimum constraints of the reporting database. Once the data is sufficiently clean, rows in the proprietary table object which contain child data in arrays, must be exploded, or flattened, to create additional rows to be inserted.

Consider the following:

A table is defined to have two columns, X and Y

The table contains one row with values of [{X: 1, Y: [1,2]}]

The table is then flattened, specifying Y as the column to flatten

The output of the table is now two rows [{X:1, Y:1}, {X:1, Y:2}]

If the table contains multiple arrays, it may be necessary to flatten the table multiple times. Once the table has been appropriately flattened, columns may be:

Renamed

Dropped if they are not needed

Added with static values including, but not limited to, batch ID, customer ID, etc. or with dynamic lookup values After the data has been transformed, it is then inserted into the reporting database 6090 to be used in the report execution process which queries two sources, the reporting database 6090 and the client storage 6086 which contains the most recently cached flowsheet encounter data in order to display the results in the UI on the end-user computer 6096, for example.

Figure 55E:
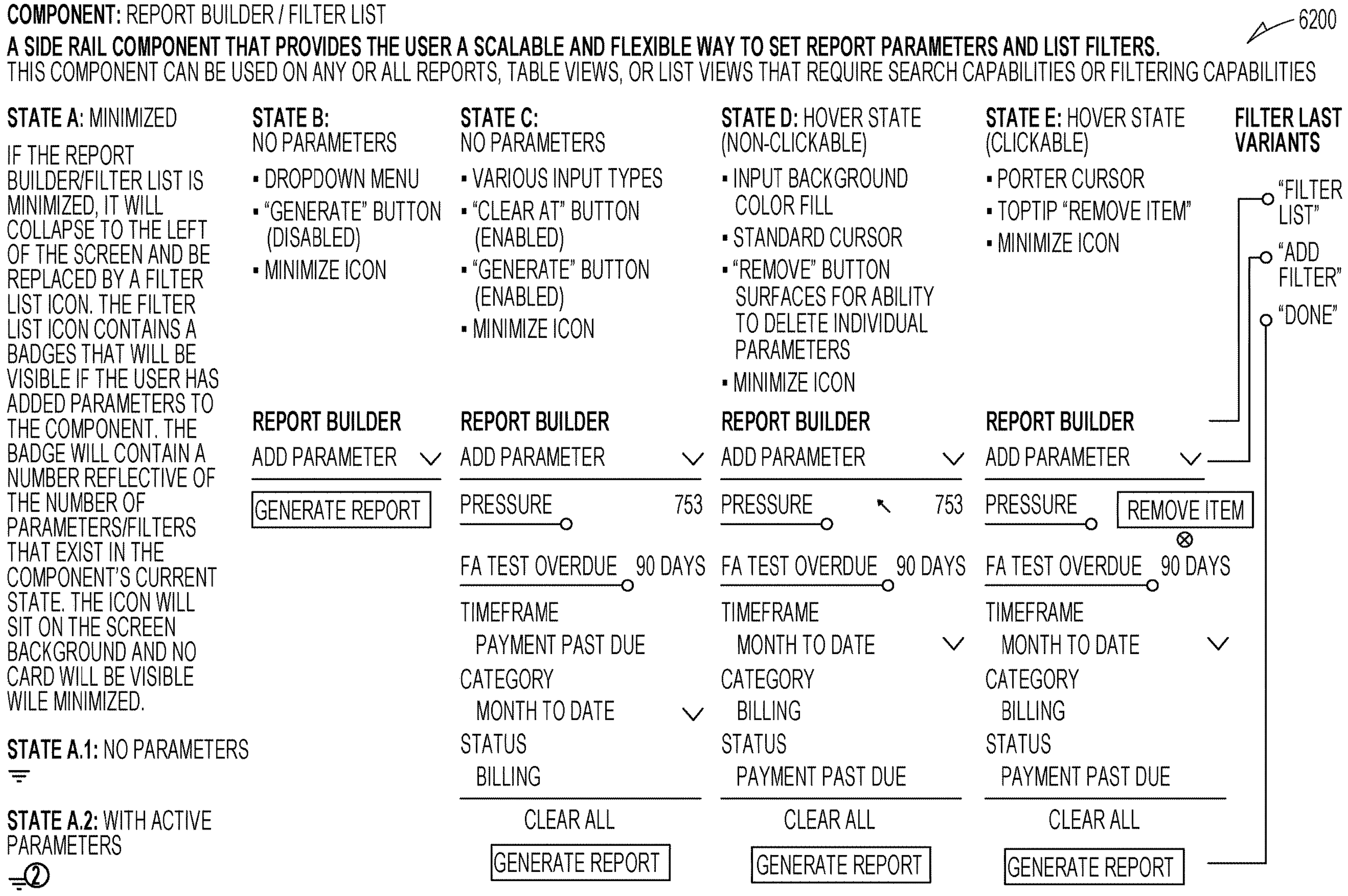
FIG. 55E illustrates the report builder parameter selection interface in a sample embodiment.

During use, an Interface 6200 (FIG. 55E) enables a user to select a report from a dropdown list. Once the report has been selected, the UI will make an HTTP request for the available parameters for the report specified from the UI API. FIG. 55E illustrates the report builder parameter selection interface 6200. Examples of the parameters which can be used include, but are not limited to, procedure codes, diagnosis codes, number of days since a procedure occurred, clinical data elements, and next appointment status. After the UI receives the response to the HTTP request, a list of parameters is then displayed. This list allows the end-user to dynamically add parameters for the specified report. Those skilled in the art will appreciate the ability to select multiple parameters using Boolean logic to specify whether all the parameters must match (AND Logic) or only some of the parameters must match (OR Logic). It is known that not all the parameters are required but there will always be at least one required parameter. Until all the required parameters have been added and set by the end-user, the report cannot be executed.

Figure 55F:
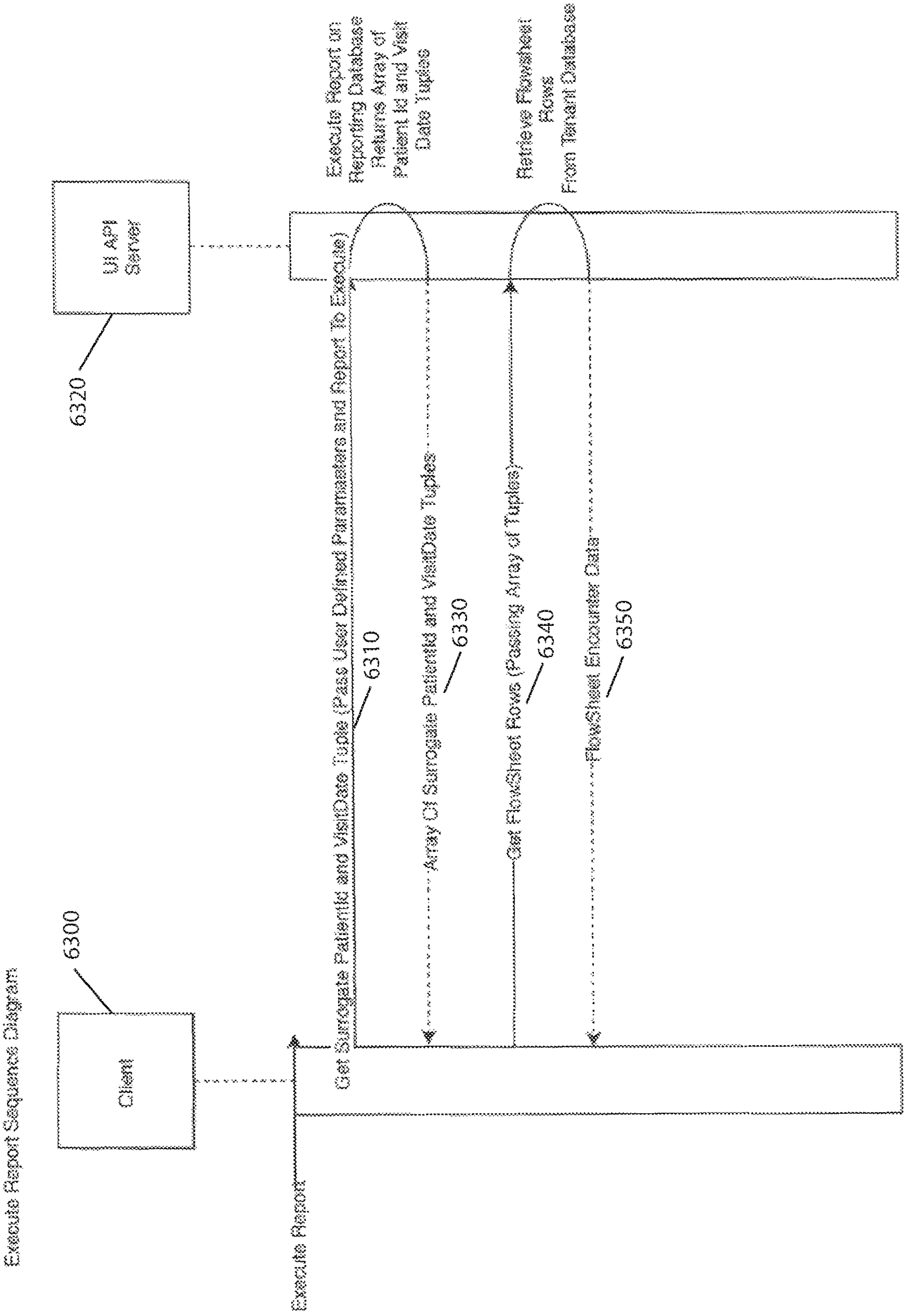
FIG. 55F illustrates a sequence diagram for executing a report in a sample embodiment.

FIG. 55F illustrates a sequence diagram for executing the report. Once all the required parameters have been added, the end-user (client 6300) may then click a button to generate, or execute, the report HTTP request with the user-defined parameters. After the button to execute the report has been clicked, the UI app of the client 6300 will make an HTTP request 6310 to a controller in the UI API server 6320. The controller is responsible for setting the correct customer ID context, ensuring that the current user has access to the specified report, and calling the correct Stored Procedure in the Reporting RDBMS 6084. The Stored procedure executes a series of queries and returns an array of Visit Date and Patient ID tuples 6330. Once the Stored Procedure has finished execution, the array of Visit Date and Patient ID Tuples is returned to the UI App. The UI App then makes another HTTP request 6340 to another controller in the UI API passing the list of Visit Date and Patient ID Tuples. The controller then executes a stored procedure on the Client Database which returns Flowsheet Encounter Data filenames 6350 for the specified visit dates. Once the list of filenames are returned to the controller, the application will loop through all of the unique patient IDs in the array of tuples that was passed as a parameter, and load the encounter data using the specified filenames retrieved from the stored procedure. Once the encounter data has been loaded from the filesystem, a summary row is generated which contains summary information for all columns specified in the flowsheet. An example of summary information could be the number of injections, by type, listed in the procedure column. Another example of summary row information could be for a patient's Visual Acuity (VA).

It is often helpful to know what a patient's best VA or worst VA over the course of care. The summary row would analyze all the historical data for a patient and insert the patient's worst VA and best VA into the summary row allowing the provider to view and evaluate years' worth of data in seconds. In order to evaluate years' worth of data without a summary row, a Clinical Professional would need to undertake the time consuming task of reviewing all Vision Tests, or Refractions, a patient has had, often having multiple refractions per visit, sometimes over the course of 10+ years of treatment. Finally, the API will then return an array of flowsheet data to the UI app which represents the group of patients which match the report type and user-defined parameters.

The UI app will then process the flowsheet data and render the relevant data in the appropriate rows and columns as shown, for example, in FIG. 55B. The columns that are displayed are configurable based on the type of procedures, diagnoses, next appointment status or date, etc., selected as parameters for a report. Based on the parameters specified, an HTTP request will be made to the Flowsheet configuration controller, which will return the flowsheet configuration which contains the columns to display. This allows the Clinical Professional the ability to only see the most relevant data for the group of patients that they may be reviewing.

Figure 56A:
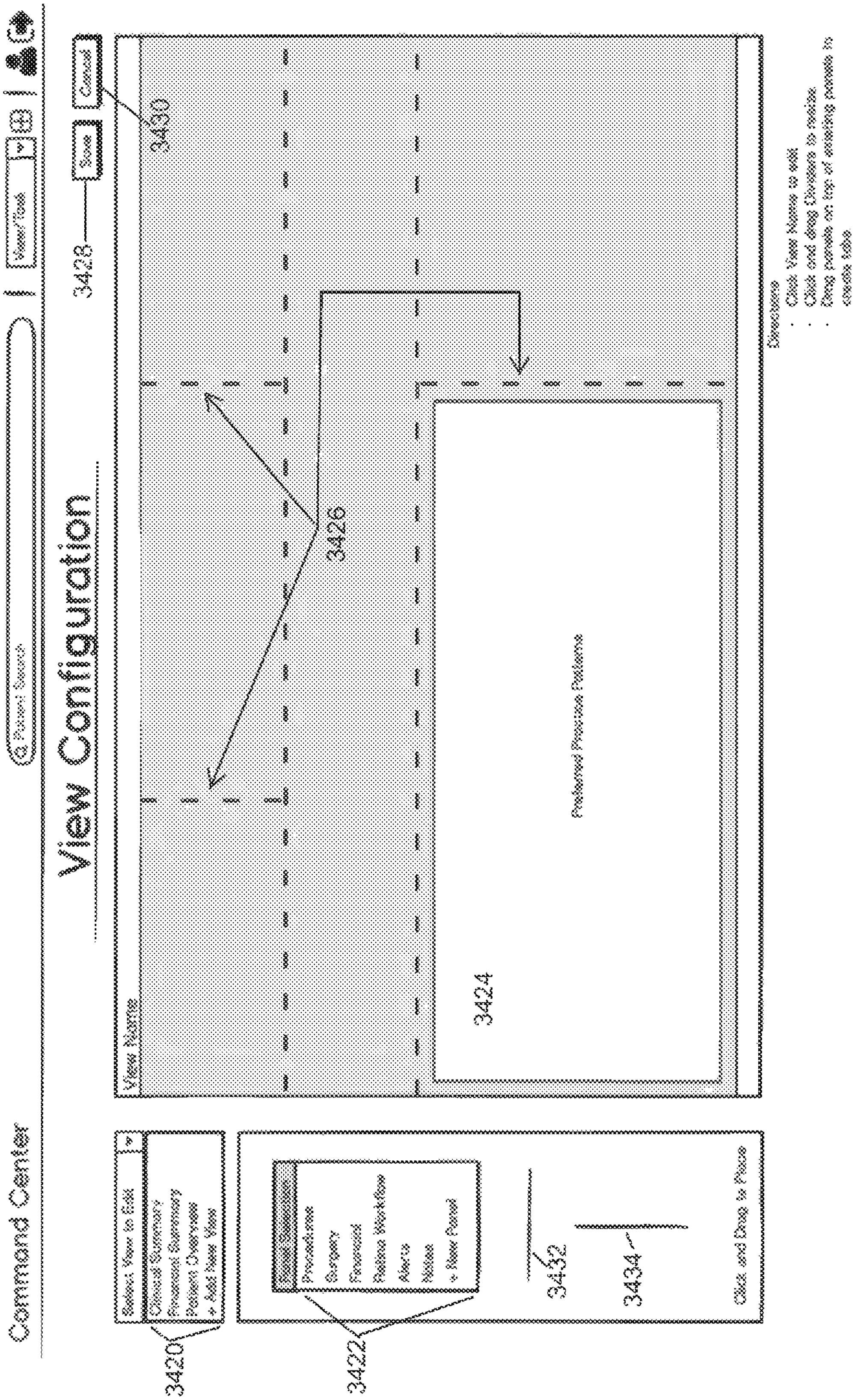
FIG. 56A illustrates the View Configuration page that provides the user a mechanism to create or modify dynamic dashboards to accommodate their unique requirements in accordance with the second embodiment.

The View Configuration page presented in FIG. 56A provides the user a mechanism to create or modify dynamic dashboards to accommodate their unique requirements. These dashboards are referred to herein as Command Center Views. The user identifies the view to be created or modified by selecting the appropriate option from the drop down menu 3420. Once the view has been selected, the user will select a panel to place in the view from the list 3422. Once the panel has been anchored in the View 3424, the dimensions of the panel may be adjusted by means for manipulating the panel frame(s) 3426. When the user is finished creating or modifying the view, the user may save (3428) or cancel (3430) their actions by selecting the associated buttons. Additional horizontal dividers 3432 and vertical dividers 3434 can be dragged and dropped onto the View in order to create new display panels. The dividers also can be removed by clicking on the desired divider and dragging it off the View.

Figure 56B:
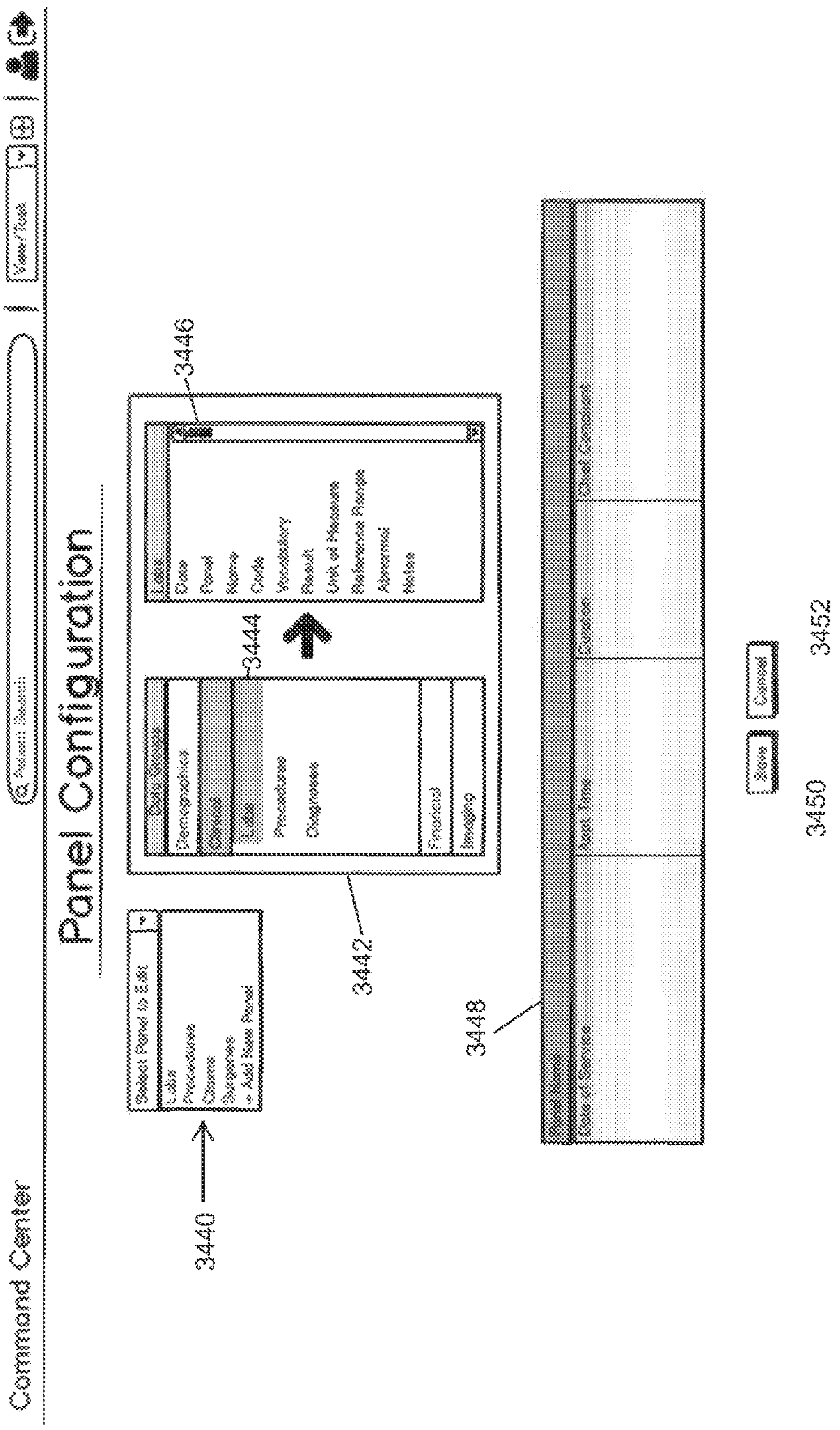
FIG. 56B illustrates the Panel Configuration page that provides the user a mechanism to create or modify display panels to use when populating the dynamic dashboards as described in FIG. 56A.

The Panel Configuration page presented in FIG. 56B provides the user a mechanism to create or modify display panels to use when populating the dynamic dashboards as described in FIG. 56A. The user identifies the panel to be created or modified by selecting the appropriate option from drop down menu 3440. The user then selects data to populate the panel from the Data Selector 3442. Available data 3444 is selected and migrated to the panel's Column List 3446. Users may also add custom fields allowing them to track any data relevant to the user. A preview of the panel 3448 is presented and updated as the user makes changes. When the user is finished creating or modifying the panel, the user may save 3450 or cancel 3452 their actions by clicking the associated buttons. The panels from the drop down menu 3440 thus may provide a template for creating a customized Command Center where all information desired by the user may be accessed without leaving the Command Center.

System Implementation

The Command Center user interface embodiments described above with respect to FIGS. 1-56 are characterized by their ability to present large volumes of dynamic data in a single screen whereby the data may be navigated without leaving the screen. For example, the data is either available in a display window, behind a tab, or available via a pop-up window and is thus accessible without leaving the display screen. To enable such processing to occur without unacceptable delay in data presentation, and to enable the display panels and flowsheet panels to be reconfigured as described, a Command Center architecture has been designed that provides for flexibility in storage and presentation of dynamic data as well as dynamic caching techniques that allow for prompt presentation. As with the first embodiment described above, two-way auto-population techniques are also implemented whereby changes made in the Command Center are not only reflected in the screen display but also the associated electronic medical record is auto-populated as well without leaving the Command Center display screen. The system design will now be described starting with FIG. 57.

Figure 57:
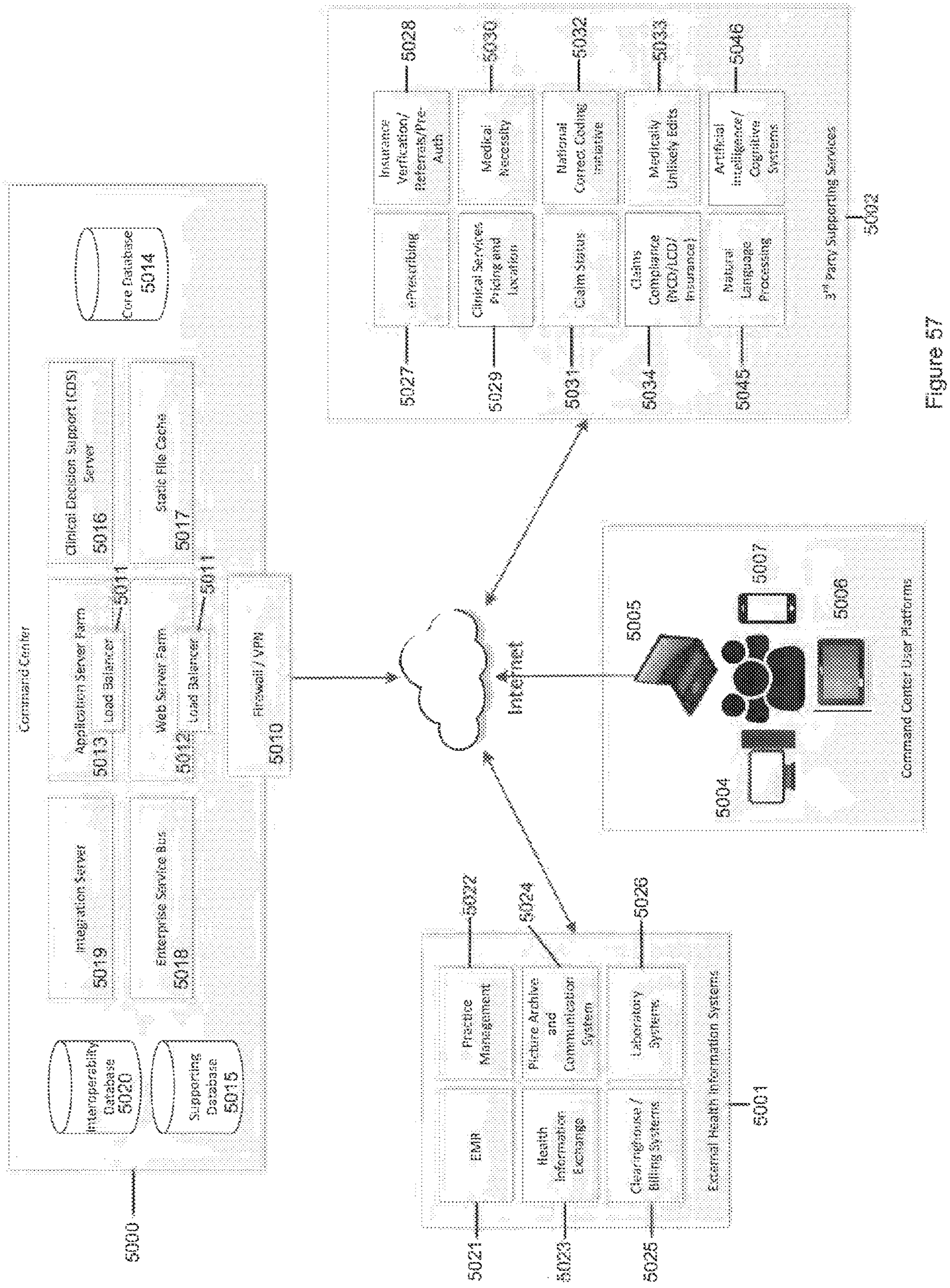
FIG. 57 illustrates the Command Center architecture and connectivity to external Health Information Technology systems and third party services in accordance with the tool described herein.

FIG. 57 illustrates the Command Center architecture 5000 and connectivity to external Health Information Technology systems 5001 and third party services 5002. The Command Center architecture 5000 is a multi-tenant cloud-based web application. As known by those skilled in the art, multi-tenant means that the application is deployed once and all customers access the same server. Data is segregated by the application so that customers can only access their own data. The Command Center is accessible over the Internet via user platforms 5003 that implement a modern web browser (e.g. Internet Explorer 10, Google Chrome) on a desktop computer 5004, laptop 5005, tablet 5006, or a smartphone 5007 with internet connectivity.

The Command Center architecture 5000 illustrated in FIG. 57 is one embodiment of how the system can be configured to support a large user base. For security purposes, access to the cloud platform containing the Command Center is governed by a firewall and Virtual Private Networks (VPNs) 5010. Additionally, end to end encryption is an inherent part of the Command Center architecture 5000 as the Command Center architecture 5000 is optimized to meet the highest privacy and security expectations. Each component allows for both the application of current high strength encryption (ex. AES 256) as well as continuous implementation of evolving data protection and security best practices. The Command Center architecture 5000 configuration supports proven high-availability and disaster recovery practices, including fully encrypted off-site backup and redundant, geographically dispersed operations. Load balancers 5011 distribute the client requests to the most available web server in the web server farm 5012 to optimize response time. The web servers in the web server farm 5012 pass requests through the load balancer 5011 to the application server farm 5013 to continue processing the client requests. The application servers of the application server farm 5013 process the requests and access data from the core database 5014 and supporting database(s) 5015. Depending on the client request, the application servers may interact with the Clinical Decision Support Server 5016 where the primary business logic resides. Once processed, the web server returns the results of the client request back to the client for display. Static files are optimized for retrieval by residing on a dedicated server (static file cache) 5017 where they are cached and optimized for this purpose.

The exchange of information between external health information technology (HIT) systems 5001 and the Command Center 5000 is managed by dedicated servers designed to optimize system throughput and secure communications. All communications take place through a secure VPN 5010 connection. If the integration method is message-based, the sending HIT system 5001 will transmit messages to the Enterprise Service Bus 5018. However, if communication is based on an API standard, the sending HIT system 5001 will communicate with the Integration Server 5019. Both of these servers 5018, 5019 communicate directly with the Interoperability database 5020 and, in turn, with the core and supporting databases 5014, 5015. While communications with third party services 5002 are largely outbound from the Command Center 5000 to the services, it is possible to receive inbound communications. These third party communications will also be handled through the Enterprise Service Bus 5018 and the Integration Server 5019. As illustrated in FIG. 57, examples of HIT systems 5001 include Electronic Medical Records (EMRs) 5021, Practice Management Systems 5022, Health Information Exchanges (HIEs) 5023, Picture archiving and communication systems (PACS) 5024, claims-based systems such as Clearinghouses and Insurance Companies billing systems 5025, and Laboratory Systems 5026.

In exemplary embodiments, many third party supporting services 5002 are integrated to provide feedback and advice. Examples of these services include ePrescribing 5027, Insurance verification including referrals and pre-authorizations 5028, clinical pricing and location services 5029 used to find the best value on purchasing medications, procedures and imaging services, medical necessity checking 5030 to verify a procedure or medication is associated with a correct ICD10 code supporting its use, claim status checking 5031, services in support of the National Correct Coding Initiative 5032, Medically Unlikely Edits 5033 provided by Center of Medicare and Medicaid Services (CMS) to proactively ensure claims are coded correctly to prevent issues in billing, and claims compliance services 5034 which evaluate claims against CMS National Coverage Determination (NCD) and Local Coverage Determination (LCD) guidelines as well as local insurance regulations all in an effort to establish and document medical necessity and to document same in support of streamlined billing. Natural language processing program 5045 and artificial intelligence/cognitive systems 5046 may also be provided to, for example, provide the clinical decision support features described with respect to FIGS. 72A-72C. In exemplary embodiments, the NCD and LCD guidance is programmed into the Command Center 5000 so that alerts may be generated when a physician attempts to follow a treatment protocol that is non-compliant with the NCD and LCD guidance.

Those skilled in the art will appreciate that data latency may be improved by storing the data in the static file cache 5017 in the server of the distributed network of servers that is closest to the geographic location of the patient's appointment. In an exemplary embodiment, the server closest to the geographic location of the patient's appointment could contain data only for today's patients so that there is less data to query, thus improving the access speed for the data. Also, any data that is not stored locally may be cached locally after it has been accessed for the first time as it is more likely to be accessed a second time, thereby speeding up the data access. This architecture implements Proximity Request storage whereby data accessed most frequently is stored geographically closer to the user to reduce the time it takes to travel over the Internet. This approach is used by Netflix and others when hosting large movie files. In the present case, the most relevant patient data is stored within proximity of where it is stored. Relevant patient data is for patients that have been accessed in the past few days and any patients with an upcoming appointment. Having a smaller local subset of data makes the whole network operate more efficiently.

Figure 58:
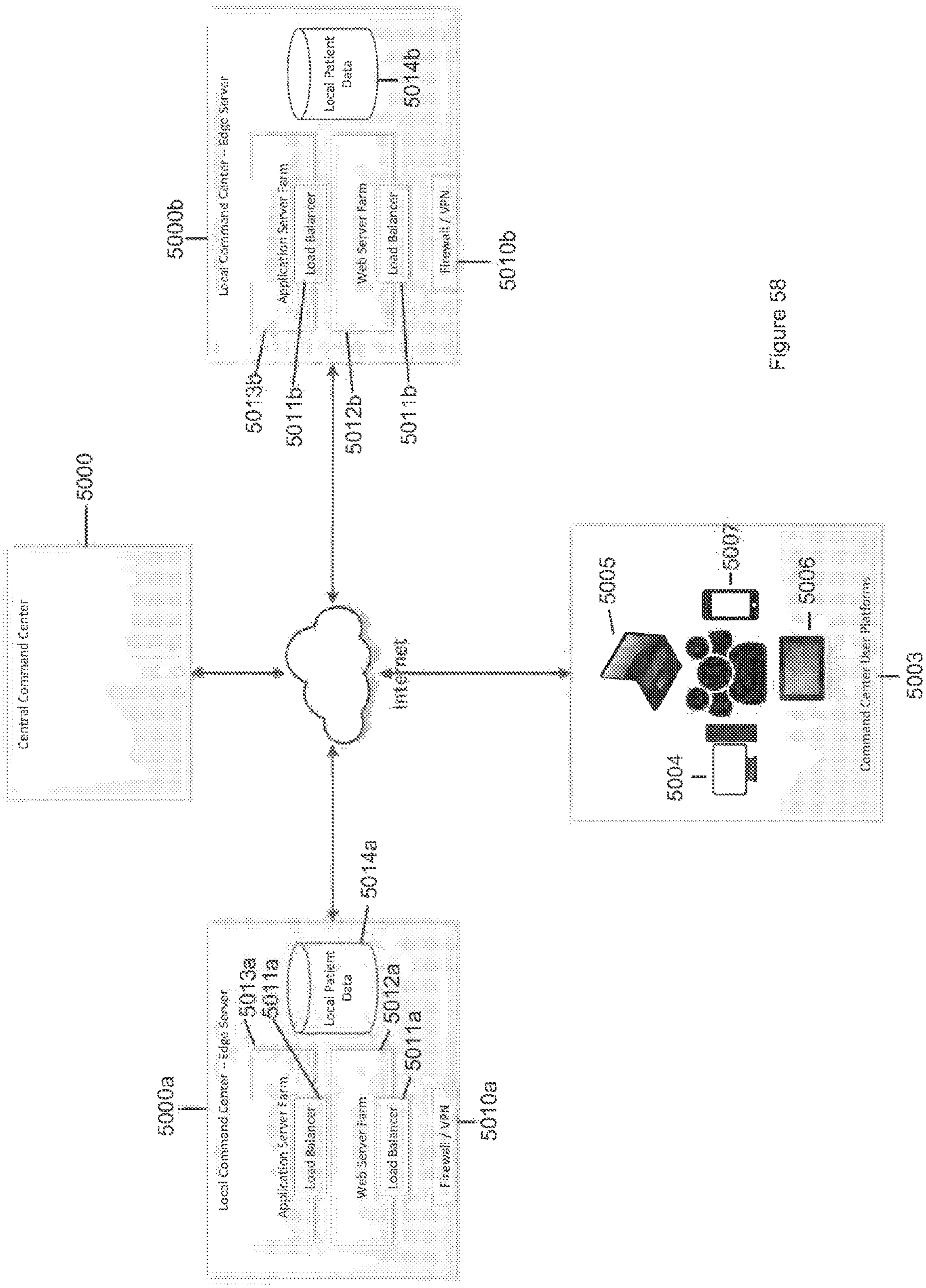
FIG. 58 illustrates the architecture of a central controlling server platform and multiple geographically distributed edge server platforms.

FIG. 58 illustrates the architecture of a central controlling server platform 5000 and multiple geographically distributed edge server platforms 5000*a* and 5000*b*. Each edge server platform 5000*a*, 5000*b* includes a firewall/VPN 5010*a*, 5010*b*, load balancers 5011*a*, 5011*b*, web servers 5012*a*, 5012*b*, application servers 5013*a*, 5013*b*, and a local Patient Database 5014*a*, 5014*b*. On a nightly basis, data for patients with appointments the next calendar day is transferred to the edge server located geographically closest to the user's primary access point as determined by IP address and stored in the local Patient Database 5014*a*, 5014*b*.

When a user requests data using platforms 5003, it is first attempted to be retrieved from the closest edge server 5000*a*, 5000*b* based on the user's location and proximity to the server. If the closest edge server 5000*a*, 5000*b* is not available, access to the central server 5000 is requested. In this configuration, the central server 5000 may be the closest geographically, in which case the user request is just processed on the central server 5000. If the data was only available on the central server 5000, in addition to returning the data to the user 5003, it is also made available on the geographically closest edge server 5000*a*, 5000*b*. This allows subsequent requests to be completed more quickly. Data is stored on the edge servers 5000*a*, 5000*b* for a pre-determined number of days after it has been last accessed because it is more likely to be accessed during this time period. After this time period has expired the data is purged from the local data storage 5014*a*, 5014*b*. All user entered data is always stored on the central server 5000 first and then propagated to the edge servers 5000*a*, 5000*b*.

This architecture has several advantages. In particular, the most likely data (patients with appointment during the current day and those that have been accessed in the past days) is made available at the closest geographic server. The response time to complete user's requests are completed faster because network latency is reduced due to a shorter physical distance, but also because queries resolve faster due to smaller datasets being stored on the edge servers. The distributed approach also makes the whole architecture more efficient, because requests handled by the edge servers 5000*a*, 5000*b* reduce the load on the central server 5000.

Figure 59A:
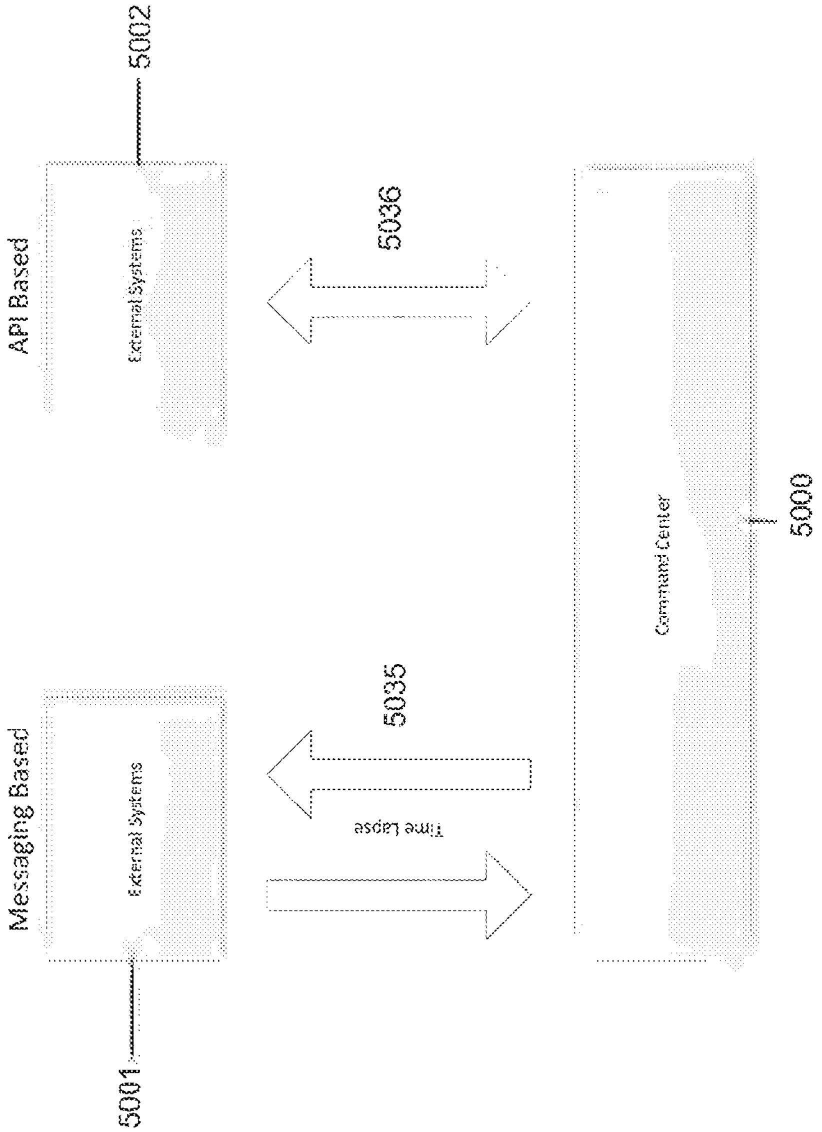
FIG. 59A illustrates integration of the Command Center with the user's existing Health Information Technology (HIT) and third party services using either industry standard message-based protocols or API-based methods in accordance with the tool described herein.

As illustrated in FIG. 59A, the Command Center 5000 is designed to be integrated with the user's existing Health Information Technology (HIT) 5001 and Third party services 5002 using either industry standard message-based protocols 5035 or API-based methods 5036. The interconnection between systems is designed to be hi-directional, in that data can be sent and received from these external systems. Those skilled in the art will appreciate that these and all messages transmitted herein are transmitted in compliance with HIPAA requirements or other global privacy and security regulations using transmission media that enable such compliance.

Figure 59B:
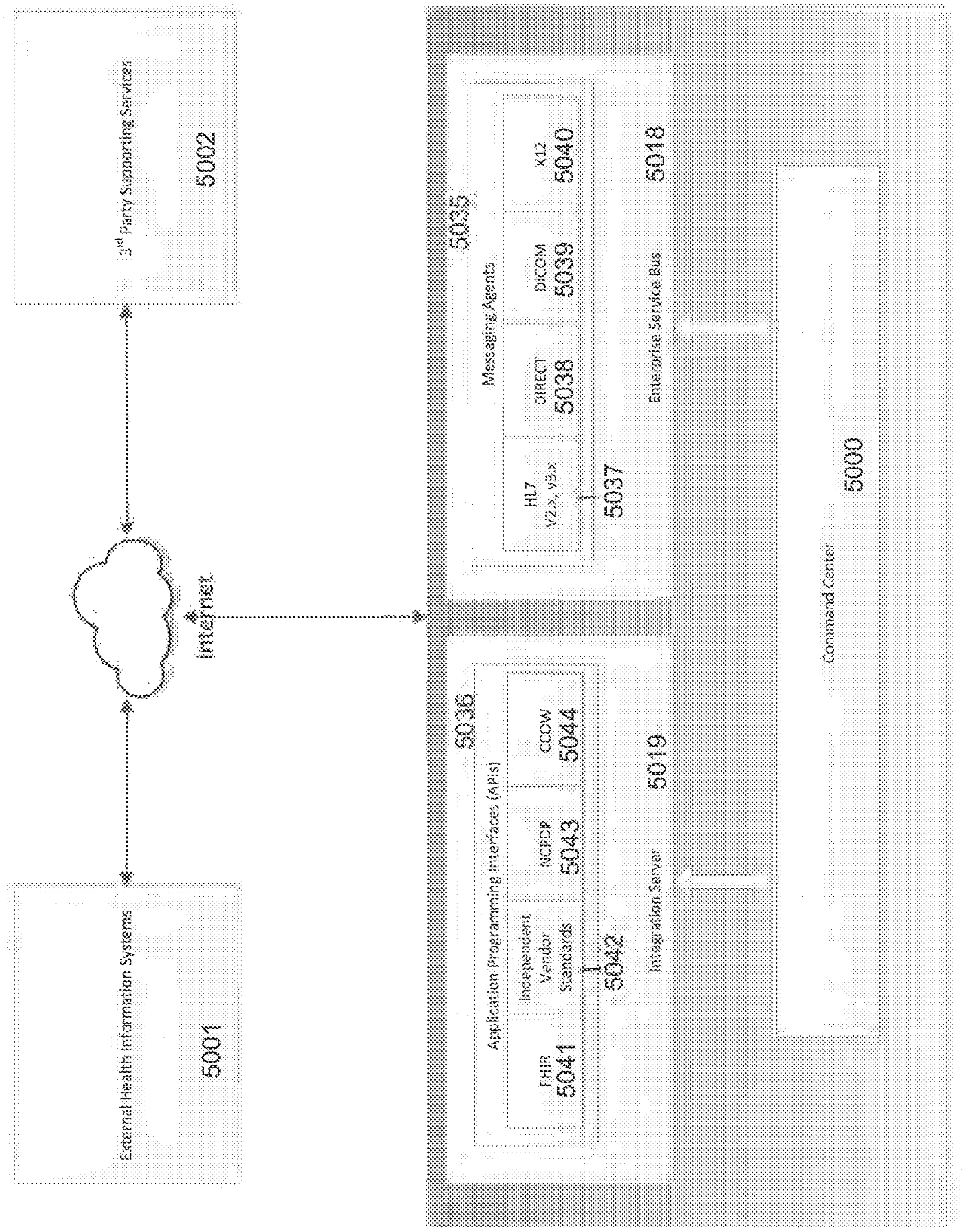
FIG. 59B illustrates systems integration standards used to communicate between the Command Center and external Systems in accordance with the tool described herein.

Systems integration standards used to communicate between the Command Center 5000 and External Systems 5001, 5002 are depicted in detail in FIG. 59B. The external systems have been previously discussed, so the focus here is on communication protocols. Integration between systems uses a variety of industry standards methods. The integrations allow the external systems 5001, 5002 to share data with Command Center 5000. Communication protocols can be grouped into two categories: message-based protocols 5035 and API-based protocols 5036. Message-based protocols 5035 are managed through an Enterprise Service Bus 5018. Enterprise Service Bus 5018 is designed to quickly and efficiently handle large volumes of messages ensuring that all of the messages are processed in order. Examples of message-based protocols 5035 are HL7 v2.x and v3.x (5037). V2.x is the most widely used healthcare integration standard and v3.x is similar to v2.x but uses the XML standard for encoding messages. DIRECT (5038) is a SMTP-based message protocol and is used for direct transmission of secure email messages. The Digital Archive and Communications in Medicine (DICOM) standard (5039) is used in tandem with a PACS system 5024 for processing images. The X12 standard (5040) is for the exchange of claims and billing data.

On the other hand, API-based messaging standards 5036 are managed by the Integration Server 5019. The supported standards include the Fast Healthcare Interoperability Resources (FHIR) standard 5041, several independent Vendor standards 5042, and the National Council for Prescription Drug Programs (DCPDP) standard 5043 used for ePrescribing. FHIR is the next generation method for integrating with HIT 5001 systems, specifically EMRs 5021 and (while not yet approved) is being widely adopted by EMR companies. Several vendors have also emerged that are extending FHIR and in some cases creating their own API-standards for achieving interoperability. Exemplary embodiments of the Command Center 5000 will incorporate each of these standards as they achieve critical mass in the market.

A major challenge in EMR integration is sharing context so that when the EMR user selects a patient other applications like the Command Center 5000 should display information about the same patient to prevent issues associated with accidentally viewing different patients. The Clinical Context Object Workgroup (CCOW) standard 5044 is designed to be used by separate applications to share this context. By using CCOW 5044, the EMR 5021 itself can communicate with the Integration Platform 5019 and the Command Center 5000.

Figure 60:
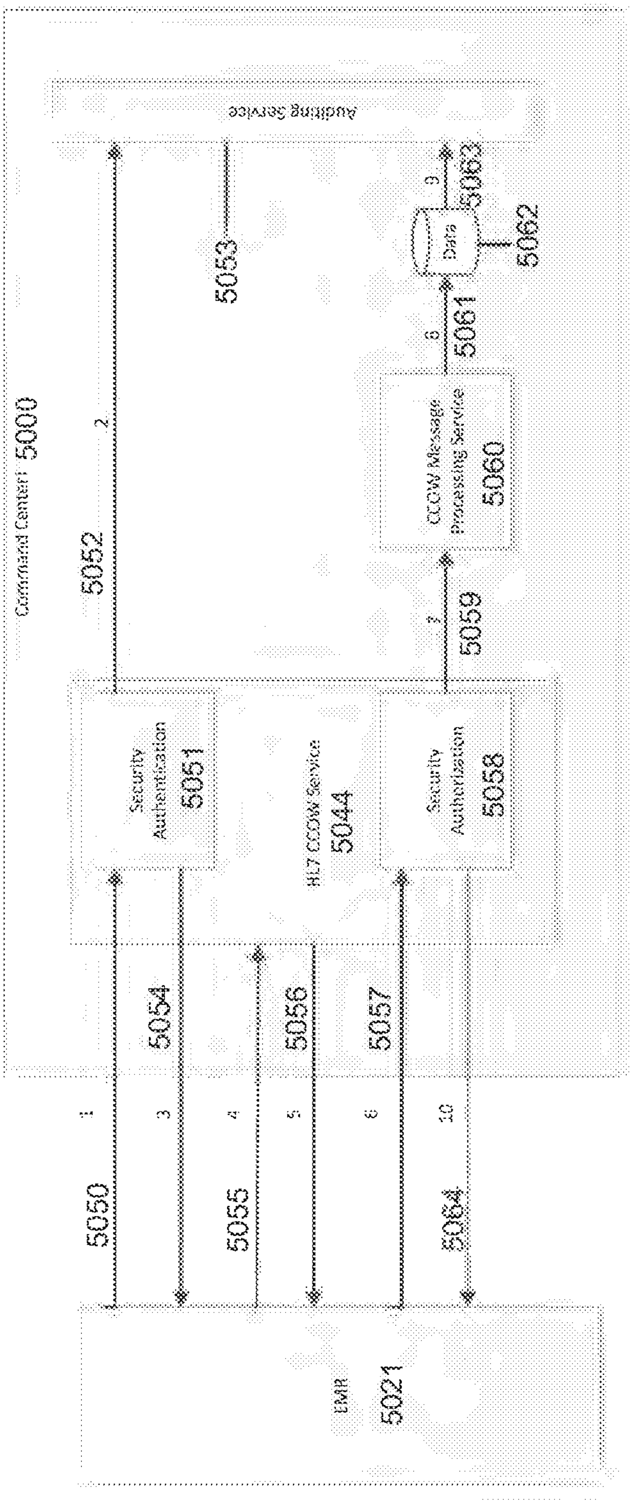
FIG. 60 illustrates an overview of the industry standard CCOW workflow and the various components involved in several transactions in accordance with the tool described herein.

FIG. 60 illustrates an overview of the industry standard CCOW workflow and the various components involved in several transactions. As illustrated, the first step is sending authentication data 5050, typically a user account and password from the EMR 5021 to the Command Center CCOW Security Authentication Service 5051. The service 5051 authenticates the user and sends the request 5052 to the Command Center Auditing Service 5053 for long term storage. Once authenticated, the Security Authentication Service 5051 returns a token 5054 back to the EMR 5021 for use in further transactions. Once authenticated, if the user selects a patient, the Patient's identifying information along with the authentication token 5055 are sent to the Command Center 5000 using HTTP-based protocols. Once complete, the Command Center 5000 will now display the same patient as the EMR 5021. Upon a successful operation, CCOW Service 5044 will return a success message 5056. In the event new data is entered into the EMR 5021 that is required to be transferred to the Command Center 5000, it can be sent at 5057 via CCOW to the Command Center 5000. The first step is to check that the user is authorized for this action at 5058. If the user is not authorized, a denial of service message 5064 is returned to the EMR 5021. If the action is authorized, the message is forwarded at 5059 to the CCOW Message Processing Service 5060 where, upon processing, the message is sent at 5061 to the database 5062 where it is stored. The change in data is also sent at 5063 to the Auditing Service 5053 for long term storage. Upon successful completion of the transaction, a success message 5064 is returned to the EMR at 5064.

Figure 61:
FIG. 61 illustrates a standard workflow when data is received from an external system through any of the messaging standards or API methods in accordance with the tool described herein.

When data is received from an external system 5001 through any of the messaging standards 5035 or API methods 5036, a standard workflow is followed as depicted in FIG. 61. The first step (5080) is to receive data using the previously discussed standards. The message is parsed and the patient identifying information is extracted so the correct Patient can be identified (5081). Once the patient is identified, the data is standardized (5082) so it can be effectively used in the Command Center 5000 and then stored (5083). The last step in the process is to evaluate the data (5084) using a variety of mechanisms using advanced analytics as will be discussed below.

Figure 62:
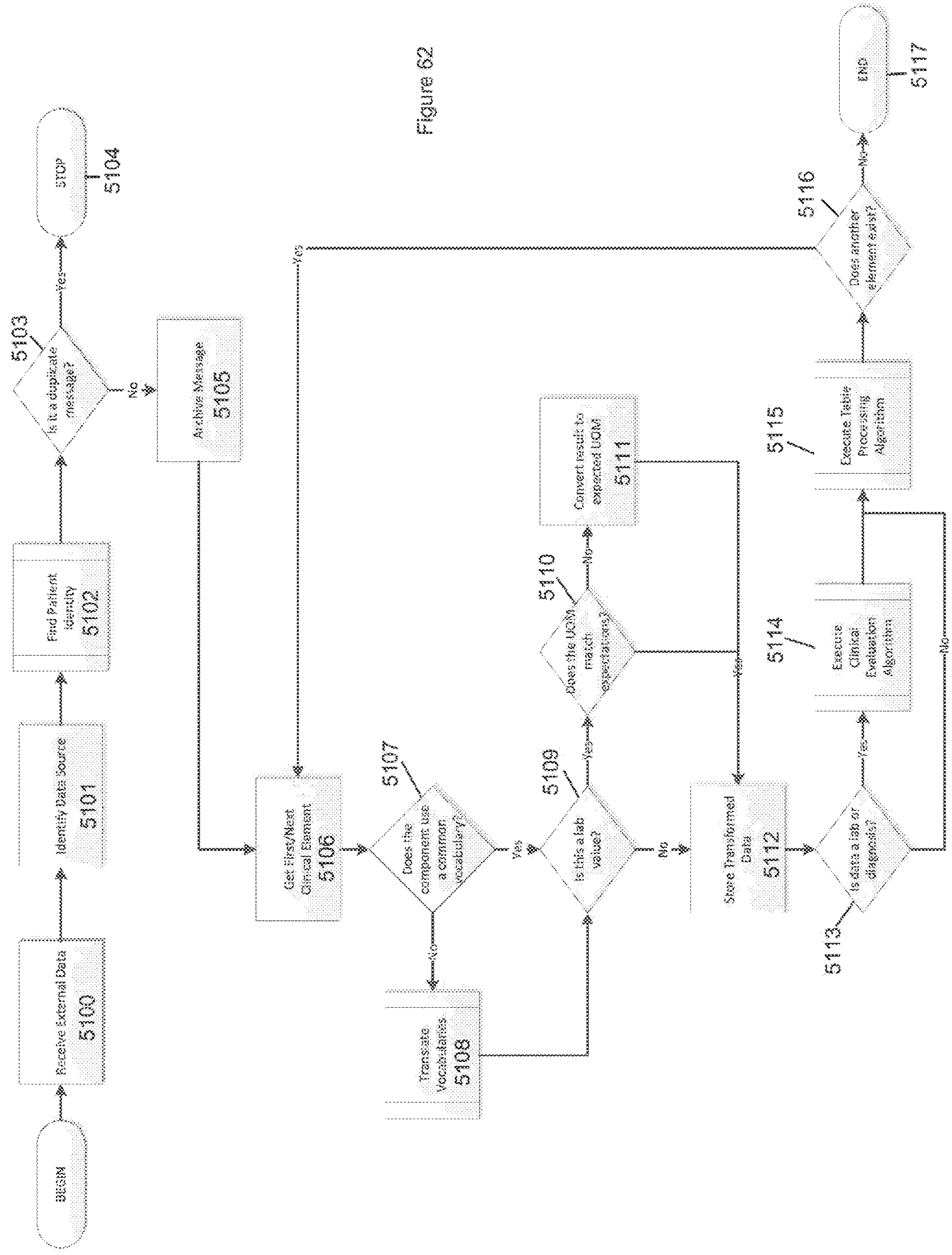
FIG. 62 illustrates a detailed flowchart of the data import process in accordance with the tool described herein.

FIG. 62 illustrates a more detailed flowchart of the data import process. As illustrated, the process begins when External Data is received (5100). The first step is identifying the source of the data (5101) to ensure it is from a trusted source and allows the Command Center 5000 to associate it with the proper customer account. Next, the patient's internal identity must be located (5102) using industry standard mechanisms, such as a Master Patient Index. Once the customer and patient have been identified, it can be determined if the message is a duplicate (5013). If the message is a duplicate, the message may be abandoned (5104) because it has already been processed. This step is necessary to prevent duplicate data and reduce the number of messages processed because the Command Center 5000 cannot control what messages External Systems 5001, 5002 will send. If the message is not a duplicate message, the message can be stored for archival purposes along with a message digest to facilitate searching for duplicate messages (5105).

Messages can often contain multiple relevant pieces of information, so the Command Center 5000 selects the first data element for processing (5106) and then examines to see if the element is using a common vocabulary (5107). If it is not, using existing lookup and translation tables, the Command Center 50000 translates (5108) the element's code to the common vocabulary used by the Command Center 5000. These standards include ICD-10 (diagnoses), CPT (procedures), RxNorm (medications), and LOINC (labs) codes. Next, if this element is a lab value 5109, the Command Center 5000 checks (5110) to see if the unit of measure is the UOM used for this lab in the Command Center 5000. If it is not, the value is converted 5111 using basic math (ex. Converting 10 centimeters to 1000 mm or 6.1 mmol to 106 mg/dL). If the element is not a lab value or has been converted, the data is saved (5112) to the Command Center clinical tables in core database 5014, for example. The clinical tables are designed using common industry standards for storing relational clinical data. If the data is a lab or diagnosis 5113, the data is evaluated to see if the new data is an improvement or decline from the last similar value 5114 by executing the Clinical Evaluation Algorithm described below with respect to FIG. 63. After evaluating the data, the data is processed to see if the data should be added to a Command Center flowsheet (5115) (see Flowsheet description). Once these steps are complete, the processing algorithm looks for another element in the message (5116) and, if another element is present, the process starts over at step 5106; otherwise the process terminates at 5117.

Lab and Diagnosis Data Evaluation

A key feature of the Command Center 5000 is its ability to evaluate lab and diagnosis data to determine if the patient is improving or getting worse based on a comparison of past lab data and diagnosis history and to present that information to the user in an easily recognizable way, using an icon such as health icons 2766, 2768 (FIG. 28), for example. This evaluation can then be used by the clinician to make faster decisions. FIG. 63 illustrates a flowchart of the Clinical Evaluation Algorithm. As illustrated, when a new lab value is received (5200), if the result is numerical (5201), the lab code is looked up in the ClinicalComparator table 5210 using the LOINC vocabulary and the lab code (5202). If a comparator exists (5203), the algorithm retrieves (5204) the most recent previous lab result of the same code for the same patient. If a comparator does not exist or no previous results exist (5205), the algorithm is complete (5206). If a previous value exists at 5205, the data is evaluated (5207). For example, the algorithm receives an A1c lab result of 6.7 mg/dL (we know the UOM is mg/dL because it was converted in FIG. 62 at steps 5110 and 5111). The algorithm searches the ClinicalComparator table 5210 using the search parameters Vocabulary=LOINC (5211), Code=4548-4 (5212). Since a Comparator is found, the previous result is retrieved at 5204, which in this example is 6.5 mg/dL. Each Comparator Record stores whether or not a lab result is getting better 5213 or worse 5214 based on if it is higher or lower than the previous value. In the example of an A1c lab test, the betterValidator=lessThan and the worseValidator=greaterThan. So the evaluation at step 5207 determines the current value 6.7 is higher or greater than the previous value 6.5, which matches the worseValidator. Once the evaluation is complete, if the new value is worse (5215), the lab record is marked as "worse" (5216) and either "declining" or "rising" based on matching lessThan or greaterThan. On the other hand, if the new value is better (5217), the lab record is marked as "better" (5218) and either "declining" or "rising" based on matching lessThan or greaterThan. This pattern allows the use of four icons to better differentiate the patient's condition: better declining, better rising, worse declining, or worse rising. If the patient is neither improving nor getting worse, the evaluation is complete (5219) and the record is not marked or is marked as "no change." Those skilled in the art will recognize that this functionality can be expanded to include other clinical values measured and/or tracked within an office visit for example blood pressure and vision.

The Clinical Evaluation Algorithm can also be applied to certain Diagnosis codes where a pattern of progression is part of the patient condition. For instance, assume that a patient starts with no retinopathy and can then progresses to mild non proliferative diabetic retinopathy (NPDR) and then moderate NPDR and finally to severe NPDR. The ClinicalComparatorList table 5220 (FIG. 63) stores the information required to determine if a diagnosis is improving or not based on its position 5221 in the list signified by its grouping code 5222. In this scenario, where a new diagnosis code is received (5230), the Comparator listing is retrieved (5231). If a Comparator List exists (5232), the algorithm retrieves previous diagnosis codes (5233); otherwise it stops (5206). If previous values do exist (5234), the current diagnosis position in the list is compared against the position of the previous value in the list (5235). If the value is worse (lower) in the list (5215), the diagnosis is marked as "worse" (5216). If the new diagnosis is better (5217), the diagnosis is marked as "better" (5218). If neither is true, the evaluation is complete (5219) and the record is not marked or is marked as "no change." Thus, the output of the Clinical Evaluation Algorithm may be used to make decisions and to update the patient's medical record in the EMR accordingly.

Flowsheet

As noted above, the central focus of the Command Center 5000 is the flowsheet. In the exemplary embodiments described in detail above, the flowsheet is a Retina Flowsheet 2530 for ophthalmologists as illustrated in FIG. 15; however, those skilled in the art will appreciate that the flowsheet 2530 may be embodied in other formats (e.g., FIGS. 4, 35, and 36). As also noted above, the Command Center 5000 presents data to the screen in such a way that the user need not navigate away from the screen. So that the data may be presented without significant delay, the data is pre-processed and stored for display in the flowsheet. A frequent issue with EMR systems for a variety of reasons is slow response time. One of the reasons for the slow response is the need to retrieve data from a variety of sources, process the data, and then render it for display. The Command Center 5000 takes an improved approach. As data is received by the Command Center 500 from external sources, the Command Center 5000 dynamically determines if the data is applicable to the flowsheet, processes it and stores it in a simple database table structure described below that can be easily retrieved when requested.

Flowsheet—Images

Figure 64:
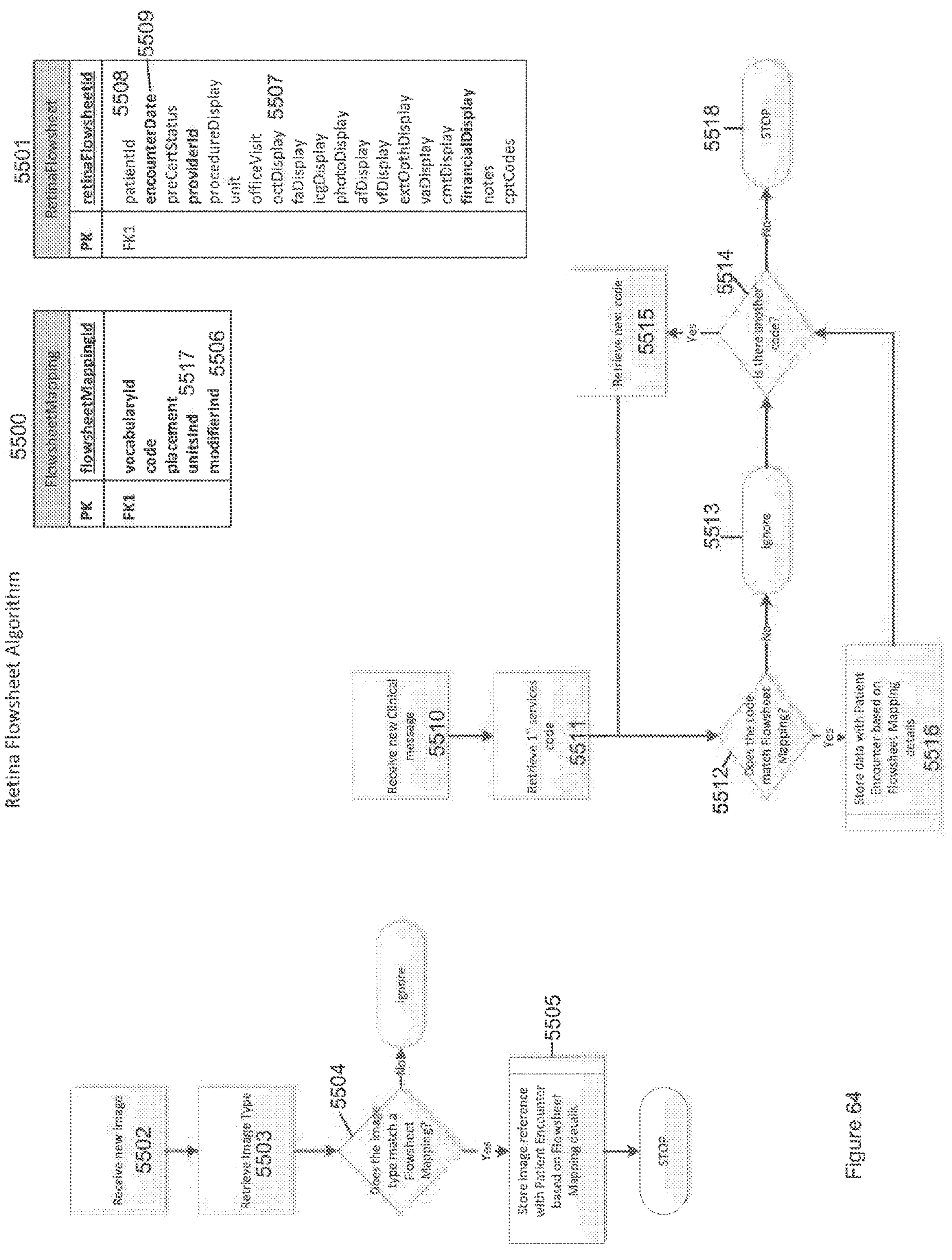
FIG. 64 provides a diagram of the tables used to determine if imported data is relevant to the Flowsheet Mapping table and to store data for display on the in the flowsheet database fields in accordance with the tool described herein.

FIG. 64 provides a diagram of the tables used to determine if imported data is relevant to the FlowsheetMapping table 5500 and to store data for display on the in the flowsheet database fields 5501. FIG. 64 also presents the logic used to process the imported data in reference to the flowsheet. For example, when new data is received by the Command Center 5000, the data includes either images or clinical data and it is determined Whether the data received should be stored for display on the flowsheet. When a new image record is received (5502), the image type is extracted (5503) from the record and the FlowsheetMapping table 5500 is searched for the image type (Vocabulary—Images, Code=Image Type). If a match is found (5504), it means the image reference should be stored and displayed on the flowsheet (5505). If a match is not found at 5504, the image is ignored. In the case of eye images, the particular eye is important so the modifiedInd 5506 will equal 1, which means when the image reference is saved, it should be associated with the correct eye side which is part of the original image record per DICOM standards. For example, if an OCT image record for the left eye is received, the image type OCT is searched for on the FlowsheetMapping table (Code=OCT). Since the image type OCT is relevant to the Retina Flowsheet as well as the eye side, the image reference along with the eye side are stored in the RetinaFlowsheet table 5501 in the octDisplay column 5507. The placement field on the FlowSheetMapping Table 5500 is the location to where the data should be saved. Instead of having an OCTDisplayOD and OCTDisplayOS columns—one for each eye, the octDisplay column and other similar columns store structured data containing reference to multiple images based on eye side. The format for this column is "OD:image reference|OS:image reference" where image reference is the name and location of the image. If this is the first data for a particular encounter date, a new record is added to the RetinaFlowsheet 5501 and the patientId 5508 and encounterDate 5509 both found in the message are saved to the table.

Flowsheet—Clinical Messages

FIG. 64 further presents the logic used to process a received clinical message in the context of the flowsheet. As illustrated, when a clinical message (medications, procedures, diagnoses) is received (5510) it typically has multiple pieces of information in the same message, so each element is processed separately. The first element is selected from the message (5511) and evaluated (5512) to determine if it belongs on the Retina Flowsheet table 5501 based on finding a matching entry in the Flowsheet table 5501. For example, a procedure J2778 Lucentis 0.5 mg is received. A query is executed on the Flowsheet Mapping table 5500 where the Vocabulary=CPT and the code=J2778. If the procedure is not found in the table, the record would be ignored (5513) and if another element exists (5514) the next element would be selected (5515) for processing. If the procedure is found in the table, the procedure data is then stored (5516) in the RetinaFlowsheet 5501 where the column is specified by the placement field. In the case of a procedure, a medication may be administered, so the units are relevant. In this case, the unitsInd 5517 in the FlowsheetMapping table 5500 would be set to 1 signaling the algorithm to save the units associated with the record in the unit column of the RetinaFlowsheet 5501. If there is another code (5514), that code will be retrieved (5515) and the process starts over; otherwise the process is complete (5518).

Flowsheet—Financial Messages

FIG. 65 illustrates a Financial Analysis Algorithm for processing financial payment information. As illustrated, when financial information is received (5600), the matching claim is located (5601) and the payment information is stored (5602). In an exemplary embodiment, a third-party a claims clearinghouse or insurance company is used to provide an electronic claims status message (5603) that is sent to determine the status of the claim. This status is then stored (5604) in the RetinaFlowsheet table 5501 in the financial display column 5605.

Preauthorization and Referral Processing

Figure 66A:
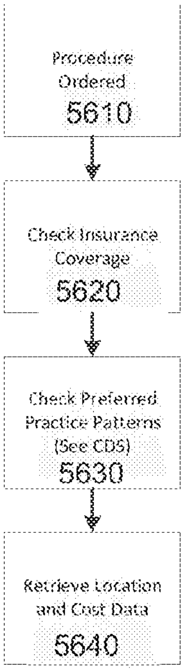
FIG. 66A illustrates generally the process for ordering a procedure in accordance with the tool described herein.

FIG. 66A generally illustrates the process the system follows when the user orders a procedure. When a procedure is ordered at 5610, the Command Center 5000 evaluates the insurance coverage at 5620. This process is described in detail in FIGS. 66B, 67 and 68 below. Next, the Command Center 5000 evaluates the Preferred Practice Patterns and other clinical decision support rules at 5630. This process is described in FIG. 72. The last step in the process is to retrieve location, if applicable, and cost data 5640. This information is then displayed in the Smart Evaluation Control panel in FIGS. 44-55.

Figure 66B:
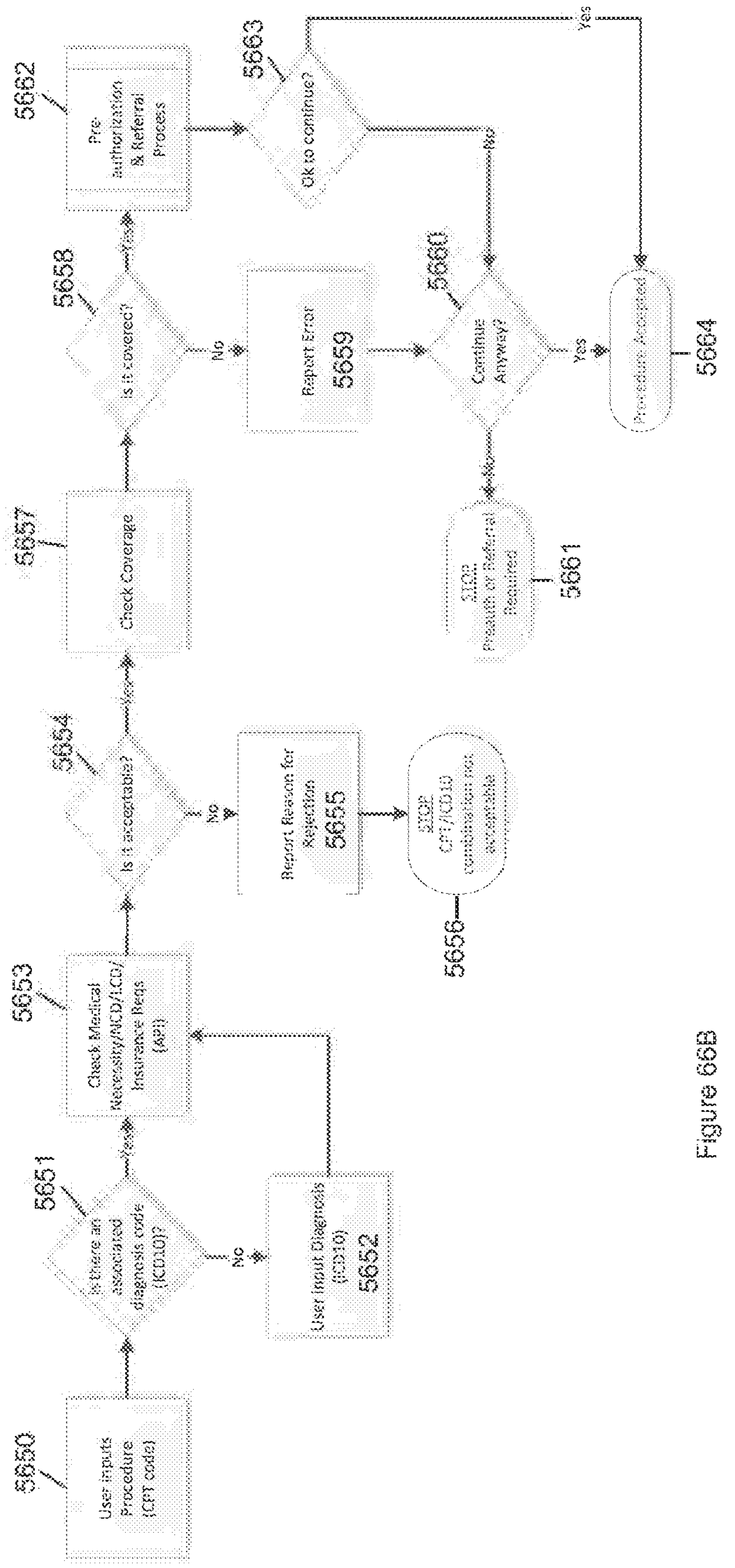
FIG. 66B illustrates the logic used to check for preauthorization and/or a referral in accordance with the tool described herein.

FIG. 66B illustrates the logic used to check for preauthorization and/or a referral. As illustrated, when a new procedure is ordered (5650), the Command Center 5000 reviews the input data (5651) for an associated ICD10 Diagnosis code. If no ICD10 Diagnosis code is found, the user is prompted to provide one (5652). Once the ICD10 Diagnosis code has been associated with the CPT procedure code, the Command Center 5000 evaluates the data against the applicable guidelines (5653) using a third party API and determines if the combination of CPT and ICD10 codes is acceptable (5654). If the input is not acceptable (5654), the user is notified of the disposition and provided with a rejection reason (5655). A rejection will terminate the process (5656). On the other hand, if the input is acceptable (5654), the system will review the patient's coverage (5657) for the procedure using a third party API. If the procedure is not covered by the patient's insurance (5658), the system will provide the user with an error code (5659). The patient will then have the Option (5660) to continue with the procedure (5664) (knowing it will be paid for out of pocket) or to decline the procedure (5661), which terminates the process. If the procedure is covered (5658), the preauthorization and referral process is invoked (5662). If the preauthorization and referral process (5662) does not approve the procedure (5663), the patient will again have the option (5660) to accept the procedure (5664) (knowing it will be paid for out of pocket) or to decline the procedure (5661), which will terminate the process. If the preauthorization and referral process (5662) approves the procedure (5663), the patient can move forward with the procedure knowing it is covered (5664).

Figure 67:
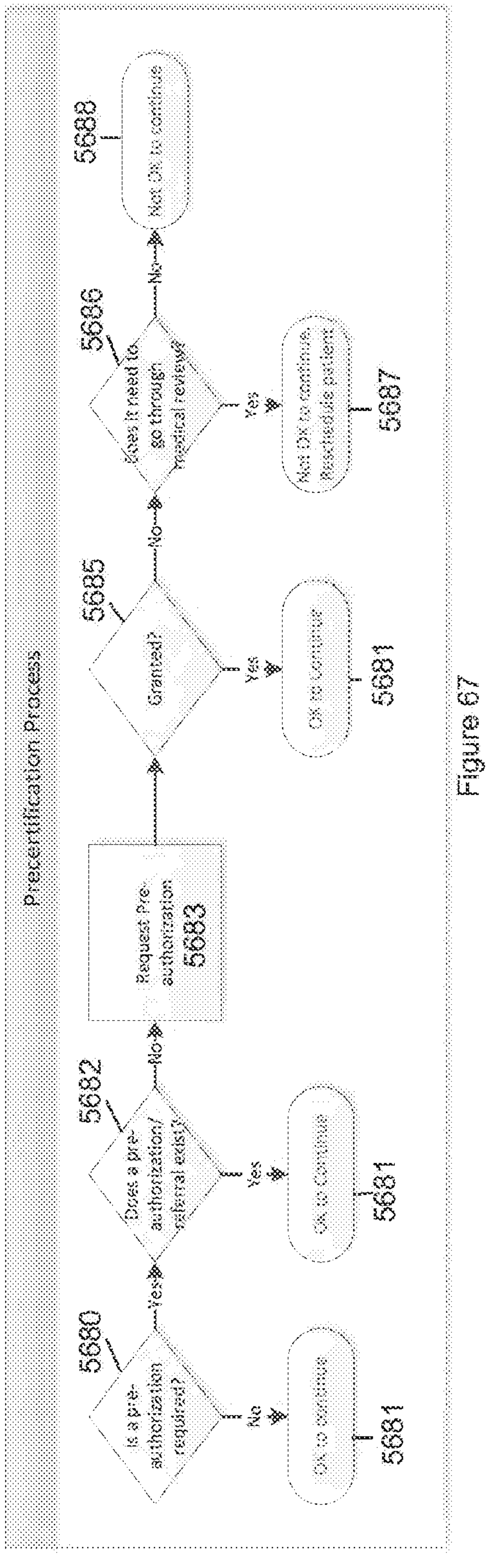
FIG. 67 illustrates the precertification process that is invoked by presentation of a CPT Procedure code and an ICD10 Diagnosis code in accordance with the tool described herein.
Figure 68:
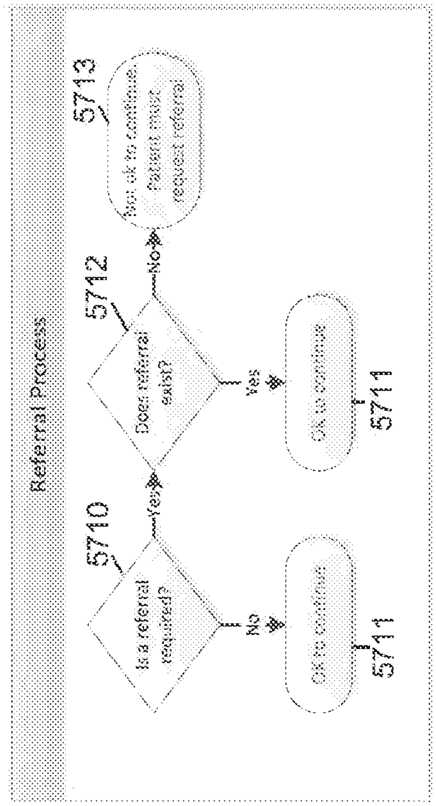
FIG. 68 illustrates the referral process that is invoked by presentation of a CPT Procedure code and an ICD10 Diagnosis code in accordance with the tool described herein.

The preauthorization and referral process (5662) described above with respect to FIG. 66B has two parallel processes, one which evaluates if the procedure requires preauthorization (FIG. 67) and another which evaluates if the procedure requires a referral (FIG. 68). The Precertification process described FIG. 67 is invoked by presentation of a CPT Procedure code and an ICD10 Diagnosis code. It is then determined using a 3rd party API whether or not a preauthorization is required (5680). If preauthorization (5680) is not required, then it is ok to proceed with the process (5681) and the process returns an approval message (5663 from FIG. 66B). If preauthorization 5680 is required, the system will then check for a pre-existing preauthorization (5682) using a third party API. If a preauthorization exists, the authorization code is stored and the procedure can continue (5681) and the process again returns an approval message (5663 from FIG. 66B). If a preauthorization does not exist, the system will request a preauthorization (5683), again using the third party API. If the request for preauthorization (5683) is granted (5685), then it is ok to proceed with the process (5681) and the process returns an approval message (5663 from FIG. 66B). If the request for preauthorization (5683) is not granted (5685), then the system will evaluate if the request for preauthorization (5683) needs to go through medical review (5686). If the request for preauthorization (5683) needs to go through medical review (5686), then it is not ok to proceed with the process (5687) and the process escapes to the negative path of 5663 in FIG. 66B to determine whether to continue anyway. If the request for preauthorization (5683) does not need to go through medical review (5686), then it is not ok to proceed with the process (5688) and the process escapes to the negative path of 5663 in FIG. 66B to determine whether to continue anyway.

The referral process illustrated in FIG. 68 is invoked by presentation of a CPT Procedure code and an ICD10 Diagnosis code. It is then determined using a third party API whether or not a referral is required (5710). If a referral (5710) is not required, then it is ok to proceed with the process (5711) and the process returns an approval message (5663 from FIG. 66B). If a referral (5710) is required, the system will determine if a referral exists. If a referral exists (5712), then it is ok to proceed with the process (5711) and the process returns an approval message (5663 from FIG. 66B). If a referral does not exist, then it is not ok to proceed with the process (5713) and the process escapes to the negative path of 5663 in FIG. 66B to determine whether to continue anyway, Data Model Overview The Command Center data model is grouped into core tables, supporting tables and interoperability tables. The core tables 5014 (FIG. 37) drive the Command Center (e.g. FIGS. 1 and 15) and store the patient demographics and insurance information, images and the patient's clinical and financial data. The supporting tables 5015 (FIG. 37) are largely used behind the scenes to drive functionality and are not directly related to a specific patient. The System Messaging tables in interoperability database 5020 (FIG. 37) support health information technology interoperability.

The Command Center data model is based on a relational database model. Each table uses a surrogate primary key. A surrogate primary key is a unique value within the table used to identify the row that is not directly tied to the data in that row. This allows any of the columns to be changed without impacting the primary key. The data is stored in two types of tables—transactional for capturing clinical and billing data as discrete data, and reporting where data is aggregated for a particular physician, practice, health system or other entity. Reporting may extract and report on any data elements captured within the Command Center 5000. These data extracts or reports can be used for clinical practice, population health management or clinical research or other purposes to improve patient health and well-being and/or the financial outcomes of a practice. Reports can be generated in real-time or batch mode executed on a pre-determine schedule and automatically delivered to interested parties.

Figure 69:
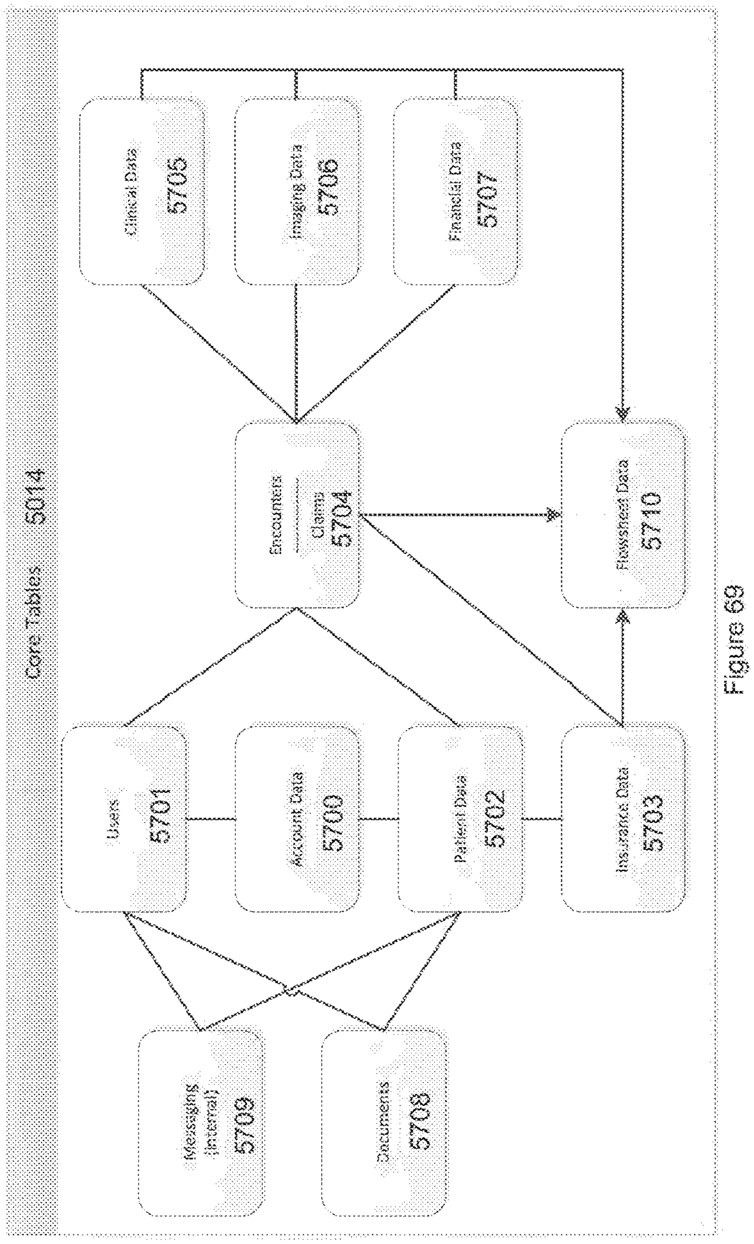
FIG. 69 illustrates the classes of data that are stored as part of the core tables in accordance with the tool described herein.

Core Tables (FIG. 69)

The core tables 5014 largely follow industry standard design patterns for storing patient, clinical and financial data in a relational format. One example embodiment of the data model is the Observational Health Data Sciences and Informatics (OHDSI) standard—(http://www.ohdsi.org/). Another has been established by OpenEHR group—http://www.openehr.org/. The classes of data illustrated in FIG. 69 are stored as part of the core tables 5014. The Account Data tables 5700 store information about customer accounts and physical locations as well as group Users and Patients so they can share information and communicate among each other. The Users tables 5701 store user accounts, credentials, personal configuration information, and data related to an individual user's profile including password and password history. Users are medical professionals such as clinicians, physicians, nurses, and billers, not patients. Patient tables 5702 store demographics and basic contact information. Insurance tables 5703 contain references to the patient's insurance information including benefits and amount paid and/or remaining deductible for the calendar year. Insurance data also includes referrals and pre-authorization information as required by the insurance company. Access to this data is compartmentalized to ensure compliance with global privacy and security regulations. The Encounter/Claim tables 5704 store encounter based data including but not limited to chief complaint, the review of systems, and the patient plan of care. Associated with encounters is claims data, which is also stored in these tables 5704. The Encounter/Claim tables 5704 are also the key set of tables that tie patient information together with the clinical and financial data. Clinical tables 5705 store data sets for vitals, procedures, diagnoses, problem lists, medications, allergies, admission/discharge information, and surgeries. Imaging tables 5706 store references to the different patient images. Example image types include fundus photography, optical coherence tomography, fluorescein angiography, indocyanine green angiography, magnetic resonance, X-ray, and ultrasound. The actual images are stored on a PACS or similar service and are not typically directly stored in the Command Center core database 5014. Financial tables 5707 include the payments by the insurance companies as well as information about claim adjustments and write-offs. The Financial tables 5707 also include a general ledger. The Document tables 5708 store key information about documents either sent or received from other providers as well as other documents pertinent to the patient care. Messaging tables 5709 hold the actual notes and messages created within the Command Center 5000 and track external notifications. Finally, the Flowsheet tables 5710 contain the processed/aggregated data used in presentation of the Flowsheets within the application.

Figure 70:
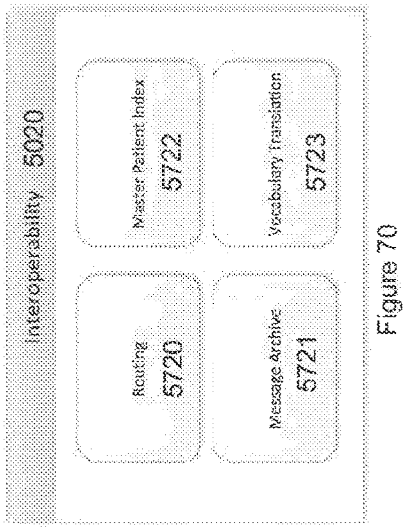
FIG. 70 illustrates the interoperability tables that are used to handle receiving and sending of data between systems in accordance with the tool described herein.

Interoperability Tables (FIG. 70)

The interoperability tables 5020 illustrated in FIG. 70 are used to handle receiving and sending of data between systems. The Routing tables 5720 store information about the connections between different systems. The Routing tables 5720 are designed to ensure data that is received are stored with the correct customer account and data that is transmitted is routed to the proper system. For auditing and debugging purposes, all inbound and outbound messages are stored in the Message Archive tables 5721. The Master Patient Index (MPI) tables 5722 are used to identify a patient record so data is properly attributed. For instance, a patient named Robert could be identified as Robert, Bob, Robbie or even Bert. The MPI tables 5722 are used to handle this patient attribution. Different systems use different vocabularies to encode data. The Vocabulary Translation tables 5723 are used to translate one system such as CPT to another like SNOMED-CT. This allows the data in the Command Center 5000 to be stored in a common format, so it is more easily processed.

Figure 71:
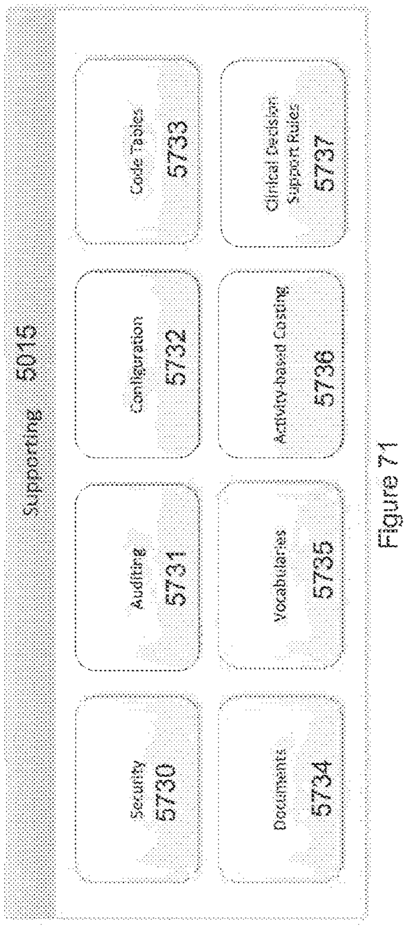
FIG. 71 illustrates the supporting tables that include tables for handling behind the scenes processing in accordance with the tool described herein.

Supporting Tables (FIG. 71)

The supporting tables 5015 in FIG. 71 include tables for handling behind the scenes processing. For example, Security tables 5730 handle authorization and authentication of user accounts and system requests. This is to ensure compliance with global privacy and security regulations. Auditing tables 5731 store data related to which user accessed which patient account and how long it was accessed, but also data about who entered or changed information within the system. The audit trail would include the date/time of the change, the user performing the action, the old data and the new data. The audit trail may be sent with any medical record requests from insurance companies, peer groups, or legal requests. The Configuration tables 5732 are used to store Application and Account-specific configuration changes. Code tables 5733 provide storage and access to common drop downs and filters used throughout the system to standardize the data and make it easier to update. The Document tables 5734 store references to the insurance benefits and guidelines, CMS NCD and LCD documents, Preferred Practice Patterns, and Clinical Practice Guidelines as well as the information unique to the Command Center 5000 such as the summary, similarities and differences between documents covering common conditions. The Vocabulary tables 5735 store the core reference tables used throughout the Command Center 5000 related to clinical data. The Vocabulary tables 5735 include but are not limited to ICD-10, CPT, RxNorm, and LOINC codes. Other examples could be SNOMED-CT or ICD-10 PCS codes. The Activity-based costing tables 5736 provide cost information related to performing procedures including but not limited to human capital expenses, material expenses, ancillary services and overhead. Finally, the Clinical Decision Support tables 5737 contain the rules and algorithm supporting data that drive the Command Center clinical decision support capabilities.

Clinical Decision Support (CDS)

The Command Center clinical decision support logic is implemented in a variety of methods. Pre-authorization, referral management, claims scrubbing, medical necessity checking for compliance with governmental and insurance regulations, and similar rules are embodied in the system through the use of third party systems. Internally, the Lab and Diagnosis Data Evaluation (FIG. 63) is an implementation of the if-then style of clinical decision support.

Figure 72A:
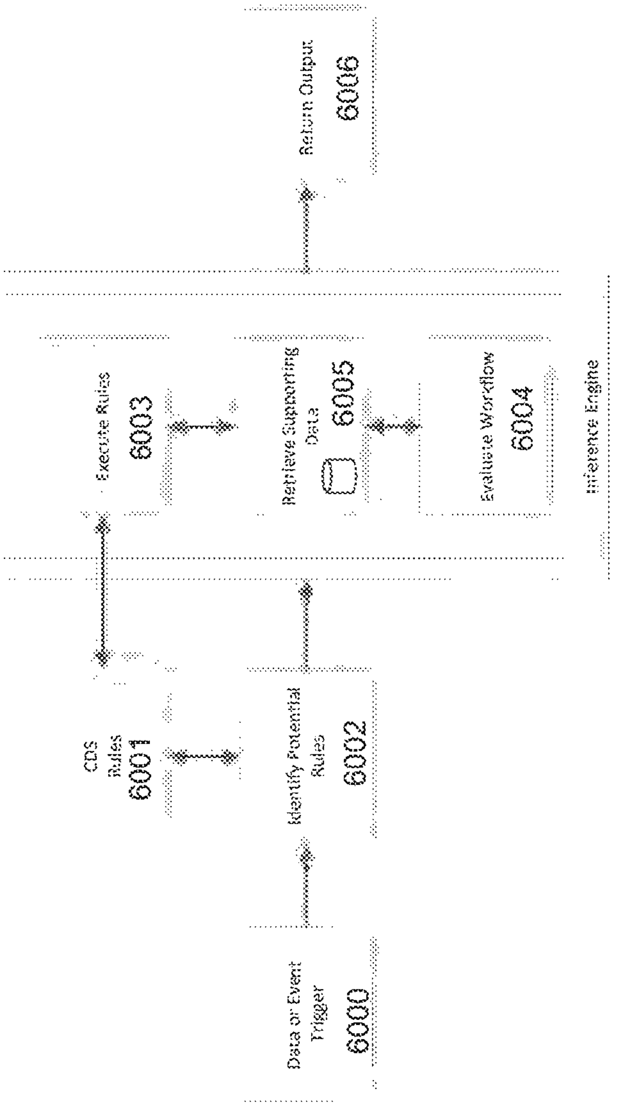
FIG. 72A illustrates an exemplary clinical decision support system in accordance with the tool described herein.
Figure 72B:
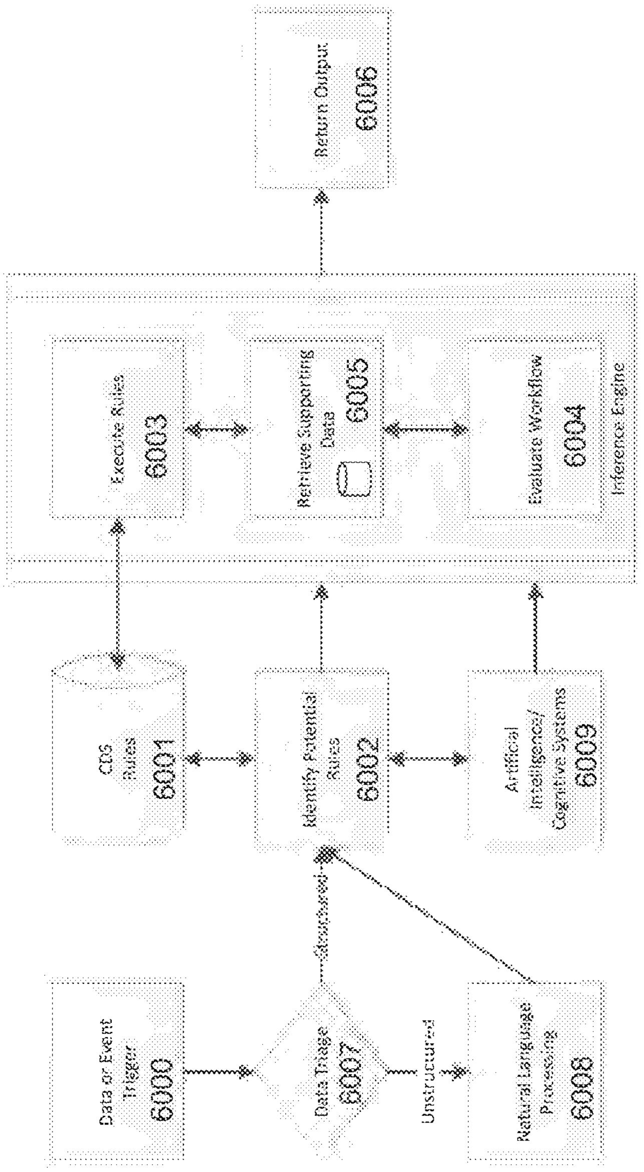
FIG. 72B illustrates an exemplary cognitive system enhanced clinical decision support system for providing cognitive enhanced guidance.

More complex clinical decision support is illustrated in FIG. 72A. In FIG. 72A, the support is handled through the use of a RETE style (pattern matching, rules-based) algorithm. A RETE rules engine or inference engine embodies a set of rules built around a data model whereby when an event is triggered 6000 (data input or a new day starts) potential rules 6001 are identified (6002) that relate to the data/event. If rules are identified, they are executed (6003) along with the evaluation of workflow rules 6004 using supporting data retrieved (6005) as needed from the patient, insurance, clinical, financial and imaging data repositories. Once complete, the outcome is returned (6006) to the requesting system for processing. Typically, the output is displayed on the screen for the user to consume or for storage in the designated database in the Command Center 5000. In exemplary embodiments, the Command Center CDS illustrated in FIG. 72A is based on the Health Level (HL7) and Object Management Group (OMG) Decision Support Standards making it flexible and compatible with other similar systems. Those skilled in the art will appreciate that the inference engine may implement conventional artificial intelligence techniques such as those provided commercially by Watson Health and Truven Health Analytics, Inc. to process received data in connection with data repositories to provide diagnostic feedback and the like.

Certain Command Center interpretations may be the product of cognitive system enhanced clinical decision support ("CDS"). As illustrated in FIG. 72B, certain guidance requests triggered at 6000 are triaged at 6007 and structured data may be simultaneously routed to the core Command Center CDS 6002 while unstructured data is routed through 3rd party commercially available Natural Language Processing services 6008. The systems 6002 and 6008 compare the incoming request against their curated knowledge base to contextually interpret the guidance as well as to provide suggestions beyond the scope of the guidelines based decision support. For example, an artificial intelligence cognitive system 6009 may continuously learn about billing and reimbursement processes, medications, insurance formularies, and patient outcomes. In such a system, an incoming medication recommendation request would then not only receive both the adopted clinical best practice recommendation but also inform the clinician of recently approved alternatives that may be both more clinically and financially effective. The cognitive system enhanced CDS of FIG. 72B may be adapted to provide guidance on: Value Management; Medication Management; Medication Pricing/Formulary Optimization; Co-Management; chart completeness; patient to treatment center matching; billing and billing code optimization; and insurance submission/audit procedures. Those skilled in the art will further appreciate that cognitive system enhanced CDS may be applied to medical records to compare medical data and to notice patterns, errors and anomalies in different entries or EMR notes. For example, when one internist is calling something a disease or has a finding yet another physician is finding something else different, or there is a disease or a billing anomaly between two different physicians, and the like. Cognitive system enhanced CDS may also be used to find discrepancies in payments, to alert physicians about inconsistent medical documentation or improper orders, to speed up the process of complying with regulations, or to alert the physician that a plan or order is inconsistent with a preferred practice plan for a patient.

Figure 72C:
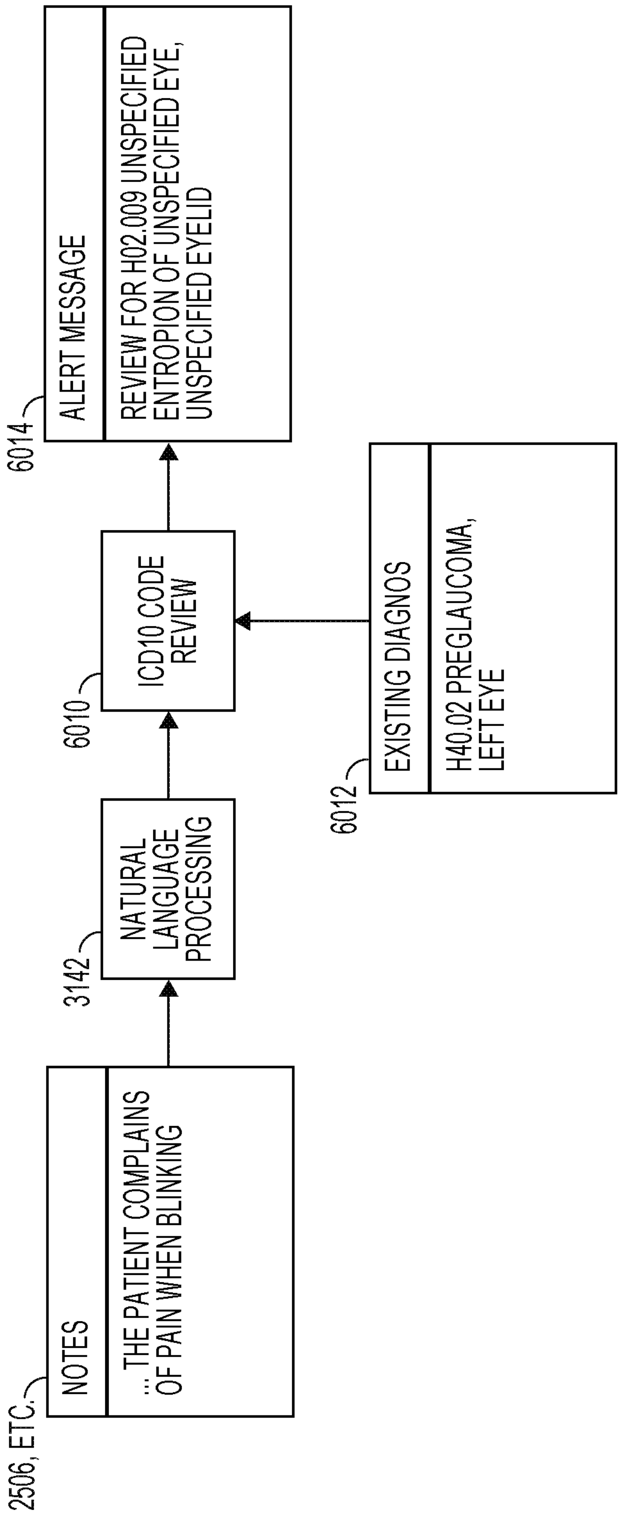
FIG. 72C illustrates an exemplary cognitive system enhanced clinical decision support system for alternative diagnosis identification.

Other embodiments of the cognitive system enhanced CDS provide direction and review of process details via Natural Language Interpretation using natural language processing (NLP) 3142 of system notes (e.g., notes 2506/2668/2701/3066/3078/et al.) described above. In FIG. 72C, visit notes 2506, etc. are parsed by NLP 3142 for alternative diagnosis identification. The unstructured data content in notes 2506, etc. is evaluated for potential ICD10 codes via Natural Language Interpretation 3142. If the potential rules process 6002 identifies ICD10 codes at 6010 not covered by existing diagnostic codes 6012, the user is alerted to the potentially viable alternative diagnosis at 6014. This code may then be selected for introduction into the Clinical Evaluation Algorithm shown in FIG. 63 for further review. The mechanics of this process may be replicated for other structured evaluation processes identifiable through Natural Language Interpretation of unstructured data.

CDS is used proactively and reactively within the Command Center 5000. Proactively, users are warned that billing certain procedures might not be covered. An example embodiment is demonstrated in FIG. 32B item 2938 where according to insurance guidelines the OCT imaging test can only be performed after 30 days have passed since the last test. In this case, the user can override the warning and proceed with the test because they deemed it medically necessary. Another example of a proactive warning is demonstrated in FIG. 32B items 2934 and 2936 where a patient is anemic to the chemical agent used to perform the ICG test so it should not be performed. Decision support is also provided in real time as users use the Command Center 5000. These rules are both clinically and financially focused to ensure lab, procedures, and imaging tests that are ordered will be covered by the insurance companies as well as to provide alternatives that may be more financially affordable for the hospital and patient but provide equivalent clinical care. Examples of these rules are demonstrated in several places including prescribing medications (FIGS. 44 and 45), ordering labs (FIGS. 46 and 47), ordering images (FIGS. 48-50), and ordering procedures (FIGS. 51-54).

Database Schema

Note Tables

Figure 73:
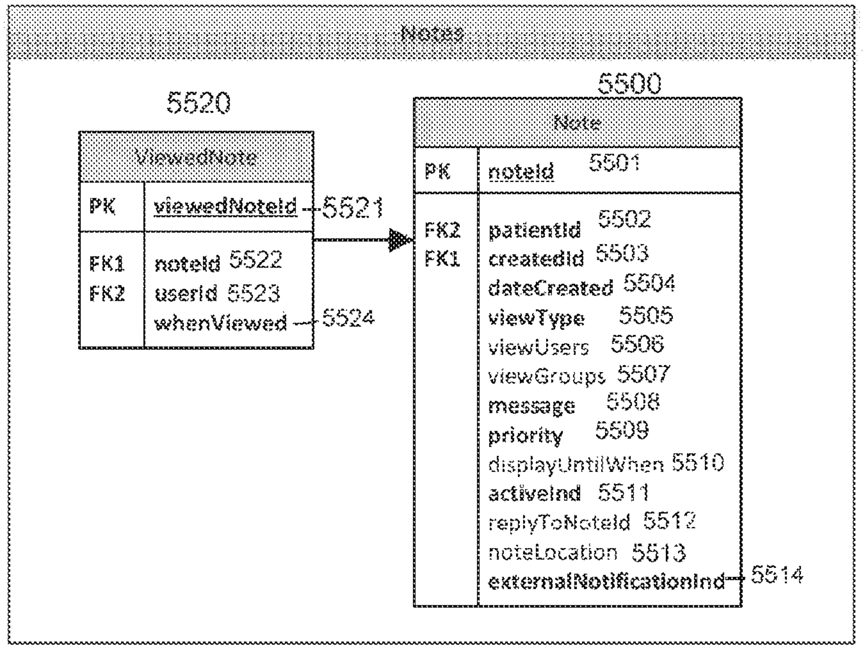
FIG. 73 illustrates a diagram of the tables used to display data on the Note tab (FIG. 39) in accordance with the tool described herein.

FIG. 73 is a diagram of the tables used to display data on the Note tab (FIG. 39). The Note table 5500 has a surrogate primary key, noteId 5501. Notes are uniquely associated to a single patient and the reference or foreign key to the patient is stored in the patientId 5502 column. createdId 5503 is a foreign key to the User that created the note. dateCreated 5504 is the date/time when the note was created. viewType 5505 determines who can see the note. If it is 0, everyone who has access to the Patient can see the note. If the value of ViewType is 1, only specific people can see the note, and if it is 2 only specific groups can see the note. The specific users are stored in the viewUsers 5506 column as a comma-separated list. viewGroups 5507 stores a comma-separated list of the groups that can see the note. The actual message is stored in the message column 5508. The priority is stored in the Priority column 5509 using the convention 0 if low, 1 if normal, 2 if high priority. The displayUntilWhen column 5510 determines how long the note is viewable. If it is null it is viewable until deleted; otherwise it is viewable until the date/time is passed. The activeInd 5511 is set to 1 if the Note can be seen and 0 if deleted or can no longer be seen based on the displayUntilWhen date/time. The activeInd 5511 column is used for convenience in that it allows faster retrieval of Notes because a date comparison is a more computationally expensive process than comparing a bit value. When the user replies to a note, the reference to the original note is stored in replyToNoteId 5512. This is a foreign key to the Note table. If there is a value in noteLocation 5513, it signifies this is a sticky note that is associated with a specific location within the Command Center 5000 (see FIGS. 18-19). The location is specific to a display panel. If it is a static display panel, i.e. the data does not change over time like an order panel, the x/y coordinates relative to the placement of the panel are stored. However, if the panel displays changing data such as rows associated to dates that change over time, the location is stored as a column and row referenced by the primary key id of the row. The externalNotificationInd 5514 stores whether or not the message should be transmitted back to the user's EMR. This process keeps the sticky note associated with the correct content, even when the content includes dynamic data such as new encounters or dates in the flowsheet.

The ViewedNote table 5520 illustrated in FIG. 73 tracks which users viewed the notes and when. The surrogate primary key is viewNoteId 5521 and the note id is stored in noteId 5522. The user who viewed the note is recorded in the userId column 5523. The date/time it is viewed is stored in whenViewed column 5524. A note can be viewed many times by the same user, but only the first time the note is viewed is it recorded in the ViewedNote table 5520.

Alert Tables

Figure 74:
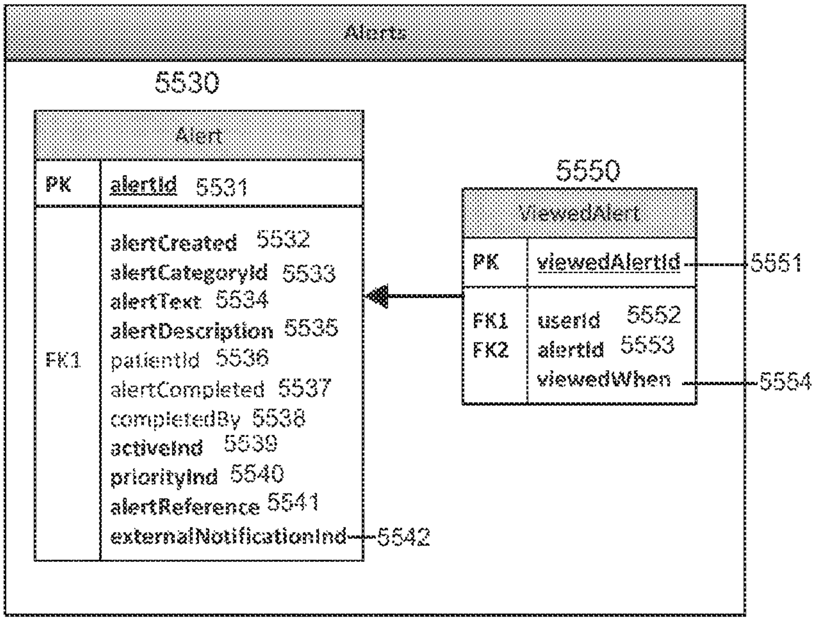
FIG. 74 illustrates a diagram of the tables used to display Alerts that are generated for a patient in accordance with the tool described herein.

FIG. 74 is a diagram of the tables used to display Alerts 5530 that are generated for a patient. The surrogate primary key id is alertId 5531. The alertCreated column 5532 holds the date/time of when the alert is created. The alertCategoryId column 5533 is a method of categorizing the alert, so they can be displayed in proximity or used in the appropriate places in the application. The column in the table is a foreign key to a code table (not depicted), but example categories are Insurance, General Wellness, Diabetes, and Billing. alertText 5534 is a short title used for the purpose of display, while alertDescription 5535 is a longer description of the alert. If the alert is associated with a patient, the patientId 5536 is stored. When the alert is completed, the date/time is stored in alertCompleted 5537 and the completedBy column 5538 stores the user who completed (deletes) the alert. If an alert is active (not deleted) the alertInd 5539=1; otherwise it is 0. Use of this column increases the speed of data retrieval. The alert priority (low, normal or high) is stored in priorityInd 5540. The values are 0 if low, 1 if normal, 2 if high priority. alertReference 5541 is used to store information about the rule/conditions that applied at the time the alert was created to better understand how the system is working. It is not intended for viewing, only troubleshooting and research. Finally, the last column externalNotificationInd 5542 is 0 if it is not transmitted back to the EMR 5021 and 1 if it was transmitted.

The ViewedAlert table 5550 illustrated in FIG. 74 stores data about which users have viewed the alerts and when they viewed it. The surrogate primary key is viewedAlertId 5551. The Alert Id is stored in alertId 5552 and the user is stored in userId 5553. The date/time the alert was viewed is stored in the whenViewed column 5554. An alert can be viewed many times by the same user, but only the first time the alert is viewed is it recorded in the ViewedNote 5550 table.

View/Panel Tables

The Command Center 5000 supports multiple configurations of the data based on the user's interests, patient's condition and task being performed. The ViewLayout table 5570 illustrated in FIG. 75 stores the panels and tabs that make up the view and how they are positioned. The Panel table 5580 illustrated in FIG. 76 stores references to the data displayed within a panel. FIGS. 75 and 76 contain the table diagrams, while FIGS. 77 and 78 are examples of the XML used to store the layout and panel information. The ViewLayout table 5570 and the Panel table 5580 thus store the configuration information generated when the view screens are configured, as described above by way of example with respect to FIGS. 41A, 41B and FIGS. 55-56.

As illustrated in FIG. 75, the ViewLayout table 5570 has a surrogate primary key called viewLayoutInd 5571. The name of the layout used for display purposes is stored in the name column 5572. The actual XML that contains the layout is stored in the gridXML column 5573. If the userid column 5574 is null, the view is a default system view that every user can use the first time they login. The userid 5574 relates custom Views to the User who created them. The defaultInd column 5575 denotes the initial layout for each view so the user can reset the View to the default.

As illustrated in FIG. 76, the Panel table 5580 has a surrogate primary key called panelId 5581. The name of the layout used for display purposes is stored in the name column 5582. The columnXML 5583 store the actual XML that defines how the panel is laid out. Like the ViewLayout table 5570, the Panel table 5580 has Panels specific to users as stored in the userId column 5584 and a defaultInd column 5585 allowing the user to reset a panel presentation.

View XML

The view XML illustrated in FIG. 77 provides means for moving and storing the different display panel and flowsheet views in exemplary embodiments. As illustrated, the view XML contains a collection of panels 5590 and tabs 5591. Within each panel 5590 is the panelId 5593 that links to the Panel tab 5591, its position 5594 and whether or not it is stacked 5595 with the preceding panel, which allows for the positioning of tabs. Whether or not each panel is fixed 5596 in position or moveable is also saved. For tabs, the position 5597 on screen for the tabs to be displayed is stored. Then each tab with reference to a panelId 5598 and its order of display is stored 5599.

PanelXML

The panel XML illustrated in FIG. 78 provides means for setting up the display panels and flowsheets in exemplary embodiments. As illustrated, the panel XML contains a collection of columns 5601. For each column, the name of the column 5602 is specified along with the source 5603 where it comes from (e.g. Table=Labs Column=LabDate) the width 5604 of the column and the order the columns 5605 are also tracked.

Guidelines

Figure 79:
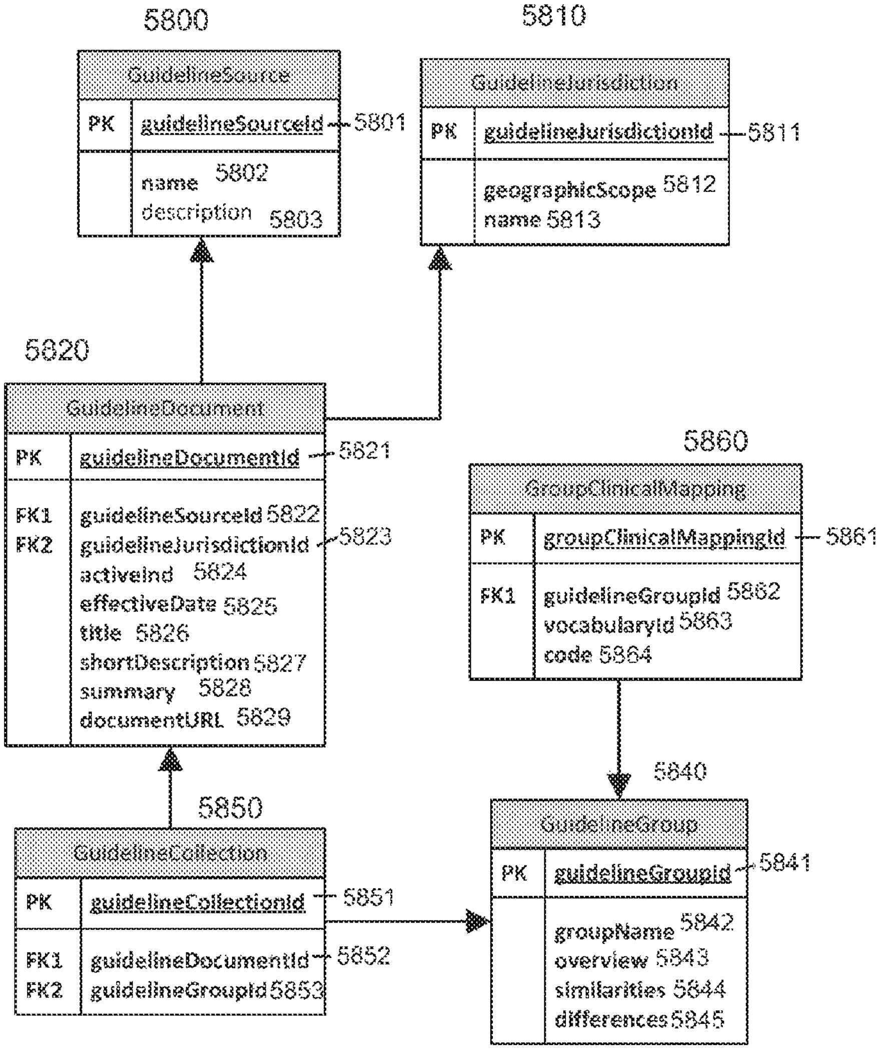
FIG. 79 illustrates the guideline tables that are used to store individual guidelines, groups of guidelines in order to store common information about the group, and associations of those groups with clinical codes (such as ICD10, CPT, RxNorm) in sample embodiments.

The Guideline tables illustrated in FIG. 79 are used to store individual guidelines, groups of guidelines in order to store common information about the group, and associations of those groups with clinical codes (such as ICD10, CPT, RxNorm) to enable physicians to assimilate the information quickly. GuidelineSource 5800 is a reference table that contains the source of the Guideline. For example, insurance company, a professional society in the case of Preferred Practice Patterns, or the government. The surrogate primary key is guidelineSourceId 5801. The name 5802 is for display purposes and the description 5803 provides more detail. GuidelineJurisdiction 5810 is a reference table that contains geographic locale references. These are applied to the Guidelines to understand where they apply. For instance, insurance guidelines are usually state specific. The surrogate primary key is guidelineJurisdictionId 5811. The geographicScope 5812 is country, state, or region and the name 5813 specifies the specific jurisdiction, so in the case of New Jersey, the geographicScope would be state and the name would be New Jersey. The core table is GuidelineDocument 5820. The GuidelineDocument table 5820 stores information about individual Guidelines. The guidelineDocumentId 5821 is a surrogate primary key. The guidelineSourceId 5822 is a foreign key to the GuidelineSource table 5800 so that it is known where the guideline originates. The guidelineJurisdictionId 5823 is a foreign key to the GuidelineJurisdiction table 5810 so that it is known where the guideline is used. The activeInd 5824 is 1 if it is active and 0 if it is not. This column is used to make retrieval easier. The effectiveDate 5825 is the date when the Guideline is effective, so guidelines can be added before they are actually used. Title 5826 is used for display purposes, while shortDescription 5827 and summary 5828 provide more detailed information about the Guideline. The documentURL 5829 is a link to the actual guideline document for retrieval and display. The Guideline document, usually a PDF, would be stored in the static File Cache 5017 in FIG. 57.

Individual guidelines are then grouped into a collection so an overview can be provided of the guidelines and information about how they are similar and different. This allows the physician to easily assimilate complex information when minute differences may be buried in hundreds of pages of documentation. The GuidelineGroup 5840 table has a surrogate primary key guidelineGroupId 5841, a groupName 5842 for display purposes and then several text fields to capture the overview 5843, similarities 5844 and differences 5845 about the group. The Guidelines are then grouped into a collection using the GuidelineCollection 5850 table. The surrogate primary key is guidelineCollectionId 5851 and the other columns are foreign keys—guidelineDocumentId 5852 and guidelineGroupId 5853. It will be appreciated that these entries enable the user to aggregate all of the guidelines together and to write and store a common overview that outlines the similarities and differences in the guidelines.

The last table related to Guidelines is the GroupClinicalMapping 5860 table. Table 5860 maps clinical codes to GuidelineGroups 5840. Table 5860 has a surrogate primary key groupClinicalMappingId 5861, a foreign key guidelineGroupId 5862 to the GuidelineGroup 5840 table, a vocabularyId 5863 identifying the vocabulary being used and the code 5864 that can be searched. The GroupClinicalMapping table 5860 allows users to easily search for collections of guidelines that apply to a specific clinical code (ICD10, RxNorm, CPT, or other codes) or see at a glance a set of guidelines based on patient specific data (see FIG. 42).

Utilization of Rows in User Interface

Figure 80:
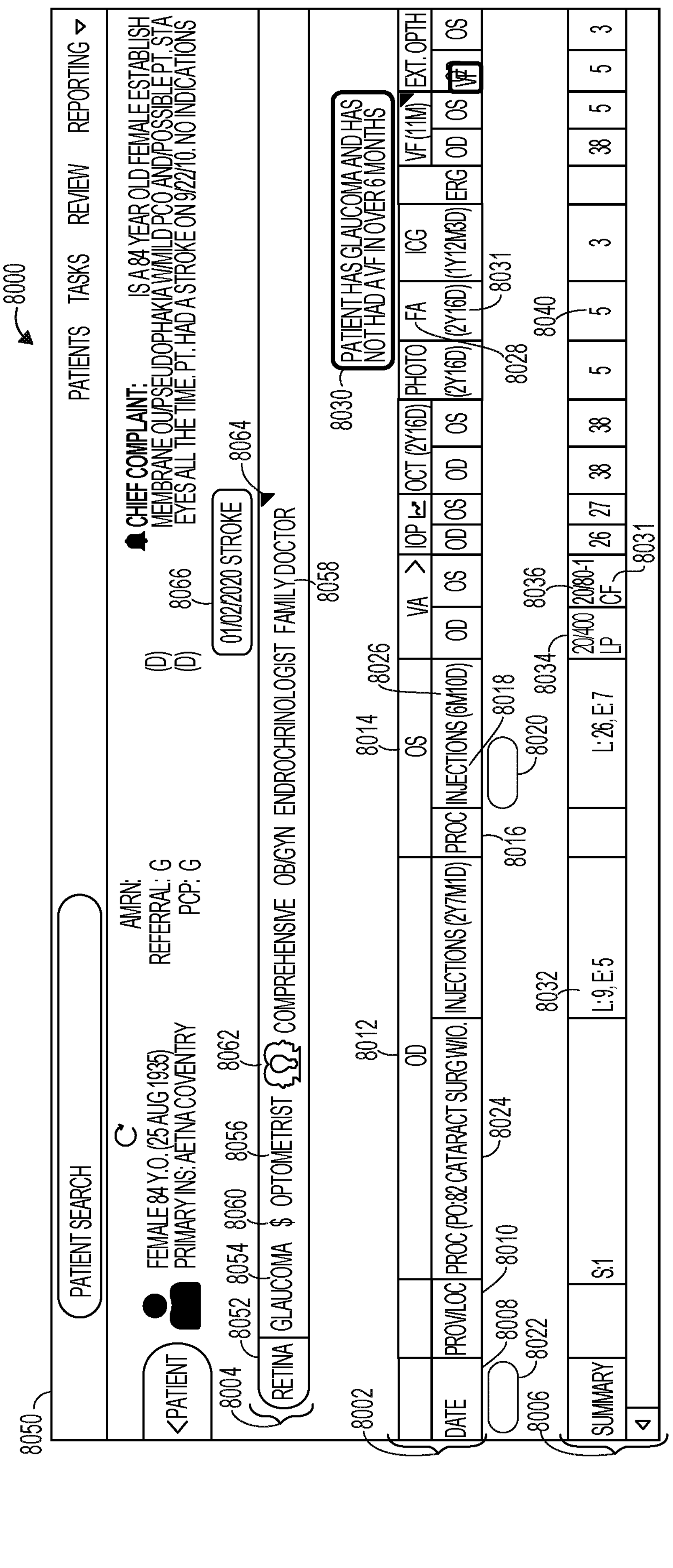
FIG. 80 illustrates how three rows in the user interface may convey much information for a healthcare professional in sample embodiments.

FIG. 80 illustrates how three rows or panels in the user interface 8000 may convey much information for a healthcare professional in sample embodiments. Header 8002 is an example of a header that can appear on each individualized specialty-based provider's actionable dashboard. As illustrated at 8004, different actionable dashboards that have been particularly designed for different providers of different specialties may be accessed. As illustrated, a summary row 8006 may be provided on each individualized dashboard for each doctor, specialist, or other user and may be specialized for each user.

Referring back to header 8002, which also represents the column where all rows underneath would have information related to this description, the date is represented at 8008. The date is the time, day, and/or date of the encounter of a patient or a group of patients that the encounter/action took place. The initials or name of the provider who cared for the patient or if just testing, would be the location or the test done. In one common embodiment, the provider's initials are presented at 8010, which may also include a location, as providers can have multiple offices. An abbreviation, description, or identifying factor of which office that provider saw and had the encounter with a patient would be listed at 8010. 8022 shows an example of one of many patient encounters over time.

An example of a column that is a procedure and, in this case, is divided into the side of the body is shown at 8012. OD is displayed, which in eye care means right and in this example, means the right eye. In the case of orthopedics, 8012 could reference the right knee. Similarly, 8014 represents the left column or the left eye, where OS represents the left eye or left knee in this example. As illustrated, the OS or left column of the header can be a procedure 8016. Under the column of the left eye is listed, by encounter, identifying procedures such as injections 8018. Item 8020 shows a focal procedure that has been performed (e.g., injection of Eylea), while 8022 shows the date of service being Mar. 21, 2017.

As illustrated at 8024, the header 8002 may also show that a cataract surgery has been done and that a postoperative period is counting down. The header 8002 may also show that injections 8026 were last performed six months and ten days ago. Another data element 8028, such as FA, may be shown over time. 8030 shows the last time this test or item was done. In this case, it was 2 years and 16 days ago. Header 8002 also includes a pop-up 8030 of underlying information. In this case, the patient has a diagnosis of glaucoma and has not had a visual field in over six months.

The summary row 8006 shows how not only is the total number of something that had occurred in the rows above counted, but it can be divided according to what was performed. So, it is a smart summary column. In this case, 8032 demonstrates that there were twenty-six Ls and seven Es of which one E (Eylea) is shown at 8020. Not shown in the diagram, would be the dates of service/encounters. This can measure or count anything. This happens to be an example of a retina doctor who does injections in the right eye in this case, and used "L," which stands for Lucentis times and "E," which stands for Eylea. 8034 similarly demonstrates the summary cell in a column of the left eye. 8036 shows the vision in the left eye is 20/80-1 and could also reflect the best number or event that occurred in the entire row overall of dates of service, and can be highlighted to inform the user that it is the best value. 8038 shows CF. In this illustration of a retina surgeon, CF means count fingers, which is very bad vision and is, therefore, red. For the first time in this illustration, a retina surgeon can know, over the time that the doctor has been delivering services, or any doctor, what is being reflected in encounters and rows above. The best vision was 20/80 (8036). The worst was count fingers (8038). This can also be the best blood pressure and the worst blood pressure. Every different specialty in medicine has different ways that it would like to measure the highs and lows in a column. 8040 simply shows the counting of the number that had occurred in all of the encounters. In this case five FAs 8028.

It is important to note that the tool can measure anything in the row and display it in multiple different ways. The choice could be just to see the high and low as in 8036 and 8038 over a short period of one year or over as many years as there have been encounters. It can also be set to show percentage changes over time. In any case, this summary provides a tremendous amount of information to the provider for enabling rapid decisions.

A panel 8050 may be located at the top, side, or bottom of the display in FIG. 80 and may provide access for each specialist to different types of healthcare providers or different doctors who want to customize the display. Any type of doctor or dentist or other health care provider of any specialty can be listed. As few or as many as have actionable dashboards that can be accessed immediately with direct access by simply clicking on the specialist's name. For instance, the specialists may be retina doctors 8052, glaucoma doctors 8054, or an optometrist 8056. All three happen to be types of eye doctors. All three could be in the same practice, separate practices, or even in different countries. Each, when clicked on, pulls up an actionable dashboard specially designed for them or their practice in that specialty. 8058 provides an example of a non-eye doctor, in this case, the family doctor.

It is important to note that any health care provider, if given permission by the patient, and each specialty noted in FIG. 80 could see the actionable dashboard of the other specialists for as little or as much as each would allow. There is some information in an actionable dashboard to each specialist, practice, or doctor that they might not want others to see, which can be hidden (e.g., payments and costs). In addition, next to each actionable dashboard can also be additional information that can also be pulled up instead of the actionable dashboard itself. For instance, a dollar sign 8060 could be for providing for each practice or actionable dashboard, payments, costs or any financial matter that can pop-up to show a different type of financial dashboard. 8062 shows an example that can pull up any type of additional information, such as a shared care dashboard between different providers.

8064 illustrates that an entire cell can alert all of the other providers of something important. It can be a color change, or flash, or blink. When activated, it represents that there is some type of important event, for instance, that all providers should know. A pop-up 8066 also may be shown at all times or by hovering over 8064. The popup could represent whatever the important item is to be alerted. For instance, a new diagnosis like the patient had a stroke on Jan. 2, 2020, which all providers would like to know. It can also inform all providers that the patient missed an appointment that was very important with that doctor. So, that all specialist would know that and be able to remind the patient.

It will be further appreciated that the actionable dashboard may further include a communication center where users can send messages to each other in a HIPAA compliant way. In other words, a physician, while seeing a patient, can send a message to their chief technician or the office manager to talk about following up on a patient or also to the billing office that there is a billing problem. Then, staff can report back to the doctor and this message can be imbedded into the smart actual dashboard so that the next time a doctor sees the patient through icons and columns of correspondence of communication within the practice, the doctor can pull up what was the response to a message they had sent earlier. This response can be read live while treating the patient so that the doctor can take it into perspective while making decisions. The messaging system, attachments or anything else can be sent to the doctor or health care provider in any way that they would want. Whether through email or the internal messaging system or as a tickler system within the EMR system that automatically toggles back and forth to the actionable dashboard, so the doctors can see their messages at the end of the day or the end of the week, or while seeing the patient. It really helps organize the doctor's life, so this actionable dashboard becomes the communication hub, the switchboard, for the entire practice, while communicating with the health care provider.

Figure 81:
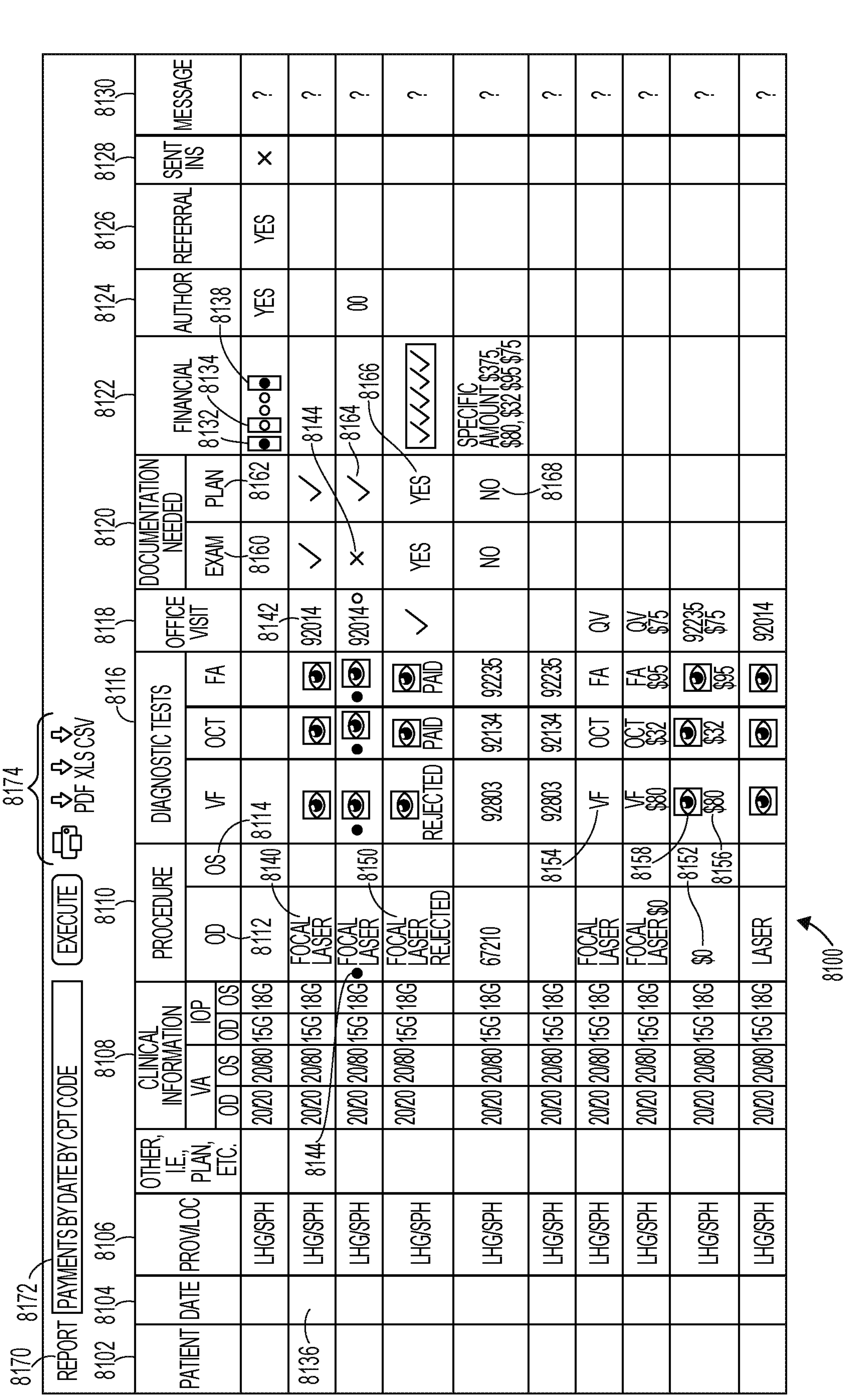
FIG. 81 demonstrates a display that enables a healthcare provider while delivering medical care to a patient to participate in revenue cycle management.
Figure 82A:
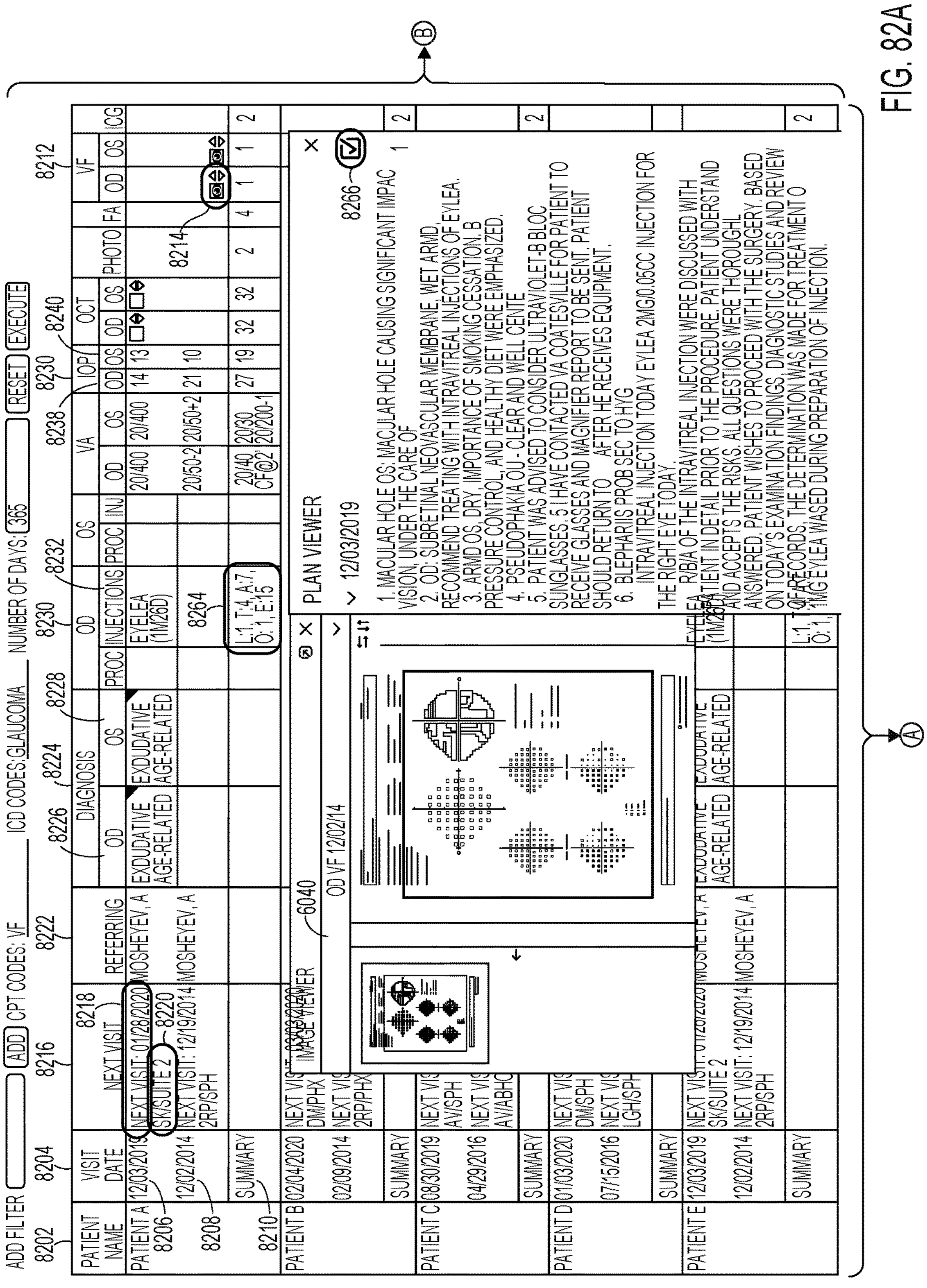
FIGS. 82A-82D all together illustrate a display of a report that can be run by user of the tool described herein in sample embodiments.
Figure 82B:
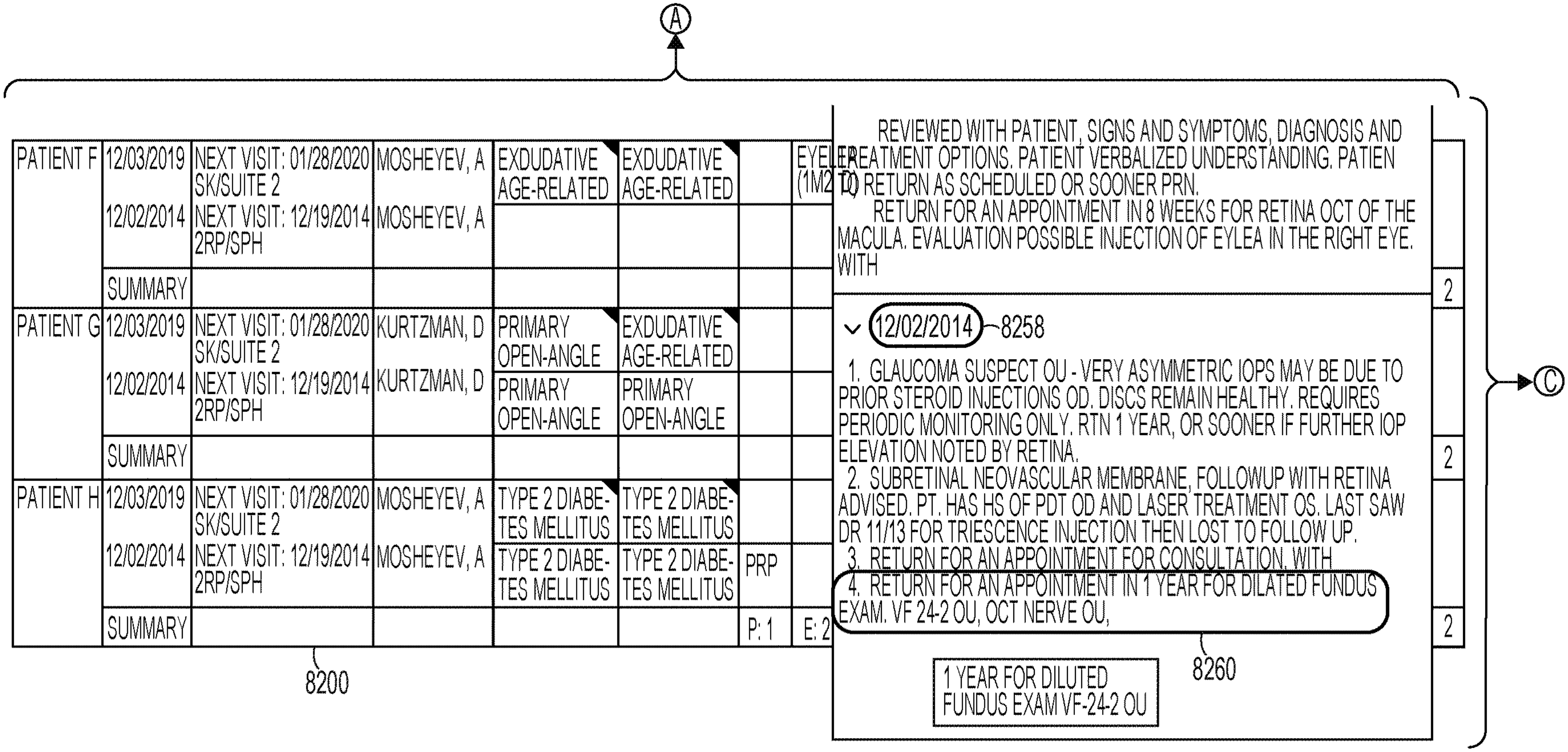
Figure 82C:
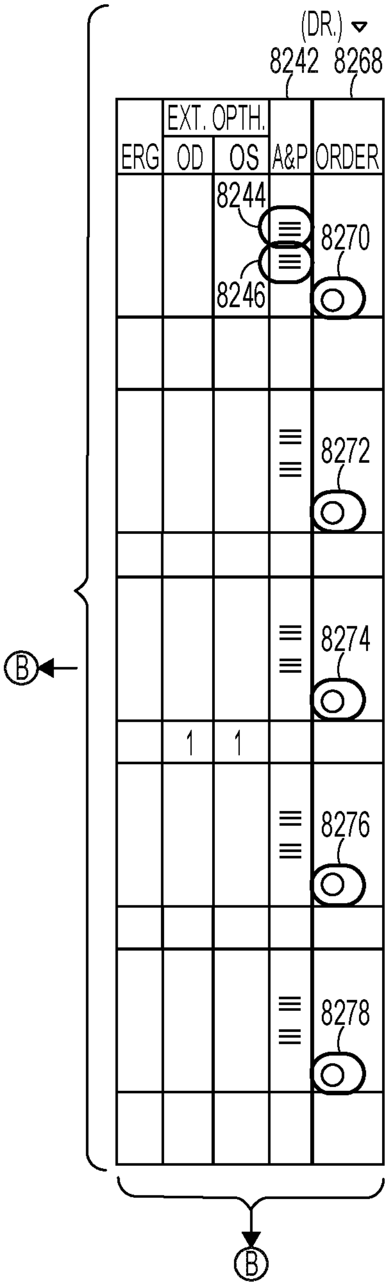
Figure 82D:
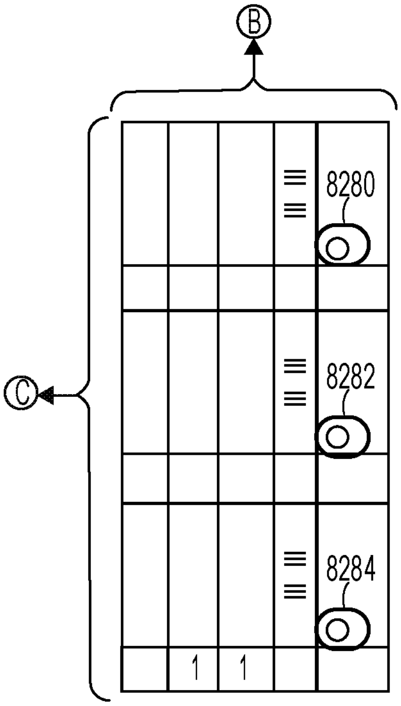

FIG. 81 demonstrates a display that enables a healthcare provider while delivering medical care to a patient to participate in revenue cycle management. Without interrupting medical care, the healthcare provider may understand what things cost, whether they have been authorized to do something like a procedure, and whether the previous claims were rejected or paid. Critical compliance issues of properly following the laws can now be often confirmed because if the healthcare provider was paid for something and the services was not performed, the failure to perform the service would be detected. The billers know when charges are paid or rejected and the corresponding diagnosis and CPT codes, but this embodiment correlates the financial with clinical as the doctor is seeing the patient without interrupting the patient flow.

The display 8100 shows a particular patient's name or the name of a number of patients at 8102. The date of a particular encounter is shown at 8104. The patient data can be seen over many encounters listed in the different rows. The provider who delivered the service as well as the location of the provider who saw the patient is provided at 8106. The clinical information that can be displayed simultaneously for the doctors to be able to care for the patient is provided at 8108. This clinical information is different for all medical specialties. Eye doctors might look at vision. Family doctors might look at blood pressure or blood sugar.

A column of procedures 8110 that were performed are defined that need to be measured by specialty. Every specialty might have different procedures and the tool can have multiple columns for different procedures. 8112 and 8114 demonstrate that a procedure can be on different sides of the body. 8112 represents the right (in eye care—OD) side while 8114 represents the left side of the body (in eye care—OS). In orthopedics, procedures of the right knee and left knee could be populated.

8116 provides an example three types of different diagnostic tests usually performed and billed in an eye doctor's office (e.g., VF, OCT, and FA) but any diagnostic test or other CPT code could be in these columns. 8118 is the office visit that was charged as there are different levels of office visits that a provider can charge at different times. 8120 illustrates whether proper documentation was needed or not needed to be able to bill any of the procedures, diagnostic tests, or office visits.

A financial column 8122 may include an authorization column 8124 where providers as they are seeing patients can actually know whether or not the insurance company has authorized the procedure. A referral column 8126 may indicate whether the proper referral from a family doctor to a specialist was received. A sent insurance column 8128 may be used to indicate whether insurance information has been received for the patient, while message column 8130 may provide messages or tasks that manually or automatically can be created by the user or anyone in the practice to communicate to the user. Financial column 8122 may include many different ways of indicating to a doctor or provider the financial information. For instance, indicator 8132 could be red which could mean rejected, or green for paid, or yellow for partially paid. Another indicator 8134 that is associated with one of the other columns representing something performed and charged by the user that particular date 8136 may also be provided. A third indicator 8138 could be red, yellow or green to represent payments or express costs and corresponding to another of the charges for date 8136. 8140 demonstrates that a focal laser type surgery was performed on a particular encounter date. Indicator 8132 could be associated with the focal laser type surgery 8140 and represents, if red, that the insurance company rejected payment and nothing was paid. Indicator 8134 could relate to whether another item performed on date 8136 was paid. Similarly, indicator 8138 could correlate with whether office visit 8142 was paid.

Instead of all indicators of payment being on one row together in column 8122, the indicators could instead be in the column next to the medical service charged for. In addition, an indicator 8144 may show that there was rejection right next to the procedure, in this case the focal laser, as there is a red dot 8144 which correlates to zero payment. This type of indicator can instead of being all in one column 8122 also can be in each column associated directly with what was done as at indicator 8146 where icon 8148 shows that a VF was performed. Indicator 8150 shows the procedure focal itself can be red or even written 'rejected'. Similarly, a zero 8152 may be used to show rejected payments. Indicator 8154 demonstrates that a VF was performed but could be highlighted green meaning it was fully paid or red if it was rejected. On the other hand, the amount paid 8156 could in the same cell next to, above or below what was performed, in this case $80.

The healthcare provider may also confirm that something was done or if they want to see the actual item being billed or to interpret it. For example, icon 8158 would allow the healthcare provider to click on it and actually the image itself comes up and an interpretation could be seen. If no image is attached, they might discover that it was not done and billed incorrectly, so the healthcare provider could elect to return the money to the insurance company. This decision may be made rapidly while examining a patient. Additionally, a lack of documentation may be indicated in column 8120. Because doctors often use scribes or assistants, they may have inadvertently not completed the chart. Column 8160 is an exam column, while column 8162 is a plan column. Perhaps they are completed or not, but instantly doctors can see whether a check mark 8164 has been provided to indicate that documentation has been completed. Alternatively, the word 'yes' 8166 or any other appropriate word or indicator may indicate that the documentation has been provided, while the word 'no' 8168 or other appropriate word or indicator may indicate that the documentation has not been completed. 8144 could be a 'X' noting that the indicated documentation was not completed. In this fashion, doctors instantly can be informed and take action to complete the chart.

Doctors may have an interest in running a report on any of the elements, columns or rows to identify payments in one patient or a group of similar patients. 8170 depicts the ability to run a report. The type of report that is requested may be indicated at 8172, where patient list 8102 may list a whole group of patients, perhaps sharing a common insurance company, but doctors can quickly make decisions because they have at their access not only the exact financial information, but in context for each individual patient can understand what was really done that day, how the patient's care was performed, what tests were or were not completed and whether they were paid properly or improperly or, from a compliance point of view not documented correctly as indicated in column 8120. The user may elect to export the data at 8174.

In sample embodiments, the indicators 8132, 8134, or 8138 could be selected to bring up a ledger that matches each CPT code individually with payments. Here the exact row of the date of service with all the CPT codes one or more done that day and payments can all be brought up as described above with respect to FIG. 13B.

Summary Reports

Another aspect of the tool is the reporting mechanism. Because the actionable dashboard also stores most everything that is important to the doctor, literally anything can be reported, and columns can be compared to rows and any information that it stores, whether it is financial or not, all reports can be written and created from this actionable dashboard. FIGS. 82A-82D all together illustrate a display of a report 8200 that in addition to identifying information on the patient and specific information that the report pertains to enables to user to bring up and analyze more information by going into the patient's medical record, EMR, PM system in the context of the report itself. The interface in FIGS. 82A-82D all together provide all the relevant information necessary for a user to evaluate the situation, identify the similarities or differences in a group of patients, provide direct access to more information such as images and plans allowing the user the ability to then in context correlate this additional information to other information and to edit notes and make notes in context and to even place orders for actions to be taken.

FIGS. 82A-82D all together illustrate one of countless reports 8200 that can be run by user of the tool. This example happens to ask the question "show me all patients in the practice who have the diagnosis of glaucoma and have not been seen in greater than 365 days." FIG. 80 illustrated at 8030 how an alert could be shown on a single patient, for example, showing a single patient having "glaucoma but no visual field in six months". But an alert or a report can be for any set length of time. The tool thus allows individual patients to have alerts as the patient is being examined by the doctor or all patients in a practice or any subset in a report.

8202 is the patient name. By way of example, there are eight rows, so in this illustration, there would be eight patient names in the row 8202 and more patients in the report can be scrolled or on different pages. 8204 lists the visit date or encounter of that patient that the report is evaluating and reporting on. 8206 in one embodiment might show the date of the most recent visit of the patient, in this case, Dec. 3, 2019. Note, a report before it is run the user can specify any dates or any data to be presented in the rows and columns. In the example 8208, a visit date of Dec. 2, 2014 is indicated. The subject in this example of the report may identify patients in the practice, for instance, who have not had a particular test. In this example, the VF (visual field) 8212, which indicator 8214 shows that the last visual field done was Dec. 2, 2014 (8208). This is the subject of this report, so in this patient's case (Patient A under column 8202) the patient has not had a visual field as shown at 8208 and 8214 since Dec. 2, 2014.

In addition to particular dates of service at 8206 and 8208, row 8210 can also be included for each patient in the report as a summary. FIG. 80 at 8006 illustrates the summary row features. Much information can be gathered about this patient by the summary row taken into consideration while looking at dates from rows 8206 and 8208.

The next scheduled visit may be indicated at 8216, showing the date at 8218 and the location at 8220.

8222 may indicate the referring doctor, while 8224 may indicate the diagnoses of the patient (ICD-10). 8226 indicates the diagnoses for the right side of the body. In this case, an eye doctor's example, right is OD. On the other hand, 8228 indicates the diagnoses of the left side of the body, where OS is the abbreviation for the left eye. All diagnosis recorded for any date can be seen by hovering or clicking.

8230 indicates a column of the right eye where anything can be followed. In this example, injections 8232 are listed. 8234 shows that an injection was done for this patient at the most recent visit (row 8206, Dec. 3, 2019).

8236 indicates a clinical measurement column. In this case, in the field of ophthalmology, IOP, which is intraocular pressure, which happens to be related to glaucoma, is the subject of the report. 8238 shows right eye readings over time. In this case, 8206 is the last visit, while 8208 is the visit when the last visual field was done. On the other hand, 8240 shows the measurements of the pressure for the left eye in the two visits reported at times 8206 and 8208.

Column 8242 illustrates where on the two visits that the report was told to show for the dates 8206 and 8208 the respective plans 8244 and 8246 that the doctors had written for the respective days.

Without leaving the screen, the user may also directly access the visual field by selecting or hovering over the icon 8214. Upon selection, image viewer 8248 may bring up a visual field 8250 from Dec. 2, 2014. 8252 is the image itself. Now, the doctor can actually see if there was a problem when the last visual field was performed and interpret in context, but the doctor might want another concurrently active window for display. For instance, and its logical for this report, by clicking on plans 8244 and/or 8246 the doctor may access the plan viewer 8254 that shows simultaneously plans 8256 (for Dec. 3, 2019) and 8258 (for Dec. 2, 2014).

8260 illustrates how the doctor can read the two relevant plans and instantly determine that the doctor on Dec. 2, 2014 had written that they wanted to see the patient "one year for dilated fundus exam, visual field 24-2" (shown enlarged at 8262). The user now realizes that the patient should have seen this doctor four years earlier and can even see by looking at image 8252 a visual field (VF) back then (Dec. 2, 2014) can determine if, back at that time, the VF was abnormal. Shown in this example is the fact that 8264 in the summary row shows this patient has had many injections of different kinds in this right eye. This is enough information to speculate since all of these types of injections are for a certain retina condition and when looking at 8234 it becomes apparent that in fact, Eylea, was performed on the most recent visit at 8206. The reviewer can look at the plan 8256 and see from the note the fact that the patient had glaucoma was not even mentioned and certain conclusions could be reached for what has happened that resulted in the visual field not being performed in five years. Now, the doctor can even edit in context a plan or note by selecting to edit at 8266 and to edit the note and input the accurate up to date note or create a message. Now the doctor can take action and open up an ordering panel which can be accessed by any means on the screen by popping up a window as described with respect to FIGS. 34A and 34B. The ordering can be for all the patients at 8268 or each patient may be selected individually at 8270 8284 as the doctor evaluates each patient one by one to see the common problems and repeating the steps noted for a patient A again in patients B through H. If more information is needed for any patient A through H, by selecting the name A through H, the health-care provider may open the individual patient actionable dashboard or take the user to the EMR of that patient.

It is important to note that for the statement 8262 written or the scheduled appointment, the visual field follow up ordered by the doctor wanting to see patient in one year for a VF as seen in 8262, the doctor at the time of reviewing this report can take action. However, the statement 8262 of a visual field in one year could, through NLP, and machine learning could have already been discovered four years ago when the doctor said they wanted the patient to return. In one embodiment, the tool could have sent an automatic task to the appropriate person in the practice, informing them of the importance of this patient keeping a scheduled appointment. Additionally, if the appointment is not scheduled, as indicated by the plan, an automatic task would be sent indicating a return exam visit and a certain diagnostic test is needed. An automatic task could in some embodiments at that time have looked exactly like what is seen in this report but row 8206 would not be the date of service of the report which ran the last time the patient was seen, but rather whatever date would be when the task was generated of the last appointment the patient was seen.

By way of example, if through NLP and ML and artificial intelligence or even if there had been a scheduled appointment by the doctor who wanted to see the patient in a year for a visual field, in this case from Dec. 2, 2014, was missed or canceled or the event did not occur at that time, the tool would send an automatic task, not depicted with all the information from row 8208 along with the most recent visit, closest to the canceled and/or missed appointment or an appointment that never was scheduled. Through machine learning and NLP, all of this information would go as an automatic task to the appropriate person who could then immediately discover the urgency and need and place an order from this task, including linked to the task a mechanism up, properly schedule the appointment and visual field or Whatever diagnostic test or procedure that might have been missed but the tool now discovers had been planned. The task includes the needed information to act with direct accessed with no more than a click to information in the display that enables the user to efficiently make a decision and take action.

The tool offers a three-tiered safety net for capturing potential mistakes and/or improving medical care. The auto task system can discover instantly when something that was ordered, needed to be evaluated or measured or performed and automatically send the task. In addition, an alert system goes into effect so that whichever doctor or user that next sees this patient for any reason which could be within the practice itself or if it is so urgent that any or all doctors or users of other actionable dashboards could be alerted about a critical event as is programmed and chosen as truly an urgent or critical event and light. This way, the patient can be reminded of the importance of making an appointment and also the treating doctor or treating practice, the next time the patient comes in in a variety of ways can be alerted that in this case the visual field (VF) is needed as described as an example of a report in FIGS. 82A-82D. FIG. 80, described above, illustrates how the alert may function. Even the patient can be reminded because through the portal or text messaging or other method automatically a message/task can be sent to the patient that a test (VF) is needed.

So, the tool offers three-tiered safety net with alert at the point of care, and automatic task option to the user and finally as described in FIGS. 82A-82D, an actionable fully evaluative report that can be run at any time. If the embodiment that allows for the automatic tasks and alerts is in fact acted upon, then this patient would not even have been on this report because the necessary care would have been provided. As noted above, even the patient can be alerted of an important visit, test or procedure that should have occurred and therefore be scheduled. Presenting this information to the user in rows and columns is an efficient way to allow the user to quickly make decisions, but in other embodiments it is not limited to rows and columns, it could be anywhere on a screen and does not necessarily have to have all this information it could be a part of the information or even comprehensive information, with the entire actionable dashboard sent in a task with just the most important rows and columns highlighted in any manner to quickly draw the attention of the user to the issue and the action that needs to be taken so in context the entire patient situation can be shown. Direct access to more information in the EMR or link anywhere can be connected to a task, alert or report. Through natural language processing, machine learning and AI just the important information can also be sent. In one embodiment of the tool, when the action is self-evident because of orders previously placed by the doctor, even without human interaction, the proper scheduling of the patient can occur, when the doctor had already in the past placed the order.

Patient Scheduling/Triaging System

In other embodiments, a medical guidance system is provided that helps doctors, and just as importantly, their staff, avoid mistakes. The medical guidance system offers preferred practice pattern advice, as set by a practice and supported by the medical literature, it helps with scheduling patients and makes certain that patients needing appointments and follow up appointments do not fall through the cracks and gives them timely appointments based on the risk that can be evaluated through algorithms of the medical guidance system. It also properly triages patient queries.

The medical guidance system addresses and solves the following issues:

1. Scheduling of patients with automated methodology to help ancillary medical staff (i.e. receptionists), call centers, and doctors to prevent patients from falling through the cracks by prioritizing the risks of symptoms and diseases, and associating these with past procedures, diagnostic tests and other critical items that need to be evaluated. In this way, staff and physicians are guided as to which patients needs the timeliest interventions, appointments and follow up.

As an example, as a patient is checking out from an appointment, the algorithm double checks that a mistake did not occur, what was ordered in regards to follow up, and if the prescribed follow up time period is not able to be done provides guidance to those that are scheduling about the potential risk of not precisely following what has been ordered so that if the doctor or staff needs to be asked and notified that there is a problem in scheduling, this is done so that a patient is not placed at undue risk. In addition, if a patient with certain high-risk diagnoses, procedures, diagnostic tests and symptoms misses an appointment, he or she is identified. What normally happens when patients miss appointments is that they are put into a recall system or the patient is called directly. However, there is currently no system available that identifies high-risk conditions, procedures and diagnostic tests and tracks the patient's attendance at the related appointments. The medical guidance system identifies which patients require strict follow up care and cannot be missed. It tracks patients who might miss multiple appointments, whether the patient cancels or the doctor's practice cancels, and what the risk is to that particular patient if he or she is not scheduled in a certain period of time. In addition, risks are calculated and tasks created for anyone in the office, including the office manager and receptionist, and depending on the risk, the task list can even be elevated to the physicians themselves.

A patient scheduling risk identifier identifies patient risks based on their medical history and can be applied to any domain that schedules patients. This includes all fields of medicine: ophthalmology, dentistry, chiropractic, podiatry, etc., and also includes practitioners such as physicians' assistants, nurses, hospitals, and emergency rooms. The patient scheduling is performed under a variety of circumstances as they leave the practice from a current visit, by calling reception, email, portal, etc. Also, scheduling can occur when patients are not in the office. Patients can call, or even through email, portal or other electronic means request information for an appointment and a receptionist or call center might answer with little clinical knowledge and, using the medical guidance system, all of the ancillary staff can ask certain questions or patients may electronically fill out questions relevant to scheduling. Precise calculations can be created through formulas to then give guidance on a time period for scheduling and if it cannot be calculated or there is an increased risk, referral to the physician or their assistant to make a decision about a particular patient. For example, who is making the telephone call is taken into account. If it is a referring doctor in a subspecialty that clearly would know what constitutes a medical emergency, like another eye doctor, who certainly knows an emergency in regard to eyes versus a foot doctor might not be as knowledgeable when they refer a patient with diabetes about eyes. All important data points related to scheduling an appointment are collected and evaluated to determine the speed at which a patient needs to be seen for an evaluation. If the patient cancels an appointment the same sort of evaluation can occur but, in this case, the patient is not calling, rather, the risk for that patient who "missed" an appointment can be calculated. The question can be discovered not by what patient says but by auto populating from what is in the patient's chart. For instance, a procedure that had been done and normally follows up post-operatively in 30 days, if the patient cancels it at 30 days and then misses another appointment a week later, this is a much higher risk than a person who did not have a procedure that required a follow up unless, of course, symptoms are dramatic, all of this is measured against the patient's disease state, diagnoses and past history. All are calculated to give guidance to ancillary staff to help medical practices schedule properly, as patients are checking out, as patients who are new or existing patients call in for appointments or as patients miss appointments due to either cancelling or the provider cancels.

The medical guidance system also provides methods for determining that patients are properly followed up for an office visit with the correct provider. This method becomes important because patients can be lost in the shuffle of so many different specialists. If a patient comes into a multi-specialty practice of any kind, and even if there are only three specialists, a patient can be scheduled with the wrong provider. By way of example, in ophthalmology there may be in one office a general ophthalmologist, an optometrist, a retina surgeon and a glaucoma surgeon. A patient with diabetes and glaucoma may see the retina surgeon four times a year and the glaucoma surgeon three times a year. The front desk or the patient may get confused as to which doctor to see. For instance, if the glaucoma doctor sees the patient and does not schedule the patient to return to the retina doctor, who handles another type of disease, not infrequently, patients can be totally lost and the wrong provider is assigned to give care. While one provider may be taking care of one disease state. (i.e. glaucoma), the other state (i.e., diabetic eye disease or macular degeneration), may be lost to follow up to that retina doctor. The same can be true in a multispecialty practice of internists, cardiologists and pulmonologists. The internist has a good rapport with the patient and sees them on a regular basis, and does not realize that the patient did not keep an appointment with their cardiologist; whether it be that the patient cancelled or the cardiologist cancelled, the internist may be assuming that someone in the practice, such as an ancillary staff member, is making an appointment for the cardiologist, but that may never happen. Each time the patient comes back in to see the internist, it is possible the internist might not know this. This tracking system identifies all these situations in medicine: it is able to see when a patient is supposed to return for a visit, what the high-risk scenarios are, whether there was a procedure that always requires a follow up with a particular doctor, whether that does or does not occur, and reminds any doctor in the practice that they should consider sending a patient back to another doctor. Not only are there indicators and alerts sent to the doctor who sees the patient, but these can be sent to the original doctor whose appointment has been missed, to the practice manager, or to anyone else in the practice to double-check whether a particular patient should be seeing a particular doctor and has been lost in the shuffle of so many visits. This kind of mistake also can happen in health systems and hospitals where a patient who is not knowledgeable about medicine makes the assumption that each doctor talks to one another and shares records; therefore, the patient may assume that if one doctor does not suggest that the patient sees another doctor, that the original doctor will be taking care of everything and the patient does not need follow-up care from a different doctor. This is a regular occurrence in medicine and puts patients at tremendous risk, because if they do not get to the specialist when the disease is most treatable, the patient might not be cured.

The medical guidance system also identifies if there are results from tests ordered and letters from outside doctors that can become just "attachments" within an EMR and get lost. The medical guidance system triages attachments by their critical nature, and alerts are provided if the attachments have not been opened by particular doctors, including identifying the doctors most specified to interpret the attachments (often the ordering physicians). For instance, in a multispecialty practice, if the pathology results of a biopsy of a skin lesion come back and the family doctor sees the results, but the dermatologist who ordered the biopsy does not see the results, an alert is sent out. This is an example of where the family doctor could make the assumption that the dermatologist sees the results, but that assumption would be incorrect.

The medical guidance system also includes a pre-patient visit analyzer that helps the physicians identify the patients they will see in the future, which could be today's patients, future patients, or any future patients with particular disease states requiring certain procedures or diagnostic tests. This feature presents the doctors with the information they need to prepare for these visits, or to find errors in scheduling, tests, etc. For instance, this feature lets the doctor know what is scheduled for today for that patient, when the patient last had similar tests, what their disease states are, what the likelihood is that they might need additional tests or another type of procedure, and even whether or not something might have been scheduled in error because information from the previous visit does not match up. For instance, if the plan says injection in the left eye but the schedule says injection in the right eye, the tool can discover that and warn the doctor to be very careful with this particular patient. The doctor may receive a summary identifying what had been done in the past, i.e. diagnostics, procedures and through algorithms that are tailored to each practice and specialty, be alerted so that the doctor can plan for what happens this day or a future day for that patient or a group of patients. It is also helpful for managers to properly staff the doctor, which will reduce waiting time for patients, because if managers are able to know how many tests are likely to be scheduled in addition to what has been scheduled and what procedures are scheduled, managers can plan how many technicians, scribes or other support staff are needed for each doctor for that day or a week in advance.

The medical guidance system also enables physicians to pull up—as can their staff at any time, on any day, or in any office—any past patients seen in any office or a particular patient seen with certain disease states or procedures or diagnostic tests and see what was done on any given time period or visit. This is especially useful if the doctor references the record on the same day or shortly thereafter when the patients are fresh in their memory. Doctors can make certain that their examinations were filled out correctly, and these summaries enable the doctor to see what they are missing in documentation and what has not been ordered and/or they see everything that was performed diagnostically and procedurally and recall that a mistake might have occurred therefore allowing them to correct billing or the documentation in the chart before it is finalized while the patient examination is fresh in their mind. They might also see that a diagnostic test should have been done but during the busy day, they might have missed something and then at the end of the day they can quickly discover that something should have been done and order it for the next visit. They might even send a message through the system that has been created to ask that the patient come in sooner than the next scheduled appointment to get something done that might have been missed; or they could even call the patient. The user of the medical guidance system may also toggle between the summary page of all the patients seen on a day and instantly open up either a command center that summarizes that patient's entire historical data or the patient's chart in the EMR for further identification. This medical guidance system is the "bird's-eye view" of what will happen in any particular time period for any group of patients in an entire day or otherwise. This allows a doctor to home into the patient's chart and/or another summary page, such as the command center, and then quickly toggle back to the summary of all the patients seen that day.

The medical guidance system further enables doctors to create indicators for clinical support and preferred practice patterns. In particular, the doctors can set indicators for preferred practice patterns that would be able to be shown at the end of the day or other days through rows and columns what the doctor personally wants to say is an important thing to do or measure depending on the patients' diagnoses. Procedures performed, symptoms, or other indicators can be alerted to the doctor. Tasks are created to warn doctors and the reporting systems measure these impacts.

The medical guidance system further enables doctors and their practices to track lack of authorizations, payments or rejections at the very earliest moment. Current systems require user-driven reports to be run manually to identify items that have not been paid or are rejected by insurance carriers. Most insurance companies send payment for hundreds of separate patient claims on the same electronic check that is then posted automatically to many different patient accounts without inspection or review by a billing or staff member. This electronic process was developed to reduce workloads on staff who before were required to read the explanation of benefits and apply the payment manually to each individual claim item in the billing system, which allowed for greater oversight of incorrect payments and rejections. Practices are now being forced to identify potential problems like lack of referrals, lack of authorizations, and documentation errors through cumbersome reports that then require personnel to research, correct, and resubmit to rectify. For instance, a provider may not be credentialed with the patient's insurance carrier because they are new to the practice. Practices can sustain huge loses if an error like this is not identified quickly. The medical guidance system enables individual CPT codes to be tracked instantly when rejected depending on the algorithm and the severity including the amount, specific insurance payors, and/or patients with high deductible plans. All pertinent data is analyzed and an indicator in a summary sheet or a task can be created to alert the appropriate staff members and physicians allowing the practice users to make corrections rapidly. Based on practice/user specifications—fully automated queries can generate indicators viewed with EC2 live while treating the patient, generate tasks to be worked by staff members, send automatic notifications to users identifying trends and errors immediately upon receipt of a rejection to prevent further errors, and drop rejected items into an open task system to be resolved and tracked by the appropriate staff. The medical guidance system informs multiple user groups within a practice ensuring proper communication of potential problems, patterns, and trends that impact every area of the business efficiently and rapidly, thereby improving the delivery of patient care and revenue cycle management.

Another embodiment of the medical guidance system automates the process of scheduling patients for new or return appointments as well as the need to respond and prioritize when patients call with issues or concerns. Scheduling can be initiated in a number of ways from a patient calling the first time for an appointment or if the patient is calling with an emergency or to schedule a required follow up visit. Also, an appointment may be initiated by a referring doctor calling directly to the office to schedule an appointment for a new or existing patient. In one embodiment, the complete past history of important data regarding the patient is available to determine how quickly and with which provider a patient may need to be scheduled. Human interaction can create misunderstandings, misinformation, and all the data about the patient may not be known. However, proper scheduling may be performed utilizing the known complete past history of important data including diagnosis, treatments and medications already integrated into the tool from the EMR.

FIG. 83 illustrates an embodiment of a patient scheduler and triage system implemented in a flowsheet table. The first step is identifying the patient to make sure there are past data elements in the system, which even if not in the practice being scheduled for, the tool integrates with all data bases, appointments, and encounters that the patient may have ever had. So, the tool cross-references and discovers issues of concern and important features when scheduling for that individual patient.

A medical record number 8301 is automatically inputted as this patient is checking out in the office for a future appointment. If it is on the phone, portal, or other mechanism where it is not automatically confirmed, the system asks for or automatically inputs medical record number 8301. The name of the patient 8302 and date of birth 8303 is also provided along with the last four digits of the social security number 8304. 8305 depicts that the patient is checking out from an office visit today and scheduling for a future appointment, while 8306 indicates that the patient is calling to schedule. 8307 indicates that a referring doctor called to schedule an existing patient, while 8308 indicates that a referring doctor called to schedule a new patient. 8309 indicates that a patient called not for a particular scheduled appointment, but rather called for a concern, question, or issue of any kind. 8310 indicates that the patient contacted the doctor's office through a patient portal or patient scheduling system.

A patient encounter is recorded, dated, and time stamped at 8311 using the information gathered at 8301-8310.

8312 illustrates a method of selecting what the current issue is which is most important. If a patient calls with symptoms, the system can relate new symptoms to any major diagnosis, or past procedures. A diagnosis that was selected within the last year or any time frame is illustrated at 8313. The symptom or diagnosis may relate to a certain part of the body. In this illustration, the right eye 8314 includes rows that actually identify by codes that are internationally approved for active disease, inactive disease, or even scarring which is the least active of all. The same process, by the international codes, ICD 10, 9 or other is repeated for 8315, the left side of the body. 8316 indicates that the code is occurring in both sides of the body. The codes depicted happen to be retina conditions in the eye that are known to have certain risk factors.

8317 notes the last time any procedure or injection was performed and the system knows the more recent the procedure or the higher the risk, factors in the acute or not acute nature. For instance, certain surgical procedure actually have postoperative periods of one week, one month, three months based on regulations as well as risk factors of when the patient is totally healed.

8318 indicates any relevant clinical measurement that is important that has been followed for that patient. The worst the clinical element compared to 8317 or the diagnosis in 8314, 8315, and 8316 increase the risk factors and help the system know the interaction of the event or encounter that is defined in 8311. The system knows the diagnostic test or measurement that has been used to follow or multiple diagnostic tests that have been used to follow conditions in 8313, 8314, 8315, and 8316 that also impact 8317 and 8318.

8320 indicates whether all patients sign consents when any procedure is performed, which list the specific risk factors and complications that occur with every procedure and through natural language processing and actually inputting, the system knows what the risks are and correlate them to 8317 and the procedures.

Whenever 8317, 8318 or 8319 are performed, the user and doctor inputs a plan of action assessment into each plan at 8321 and in that note it is explained the patient goals and possible risks or complications. 8317 or 8319 indicates whether it is a special type of diagnostic test such as an angiogram or if an injection as occurred in the arm or elsewhere as well as the treatment effect is expected to be, including if medications have been prescribed and that is the action taken in 8317 cross referencing of allergies, expected outcomes, adverse events. 8322 will identify if in the plan or EMR particular risks or symptoms may occur from the treatment.

8323 identifies if in the EMR or plan there is a timing issue that is of particular concern or consideration. For instance, if after a treatment pain is expected for 24 hours if a patient calls 10 hours later the risk is low but if the pain continues for 48 hours the risk is higher.

8324 is the symptoms if in fact the patient has at 8311 and at 8309 or 8310 contacted the practice in some form what the patient is reporting The systems as noted elsewhere can prompt the patient to answer certain questions yes/no to evaluate the symptoms and the patient respond yes or not but the symptoms factors in all of the data to be able to prompt correctly the questions for that particular patient based on 8312, 8317, 8318, and 8319 and through techniques of NLP, machine learning and AI, and other techniques they have what is written in 8320, 8321, 8322, and 8323. 8323 specifies the timeliness of a complaint. For instance, if there is a procedure for 8317 and it is expected the patient will have pain for 24 hours and the patient calls for pain, there does not need to be a necessary emergent visit but if there is pain reported 24 hours or more the system will know the timing of this system in regards to expected versus not expected for 8317 or 8319. 8325 will prompt the patient if 8324 is more than a symptom but perhaps there is a complaint or condition that 8317 or 8312 are associated so another series of questions can prompt the patient.

8326 is for the special situations that the patient has cancelled, no showed or the doctor is cancelling an appointment and the risk factor associated with how quickly this patient needs to come in is evaluated.

8327 indicates whether it is through a patient portal contact or other method and not through a phone call an entirely different way of prompting rather than responding yes or no on the phone or by human interaction by actually inputting the invention tells them to input from these prompted questions this would need to be more of a manual total automated communication with no human interaction like a call center of scheduling person.

8328 indicates the preferred practice plans, clinical decision support and other means that can be suggested and evaluated when processed taking into the account the rest of the situations and what had been programmed in the system in one embodiment in an actionable dashboard that the user who is caring for this patient had set. Now taking all that into consideration 8329 allows a conclusion of how soon a patient should be seen at 8330, 8331, 8332, or 8333.

8334 indicates when the system cannot form a conclusion and now the doctor or appropriate representative in the practice must be contacted. The indication can be a message or task or phone call or personal contact from a scheduler in the same office who is now asked to present the situation to the doctor. A task message or any other message may be used as described herein so that the doctor can make an informed efficient decision.

8335 demonstrates the tool would also interact with the practice management system or clearinghouse or billing company and knows for that patient if any money is owed or other financial issues or whether a referral or authorization is needed and can send this information to the billing department, clinical department so when the patient presents for the appointment an authorization is already received and the automated computer or the human being in addition to scheduling the appointment with the patient can mention please bring 'X' amount of money owed or the following needs to be done to be able to be seen.

Thus, in this embodiment, the actionable dashboard acts as a patient triage and scheduler, assisting receptionists and in some embodiments scheduling appointments. If human interaction is warranted, because a patient initiates contact with the practice by way of a telephone call or through a patient portal or automatically and can answer some questions, the dashboard is programmed to identify certain issues or symptoms that a patient may have and evaluate the importance of time and the danger to that individual patient. This is done based on data that had been previously entered in the actionable dashboard in some embodiments in rows and columns. If the patient had any kind of procedure, surgical, injections, or had been given any type of new medication or an action taken that could impact the patient, i.e. an allergic reaction, pain, or any other factor, the actionable dashboard is aware that this patient is at risk and can schedule an appointment. Based on the risk identified by the invention, the patient will be scheduled either emergently, in one day or other period indicated according to the risk factor.

Whenever a user performs a procedure, an action, or prescribes a medication, patients have to consent to actions, especially the procedural and surgical ones. This could include injections, laser, biopsies or the like. At the time of consent, the risks and side effects are explained to the patient and the patient signs permission to have the specific procedure be performed. The consent allowing treatment to be done is stored within the EMR system. Additionally, when a provider performs a procedure the doctor explains and notes in their plan or elsewhere, what the side effects and risks to this procedure can be. Through natural language processing and machine learning, all of this is known and interpreted by one of the embodiments and takes into account the risks of each of the symptoms, side effects that can occur and how much of a risk it is to the person. The moment a patient contacts the provider by any means, whether through the portal or a telephone call by this communication being inputted into the system the tool identifies any side effects, risks, symptoms or signs that could be related to the procedure or prior action or medical service delivered by the provider. Any possible complications, problem, ineffective treatment, or worsening from treatment or medical services or medications prescribed, in one embodiment this is measured, evaluated, processed and displayed in multiple ways and can be help direct a human scheduler, if they are inputting this. The tool can also make automated contact and response to a scheduling module, which then schedules appropriately the patient as needed based on determined risk. The same is true when a patient misses, no shows, or cancels an appointment or the user and the doctor cancel an appointment. Unbeknownst to the doctor, are the risks of delay of care and evaluation when patient appointments are not kept for any reason, including even the practice cancels an appointment perhaps when they cancel. The patients being canceled by the practice can be evaluated and risk to cancellation measured with proper scheduling of the patient to limit risk performed. For instance, if it is a postoperative visit, after a major procedure, or the patient has been having some symptoms that are high-risk and have been inputted into the plan and through natural language processing, the risks are known so when this patient is being re-scheduled because the practice cancels, when this patient should be re-scheduled, can also automatically occur based on risk factors or human interaction and the tool displays the appropriate scheduling action. This is critical because the doctor can go on vacation and cancel important follow up for patients. Receptionists who re-schedule the patient are not doctors or trained professionals who really understand the risk factors of delaying care. The tool can evaluate and identify the proper time for re-scheduling. Note, the risks, complications or expected results for any action or medical service that a doctor or user does, is inputted into the system. The tool integrates with EMR and PM system and already has the data.

The tool knows, the diagnosis, the doctor previously entered with treatments and when performed. All interpreted together with natural language processing and the complaints and symptoms of the risk can be identified. Once an appointment is missed or a patient contacts the office for any reason, the risk factor for this patient is identified by the tool with input from the scheduler, phone triage person or automated selection by the patient.

The tool also can work with the human being that makes the telephone call or portal contact is the invention knows all the diagnosis, the procedures, and the risk of complications and symptoms. When the patient makes contact, very similar to in automated phone calls, like when you try to make a ticket on an airplane, certain questions are asked to the user to then hit one, two, or say yes, no. So, when the patient calls, the questions would be: state you name, what is your date of birth, and what are the last four digits of your social security number. The invention then has the identifying information and can then lead with certain questions that the tool can determine is a high-risk for that patient. For instance, "I see you had the following procedure when you were last in the office on . . . . We would like to ask you a series of questions to identify how to best answer your questions and schedule you if needed." Are you having the following symptoms? Press 1 if yes or say yes or press 2 if no. Are you having the following situation . . . ? Press 1 if yes, press 2 for no or say no, or if uncertain, press 3. FIGS. 84A-84C illustrate sample questions for the patient.

This would continue depending on what the tool has identified that the user had inputted in the past and through preferred practice plans and the understanding of those conditions, a series of questions of importance can be asked. NLP, AI, and machine learning all can see and interpret what has been inputted in the EMR. The questions then are tailored appropriately for the patient. The concluding statement could be "We understand you have said, after you receive certain medical service on the date last seen, and you are calling because you are saying that you have symptom X, concerns Y, new developments Z." Press or say yes if this is the question you are calling about. Press or say no if it is not the question. The tool based on the responses, can make recommendations transferring the patient to this scheduling office.

Figure 84E:
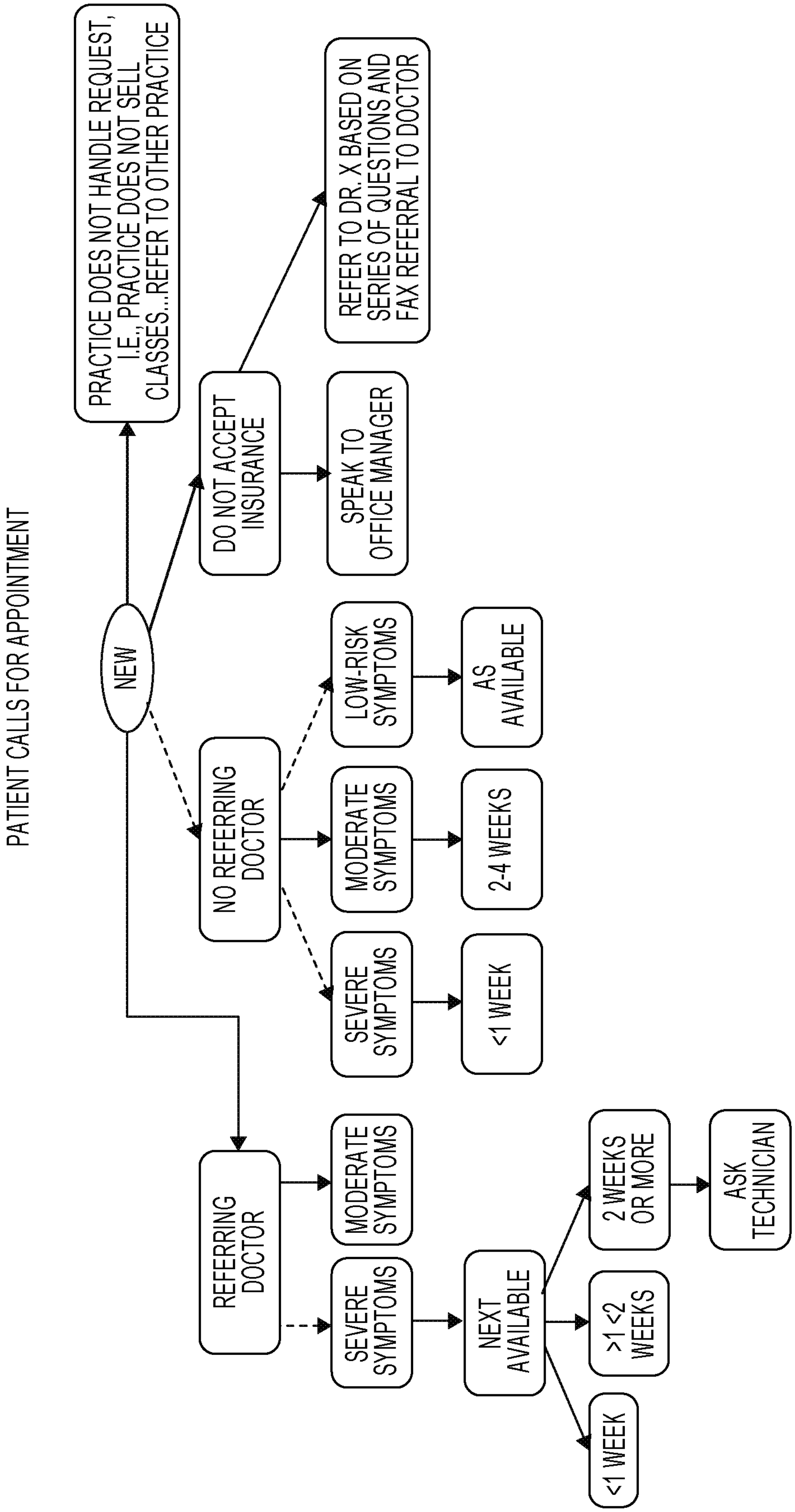
FIG. 84E illustrates a flow for handling patient calls for an appointment.

Clinical staff that will have to make the decision when a scheduler or receptionist requests direction. When a patient is seen in the office and is checking out to get an appointment and something does not match up, the tool can confirm the orders the doctor placed for scheduling is followed by the receptionist. If not, the tool can warn the receptionist or the patient if they are scheduling themselves through the computer check out process. All can be double-checked by the tool and if there is an alert or human interaction needed, it occurs. The provider have far fewer issues to address because the automated process of the tool can work more accurately, efficiently, and quickly to solve all these problems. No longer do patients get lost in the mix of waiting for a return phone call or being scheduled incorrectly. But, when the doctor is contacted because the invention is unable to come up with an answer or the patient, needs to contact the doctor for other issues, the doctor instantly has the task or an alert sent along with the single screen display view the tool creates, along with the issue the patient or staff have identified, and the doctor, can make an accurate recommendation on scheduling. FIG. 84D illustrates sample formulas for urgency of appointments, while FIG. 84E illustrates a flow for handling patient calls for an appointment.

In another sample embodiment, the medical guidance system may include a triage scheduling tool that allows someone who is not a sophisticated clinician the ability to rapidly understand the urgency of scheduling the patient's next appointment. To properly triage the patient and determine the urgency of when the patient should be seen next, the triage scheduling tool displays information about the patient's current condition and a computed severity index. It is important to note that this interface could be a graphical user interface or, in some cases, adapted to create a severity index using a phone system in conjunction with the task system in the tool in order to alert staff members to schedule an appointment. The severity index consists of a lower bound and an upper bound. An example of the lower bound would be 0 and the upper bound would be 10. Severity indexes with high values are understood to be more urgent for the patient to be seen. Those values which approach the maximum upper bound are understood to be emergency situations. Values which are at the lower end of the scale are known to be less important and can be scheduled at the patient's and/or clinic's convenience.

Figure 85:
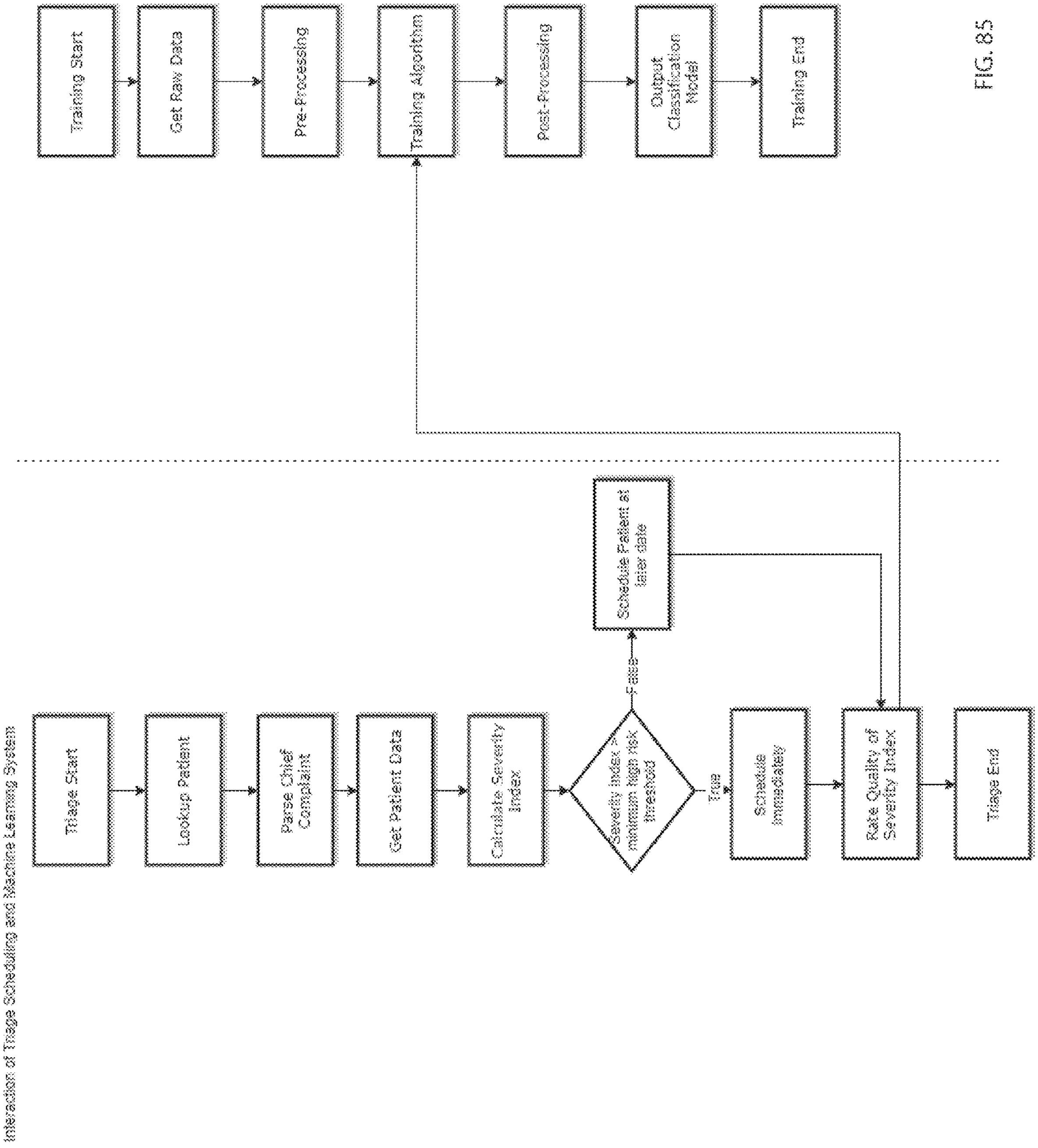
FIG. 85 illustrates the interaction of triage scheduling with a machine learning system.

FIG. 85 illustrates the interaction of the triage scheduling with a machine learning system. As illustrated in FIG. 85, in order to be able to assign a severity index to patient, the triage scheduling tool is first trained using Machine Learning techniques on millions of rows of existing patient data examining chief complaints and the various outcomes that occur based on a patient's medical history. As the system continues to train, it is understood that the severity index will become more accurate over time. An additional way the system will improve its accuracy is by creating a feedback loop whereby the staff member is able to rate the severity index as to how accurate it was. Once the staff member has assigned a rating as to how accurate it was, the feedback loop will incorporate the rating into future severity index calculations. The system shall also learn by examining when the appointments were made in relationship to available openings to determine the selected course of action. Once the system has been sufficiently trained, it will then be able to assess risk by analyzing the patient's chief complaint to create a severity index to assist staff with scheduling the patient.

The severity index is created by examining the patient's procedures, problems, observations as well as understanding the patient's chief compliant and the medical professionals notes, such as but not limited to assessment, outcomes and plans using natural language processing. The patient's complaint is classified using machine learning classification algorithms in order to classify portions of the chief complaint which are relevant to the patient's current condition. Once the text has been classified, it can then be included in a calculation in conjunction with the patient's current problem list, observation history, recent procedures.

For example, a patient may have an acute complaint which, in conjunction with a certain procedure, would require an appointment immediately because the patient is at major risk of suffering severe complications which includes, but is not limited to, blindness, death, etc. Such a situation would result in a severity index which is close to or at the upper bound indicating the need for an immediate appointment or recommendation to proceed to an emergency room. Another possible example is that the patient has an acute complaint of mild discomfort but has not had any of the following but not limited to, a recent procedure, new prescription, medical observation, etc. In such a scenario, the patient's severity index could be at the lower end of the scale indicating the patient can be scheduled at the clinic or patient's convenience The state of triage and knowing when patients are urgent and when they are not can always be improved upon in a practice. Practices handle things in different ways. Every practice has its own ideas of what they think is urgent and how to triage and questions that can be answered. But, often practices are not even implementing what they actually have written. Training is suspect and unless there is a fool-proof way where every patient is put through a computer program, which can be verified to double-check what is hopefully to happen verbally, patients will slip through the cracks. Another idiosyncrasy is often patients can be more demanding and some less demanding. Some might insist on being seen urgently because they have higher stress and others will just accept what the person on the telephone says. Even these factors need to be known. If a patient has higher stress and is pushier, that needs to be calculated and possibly the computer program bumps it out because that type of person should be seen and not just by the person on the telephone, who is an operator, but rather get someone else on the telephone who can talk to that patient or even if the patient cannot be fit in that day and the initial assessment is that it is not urgent and can wait a week, if the patient is that stressed, suggestions in the computer can then be made and someone in management calls the referring doctor to explain and the referring doctor's office can help a patient understand that the next available appointment given is appropriate.

With too few doctors, too many patients and so many diseases, there needs to be a way of figuring out which patients need to be seen when and leaving it up to whoever is answering the telephone is how the world of medicine has now and always worked. The medical guidance system can help triage the patients whereby when a patient calls for an appointment, the medical guidance system would triage the patient appropriately and then further questions can be answered by a human being if necessary. A computer answering service may triage medical appointments in urgent situations.

By tracking what the patient is looking for, or the questions or the query, the proper risks can be identified. So, even if it is not a situation where the patient is calling by telephone but rather emailing or texting and now with the days of patient portals where patients can communicate online, now more than ever it is important that there be a computer algorithm within the medical guidance system that can evaluate, assess and manage all of these patient queries.

Another aspect of the medical guidance system enables it to interface with the patient portals when they try to contact doctors or staff with questions or requests. Anything from refills of medications or symptoms and asking the doctor to communicate with them. The reality is doctors often do not have the time to communicate with each and every single patient. Therefore, medical guidance system will evaluate every query, look at the patient from a historical aspect if they are an existing patient, if they have had procedures or a risky diagnosis so that they can manage to let the doctor know when they get many queries a day, which ones might be more problematic and urgent based on patient's symptoms, diagnosis, and past procedures. If the doctor does not respond in a specified period of time, these queries will then bounce to the practice manager or anyone else to try to help practices manage the numerous requests that are coming in every day because of portals and electronic abilities. In the past, simple telephone calls were difficult to manage. Now patients can simply go online and email and text or through the portal and ask any question. This makes it very difficult to be able to assess the type of risk. In sample embodiments, natural language processing may be used to assess the risk.

The medical guidance system may also include a Smart Actionable Dashboard that enables users to send a message to each other in a HIPAA compliant way. In other words, a physician, while seeing a patient, can send a message to their chief technician or the office manager to talk about following up on a patient or also to the billing office that there is a billing problem. Then, staff can report back to the doctor and this message can be imbedded into the smart actual dashboard so that the next time a doctor sees the patient through icons and columns of correspondence of communication within the practice, the doctor can pull up what was the response to a message they had sent earlier. This response can be read live while treating the patient so that the doctor can take it into perspective while making decisions. The messaging system, attachments or anything else can be sent to the doctor or health care provider in any way that they would want. Whether through email or the internal messaging system or as a tickler system within the EMR system that automatically toggles back and forth to the actionable dashboard, so the doctors can see their messages at the end of the day or the end of the week, or while seeing the patient. This feature really helps organize the doctor's life, so this actionable dashboard becomes the communication hub, the switchboard, for the entire practice, while communicating with the health care provider.

The medical guidance system further provides the ability to tailor what is being evaluated and followed for any particular patient in regard to both scheduling appointments, scheduling laboratory work, diagnostic tests and that is problem list orientated where the system identifies a particular problem list that a patient has. A particular problem list or disease state has a very clear-cut way of providing care for the patient and even treating the disease that have been statistically and clinically evaluated. These guidelines are what the tool uses to populate but also it allows for doctors to tailor care and testing based on their clinical judgment. Patient's appointments, diagnostic tests, surgeries and even clinical findings can all he tracked over time by many different methods including columns and rows of the patient flowsheet's table. One method follows a patient over time to make certain they get correct scheduled appointments or diagnostic tests ordered, is for all the office visits or any kind of encounter the patient has (e.g., testing days, procedure days, etc.) and even forms of communication that all can be date stamped and organized chronologically or otherwise in many ways the tool allows but also in rows or columns in the flowsheet table. Columns or rows can represent many different procedures, diagnostic tests, laboratories, scheduled appointments, vaccinations that the patient receives or should receive over time. As the patient receives tests or anything necessary in any column, it is auto populated or can be inserted manually. The columns or rows may identify what procedure needs to be followed based on a problem list or condition the patient has can change so that for instance if this is followed in a flow sheet or any type of dashboard can be tied to columns and/or rows changing based on the particular disease state or problem list or symptoms that a patient has. The problem list can be anything from disease state to any ICD-10 or CPT code, symptom or even social and community problems.

By way of example in the field of obstetrics, certain clinical findings that are followed have been suggested by the American College of OB-GYN including clinical measurement findings like fundal height and according to the week's gestation, which corresponds to how many weeks the patient has been pregnant. There are set guidelines on what needs to be ordered for different weeks. All patients have their weight followed, blood pressure and may get one ultrasound done during the pregnancy or a fetal stress test perhaps. However, most healthy women will not require certain things to be followed, which can be listed in columns. Diagnostic tests such as EKGs and echocardiograms are not something that would normally be needed in a pregnant female. However, if a problem list or ICD-10 of the patient having chronic hypertension, those patients automatically need EKGs, echocardiograms and might need baby aspirin and therefore columns can appear for that patient's specially designed dashboard because the problem list of chronic hypertension was identified. A column for EKG and echocardiogram occur and based on the date it is auto populated when the EKG or echocardiogram is done in comparison to all of the times corresponding to all the rows of different dates the patient was examined or had a test done. This way a doctor can quickly be looking at a glance and see all the clinical findings of a patient, but have a dashboard automatically tailored because the patient has chronic hypertension. Further, since some of these tests are at certain periods of time dependent on the age of the patient and weeks of gestation to remind a doctor to get an EKG or echocardiogram, a particular column and/or row and or date and the cross-section of a date/row/column and the test can light up reminding the doctor to order or if a particular vaccination is needed at a particular time that column or the header can in some way alert a doctor by blinking, changing colors, etc. Each of the columns and what is needed for an individual patient can change based on different chronic diseases such as chronic hypertension and morbid obesity where a column with the heading consults needed (i.e., nutritional counseling) and when completed the day of order is noted and the day of completion all perhaps on a row of the date of action. Another of the hundreds of examples might be a patient with advanced maternal age can be another problem list which requires an entirely different group of tests and procedures need to be performed at designated times. Those tests would be programmed in and the columns would appear for that particular patient. If the patient has more than one problem list the computer will know what tests need to be ordered and when for each of the problem lists and then the dashboard is specifically tailored automatically for that patient.

The tool works as follows in the case of an obstetrics example. When a patient first comes in to see the doctor when they loam or believe they are pregnant, the doctor evaluates the patient and creates various problem lists the patient has and the doctor anticipates what that patient in particular may need over the next nine months of the pregnancy until delivery. All of this may be anticipated at the first or second visit with regimented follow up visits over the remainder of the pregnancy and very specific tests, counseling, vaccinations, treatments planned for according to the needs of the patient and the problem list that patient may have and with population health and understanding the socioeconomic and cultural and religious considerations all needs to be factored in. The doctor develops the plan of action and sets up the game plan. But the challenge is how to make certain that everything is carried out and how to check each time the patient returns for a visit. The doctor will fill out on the first visit a section on risks the patient has (i.e. chronic hypertension, diabetes, advanced maternal age, etc.) Depending on specialty and EMR they use, the doctors may have a menu of items that are sorted though and templates filled out of what to expect and is needed during the pregnancy so that the plan may be followed. However, ail of this often has to be done manually and updated manually by the doctors or their technicians, perhaps residents and if they are not careful to really comb through each problem list at every visit, things will get missed. Things might be updated for one problem, but not in a different problem and if there is overlap and therefore it can be not clear to know what did or did not happen mistakes happen and in EMR systems there is no real way to unify that in one space.

The medical guidance system may understand that these are the problems that the provider clicks off. The tool receives all the menu of items that the provider likes to provide for these patients into one single dashboard. Thereby the providers know if their patient has chronic hypertensive, diabetic and advanced maternal age and can be certain all is correctly being done. Then, columns in the actionable dashboard are updated with what all clinical and diagnostic information is needed i.e. blood pressures, did the patient get her echo, did she get her EKG. The provider then can click on perhaps an icon or representation or column or row that hosts the results and the provider can view the results and even see the test itself. Then, if a patient needs something like an ultrasound in the third trimester a future row or column lights up because all the future office visits expected can be seen in rows and alerts on rows as needed.

In obstetrics, the is usually paid one time for all the visits over the nine months. But if there is an unplanned visit because the patient comes in for a sore throat or discharge that can be separately billed so even the billings and payments can be on each row so that the provider can be involved in all aspects. If a patient misses a particular visit, the medical guidance system knows this and can send a reminder or message or alert. By having everything the provider needs to know and to evaluate that particular patient, customized columns for that patient's situation provides everything at a glance for evaluation with no information more than a click or two away and all brought up on the same screen so that the doctors do not lose track of the global situation.

Some insurance providers may only allow certain number of tests for a particular condition (i.e., in obstetrics a number of ultrasounds that are included in the "package" and others pay for each one). The tool informs the healthcare provider of all such options.

It will be appreciated that a personalized dashboard can be generated by the healthcare provider by clicking on the problems and the diagnosis that the patient has and the tool through AI and algorithms knows what is needed to be done and when, which test need ordering, which symptoms should be asked about based on each of those diagnoses. Obviously, in primary care there are a lot more diagnoses then in ophthalmology or pregnancy but they all can work with each other. The tool has a built dictionary and all doctors. seen by the patient can share dashboards. Even though the respective doctors may have separate dashboards by specialty, the healthcare providers can click on which columns are in each problem dashboard and migrate into a central dashboard—the snapshot dashboard.

Those skilled in the art will appreciate that the operations described herein are implemented in software implemented as instructions stored in instruction memory and processed in processors of one or more of the servers of the Command Center 5000 illustrated in FIG. 57 and/or the processors 32 of FIG. 14. The design of the data tables and XML structures have been laid out to enable all of the data generated for presentation to the Command Center interface of FIGS. 1 and 15, for example, to be processed in advance and stored in the presentation tables where possible in order to minimize delays in table generation. Also, the display tables are all tied to the Command Center interface so that the user need not navigate away from the Command Center interface to access any of the data described herein. The software operations may be implemented in a special purpose system of the type illustrated in FIG. 57, for example, or the software may be implemented in a general purpose computer that can also perform other processing, program execution or routines that are not part of the special purpose, while still being capable of operating for the special purpose. Alternatively, the operations can be processed by a general purpose computer selectively activated or configured by one or more computer programs stored in the computer memory, cache, or obtained over a network. When data is obtained over a network the data can be processed by other computers on the network, e.g. a cloud of computing resources.

Those skilled in the art will appreciate that the software instructions for implementing the algorithms and XML functionality described herein may be stored in conventional computer-readable storage media. Computer-readable storage media, as used herein, refers to physical or tangible storage (as opposed to signals) and includes without limitation volatile and non-volatile, removable and non-removable storage media implemented in any method or technology for the tangible storage of information such as computer-readable instructions, data structures, program modules or other data.

Although method operations can be described in a specific order, it should be understood that other housekeeping operations can be performed in between operations, or operations can be adjusted so that they occur at slightly different times, or can be distributed in a system which allows the occurrence of the processing operations at various intervals associated with the processing, as long as the processing of the overlay operations are performed in the desired way.

Those skilled in the art will appreciate that while XML is used to encode data in the illustrated embodiments, other data formats can be used, for example JSON or simple comma delimited text files. Also, those skilled in the art will appreciate that the Command Center embodiments described herein may be modified to include automated mobile messages to patients for usage of medication with feedback to the patient's Command Center along with appointment reminders, bill reminders, etc. A summary of this information may be provided in a display panel of the Command Center in succinct form for the physician. This information enables the physician to determine at a glance whether the patient is reliable or unreliable regarding taking medications, following medical directions, and the like.

It will be appreciated by those skilled in the art that while the description has been directed to particular embodiments and examples, the tool described herein is not necessarily so limited, and that numerous other embodiments, examples, uses, modifications and departures from the embodiments, examples and uses are intended to be encompassed by the claims attached hereto. For example, while detailed embodiments describe the use of systems for presenting medical and financial data related to treatment of patients by an ophthalmologist, those skilled in the art will appreciate that the medical data may relate to other medical practices such as dentistry, orthopedics, oncology, and the like. In addition, the techniques described herein may be applied to the presentation of data in other contexts, such as the presentation of stock market and other types of dynamic data. These and other features and advantages are set forth in the following claims.

The invention claimed is:

1. A computer implemented method for dynamically presenting patient-related data for a patient on a medical dashboard, the method comprising;

generating a dynamic data display comprising a medical dashboard including a first dashboard configuration describing a display layout of multiple data fields including information;

receiving, from at least one patient data source, patient-related data for the patient, the patient-related data including information received or derived from the at least one patient data source, the medical dashboard comprising a display, using the multiple data fields, of information corresponding to multiple different elements selected from the group consisting of diagnosis, symptoms, medications ordered, prescribed, taken, or administered, clinical data, life events, examination findings, diagnostic tests, images, health care provider plans, medical documents, injections, claims, authorizations and procedures performed on a patient;

storing the patient-related data in a flowsheet data structure that organizes, for each of a plurality of encounters of the patient, each of the data fields as one or more rows or columns of one type of the information received or derived from the at least one patient data source, such that at least two of the rows or columns are arranged to a time that the information was performed on or collected for the patient, generating, by at least one processor, a flowsheet configuration object that defines, for the patient, a dashboard configuration describing a display layout of multiple data fields of a medical dashboard including a flowsheet data field, the flowsheet configuration object specifying which rows or columns from the flowsheet data structure are to be displayed in the flowsheet data field and an order and visibility state of the rows or columns;

rendering and displaying, on at least one display device, the medical dashboard including the flowsheet data field by applying the flowsheet configuration object to the flowsheet data structure such that the rows or columns specified by the flowsheet configuration object are presented in the medical dashboard in accordance with the first dashboard configuration;

executing by at least one processor, clinical decision-support rules derived from at least one of clinical guidelines, insurance regulations, local or national coverage determinations, preferred practice patterns, or clinical decision-support knowledge bases, the clinical decision-support rules being applied to the patient-related data in the flowsheet data structure to determine information that is more relevant or less relevant for the patient at a given time or for at least one of a healthcare provider, administrative user or practice;

detecting, in the flowsheet data structure, a change of the patient-related data for the patient, the change including at least of one of a diagnosis, medical condition, symptom, clinical data, procedure, test result, medication order, encounter with another health care provider of the patient, a change in authorization status, a change in claim status, a change in payment status, or a change denial status;

executing display rules in response to detecting the change and based on results of execution of the clinical decision-support rules, the display being executed by parsing information from at least one patient data source to identify additional information responsive to change of patient-related data;

automatically updating, by the at least one processor, the flowsheet configuration object by adding to the flowsheet configuration object a row or column corresponding to additional patient-related data of a further different one of said elements that was not defined for display before the change of patient data to generate a modified dashboard configuration that includes an added data field corresponding to additional information from the further different element of the group based on the detected change of related data, wherein additional information comprises rows or columns of an additional type of information over time from one of medications ordered, prescribed, taken, or administered, clinical data, life events, examination findings, diagnostic tests, images, medical documents, injections, or procedures; and rendering and displaying, on at least one display device, the changed dashboard including the flowsheet data field as automatically modified by applying the updated flowsheet configuration object to the flowsheet data structure for the patient, such that the change in patient-related data and the corresponding change in the flowsheet configuration with the additional information not displayed in the first dashboard configuration is displayed in the added data field and at least one of the first dashboard displayed data fields remains visible without navigating away from the medical dashboard.

2. The method of claim 1, wherein automatically updating the flowsheet configuration object comprises removing or collapsing a data field containing less relevant information to generate the flowsheet configuration object such that the additional patient-related data is displayed without having to navigate away from the medical dashboard.

3. The method of claim 1 wherein automatically updating the flowsheet configuration object comprises identifying at least one of expanding a data field to expand a number of rows or columns of information in the data field, collapsing a data field containing less relevant information, removing a data field containing less relevant information, adding an alert, changing an appearance of information in a data field, adding a graphical representation providing access to underlying information, or adding a text link in a data field.

4. The method of claim 1, wherein automatically updating the flowsheet configuration object comprises expanding or truncating one or more data fields as a function of user specialty, condition or diagnosis or diagnoses, or life events to generate the flowsheet configuration object.

5. The method of claim 1 wherein the flowsheet configuration object includes a new window displaying additional underlying patient information.

6. A computer implemented method for dynamically presenting patient related data for a patient on a panel based medical dashboard, the method comprising:

receiving, from at least one patient data source, patient related data for the patient, the patient related data comprising information corresponding to multiple elements selected from the group consisting of diagnosis, symptoms, medications ordered, prescribed, taken, or administered, clinical data, life events, examination findings, diagnostic tests, images, health care provider plans, medical documents, injections, procedures, authorizations for medications, diagnostic tests, or procedures, claims status, payments, denials, and encounters with one or more healthcare providers of the patient;

storing the patient related data for the patient in at least one patient record repository and in an encounter oriented data structure that organizes the data for each encounter according to time;

generating, by at least one processor, a view layout object that encodes a dashboard configuration describing a plurality of concurrently displayed panels of a medical dashboard, each panel comprising at least one data field configured to display a different subset of the patient related data for the patient, the plurality of panels including at least:

a first panel configured to present, for a plurality of encounters, respective encounter level identifiers and one or more selected items of encounter level patient related data derived from the encounter oriented data structure, and at least one second panel configured to present additional patient related data associated with one or more selected encounters;

rendering and displaying, on at least one display device, the panel based medical dashboard by applying the view layout object to the encounter oriented data structure such that the plurality of concurrently displayed panels are populated with respective subsets of the patient related data;

executing, by the at least one processor, decision support rules derived from at least one of clinical guidelines, preferred practice patterns, clinical decision support knowledge bases, medical treatment guidelines, coverage determinations, payer or insurance regulations, authorization requirements, and financial or operational business rules, the decision support rules being applied to the patient related data in the encounter oriented data structure to determine, for the patient, which types of information are more relevant or less relevant at a given time or for at least one of a healthcare provider, administrative user, or practice;

detecting, from the patient related data for the patient, a change in patient status or other patient related data including at least one of a newly entered diagnosis, a newly entered or changed test result, a newly entered or changed procedure, a newly entered or changed medication order, a newly entered or changed symptom, newly entered or changed clinical data, a newly received encounter from another healthcare provider of the patient, a change in authorization status, a change in claims status, a change in payment status, or a change in denial status;

in response to the detected change and based on results of the decision support rules, automatically updating, by the at least one processor, the view layout object by at least one of:

adding a new panel definition that causes display of additional patient related data associated with the detected change, modifying a panel definition to expand a panel to display more detailed information associated with the detected change, modifying a panel definition to collapse, hide, or reduce a display size of a panel whose information is determined to be less relevant after the detected change, or modifying a panel definition to reorder the panels such that panels containing information determined to be more relevant after the detected change are presented in a different position relative to other panels; and rendering and displaying, on at least one display device, the medical dashboard using the updated view layout object such that information relating to the detected change and other patient related data determined to be more relevant are presented in a concurrently viewable dashboard.

7. The method of claim 6, wherein automatically updating the view layout object comprises changing data in at least one other of respective ones of the panels by at least one of adding a data field, expanding a data field, collapsing a data field, removing a data field, adding an alert to a data field, highlighting data in a data field, adding a graphical representation indicating access to underlying information, or adding a text link data representation, such that the medical dashboard is comprised of information from multiple data sources.

8. A computer-implemented method for generating a dynamic data display comprising a medical records dashboard, the method comprising:

receiving patient-related data for a patient from at least one patient data source, the patient-related data including a first configuration describing a layout of one or more panels including one or more data fields containing information received or derived from the at least one patient data source, the medical records dashboard comprising a display, using the one or more panels, of information corresponding to multiple elements selected from the group consisting of at least one of diagnosis, symptoms, medications ordered, prescribed, taken, or administered, clinical data, life events, examination findings, diagnostic tests, images, health care provider plans, medical documents, injections, claims, authorizations and procedures performed on a patient:

storing the patient-related data in a data structure that organizes, for the patient, the multiple elements as rows or columns of one type of information according to a time that the corresponding element or information was performed on or collected for the patient;

generating, by at least one processor, a first flowsheet configuration object comprising information describing a layout of one or more panels of the medical records dashboard, each panel including one or more data fields containing information received or derived from the at least one patient data source, the data fields corresponding to selected types of information from the elements of the group, each of the data fields corresponding to a selected type of information from an element of the group and containing one or more pieces of information corresponding to the respective type of information received or derived from the at least one patient data source;

displaying, on at least one display device, the medical records dashboard by applying the first flowsheet configuration object to the data structure to display patient-related data in selected, respective ones of the data fields or panels in accordance with the first flowsheet configuration object;

detecting a change of patient-related data for the patient;

executing display rules, by the at least one processor, in response to detecting the change of patient-related data to identify a changed flowsheet configuration object based on the detected change of patient-related data, wherein the changed flowsheet configuration object comprises an added data field, or panel and a change to a first data field, or panel of the first flowsheet configuration object;

parsing information from the at least one patient data source to identify less relevant information and relevant new information responsive to the change of patient-related data;

modifying the first data field, panel, row, or column of the first flowsheet configuration object containing less relevant information to reduce an amount of information identified as less relevant by reducing at least one of a data field, panel, rows or columns and thereby reducing a size of the first data field or panel to make room for the added data field or panel; and displaying on the at least one display device the medical records dashboard based on the changed flowsheet configuration object, the relevant new information not displayed in the first flowsheet configuration object displayed in the added data field or panel.

9. The method of claim 8 wherein the changed dashboard configuration flowsheet configuration object is different from the first dashboard configuration flowsheet configuration object by at least one of expanding a data representation, truncating the data representation, adding a data representation, removing a data representation, adding an alert to the data representation, highlighting a data representation, changing an appearance of a data representation, adding a graphical representation indicating access to underlying information, or adding a text link data representation.

10. The method of claim 8 wherein the changed dashboard configuration flowsheet configuration object enables a user to access and cause display of stored underlying patient information linked to the medical records data populated into the data fields or panels in the medical records dashboard for the patient.

11. The method of claim 10 wherein the changed configuration flowsheet configuration object enables a user to access underlying patient information from an underlying patient information data source by providing a selectable icon, indicator, graphical marker or displayed visual representation in one of the data fields or panels to access the linked underlying patient information.

12. The method of claim 10 wherein the underlying patient information comprises an image, diagnostic test, or a plan.

13. The method of claim 10 wherein the underlying patient information is displayed in a new panel of the dashboard.

14. The method of claim 8 wherein modifying the first configuration flowsheet configuration object comprises at least one of expanding a data field to expand the amount of information in the data field, collapsing a data field containing less relevant information, removing a data field containing less relevant information, adding an alert, changing an appearance of information in a data field, adding a graphical representation providing access to underlying information, or adding a text link in a data field.

15. The method of claim 6 wherein the operations further comprise:

executing rules based on artificial intelligence adaptive learning engine techniques, natural language processing programs, or conventional business logic to detect a change of patient data; and executing display rules in response to detecting the change of patient data to generate an updated view layout object based on the detected change of patient data.

16. The method of claim 1 wherein detecting a change of patient-related information comprises detecting a change in at least one of a current procedural terminology (CPT) code, an international classification of disease (ICD) code, a systematic nomenclature of medicine (SNOMED) code, or medical treatment guidelines.

17. The method of claim 1, wherein the at least one of symptoms, medications, clinical data, examination findings, diagnostic tests, images, medical documents, healthcare provider plans, life events, injections, authorizations, claims, and procedures are represented in at least one of the at least one data field using respective icons, indicators, graphical markers, or displayed visual representation, identifying existence of underlying patient data corresponding to at least one of the clinical data, an examination finding, a diagnostic test, an image, a medication, a medical document, a healthcare provider plan, a life event, an injection, an authorization, a claim, and a procedure.

18. The method of claim 17 and further comprising enabling a user to access underlying information of at least one of symptoms, clinical data, examination findings, diagnostic tests, images, medical documents, healthcare provider plans, life events, claims, injections, authorizations, claims, and procedures by providing a selectable icon, indicator, graphical marker or displayed visual representation in one of the data fields to access linked underlying patient information.

19. The method of claim 18, wherein the selection of an icon, indicator, graphical marker or displayed visual representation comprises clicking or hovering over the icon, indicator, graphical marker or displayed visual representation using a pointing device.

20. The method of claim 1, and further comprising enabling a user to edit the data provided in at least one of the respective data fields to auto-populate edits made in the at least one of the respective data fields to the at least one data source.

21. The method of claim 1, wherein the at least one patient data source includes one or more of an electronic health record system, and one or more additional electronic health record system, health record systems, healthcare information technology system, a health information exchange, patient portal, shared care system, telemedicine, diagnostic equipment, picture archiving and communication system, claims-based system, insurance companies billing system, laboratory system, image management system, practice management system, or artificial intelligence engine.

22. The method of claim 1, wherein the received information comprises health care provider order information received from the data source.

23. The method of claim 1, and further comprising displaying a means for placing an order, prescribing a medication, a procedure, diagnostic test, image, medical service.

24. The method of claim 1, wherein automatically updating the flowsheet configuration object comprises adding, expanding, removing or truncating one or more rows, columns, or data fields as a function of a shared care information, user specialty, condition or diagnosis, or life events.

25. The method of claim 1, wherein information received from or derived from the at least one data source includes information corresponding to more than one provider sharing care of the patient, and where detecting a change of patient-related data comprises detecting a change in patient-related data corresponding to a different provider.

26. The method of claim 1, wherein information received from or derived from the at least one data source includes information corresponding to more than one provider sharing care of the patient from different medical practices, and wherein automatically updating the flowsheet configuration object comprises adding one or more rows, columns, or data fields from another provider that shares the care of the patient from a different medical practice.

27. The method of claim 6, wherein the at least one of symptoms, medications, clinical data, examination findings, diagnostic tests, images, medical documents, health care provider plans, life events, authorizations, claims, injections, and procedures are represented in at least one of the at least one data field using respective icons, indicators, graphical markers, or displayed visual representation, identifying existence of underlying patient data corresponding to the symptoms, clinical data, examination findings, diagnostic tests, images, medications, medical documents, health care provider plans, life events, claims, injections, and procedures.

28. The method of claim 27 and further comprising enabling a user to access underlying information of at least one of symptoms, clinical data, examination findings, diagnostic tests, images, medical documents, health care provider plans, life events, claims, injections, and procedures by providing a selectable icon, indicator, graphical marker or displayed visual representation in one of the data fields to access linked underlying patient information.

29. The method of claim 6, and further comprising enabling a user to edit the information provided in at least one of the respective panels and to auto-populate edits made in the at least one of the respective data fields or panels on the viewable dashboard to the at least one data source.

30. The method of claim 6, wherein the executed display rules are derived from local or national guidelines, local or national coverage determinations, preferred practice patterns, or clinical decision support knowledge base.

31. The method of claim 6, wherein the data fields are reordered or grouped by execution of the display rules.

32. The method of claim 6, wherein the configuration rules are identified based on a changed parameter value or.

33. The method of claim 6, and further comprising displaying a means for placing an order, prescribing a medication, a procedure, diagnostic test, image, medical service.

34. The method of claim 23, wherein automatically updating the view layout object comprises adding, removing, hiding, expanding or truncating one or more data fields as a function of user specialty, condition or diagnosis, or life events, or clinical decision support.

35. The method of claim 6, wherein the patient data from the at least one patient data source includes information corresponding to more than one provider sharing care of the patient wherein detecting a change of patient data comprises detecting a change in patient data corresponding to another provider that shares the care of the patient.

36. The method of claim 6, wherein patient data from the at least one patient data source includes information corresponding to more than one provider sharing care of the patient, and wherein automatically updating the view layout object comprises modifying a data field from another provider that shares the care of the patient.

37. The method of claim 8, wherein the at least one of symptoms, medications, clinical data, examination findings, diagnostic tests, images, medical documents, health care provider plans, life events, claims, injections, claims, authorizations and procedures are represented in at least one of the at least one data field or panel using respective icons, indicators, graphical markers, or displayed visual representation, identifying existence of underlying patient data corresponding to at least one of clinical data, an examination finding, a diagnostic test, an image, a medication, a medical document, a healthcare provider plan, a life event, an injection, an authorization, a claim, and a procedure.

38. The method of claim 37 and further comprising enabling a user to access underlying information of at least one of symptoms, clinical data, examination findings, diagnostic tests, images, medical documents, health care provider plans, life events, claims, injections, claims, authorizations, and procedures by providing a selectable icon, indicator, graphical marker or displayed visual representation in one of the data fields or panels to access linked underlying patient information.

39. The method of claim 38, wherein the selection of an icon, indicator, graphical marker or displayed visual representation comprises clicking or hovering over the icon, indicator, graphical marker or displayed visual representation using a pointing device.

40. The method of claim 8, wherein the executed display rules are derived from local or national guidelines, local or national coverage determinations, preferred practice patterns or clinical decision support knowledge base.

41. The method of claim 8, wherein the data fields or panels are reordered or grouped by execution of the display rules.

42. The method of claim 8 wherein the configuration rules are identified based on a changed parameter value or clinical decision support.

43. The method of claim 8, wherein the received patient-related data comprises order information or information received from the at least one data source.

44. The method of claim 8, wherein patient-related data received from or derived from the at least one patient data source includes information corresponding to more than one provider sharing care of the patient, and wherein modifying the first dashboard configuration comprises removing, hiding, adding, expanding or truncating one or more data fields or panels as a function of user specialty, condition or diagnosis or diagnoses, detected change of patient data, life events, or clinical decision support.

45. The method of claim 8 wherein patient-related data received from or derived from the at least one patient data source includes information corresponding to more than one provider sharing care of the patient, and wherein the display rules are identified based on modifying the first configuration flowsheet configuration object to add one or more data fields or panels from another provider that shares the care of the patient.

46. The method of claim 8, wherein information received from or derived from the at least one patient data source includes information corresponding to more than one provider sharing care of the patient, and wherein the data fields are added, reordered or grouped by execution of the display rules that include data from another provider that shares the care of the patient.

47. The method of claim 1 wherein executing the display rules comprises identifying less relevant information, and wherein executing display rules comprises compiling a final dataset containing the relevant and less relevant information wherein the changed dashboard configuration is stored in a flowsheet configuration object containing definitions and constraints outlining information to be displayed.

48. The method of claim 1, and further comprising:

preprocessing patient-related data from the at least one patient data source, including the changed patient-related data; and generating an object optimized for displaying information in the modified medical dashboard.

49. The method of claim 48 wherein the flowsheet configuration object is populated with information using the generated object optimized for displaying the information to minimize time required for displaying the changed dashboard configuration.

50. The method of claim 49 and further comprising using proximity request storage to store the object optimized for displaying the information.

51. The method of claim 1 wherein executing the display rules to generate a flowsheet configuration object modifies the dashboard configuration based on a specified medical specialty and wherein the medical dashboard further comprises selectable dashboard configurations, each specific to a medical specialty, such that selection of a dashboard configuration specific to the medical specialty results in a dashboard configuration that includes medical information for the patient specific to that specialty.

52. The method of claim 51 wherein the selected dashboard configuration specific to the medical specialty includes medical information of a patient configured for the medical specialty that includes at least one link to access underlying data related to the patient.

53. The method of claim 6, wherein automatically updating the view layout in response to detecting the change of patient-related data comprises:

preprocessing patient information from the at least one patient data source, including the changed patient data; and generating an object optimized for displaying information in the modified medical dashboard.

54. The method of claim 53 wherein the view layout object is populated with information using the generated object optimized for displaying the information to minimize time required for displaying the changed dashboard configuration.

55. The method of claim 54 and further comprising using proximity request storage to store the object optimized for displaying the information.

56. The method of claim 8, wherein automatically updating the first configuration flowsheet configuration object in response to detecting the change of patient-related data comprises:
- preprocessing patient information from the at least one patient data source, including the changed patient data; and
- generating an object optimized for displaying information in the modified medical dashboard.

57. The method of claim 56 wherein the first configuration flowsheet configuration object is populated with information using the generated object optimized for displaying the information to minimize time required for displaying the changed dashboard configuration.

58. The method of claim 57 and further comprising using proximity request storage to store the object optimized for displaying the information.

59. The method of claim 1 wherein automatically updating the flowsheet configuration object is performed such that the changed flowsheet configuration object dashboard configuration includes a link in the additional data field to underlying information associated with the additional information.

60. The method of claim 59 wherein selection of the link causes display of the underlying information such that both the information relating to the detected change and other relevant patient-related data remain visible and accessible to enable user interaction.

61. The method of claim 6 wherein the at least one data field of the dashboard configuration is modified to reduce an amount of information identified as less relevant by reducing a number of rows or columns and thereby reducing a size of the at least one data field.

62. The method of claim 1, further comprising:
- executing rules based on artificial intelligence adaptive learning engine techniques, natural language processing programs or conventional business logic to detect a change of patient data; and
- executing display rules in response to detecting the change of patient data to generate a flowsheet configuration object based on the detected change of patient data.

63. The method of claim 8, further comprising:
- executing rules based on artificial intelligence adaptive learning engine techniques, natural language processing programs or conventional business logic to detect a change of patient data; and
- executing display rules in response to detecting the change of patient data to generate a flowsheet configuration object based on the detected change of patient data.

64. The method of claim 1 wherein automatically updating the flowsheet configuration object further comprises removing from the flowsheet configuration object a row or column corresponding to information determined to be less relevant after the change to make room for the added row or column corresponding to additional patient-related data of a further different one of said elements that was not defined for display before the change.

65. The method of claim 1 wherein automatically updating the flowsheet configuration object further comprises modifying the flowsheet configuration object to collapse, hide, or reduce a display size of one or more rows or columns corresponding to information determined to be less relevant after the change.

66. The method of claim 1 wherein automatically updating the flowsheet configuration object further comprises modifying the flowsheet configuration object to expand, emphasize, group, or reorder one or more rows or columns corresponding to information determined to be more relevant after modification.

67. The method of claim 1 wherein generating the flowsheet configuration object further comprises one or more constraints outlining what patient-related data should be displayed in the rows or columns.

68. The method of claim 1 wherein the flowsheet configuration object comprises an XML or JSON data structure defining a collection of data fields and, for each data field, attributes specifying a data field identifier, a display position, a stacking state, and a set of rows or columns to be rendered within the data field.

69. The method of claim 1 wherein executing, by at least one processor, clinical decision-support rules is performed by querying a clinical comparator database table that stores a plurality of rules, each rule mapping a clinical data code to a validator, and applying the validator to a current data value and a previous data value from the flowsheet data structure.

70. The method of claim 1 wherein storing the patient-related data in a flowsheet data structure comprises storing one or more presentation tables containing pre-processed and aggregated data dynamically updated from external sources, the presentation tables being optimized for retrieval to minimize latency in generating the medical dashboard.

71. The method of claim 1 wherein executing the clinical decision-support rules comprises processing unstructured text notes within the flowsheet data structure using a natural language processing engine to identify clinical concepts and applying the rules to the identified clinical concepts.

72. The method of claim 1, wherein detecting the change of the patient-related data comprises determining that at least one of the clinical data, test result, or vital sign has changed by more than a predefined clinical threshold stored in a rules repository, and wherein only changes exceeding the predefined clinical threshold cause the flowsheet configuration object to be automatically updated.

73. The method of claim 1, further comprising receiving, from a user, an override input that prevents automatic removal or collapsing of at least one data field identified as less relevant by the clinical decision-support rules, and modifying the flowsheet configuration object to maintain visibility of the corresponding rows or columns responsive to the override input.

74. The method of claim 1, wherein automatically updating the flowsheet configuration object comprises modifying the flowsheet configuration object to restrict the rows or columns displayed in the flowsheet data field to a configurable time window relative to the detected change of patient-related data.

75. The method of claim 6, wherein automatically updating the view layout object further comprises assigning priority scores to panel definitions based on outputs of the decision support rules and ordering the panels in the medical dashboard according to the priority scores.

76. The method of claim 6, wherein the panel definitions include a panel type attribute selected from the group consisting of summary, condition-specific, workflow, imaging, and financial, and wherein automatically updating the view layout object comprises changing visibility or position of panels based at least in part on the panel type attribute.

77. The method of claim 8, wherein generating the first flowsheet configuration object further comprises selecting one of a plurality of predefined configuration templates corresponding to clinical scenarios including at least preoperative, postoperative, and chronic-disease-management scenarios.

78. The method of claim 8, further comprising storing, in association with the patient, a version history of the flowsheet configuration object including a previous configuration and the changed dashboard configuration, and enabling a user to revert the medical records dashboard to the previous configuration.

79. A data command center visual display system for dynamically presenting patient-related data for a patient on a medical dashboard, the system comprising:

at least one processor;

at least one memory storing instructions executable by the at least one processor;

at least one patient data source interface configured to receive, from at least one patient data source, patient-related data for the patient, the patient-related data including information corresponding to multiple different elements selected from the group consisting of diagnosis, symptoms, medications ordered, prescribed, taken, or administered, clinical data, life events, examination findings, diagnostic tests, images, health care provider plans, medical documents, injections, claims, authorizations, and procedures performed on the patient;

a flowsheet data structure stored in the at least one memory and configured to organize, for each of a plurality of encounters of the patient, the patient-related data such that, for each of a plurality of data fields of the medical dashboard, the flowsheet data structure stores one or more rows or columns of one type of the information received or derived from the at least one patient data source, with at least two of the rows or columns arranged according to a time that the information was performed on or collected for the patient;

at least one flowsheet configuration object stored in the at least one memory and generated by the at least one processor, the flowsheet configuration object defining, for the patient, a dashboard configuration describing a display layout of multiple data fields of the medical dashboard including a flowsheet data field, the flowsheet configuration object specifying which rows or columns from the flowsheet data structure are to be displayed in the flowsheet data field and an order and visibility state of the rows or columns;

a medical dashboard module configured, when the instructions are executed by the at least one processor, to:

generate a dynamic data display comprising the medical dashboard including a first dashboard configuration describing a display layout of the multiple data fields including information received or derived from the at least one patient data source; and render and display, on at least one display device, the medical dashboard including the flowsheet data field by applying the flowsheet configuration object to the flowsheet data structure such that the rows or columns specified by the flowsheet configuration object are presented in the medical dashboard in accordance with the first dashboard configuration;

a clinical decision-support module comprising at least one rules engine configured to execute clinical decision-support rules derived from at least one of clinical guidelines, insurance regulations, local or national coverage determinations, preferred practice patterns, or clinical decision-support knowledge bases, the clinical decision-support rules being applied to the patient-related data in the flowsheet data structure to determine information that is more relevant or less relevant for the patient at a given time or for at least one of a healthcare provider, administrative user, or practice;

a change detection module configured to detect, in the flowsheet data structure, a change of the patient-related data for the patient, the change including at least one of a diagnosis, medical condition, symptom, clinical data, procedure, test result, medication order, encounter with another health care provider of the patient, a change in authorization status, a change in claim status, a change in payment status, or a change denial status;

display rules module configured to execute display rules, in response to detecting the change and based on results of execution of the clinical decision-support rules, by parsing information from at least one patient data source to identify additional information responsive to the change of patient-related data; and a configuration update and rendering module configured, when the instructions are executed by the at least one processor and in response to the display rules module identifying the additional information, to:

automatically update the flowsheet configuration object by adding to the flowsheet configuration object a row or column corresponding to additional patient-related data of a further different one of said elements that was not defined for display before the change of patient data, to generate a modified dashboard configuration that includes an added data field corresponding to additional information from the further different element of the group based on the detected change of related data, the additional information comprising rows or columns of an additional type of information over time from one of medications ordered, prescribed, taken, or administered, clinical data, life events, examination findings, diagnostic tests, images, medical documents, injections, or procedures; and render and display, on the at least one display device, the changed dashboard including the flowsheet data field as automatically modified by applying the updated flowsheet configuration object to the flowsheet data structure for the patient, such that the change in patient-related data and the corresponding change in the flowsheet configuration with the additional information not displayed in the first dashboard configuration is displayed in the added data field and at least one of the first dashboard displayed data fields remains visible without navigating away from the medical dashboard.

80. The system of claim 79, wherein the at least one memory further stores an object optimized for displaying information in the changed medical dashboard, the object being generated by preprocessing patient-related data from the at least one patient data source, and the system further comprises a proximity request storage configured to store the object optimized for displaying the information to minimize time required for displaying the changed dashboard configuration.

81. A data command center visual display system for generating a dynamic data display comprising a medical records dashboard, the system comprising:

at least one processor;

at least one memory storing instructions executable by the at least one processor;

at least one patient data source interface configured to receive, from at least one patient data source, patient-related data for a patient, the patient-related data including a first configuration describing a layout of one or more panels including one or more data fields containing information received or derived from the at least one patient data source, the medical records dashboard comprising a display, using the one or more panels, of information corresponding to multiple elements selected from the group consisting of diagnosis, symptoms, medications ordered, prescribed, taken, or administered, clinical data, life events, examination findings, diagnostic tests, images, health care provider plans, medical documents, injections, claims, authorizations, and procedures performed on the patient;

a data structure stored in the at least one memory and configured to organize, for the patient, the multiple elements as rows or columns of one type of information according to a time that the corresponding element or information was performed on or collected for the patient;

at least one first flowsheet configuration object stored in the at least one memory and generated by the at least one processor, the first flowsheet configuration object comprising information describing a layout of the one or more panels of the medical records dashboard, each panel including one or more data fields containing information received or derived from the at least one patient data source, the data fields corresponding to selected types of information from the elements of the group, each of the data fields corresponding to a selected type of information from an element of the group and containing one or more pieces of information corresponding to the respective type of information received or derived from the at least one patient data source;

a dashboard rendering module configured, when the instructions are executed by the at least one processor, to display, on at least one display device, the medical records dashboard by applying the first flowsheet configuration object to the data structure to display patient-related data in selected, respective ones of the data fields or panels in accordance with the first flowsheet configuration object;

a change detection module configured to detect a change of patient-related data for the patient;

at least one decision-support module comprising a rules engine configured to execute display rules and clinical decision-support rules derived from at least one of clinical guidelines, insurance regulations, local or national coverage determinations, preferred practice patterns, or clinical decision-support knowledge bases, the rules being applied to the patient-related data in the data structure to determine information that is more relevant or less relevant based on the detected change of patient-related data; and a configuration update module configured, when the instructions are executed by the at least one processor and in response to the change detection module detecting the change of patient-related data and the decision-support module applying the display rules, to automatically modify the first flowsheet configuration object to generate a changed flowsheet configuration object describing a changed dashboard configuration by at least one of:

adding a data field in one of the panels corresponding to additional patient-related data of a type that was not defined for display before the detected change;

expanding a data field to expand a number of rows or columns of information in the data field;

collapsing or removing a data field containing less relevant information;

adding an alert to a data field;

changing an appearance of information in a data field;

adding a graphical representation providing access to underlying information; or adding a text link data representation; and to render and display, on the at least one display device, the medical records dashboard according to the changed flowsheet configuration object such that the change in patient-related data and corresponding additional information are displayed in the medical records dashboard and at least one data field from the first configuration remains visible without navigating away from the medical records dashboard.

82. The system of claim 81, wherein the at least one patient data source interface is further configured to receive patient-related data corresponding to more than one provider sharing care of the patient, and wherein the configuration update module is further configured to, in response to the received patient-related data corresponding to more than one provider sharing care of the patient, add one or more data fields or panels to the medical records dashboard corresponding to information from another provider that shares care of the patient.

83. The method of claim 8 wherein generating the flowsheet configuration object further comprises one or more constraints outlining what patient-related data should be displayed in the rows or columns.

84. The method of claim 8 wherein the flowsheet configuration object comprises an XML or JSON data structure defining a collection of data fields and, for each data field, attributes specifying a data field identifier, a display position, a stacking state, and a set of rows or columns to be rendered within the data field.

85. The system of claim 79, wherein the at least one patient data source interface is further configured to receive patient-related data corresponding to more than one provider sharing care of the patient, and wherein the configuration update module is further configured to, in response to the received patient-related data corresponding to more than one provider sharing care of the patient, add one or more data fields or panels to the medical dashboard corresponding to information from another provider that shares care of the patient.

86. The system of claim 79 wherein the flowsheet configuration object comprises an XML or JSON data structure defining a collection of data fields and, for each data field, attributes specifying a data field identifier, a display position, a stacking state, and a set of rows or columns to be rendered within the data field.

87. The system of claim 81 wherein executing, by at least one processor, clinical decision-support rules is performed by querying a clinical comparator database table that stores a plurality of rules, each rule mapping a clinical data code to a validator, and applying the validator to a current data value and a previous data value from the flowsheet data structure.

88. The system of claim 81 wherein executing the clinical decision-support rules comprises processing unstructured text notes within the flowsheet data structure using a natural language processing engine to identify clinical concepts and applying the rules to the identified clinical concepts.

89. The system of claim 81, wherein generating the first flowsheet configuration object further comprises selecting one of a plurality of predefined configuration templates corresponding to clinical scenarios including at least preoperative, postoperative, and chronic-disease-management scenarios.

90. The system of claim 81 and further comprising:

preprocessing patient-related data from the at least one patient data source, including the changed patient-related data; and generating an object optimized for displaying information in the modified medical dashboard.

91. The system of claim 90 wherein the flowsheet configuration object is populated with information using the generated object optimized for displaying the information to minimize time required for displaying the changed dashboard configuration.

92. The system of claim 91 further comprising using proximity request storage to store the object optimized for displaying the information.

93. The system of claim 79 wherein generating the flowsheet configuration object further comprises one or more constraints outlining what patient-related data should be displayed in the rows or columns.

* * * * *